United States Patent
Hamers et al.

(10) Patent No.: US 11,286,621 B2
(45) Date of Patent: Mar. 29, 2022

(54) AQUEOUS SURFACE TREATMENT COMPOSITION FOR PAPER AND BOARD

(71) Applicant: BASF SE, Ludwigshafen (DE)

(72) Inventors: Christoph Hamers, Schifferstadt (DE); Konstantino Karanikas, Sparta, NJ (US); Kenneth Barrett, Del Mar, CA (US); Zheng Tan, Ewing, NJ (US)

(73) Assignee: BASF SE, Ludwigshafen (DE)

( * ) Notice: Subject to any disclaimer, the term of this patent is extended or adjusted under 35 U.S.C. 154(b) by 445 days.

(21) Appl. No.: 15/752,285

(22) PCT Filed: Aug. 12, 2016

(86) PCT No.: PCT/EP2016/069288
§ 371 (c)(1),
(2) Date: Feb. 13, 2018

(87) PCT Pub. No.: WO2017/029238
PCT Pub. Date: Feb. 23, 2017

(65) Prior Publication Data
US 2019/0271115 A1   Sep. 5, 2019

Related U.S. Application Data

(60) Provisional application No. 62/205,609, filed on Aug. 14, 2015.

(51) Int. Cl.
| | | |
|---|---|---|
| *D21H 19/54* | (2006.01) | |
| *C12P 19/14* | (2006.01) | |
| *C12P 19/16* | (2006.01) | |
| *C12P 19/18* | (2006.01) | |
| *C12P 19/22* | (2006.01) | |
| *D21H 17/28* | (2006.01) | |
| *D21H 27/40* | (2006.01) | |
| *D21H 21/18* | (2006.01) | |
| *D21H 25/06* | (2006.01) | |

(52) U.S. Cl.
CPC ............ *D21H 19/54* (2013.01); *C12P 19/14* (2013.01); *C12P 19/16* (2013.01); *C12P 19/18* (2013.01); *C12P 19/22* (2013.01); *D21H 17/28* (2013.01); *D21H 21/18* (2013.01); *D21H 27/40* (2013.01); *D21H 25/06* (2013.01)

(58) Field of Classification Search
CPC ........ D21H 19/54; D21H 17/28; D21H 25/06; C12P 19/14; C12P 19/16; C12P 19/18; C12P 19/22
See application file for complete search history.

(56) References Cited

U.S. PATENT DOCUMENTS

| | | | |
|---|---|---|---|
| 4,169,810 A | 10/1979 | Gunther et al. | |
| 5,482,514 A | 1/1996 | Von Raven | |
| 5,902,454 A | 5/1999 | Nelson | |
| 6,426,382 B1 | 7/2002 | Farrar et al. | |
| 6,723,846 B1 | 4/2004 | Metzger et al. | |
| 6,890,454 B2 | 5/2005 | Farrar et al. | |
| 6,893,473 B2 | 5/2005 | Neogi et al. | |
| 7,273,740 B2 | 9/2007 | Callen et al. | |
| 7,323,336 B2 | 1/2008 | Callen et al. | |
| 7,407,677 B2 | 8/2008 | Callen et al. | |
| 8,338,131 B2* | 12/2012 | Callen .................. | C12N 9/2411 435/41 |
| 8,349,464 B2 | 1/2013 | Wicher et al. | |
| 9,062,295 B2 | 6/2015 | Callen et al. | |
| 9,701,950 B2* | 7/2017 | Callen .................. | C12N 9/2417 |
| 10,066,222 B2* | 9/2018 | Callen .................. | C12N 9/2411 |
| 2009/0250183 A1 | 10/2009 | Hayes et al. | |
| 2011/0039308 A1* | 2/2011 | Slupska ............... | C12N 9/2428 435/101 |
| 2011/0230601 A1 | 9/2011 | Nieberle et al. | |
| 2015/0197891 A1 | 7/2015 | Van Der Maarel et al. | |

FOREIGN PATENT DOCUMENTS

| | | |
|---|---|---|
| CN | 103946448 A | 7/2014 |
| EP | 0257412 A1 | 3/1988 |
| EP | 0273770 A2 | 7/1988 |
| EP | 0470871 A1 | 2/1992 |
| EP | 0690170 A1 | 1/1996 |
| EP | 1109927 A0 | 6/2001 |
| EP | 121442 A0 | 6/2002 |
| GB | 871937 | 7/1961 |
| JP | 2009243013 | 10/2009 |
| JP | 2011506794 | 3/2011 |
| WO | 97/45590 A1 | 12/1997 |
| WO | 99/42490 A1 | 8/1999 |
| WO | 01/34784 A1 | 5/2001 |
| WO | 02/14393 A1 | 2/2002 |
| WO | 2006/124869 A1 | 11/2006 |
| WO | 2006/124871 A1 | 11/2006 |
| WO | 2007/000419 A1 | 1/2007 |

(Continued)

OTHER PUBLICATIONS

International Preliminary Report on Patentability and Written Opinion dated Feb. 20, 2018 in PCT/EP2016/069288 (English Translation only), 8 pages.

Napaporn Atichokudomchai, et al., "Reaction Pattern of a Novel Thermostable α-amylase", Carbohydrate Polymers, vol. 64, Issue 4, Jun. 16, 2006, pp. 582-588.

Rani Gupta, et al., "Microbial α-amylases: a biotechnological perspective", Process Biochemistry 00, 2003, pp. 1-18 and cover page.

(Continued)

*Primary Examiner* — Iqbal H Chowdhury
(74) *Attorney, Agent, or Firm* — Marshall, Gerstein & Borun LLP

(57) ABSTRACT

Embodiments disclosed herein provide enzymatic formulations comprising a polypeptide having amylase activity for producing a paper product. Also provided are aqueous surface treatment compositions for paper and board comprising degraded starch. Further provided are methods for producing paper and board using the aqueous surface treatment composition, and to corrugated boards produced from this paper.

24 Claims, No Drawings

Specification includes a Sequence Listing.

(56) References Cited

FOREIGN PATENT DOCUMENTS

| | | | |
|---|---|---|---|
| WO | 2007/000420 A1 | 1/2007 |
| WO | 2007/055911 A1 | 5/2007 |
| WO | 2007/055912 A1 | 5/2007 |
| WO | 2008/080093 A2 | 7/2008 |
| WO | 2008/092919 A1 | 8/2008 |
| WO | 2010/003054 A1 | 1/2010 |
| WO | 2010/088447 A1 | 8/2010 |
| WO | 2011/039185 A2 | 4/2011 |
| WO | 2012/076163 A2 | 6/2012 |
| WO | 2013/034106 A1 | 3/2013 |
| WO | 2013/044867 A1 | 4/2013 |
| WO | 2014/003556 A1 | 1/2014 |

OTHER PUBLICATIONS

Catherine L. Lawson, et al., "Nucleotide Sequence and X-ray Structure of Cyclodextrin Glycosyltransferase from Bacillus circulars Strain 251 in a Maltose-dependent Crystal Form", Journal of Molecular Biology, vol. 236, Mar. 1994, pp. 590-600.

Eugene W. Myers, et al., "Optimal Alignments in Linear Space", Computer applications in the biosciences : CABIOS, vol. 4, Issue 1, 1988, pp. 11-17.

Toby H. Richardson, et al., "A novel, High Performance Enzyme for Starch Liquefaction. Discovery and Optimization of a Low pH, Thermostable alpha-amylase", The Journal of Biological Chemistry, vol. 277, No. 29, Jul. 19, 2002, pp. 26501-26507 and cover page.

U.S. Appl. No. 15/035,959, filed May 11, 2016, US 2016-0265162 A1, Holger Kern.

U.S. Appl. No. 15/129,986, filed Sep. 28, 2016, US 2017-0183821 A1, Matthew Buchan.

U.S. Appl. No. 15/322,367, filed Dec. 27, 2016, Christoph Hamers.

U.S. Appl. No. 15/518,514, filed Apr. 12, 2017, US 2017-0233950 A1, Hans-Joachim Haehnle.

U.S. Appl. No. 15/536,552, filed Jun. 15, 2017, US 2017-0362776 A1, Hans-Joachim Haehnle.

International Search Report dated Feb. 13, 2017, in PCT/EP2016/069288, filed Aug. 12, 2016.

* cited by examiner

AQUEOUS SURFACE TREATMENT COMPOSITION FOR PAPER AND BOARD

BACKGROUND

Field

The present disclosure relates to an aqueous surface treatment composition for paper and board comprising degraded starch. The present disclosure further relates to a method for producing paper and board using the aqueous surface treatment composition, and to corrugated boards produced from this paper.

Description of the Related Art

Starch surface treatment on paper web materials is extensively used in various paper products and grades. Substantial portions of the starch used in the paper surface treatment, such as by various types of size-press or coating devices, are modified starches such as ethylated starches, oxidized starches, which are quite expensive compared to unmodified starches. On-site oxidative starch modification, such as carried out by ammonium persulfate oxidations (or catalytic peroxide oxidations) of Pearl starch in the jet cooker, has also been used in the paper industry for providing a starch based surface treatment composition with reduced costs. On-site oxidative hydrolysis modification of starches, however, generate unstable oxidation groups on the starch macromolecules as well as on the oxidatively degraded carbohydrate derived products, all of which are susceptible to yellowing or color reversions, reducing the brightness and whiteness of the surface treated papers. This deleterious effect is especially costly, when optical brightening agents (OBAs) are used on the paper surface (or inside paper web) and the effectiveness of the expensive OBAs is substantially reduced by these yellowing starch products. Enzymatic modification of starch by amylase has also been practiced in paper industry for providing surface size or coating compositions. However, many of the commercial amylase enzymes, suffers from lack of sufficient thermostability or pH stability which makes them susceptible to inactivation by industrial process condition variations. The dose of enzymes required of traditional amylase, and the need of careful control on process conditions to avoid inactivation or to avoid process upsets due to non-uniform viscosity development, have put some limitations on the cost, use range, or industrial methods/devices of amylases in paper surface treatment applications. There is a need to further improve amylase dose effectiveness for reducing cost and reducing the enzyme (protein) carry over to the products. There is also a need to provide an enzyme modified starch surface treatment composition with improved process stability, uniform viscosity control, and expanded range of surface treatment methods.

An important requirement in the packaging paper segment is the strength of the paper, since an important basis for such paper are recycled fibers, which lose length as a result of the recycling and hence lead to a successive decrease in the strength of the paper. To enhance the qualities of the paper, the paper stock is often admixed with assistants such as wet and dry strength agents, such as cationic and anionic polyacrylamide or polyvinylamine, retention agents, and sizing agents. The effect of cationic strengtheners in the paper stock, however, is partly undone by anionic compounds from the recycling process. Attempts are therefore made to obtain additional strength through the adding of assistants to the paper sheet, in the size press, for example.

In surface sizing it is the paper sheet that is coated. Surface sizing agents employed are often gelatin or derivatives of starch. Starch of this kind, added as a surface sizing agent, likewise has a strengthening effect. But it is not possible to increase strength by starch ad infinitum. There is an upper limit as it comes to the amount of starch, which can be used for sizing purposes. Therefore it was an object of the present disclosure to provide a surface treatment composition which makes it possible to add more than 60 kg degraded starch per ton paper (solid). Another object of the present disclosure is to prove improved pick up of starch-containing surface treatment at same solid content or at higher solid content.

SUMMARY

1. Use of an enzymatic formulation for producing a paper or board surface treatment composition, comprising:
    (a) providing an enzymatic formulation comprising a polypeptide having an amylase activity;
    (b) providing a starch; and
    (c) contacting the enzymatic formulation with the starch, thereby hydrolyzing the starch to produce a paper surface treatment composition comprising degraded starch having a weight-average molecular weight (Mw) in the range from 10,000 to 12,000,000 and a polydispersity index (Mw/Mn) of 1.3 to 49.

2. The use of Embodiment 1, for the production of a paper product.

3. The use of Embodiment 1, for the production of a paper product having improved surface quality.

4. The use of Embodiment 3, wherein the surface quality of the paper product is selected from the group consisting of water resistance, a barrier property for moisture, vapor, oxygen, oil, or grease, resistance to fuzz, reduced abrasiveness, a printing property, a surface charge property, ink/color/dye fixation, and bonding or surface strength.

5. The use of any one of Embodiments 2-4, wherein the paper product is photocopy paper, computer printer paper, notebook paper, notepad paper, typewriter paper, newspaper, magazine, cardboard, corrugated board, paper-based packaging material, or paper-based printing and writing material.

6. The use of any one of Embodiments 1-5, wherein the enzymatic formulation comprises a glucoamylase and/or a debranching enzyme.

7. The use of any one of Embodiments 1-5, wherein the enzymatic formulation does not comprise a glucoamylase and/or a debranching enzyme.

8. The use of any one of Embodiments 1-7, wherein the enzymatic formulation further comprises a protease, a lipase, a peroxidase, a laccase, a tyrosinase, a cellubiohydrolase, a glucose oxidase, a transferase, a glycosyl transferase, a pectinase, an esterase, a cellobiose oxidoreductase, a glyoxal oxidase, an epimerase, an invertase, a chlorophyllase, or any combination thereof.

9. The use of any one of Embodiments 1-8, wherein the paper surface treatment composition comprises 1 to 40 wt % of the degraded starch.

10. The use of any one of Embodiments 1-9, wherein the paper surface treatment composition comprises 2 to 30 wt % of the degraded starch.

11. The use of any one of Embodiments 1-10, wherein the degraded starch has a weight-average molecular weight Mw of in the range from 400,000 to 5,000,000 and a polydispersity index (Mw/Mn) of 10 to 49.

12. The use of any one of Embodiments 1-11, wherein the degraded starch has a polydispersity index (Mw/Mn) of less than 45.

13. The use of any one of Embodiments 1-11, wherein the degraded starch has a polydispersity index (Mw/Mn) of less than 40.

14. The use of any one of Embodiments 1-11, wherein the degraded starch has a polydispersity index (Mw/Mn) of less than 35.

15. The use of any one of Embodiments 1-11, wherein the degraded starch has a polydispersity index (Mw/Mn) of less than 30.

16. The use of any one of Embodiments 1-11, wherein the degraded starch has a polydispersity index (Mw/Mn) of less than 25.

17. The use of any one of Embodiments 1-11, wherein the degraded starch has a polydispersity index (Mw/Mn) of less than 20.

18. The use of any one of Embodiments 1-11, wherein the degraded starch has a polydispersity index (Mw/Mn) of less than 15.

19. The use of any one of Embodiments 1-11, wherein the degraded starch has a polydispersity index (Mw/Mn) of less than 10.

20. The use of any one of Embodiments 1-11, wherein the degraded starch has a polydispersity index (Mw/Mn) of less than 7.5.

21. The use of any one of Embodiments 1-11, wherein the degraded starch has a polydispersity index (Mw/Mn) of less than 5.

22. The use of any one of Embodiments 1-21, wherein the polypeptide having an amylase activity has at least 80% identity to SEQ ID NO:12 (SEQ ID NO:2 of U.S. Pat. No. 7,273,740 of Table 3).

23. The use of any one of Embodiments 1-21, wherein the polypeptide having an amylase activity has at least 80% identity to any one of amino acid sequences disclosed in Table 3 and 4.

24. The use of any one of Embodiments 1-21, wherein the polypeptide having an amylase activity is any one of those set forth in Tables 1 & 2.

25. A method for producing a paper or board surface treatment composition, comprising:
(a) providing a polypeptide having an amylase activity;
(b) providing a starch; and
(c) contacting the polypeptide of (a) with the starch of (b), thereby hydrolyzing the starch to produce a paper surface treatment composition comprising degraded starch having a weight-average molecular weight (Mw) in the range from 10,000 to 12,000,000 and a polydispersity index (Mw/Mn) of 1.3 to 49.

26. The method of Embodiment 25, wherein the paper surface treatment composition is for treating photocopy paper, computer printer paper, notebook paper, notepad paper, typewriter paper, newspaper, magazine, cardboard, corrugated board, or paper-based packaging material.

27. The method of Embodiment 25 or 26, wherein the paper surface treatment composition comprises 1 to 40 wt % of the degraded starch.

28. The method of any one of Embodiments 25-27, wherein the paper surface treatment composition comprises 2 to 30 wt % of the degraded starch.

29. The method of any one of Embodiments 25-28, wherein the degraded starch has a weight-average molecular weight Mw of in the range from 400,000 to 5,000,000 and a polydispersity index (Mw/Mn) of 10 to 49.

30. The method of any one of Embodiments 25-29, wherein the degraded starch has a polydispersity index (Mw/Mn) of less than 45.

31. The method of any one of Embodiments 25-29, wherein the degraded starch has a polydispersity index (Mw/Mn) of less than 40.

32. The method of any one of Embodiments 25-29, wherein the degraded starch has a polydispersity index (Mw/Mn) of less than 35.

33. The method of any one of Embodiments 25-29, wherein the degraded starch has a polydispersity index (Mw/Mn) of less than 30.

34. The method of any one of Embodiments 25-29, wherein the degraded starch has a polydispersity index (Mw/Mn) of less than 25.

35. The method of any one of Embodiments 25-29, wherein the degraded starch has a polydispersity index (Mw/Mn) of less than 20.

36. The method of any one of Embodiments 25-29, wherein the degraded starch has a polydispersity index (Mw/Mn) of less than 15.

37. The method of any one of Embodiments 25-29, wherein the degraded starch has a polydispersity index (Mw/Mn) of less than 10.

38. The method of any one of Embodiments 25-29, wherein the degraded starch has a polydispersity index (Mw/Mn) of less than 7.5.

39. The method of any one of Embodiments 25-29, wherein the degraded starch has a polydispersity index (Mw/Mn) of less than 5.

40. The method of any one of Embodiments 25-39, wherein the polypeptide having an amylase activity has at least 80% identity to SEQ ID NO:12 (SEQ ID NO:2 of U.S. Pat. No. 7,273,740 of Table 3).

41. The method of any one of Embodiments 25-39, wherein the polypeptide having an amylase activity has at least 80% identity to any one of amino acid sequences disclosed in Table 3 and 4.

42. The method of any one of Embodiments 25-39, wherein the polypeptide having an amylase activity is any one of those set forth in Tables 1 & 2.

43. The method of any one of Embodiments 25-42, wherein the polypeptide having amylase activity is provided at 0.01 ppm to 1000 ppm based on the weight of the starch.

44. The method of any one of Embodiments 25-42, wherein the polypeptide having amylase activity is provided at 0.05 ppm to 500 ppm based on the weight of the starch.

45. The method of any one of Embodiments 25-42, wherein the polypeptide having amylase activity is provided at 0.1 ppm to 250 ppm based on the weight of the starch.

46. The method of any one of Embodiments 25-42, wherein the polypeptide having amylase activity is provided at 0.15 ppm to 150 ppm based on the weight of the starch.

47. The method of any one of Embodiments 25-46, wherein the method further comprises use of a protease, a lipase, a peroxidase, a laccase, a tyrosinase, a cellubiohydrolase, a glucose oxidase, a transferase, a glycosyl transferase, a pectinase, an esterase, a cellobiose oxidoreductase, a glyoxal oxidase, an epimerase, an invertase, a chlorophyllase, or any combination thereof.

48. The method of any one of Embodiments 25-47, wherein the method further comprises use of a glucoamylase and/or a debranching enzyme.

49. The method of Embodiment 48, wherein the debranching enzyme is a hemicellulase, an isoamylase, a beta amylase, a gamma amylase, an exo-amylase, a pullulanase, a xylanase, a mannanase, an alpha gluconase, an endocellulase, an exocellulase, or any combination thereof.

50. The method of any one of Embodiments 25-49, wherein the starch is from rice, corn, barley, wheat, legumes, potato, Tapioca, soybean oat, rye, beet or sugar cane.

51. The method of any one of Embodiments 25-50, wherein the starch is treated by chemical treatment, mechanical treatment, thermal treatment, acid treatment, oxidation, derivatization, or enzymatic treatment.

52. The method of Embodiment 51, wherein the thermal treatment comprises temperatures between 60-100° C. for 5 to 60 minutes.

53. The method of any one of Embodiments 25-52, comprising inactivating the polypeptide having an amylase activity.

54. The method of Embodiment 53, comprising inactivating the polypeptide having an amylase activity via heating.

55. The method of Embodiment 54, wherein the polypeptide having an amylase activity is heated to a temperature of more than 100° C.

56. The method of Embodiment 54, wherein the polypeptide having an amylase activity is heated to a temperature of more than 110° C.

57. The method of Embodiment 54, wherein the polypeptide having an amylase activity is heated to a temperature of more than 114° C.

58. The method of Embodiment 54, wherein the polypeptide having an amylase activity is heated to a temperature of more than 120° C.

59. The method of Embodiment 53, comprising inactivating the polypeptide having an amylase activity via direct heat injection using a supersaturated steam.

60. The method of Embodiment 53, comprising inactivating the polypeptide having an amylase activity via chemical inactivation using sodium hydroxide, potassium hydroxide, ammonium hydroxide or aqueous ammonia, soda ash (sodium carbonate), calcium hydroxide or slaked lime, sodium or potassium hypochlorite, sodium silicates, magnesium hydroxide, sodium or potassium percarbonate, sodium or potassium perborate, borax, chemical cross-linking agents based on multifunctional carboxylic acids, carbodiimides, glyoxals, aldehydes, Kymene, G-PAM, peroxyorganic acids, persulfates, Oxone, AKD sizing agents, ASA sizing agents, cationic polymers, quaternary amines, polyvinylamines, azides, or any combination thereof.

61. The method of Embodiment 53, comprising inactivating the polypeptide having an amylase activity via radiation selected from the group consisting of UV-peroxide, X-ray, gamma-ray, and electron beam.

62. A paper or board surface treatment composition, comprising degraded starch obtained by a method comprising:
   (a) providing an enzymatic formulation comprising a polypeptide having an amylase activity;
   (b) providing a starch; and
   (c) contacting the enzymatic formulation with the starch, thereby hydrolyzing the starch to produce a paper surface treatment composition comprising degraded starch having a weight-average molecular weight (Mw) in the range from 10,000 to 12,000,000 and a polydispersity index (Mw/Mn) of 1.3 to 49.

63. The paper surface treatment composition of Embodiment 62, wherein the paper surface treatment composition is for treating photocopy paper, computer printer paper, notebook paper, notepad paper, typewriter paper, newspaper, magazine, cardboard, corrugated board, or paper-based packaging material.

64. The paper surface treatment composition of Embodiment 62 or 63, wherein the paper surface treatment composition comprises 1 to 40 wt % of the degraded starch.

65. The paper surface treatment composition of any one of Embodiments 62-64, wherein the paper surface treatment composition comprises 2 to 30 wt % of the degraded starch.

66. The paper surface treatment composition of any one of Embodiments 62-65, wherein the degraded starch has a weight-average molecular weight Mw of in the range from 400,000 to 5,000,000 and a polydispersity index (Mw/Mn) of 10 to 49.

67. The paper surface treatment composition of any one of Embodiments 62-66, wherein the degraded starch has a polydispersity index (Mw/Mn) of less than 45.

68. The paper surface treatment composition of any one of Embodiments 62-67, wherein the degraded starch has a polydispersity index (Mw/Mn) of less than 40.

69. The paper surface treatment composition of any one of Embodiments 62-67, wherein the degraded starch has a polydispersity index (Mw/Mn) of less than 35.

70. The paper surface treatment composition of any one of Embodiments 62-67, wherein the degraded starch has a polydispersity index (Mw/Mn) of less than 30.

71. The paper surface treatment composition of any one of Embodiments 62-67, comprising degraded starch with a polydispersity index (Mw/Mn) of less than 25.

72. The paper surface treatment composition of any one of Embodiments 62-67, comprising degraded starch with a polydispersity index (Mw/Mn) of less than 20.

73. The paper surface treatment composition of any one of Embodiments 62-67, comprising degraded starch with a polydispersity index (Mw/Mn) of less than 15.

74. The paper surface treatment composition of any one of Embodiments 62-67, comprising degraded starch with a polydispersity index (Mw/Mn) of less than 10.

75. The paper surface treatment composition of any one of Embodiments 62-67, comprising degraded starch with a polydispersity index (Mw/Mn) of less than 7.5.

76. The paper surface treatment composition of any one of Embodiments 62-67, comprising degraded starch with a polydispersity index (Mw/Mn) of less than 5.

77. The paper surface treatment composition of any one of Embodiments 62-76, comprising degraded starch with a viscosity of 3 to 2,000 mPas at 80° C., 100 rpm.

78. The paper surface treatment composition of any one of Embodiments 62-77, modified with a cross-linking agent.

79. The paper surface treatment composition of Embodiment 78, wherein the cross-linking agent is selected from the group consisting of 1,2,3,4-Butanetetracarboxylic acid (BTCA), Poly (maleic acid), (PMA), poly(itaconic acid), citric acid, 1,6-hexamethylene bis(ethylcarbodiimide); 1,8-octamethylene bis(ethylcarbodiimide); 1,10 decamethylene bis(ethylcarbodiimide); 1,12 dodecamethylene bis(ethylcarbodiimide); PEG-bis(propyl(ethylcarbodiimide)); 2,2'-dithioethyl bis(ethylcarbodiimde); 1,1'-dithio-p-phenylene bis (ethylcarbodiimide); and 1,1'-dithio-m-phenylene bis (ethylcarbodiimide).

80. The paper surface treatment composition of Embodiment 78, wherein the cross-linking agent is selected from the group consisting of borax and glyoxal.

81. The paper surface treatment composition of any one of Embodiments 62-80, comprising a mineral, an inorganic pigment, clays, kaolin, PCC, GCC, calcium silicates, silica, plastic spheres pigments including hollow sphere pigments, expandable plastic spheres, microcrystalline celluloses, nanocrystalline cellulose, nano-frillated cellulose, colloidal MCC, TiO2, talc, alumina, or any combination thereof.

82. The paper surface treatment composition of any one of Embodiments 62-81, comprising a hemicellulose or a lignin.

83. The paper surface treatment composition of any one of Embodiments 62-82, wherein the polypeptide having an amylase activity has at least 80% identity to SEQ ID NO:12 (SEQ ID NO:2 of U.S. Pat. No. 7,273,740 of Table 3).

84. The paper surface treatment composition of any one of Embodiments 62-82, wherein the polypeptide having an amylase activity has at least 80% identity to any one of amino acid sequences disclosed in Table 3 and 4.

85. The paper surface treatment composition of any one of Embodiments 62-82, wherein the polypeptide having an amylase activity is any one of those set forth in Tables 1 & 2.

86. The paper surface treatment composition of any one of Embodiments 62-85, wherein (a) further comprises a glucoamylase and/or a debranching enzyme.

87. The paper surface treatment composition of Embodiment 86, wherein the debranching enzyme is a hemicellulase, an isoamylase, a beta amylase, a gamma amylase, an exo-amylase, a pullulanase, a xylanase, a mannanase, an alpha gluconase, an endocellulase, an exocellulase, or any combination thereof.

88. The paper surface treatment composition of any one of Embodiments 62-87, wherein the method further comprises use of a protease, a lipase, a peroxidase, a laccase, a tyrosinase, a cellubiohydrolase, a glucose oxidase, a transferase, a glycosyl transferase, a pectinase, an esterase, a cellobiose oxidoreductase, a glyoxal oxidase, an epimerase, an invertase, a chlorophyllase, or any combination thereof.

89. A method of producing a paper product, comprising:
    (a) providing a paper surface treatment composition comprising degraded starch with a polydispersity index (Mw/Mn) of 1.3 to 49;
    (b) providing a web material; and
    (c) applying the paper surface treatment composition to the web material whereby a paper product having improved surface quality is produced.

90. The method of Embodiment 89, wherein the paper product is a photocopy paper, computer printer paper, notebook paper, notepad paper, typewriter paper, newspaper, magazine, board, cardboard, corrugated board, paper-based packaging material, or paper-based printing and writing material.

91. The method of any one of Embodiments 89-90, wherein the paper surface treatment composition comprises 1 to 40 wt % of the degraded starch.

92. The method of any one of Embodiments 89-91, wherein the paper surface treatment composition comprises 2 to 30 wt % of the degraded starch.

93. The method of any one of Embodiments 89-92, wherein the degraded starch has a weight-average molecular weight Mw of in the range from 400,000 to 5,000,000 and a polydispersity index (Mw/Mn) of 10 to 49.

94. The method of any one of Embodiments 89-93, wherein the degraded starch has a polydispersity index (Mw/Mn) of less than 45.

95. The method of any one of Embodiments 89-93, wherein the degraded starch has a polydispersity index (Mw/Mn) of less than 40.

96. The method of any one of Embodiments 89-93, wherein the degraded starch has a polydispersity index (Mw/Mn) of less than 35.

97. The method of any one of Embodiments 89-93, wherein the degraded starch has a polydispersity index (Mw/Mn) of less than 30.

98. The method of any one of Embodiments 89-93, wherein the degraded starch has a polydispersity index (Mw/Mn) of less than 25.

99. The method of any one of Embodiments 89-93, wherein the degraded starch has a polydispersity index (Mw/Mn) of less than 20.

100. The method of any one of Embodiments 89-93, wherein the degraded starch has a polydispersity index (Mw/Mn) of less than 15.

101. The method of any one of Embodiments 89-93, wherein the degraded starch has a polydispersity index (Mw/Mn) of less than 10.

102. The method of any one of Embodiments 89-93, wherein the degraded starch has a polydispersity index (Mw/Mn) of less than 7.5.

103. The method of any one of Embodiments 89-93, wherein the degraded starch has a polydispersity index (Mw/Mn) of less than 5.

104. The method of any one of Embodiments 89-103, wherein the degraded starch has a viscosity of 3 to 2,000 mPas at 80° C., 100 rpm.

105. The method of any one of Embodiments 89-104, wherein the web material is made of synthetic polymers, plastics, biopolymers, or biodegradable polymers.

106. The method of any one of Embodiments 89-105, wherein the web material is uncoated or coated paper webs, rolls, sheets, pellets, tubes, pads, wraps, nonwovens, fabrics printing surfaces, paper packaging materials, boxes, plates, cups, cards, panels, trays, cushions, tissues, towels, napkins, wipes, diapers, hygienic pads/webs, corrugated boxes, liners, medium, and fiber webs comprising plastic fibers, glass fibers, biopolymer fibers, plant fivers, vegetable fibers, seaweed fibers, algae fibers, wood fibers, nonwood fibers, bagasse fibers, bamboo fibers, hemp fibers, ramie fibers, kenaf fibers, palm fibers, sisal fibers, abaca fibers, agricultural fibers, peanut shell fibers, keratin (feather) fibers, animal hair fibers, furs, corn kernel fibers, straw fibers, cotton fibers, mineral fibers, metallic fibers, ceramic fibers, silk fibers, carbon fibers, carbon nanotubes, or graphene sheets.

107. The method of any one of Embodiments 89-106, wherein the surface quality of the paper product is selected from the group consisting of water resistance, a barrier property for moisture, vapor, oxygen, oil, or grease, resistance to fuzz, reduced abrasiveness, a printing property, a surface charge property, ink/color/dye fixation, and bonding or surface strength.

108. The method of any one of Embodiments 89-107, wherein the web material is a paper web.

109. The method of any one of Embodiments 89-108, wherein the paper surface treatment composition is applied to the paper web as a sizing agent, a wet end application, a coating binder/carrier, or an adhesive agent.

110. The method of any one of Embodiments 89-108, wherein the paper surface treatment composition is applied to the paper web via size-press, metered size-press, film-press, roll coating, blade coating, rod coating, cast coating, spray coating, curtain coating, shower coatings, injections, transfer coating, water-box pick-up, or headbox.

111. The method of Embodiment 109, wherein the sizing agent is applied to the paper web via the wet end section of a paper machine.

112. A paper product having improved surface quality produced using a paper surface treatment composition comprising degraded starch having a weight-average molecular weight (Mw) in the range from 10,000 to 12,000,000 and a polydispersity index (Mw/Mn) of 1.3 to 49.

113. The paper product of Embodiment 112, wherein the paper product is a photocopy paper, computer printer paper, notebook paper, notepad paper, typewriter paper, newspaper, magazine, board, cardboard, corrugated board, paper-based packaging material, or paper-based printing and writing material.

114. The paper product of Embodiment 112 or 113, wherein the paper surface treatment composition comprises 1 to 40 wt % of the degraded starch.

115. The paper product of any one of Embodiments 112-114, wherein the paper surface treatment composition comprises 2 to 30 wt % of the degraded starch.

116. The paper product of any one of Embodiments 112-115, wherein the degraded starch has a weight-average molecular weight Mw of in the range from 400,000 to 5,000,000 and a polydispersity index (Mw/Mn) of 10 to 49.

117. The paper product of any one of Embodiments 112-116, wherein the degraded starch has a polydispersity index (Mw/Mn) of less than 45.

118. The paper product of any one of Embodiments 112-116, wherein the degraded starch has a polydispersity index (Mw/Mn) of less than 40.

119. The paper product of any one of Embodiments 112-116, wherein the degraded starch has a polydispersity index (Mw/Mn) of less than 35.

120. The paper product of any one of Embodiments 112-116, wherein the degraded starch has a polydispersity index (Mw/Mn) of less than 30.

121. The paper product of any one of Embodiments 112-116, wherein the degraded starch has a polydispersity index (Mw/Mn) of less than 25.

122. The paper product of any one of Embodiments 112-116, wherein the degraded starch has a polydispersity index (Mw/Mn) of less than 25.

123. The paper product of any one of Embodiments 112-116, wherein the degraded starch has a polydispersity index (Mw/Mn) of less than 20.

124. The paper product of any one of Embodiments 112-116, wherein the degraded starch has a polydispersity index (Mw/Mn) of less than 15.

125. The paper product of any one of Embodiments 112-116, wherein the degraded starch has a polydispersity index (Mw/Mn) of less than 10.

126. The paper product of any one of Embodiments 112-116, wherein the degraded starch has a polydispersity index (Mw/Mn) of less than 7.5.

127. The paper product of any one of Embodiments 112-116, wherein the degraded starch has a polydispersity index (Mw/Mn) of less than 5.

128. The paper product of any one of Embodiments 112-127, wherein the degraded starch has a viscosity of 3 to 2,000 mPas at 80° C., 100 rpm.

129. The paper product of any one of Embodiments 112-128, wherein the surface quality of the paper product is selected from the group consisting of water resistance, a barrier property for moisture, vapor, oxygen, oil, or grease, resistance to fuzz, reduced abrasiveness, a printing property, a surface charge property, ink/color/dye fixation, and bonding or surface strength.

130. A paper or board product comprising a degraded starch having a weight-average molecular weight (Mw) in the range from 10,000 to 12,000,000 and a polydispersity index (Mw/Mn) of 1.3 to 49.

131. The paper product of Embodiment 130, wherein the degraded starch has a weight-average molecular weight Mw of in the range from 400,000 to 5,000,000 and a polydispersity index (Mw/Mn) of 10 to 49.

132. The paper product of Embodiment 130 or 131, comprising at least 10%-90% disaccharides.

133. The paper product of any one of Embodiments 130-133, comprising at least 10%-90% trisaccharides.

134. A low dose enzymatic formulation for producing a paper product comprising a polypeptide having an amylase activity, wherein the polypeptide having the amylase activity is applied to a starch at 0.01 ppm to 1000 ppm based on the weight of the starch.

135. The low dose enzymatic formulation of Embodiment 134, wherein the paper product is a photocopy paper, computer printer paper, notebook paper, notepad paper, typewriter paper, newspaper, magazine, board, cardboard, corrugated board, paper-based packaging material, or paper-based printing and writing material.

136. The low dose enzymatic formulation of Embodiment 134 or 135, wherein the polypeptide having amylase activity is applied at 0.05 ppm to 500 ppm based on the weight of the starch.

137. The low dose enzymatic formulation of Embodiment 134 or 135, wherein the polypeptide having amylase activity is applied at 0.1 ppm to 250 ppm based on the weight of the starch.

138. The low dose enzymatic formulation of Embodiment 134 or 135, wherein the polypeptide having amylase activity is applied at 0.15 ppm to 150 ppm based on the weight of the starch.

139. The low dose enzymatic formulation of any one of Embodiments 134-138, wherein the enzymatic formulation comprises a glucoamylase and/or a debranching enzyme.

140. The low dose enzymatic formulation of Embodiment 139, wherein the debranching enzyme is a hemicellulase, an isoamylase, a beta amylase, a gamma amylase, an exo-amylase, a pullulanase, a xylanase, a mannanase, an alpha gluconase, an endocellulase, an exocellulase, or any combination thereof.

141. The low dose enzymatic formulation of any one of Embodiments 134-140, wherein the enzymatic formulation further comprises a protease, a lipase, a peroxidase, a laccase, a tyrosinase, a cellubiohydrolase, a glucose oxidase, a transferase, a glycosyl transferase, a pectinase, an esterase, a cellobiose oxidoreductase, a glyoxal oxidase, an epimerase, an invertase, a chlorophyllase, or any combination thereof.

142. The low dose enzymatic formulation of any one of Embodiments 134-141, wherein the polypeptide having an amylase activity has at least 80% identity to SEQ ID NO:12 (SEQ ID NO: 2 of U.S. Pat. No. 7,273,740 of Table 3).

143. The low dose enzymatic formulation of any one of Embodiments 134-141, wherein the polypeptide having an amylase activity has at least 80% identity to any one of amino acid sequences disclosed in Table 3 and 4.

144. The low dose enzymatic formulation of any one of Embodiments 134-141, wherein the polypeptide having an amylase activity is any one of those set forth in Tables 1 & 2.

145. A composition for producing a paper product, comprising:
   (a) an enzymatic formulation comprising a polypeptide having an amylase, a glucoamylase and/or a debranching enzyme activity; and
   (b) a paper or a paper pulp or a biomass material.

146. The composition of Embodiment 145, wherein the paper product is a photocopy paper, computer printer paper, notebook paper, notepad paper, typewriter paper, newspaper, magazine, board, cardboard, corrugated board, paper-based packaging material, or paper-based printing and writing material.

147. The composition of any one of Embodiments 145-146, wherein the polypeptide having an amylase activity has at least 80% identity to SEQ ID NO:12 (SEQ ID NO:2 of U.S. Pat. No. 7,273,740 of Table 3).

148. The composition of any one of Embodiments 145-146, wherein the polypeptide having an amylase activity has at least 80% identity to any one of amino acid sequences disclosed in Table 3 and 4.

149. The composition of any one of Embodiments 145-146, wherein the polypeptide having an amylase activity is any one of those set forth in Tables 1 & 2.

150. The composition of any one of Embodiments 145-149, wherein the debranching enzyme is a hemicellulase, an isoamylase, a beta amylase, a gamma amylase, an exoamylase, a pullulanase, a xylanase, a mannanase, an alpha gluconase, an endocellulase, an exocellulase, or any combination thereof.

151. The composition of any one of Embodiments 145-150, wherein the enzymatic formulation further comprises a protease, a lipase, a peroxidase, a laccase, a tyrosinase, a cellubiohydrolase, a glucose oxidase, a transferase, a glycosyl transferase, a pectinase, an esterase, a cellobiose oxidoreductase, a glyoxal oxidase, an epimerase, an invertase, a chlorophyllase, or any combination thereof.

152. The composition of any one of Embodiments 145-151, wherein the biomass material comprises or is derived from an agricultural crop, a byproduct of a food or a feed production, a lignocellulosic waste product, a plant residue, a waste paper, or waste paper product.

153. The method of Embodiment 152, wherein the plant residue comprise stems, leaves, hulls, husks, cobs, wood, wood chips, wood pulp or sawdust, or, the paper waste comprises discarded or used photocopy paper, computer printer paper, notebook paper, notepad paper, typewriter paper, newspapers, magazines, cardboard or paper-based packaging materials.

154. A method for producing a paper product, the method comprising:
(a) treating a paper stock with paper auxiliary and/or filler;
(b) draining the paper stock treated in (a) with sheet formation to obtain a paper web;
(c) providing a paper surface treatment composition comprising a degraded starch having a weight-average molecular weight (Mw) in the range from 10,000 to 12,000,000 and a polydispersity index (Mw/Mn) of 1.3 to 49;
(d) contacting the paper web with the paper surface treatment composition of (c); and
(e) drying the paper web contacted in (d),
whereby a paper product is produced.

155. The method of Embodiment 154, wherein the paper product is a photocopy paper, computer printer paper, notebook paper, notepad paper, typewriter paper, newspaper, magazine, board, cardboard, corrugated board, paper-based packaging material, or paper-based printing and writing material.

156. The method of Embodiment 154 or 155, wherein the paper surface treatment composition comprises 1 to 40 wt % of the degraded starch.

157. The method of any one of Embodiments 154-156, wherein the paper surface treatment composition comprises 2 to 30 wt % of the degraded starch.

158. The method of any one of Embodiments 154-157, wherein the degraded starch has a weight-average molecular weight Mw of in the range from 400,000 to 5,000,000 and a polydispersity index (Mw/Mn) of 10 to 49.

159. The method of any one of Embodiments 154-157, wherein the degraded starch has a polydispersity index (Mw/Mn) of less than 45.

160. The method of any one of Embodiments 154-157, wherein the degraded starch has a polydispersity index (Mw/Mn) of less than 40.

161. The method of any one of Embodiments 154-157, wherein the degraded starch has a polydispersity index (Mw/Mn) of less than 35.

162. The method of any one of Embodiments 154-157, wherein the degraded starch has a polydispersity index (Mw/Mn) of less than 30.

163. The method of any one of Embodiments 154-157, wherein the degraded starch has a polydispersity index (Mw/Mn) of less than 25.

164. The method of any one of Embodiments 154-157, wherein the degraded starch has a polydispersity index (Mw/Mn) of less than 20.

165. The method of any one of Embodiments 154-157, wherein the degraded starch has a polydispersity index (Mw/Mn) of less than 15.

166. The method of any one of Embodiments 154-157, wherein the degraded starch has a polydispersity index (Mw/Mn) of less than 10.

167. The method of any one of Embodiments 154-157, wherein the degraded starch has a polydispersity index (Mw/Mn) of less than 7.5.

168. The method of any one of Embodiments 154-157, wherein the degraded starch has a polydispersity index (Mw/Mn) of less than 5.

169. The method of any one of Embodiments 154-168, wherein the paper stock contains no polyvinyl alcohol fiber.

170. The method of any one of Embodiments 154-169, wherein the paper surface treatment composition is modified with a cross-linking agent.

171. The method of embodiment 170, wherein the cross-linking agent is selected from the group consisting of 1,2,3,4-Butanetetracarboxylic acid (BTCA), Poly (maleic acid), (PMA), poly(itaconic acid), citric acid, 1,6-hexamethylene bis(ethylcarbodiimide); 1,8-octamethylene bis(ethylcarbodiimide); 1,10 decamethylene bis(ethylcarbodiimide); 1,12 dodecamethylene bis(ethylcarbodiimide); PEG-bis(propyl(ethylcarbodiimide)); 2,2'-dithioethyl bis (ethylcarbodiimde); 1,1'-dithio-p-phenylene bis (ethylcarbodiimide); and 1,1'-dithio-m-phenylene bis (ethylcarbodiimide).

172. The method of embodiment 170, wherein the cross-linking agent is selected from the group consisting of borax and glyoxal.

173. The method of any one of Embodiments 154-172, wherein the paper surface treatment composition comprises a mineral, an inorganic pigment, clays, kaolin, PCC, GCC, calcium silicates, silica, plastic spheres pigments including hollow sphere pigments, expandable plastic spheres, microcrystalline celluloses, nanocrystalline cellulose, nano-frillated cellulose, colloidal MCC, TiO2, talc, alumina, or a combination thereof.

174. The method of any one of Embodiments 154-173, wherein the paper surface treatment composition comprises a hemicellulose or a lignin.

175. The method of any one of Embodiments 154-174, wherein the method further comprises a filtration process, and optionally a filtrate is generated.

176. The method of Embodiment 175, wherein the method further comprises recycling of the filtrate, and optionally fines are collected from the filtrate.

177. The method of any one of Embodiments 154-176, wherein the method further comprises a mixing process.

178. The method of any one of Embodiments 154-177, wherein the method further comprises a bleaching process.

179. The method of any one of Embodiments 154-178, wherein optionally the method further comprises addition of additional enzymes, and optionally the additional enzymes are added at multiple time points or step-wise in the method.

180. The method of any one of Embodiments 154-179, wherein the method further comprises a pre-washing or a pretreatment process.

181. The method of any one of Embodiments 154-180, wherein the paper surface treatment composition is applied to the paper web as a sizing agent, a wet end application, a coating binder/carrier, or an adhesive agent.

182. The method of any one of Embodiments 154-180, wherein the paper surface treatment composition is applied to the paper web via size-press, metered size-press, film-press, roll coating, blade coating, rod coating, cast coating, spray coating, curtain coating, shower coatings, injections, transfer coating, water-box pick-up, or headbox.

183. The method of Embodiment 181, wherein the sizing agent is applied to the paper web via the wet end section of a paper machine.

184. A paper product obtainable by the method according to any one of Embodiments 1-183.

185. A composition comprising a starch having a weight-average molecular weight (Mw) in the range from 10,000 to 12,000,000 and a polydispersity index (Mw/Mn) of 1.3 to 49.

186. An aqueous surface treatment composition for paper and board comprising 1 to 40 wt % of a degraded starch with a weight-average molecular weight Mw of in the range from 400 000 to 12 000 000 and a polydispersity of 10 to 49.

187. An aqueous surface treatment composition for paper and board comprising 1 to 40 wt % of a degraded starch obtained by treating starch with an enzymatic formulation comprising a polypeptide having an amylase activity till it has a weight-average molecular weight Mw of in the range from 400 000 to 12 000 000.

188. The aqueous surface treatment composition according to embodiment 186 or 187, wherein 0.0001 wt % to 1 wt % of the polypeptide of SEQ ID NO:12 (SEQ ID NO:2 of U.S. Pat. No. 7,273,740 of Table 3) based on the weight of starch are used to obtain the degraded starch.

189. The aqueous surface treatment composition according to any of embodiments 186-188, wherein the enzymatic formulation comprises a glucoamylase and/or a debranching enzyme.

190. The aqueous surface treatment composition according to any of embodiments 186-189, wherein the debranching enzyme is a hemicellulase, an isoamylase, a beta amylase, a gamma amylase, an exo-amylase, a pullulanase, a xylanase, a mannanase, an alpha gluconase, an endocellulase, an exocellulase, or any combination thereof.

191. The aqueous surface treatment composition according to any of embodiments 186-190, wherein the enzymatic formulation further comprises a protease, a lipase, a peroxidase, a laccase, a tyrosinase, a cellubiohydrolase, a glucose oxidase, a transferase, a glycosyl transferase, a pectinase, an esterase, a cellobiose oxidoreductase, a glyoxal oxidase, an epimerase, an invertase, a chlorophyllase, or any combination thereof.

192. The aqueous surface treatment composition according to any of embodiments 186-191, wherein the polypeptide having an amylase activity has at least 80% identity to SEQ ID NO:2 of Table 3.

193. The aqueous surface treatment composition according to any of embodiments 186-192, wherein the polypeptide having an amylase activity has at least 80% identity to any one of amino acid sequences disclosed in Table 3 and 4.

194. The aqueous surface treatment composition according to any of embodiments 186-193, wherein the polypeptide having an amylase activity is any one of those set forth in Tables 1 & 2.

195. The aqueous surface treatment composition according to any of embodiments 186-194, wherein the degraded starch is obtained by a method comprising the steps
   a) preparing a suspension of water and starch;
   b) addition of 0,0001 to 1% a polypeptide having an amylase activity which has at least 80% identity to SEQ ID NO:12 (SEQ ID NO:2 of U.S. Pat. No. 7,273,740 of Table 3); and
   c) heating the mixture comprising starch and enzyme to a temperature of 60 to 100° C. for 5 to 60 Minutes.

196. The aqueous surface treatment composition according to any of embodiments 186-195, comprising 2 to 30 wt % of a degraded starch.

197. The aqueous surface treatment composition according to any of embodiments 186-196, wherein the degraded starch has a weight-average molecular weight Mw of in the range from 400 000 to 5 000 000 and a polydispersity of 10 to 49.

198. A method for producing paper and board comprising the steps of
   a) treating paper stock with paper auxiliary and/or filler,
   b) draining the paper stock treated by a), with sheet formation, and
   c) treating the paper web obtained by b) with the surface treatment composition according to any of embodiments 186-197,
   d) and drying the paper web coated by c).

199. The method according to embodiment 198, wherein the degraded starch has a weight-average molecular weight Mw in the range from 400 000 to 12 000 000 and a polydispersity of 10 to 49 and the surface treatment composition is applied by size press application technique.

200. The method according to embodiment 198, wherein the degraded starch has a weight-average molecular weight Mw in the range from 400 000 to 5 000 000 and a polydispersity of 10 to 49 and the surface treatment composition is applied by film-press application technique.

201. A paper and board obtainable by the method according to any of embodiments 198-200.

202. A use of a paper and board according to embodiment 201 for producing corrugated board.

DETAILED DESCRIPTION

Definitions

All patents, applications, published applications and other publications referred to herein are incorporated by reference for the referenced material and in their entireties. If a term or phrase is used herein in a way that is contrary to or otherwise inconsistent with a definition set forth in the patents, applications, published applications and other publications that are herein incorporated by reference, the use herein prevails over the definition that is incorporated herein by reference.

As used herein, the singular forms "a", "an", and "the" include plural references unless indicated otherwise, expressly or by context. For example, "a" dimer includes one or more dimers, unless indicated otherwise, expressly or by context.

Paper stock (also known as pulp furnish) refers hereinafter to a mixture of water and fibrous material and, depending on the stage in the papermaking process, may further comprise filler and also paper auxiliaries. Dry paper stock is to be understood as meaning the overall paper stock composed of fibrous material and also, optionally, filler and, optionally, paper auxiliaries, without water (paper stock solids).

The term for the shaped body consisting of fibrous material alters with the mass per unit area, also referred to in the jargon as grammage. Hereinafter, paper is to comprehend a mass per unit area of 7 g/m$^2$ to 225 g/m$^2$, and board a mass per unit area of 225 g/m$^2$ and above.

Starch in this context is to be understood as any virgin or modified starch. Virgin starches may consist of amylose, amylopectin, or mixtures thereof modified starches may comprise oxidized starch, starch esters, or starch ethers.

Types of starch contemplated include virgin starches such as potato starch, wheat starch, corn starch, rice starch, or tapioca starch, preferably potato starch. The starches could also be any biomass-containing starch components from plants or agricultural residues chemically modified starches may also be used, such as hydroxyethyl or hydroxypropyl starches, or else starches which contain anionic groups, such as phosphate starch, or else cationized starches containing quaternary ammonium groups, preference being given to a degree of substitution DS of 0.01 to 0.2. This degree of substitution DS indicates the number of cationic groups present on average in the starch per glucose unit. Particularly preferred are amphoteric starches, which contain not only quaternary ammonium groups but also anionic groups such as carboxylate and/or phosphate groups, and which may optionally also have undergone chemical modification, having for example been hydroxyalkylated or alkyl-esterified. The starches may be used individually or else in any desired mixtures with one another.

The starches may be present with other hemicelluloses or polysaccharides, such as but not limited to galactomannans, xylans, arabinoxylans, glucuronoxylans, glucomannans, xyloglucans (such as Tamarind seed flour), pectins/pectate, galactans, arabinogalactans. In the case where starch used contains other polysaccharides, it is optional that hemicellulase enzymes or polysaccharide enzymes may be used in combination with the amylase for the preparations of surface starch composition of the present disclosure. In one option, xylanases (LUMINASE® PB-100, LUMINASE® PB-200) from BASF can be used. In fact hemicellulases, xylanases, and cellulases from any supply is implied, including from Novozymes, Dyadic, Dupont, and BASF. If the starchy materials contain proteins and fats, protease and lipases may optionally be used in combination with the aforementioned enzymes comprising amylase.

The starch used in the present disclosure, preferably, is a native starch, or a substantially un-modified starch. One example is the Pearl starch from Tate and Lyle. However, the starch used can also be any modified or partially modified starches, as modified by thermal treatment, by thermal-mechanical treatment, by acid hydrolysis, by oxidations, by ester derivatizations, (such as starch acetates, starch phosphates), by ether modifications or hydroxyl-alkyl derivatizations (such as hydroxypropyl starches, hydroxyethyl starches or ethylated starches, hydroxypropyl starch phosphates, carboxymethyl starches, various cationic starches, and previously enzyme modified starches, and pre-gelatinized starches. Common examples include industrial starches from A.E. Staley, Penford (Ingredion), Tate and Lyle, ADM, Cargill, Rasio, Roguette, and Amylum, to name a few.

As used herein, "carbohydrates," "saccharide" or "sugar" refers to a macromolecule consisting of carbon (C), hydrogen (H), and oxygen (O) atoms, usually with a hydrogen: oxygen atom ratio of 2:1 (as in water); in other words, with the empirical formula $Cm(H2O)n$ (where m could be different from n). Polysaccharides can have more than one saccharide and are used for the storage of energy. Monosaccharide and contain only one saccharide unit, while a disaccharide can contain two saccharide units, or two joined monosaccharides.

As used herein, "enzyme," refers to a macromolecular catalyst. They are responsible for thousands of metabolic processes that sustain life. Enzymes are highly selective catalysts, greatly accelerating both the rate and specificity of metabolic reactions. Reactions can include but are not limited to the digestion of food, cleavage or breakdown of molecules, to the synthesis of DNA. Most enzymes are proteins, although some catalytic RNA molecules have been identified. Enzymes adopt a specific three-dimensional structure, and can employ organic (e.g. biotin) and inorganic (e.g. magnesium ion) cofactors to assist in catalysis. Enzymes are usually very specific as to which reactions they catalyze and the substrates that are involved in these reactions. Complementary shape, charge and hydrophilic/hydrophobic characteristics of enzymes and substrates are responsible for this specificity. Enzymes can also show high levels of specificity such as, stereospecificity, regioselectivity and chemoselectivity. By way of example and not of limitation, some enzymes can be used to break down large molecules such as, for example, starch, polyglycosides, sugars, proteins, branched sugars, liposaccharides, APG. In some embodiments, enzymes can be used to break down a micelle and release oil.

As used herein, "glycoside hydrolase," "glycosidases" or "glycosyl hydrolases" are enzymes that can assist in the hydrolysis of glycosidic bonds in a complex sugar. The terms can be used interchangeably. These enzymes can degrade biomass such as, for example, cellulose, hemicellulose, APG, and glycosides. Glycosidases form the major catalytic machinery for the breakage of glycosidic bonds. In some embodiments, an enzyme comprising glycoside hydrolase activity is provided. In some embodiments, the enzyme can destabilize a micelle.

As used herein, "enzyme breakers" are enzymes, for example encapsulated enzymes that can be used as a delayed release breaker for hydraulic fracturing fluids. For example, encapsulated breakers may be used to delay the release of the active enzyme upon the fluid. This delay can allow higher breaker concentrations to be used without compromising the proppant transport capacity of the fracturing fluid. In some embodiments, a solid breaker can be concentrated in the fracture and not lost to the formation during fluid leak-off. In some embodiments, the enzyme breakers can be used to improve fracture conductivity by enhancing fluid clean-up.

As used herein, "cellulase" refers to an enzyme that can hydrolyze cellulose and polysaccharides to generate monosaccharides. In some embodiments, an enzyme comprising cellulase activity is provided.

The terms "polynucleotide," "oligonucleotide," "nucleic acid" and "nucleic acid molecule" are used interchangeably herein to refer to a polymeric form of nucleotides of any length, and can comprise ribonucleotides, deoxyribonucleotides, analogs thereof, or mixtures thereof. This term refers only to the primary structure of the molecule. Thus, the term includes triple-, double- and single-stranded deoxyribonucleic acid ("DNA"), as well as triple-, double- and single-stranded ribonucleic acid ("RNA"). It also includes modified, for example by alkylation, and/or by capping, and unmodified forms of the polynucleotide. More particularly, the terms "polynucleotide," "oligonucleotide," "nucleic acid" and "nucleic acid molecule" include polydeoxyribonucleotides (containing 2-deoxy-D-ribose), polyribonucleotides (containing D-ribose), including tRNA, rRNA, hRNA, and mRNA, whether spliced or unspliced, any other type of polynucleotide which is an N- or C-glycoside of a purine or pyrimidine base, and other polymers containing nucleotidic backbones, for example, polyamide (e.g., peptide nucleic acids ("PNAs")) and polymorpholino (commercially available from the Anti-Virals, Inc., Corvallis, Oreg., as NeuGene®) polymers, and other synthetic sequence-specific nucleic acid polymers providing that the polymers contain nucleobases in a configuration which allows for base pairing and base stacking, such as is found in DNA and RNA. Thus, these terms include, for example, 3'-deoxy-2', 5'-DNA, oligodeoxyribonucleotide N3' to P5' phosphoramidates, 2'-O-alkyl-substituted RNA, hybrids between DNA and RNA or between PNAs and DNA or RNA, and also include known types of modifications, for example, labels, alkylation, "caps," substitution of one or more of the nucleotides with an analog, internucleotide modifications such as, for example, those with uncharged linkages (e.g., methyl phosphonates, phosphotriesters, phosphoramidates, carbamates, etc.), with negatively charged linkages (e.g., phosphorothioates, phosphorodithioates, etc.), and with positively charged linkages (e.g., aminoalkylphosphoramidates, aminoalkylphosphotriesters), those containing pendant moieties, such as, for example, proteins (including enzymes (e.g., nucleases), toxins, antibodies, signal peptides, poly-L-lysine, etc.), those with intercalators (e.g., acridine, psoralen, etc.), those containing chelates (of, e.g., metals, radioactive metals, boron, oxidative metals, etc.), those containing alkylators, those with modified linkages (e.g., alpha anomeric nucleic acids, etc.), as well as unmodified forms of the polynucleotide or oligonucleotide.

As used herein, "sequence identity" or "identity" or "homology" in the context of two protein sequences (or nucleotide sequences) includes reference to the residues in the two sequences which are the same when aligned for maximum correspondence over a specified comparison window. The portion of the amino acid sequence or nucleotide sequence in the comparison window can comprise additions or deletions (i.e., gaps) as compared to the reference sequence for optimal alignment of the two sequences. When percentage of sequence identity is used in reference to proteins it is recognized that residue positions which are not identical often differ by conservative amino acid substitutions, where amino acids are substituted for other amino acid residues with similar chemical properties (e.g. charge or hydrophobicity) and therefore do not change the functional properties of the molecule. Where sequences differ in conservative substitutions, the percentage sequence identity can be adjusted upwards to correct for the conservative nature of the substitutions. Sequences, which differ by such conservative substitutions are said to have "sequence similarity" or "similarity". Means for making these adjustments are well known to persons skilled in the art. The percentage is calculated by determining the number of positions at which the identical amino acid or nucleic acid base residue occurs in both sequences to yield the number of matched positions, dividing the number of matched positions by the total number of positions in the window of comparison and multiplying the result by 100 to yield the percentage of sequence identity. Typically this involves scoring a conservative substitution as a partial rather than a full mismatch, thereby increasing the percentage sequence identity. Thus, for example, where an identical amino acid is given a score of 1 and a non-conservative substitution is give a score of zero, a conservative substitution is given a score between 0 and 1. The scoring of conservative substitutions is calculated, e.g. according to the algorithm of Meyers and Miller (*Computer Applic. Biol. Sci.,* 1998, 4, 11-17).

As used herein, "substantially complementary or substantially matched" means that two nucleic acid sequences have at least about 90% sequence identity. Preferably, the two nucleic acid sequences have at least about 95%, 96%, 97%, 98%, 99% or 100% of sequence identity. Alternatively, "substantially complementary or substantially matched" means that two nucleic acid sequences can hybridize under high stringency condition(s).

In general, the stability of a hybrid is a function of the ion concentration and temperature. Typically, a hybridization reaction is performed under conditions of lower stringency, followed by washes of varying, but higher, stringency. Moderately stringent hybridization refers to conditions that permit a nucleic acid molecule such as a probe to bind a complementary nucleic acid molecule. The hybridized nucleic acid molecules generally have at least 60% identity, including for example at least any of 70%, 75%, 80%, 85%, 90%, or 95% identity. Moderately stringent conditions are conditions equivalent to hybridization in 50% formamide, 5×Denhardt's solution, 5×SSPE, 0.2% SDS at 42° C., followed by washing in 0.2×SSPE, 0.2% SDS, at 42° C. High stringency conditions can be provided, for example, by hybridization in 50% formamide, 5×Denhardt's solution, 5×SSPE, 0.2% SDS at 42° C., followed by washing in 0.1×SSPE, and 0.1% SDS at 65° C.

Low stringency hybridization refers to conditions equivalent to hybridization in 10% formamide, 5×Denhardt's solution, 6×SSPE, 0.2% SDS at 22° C., followed by washing in 1×SSPE, 0.2% SDS, at 37° C. Denhardt's solution contains 1% Ficoll, 1% polyvinylpyrolidone, and 1% bovine serum albumin (BSA). 20×SSPE (sodium chloride, sodium phosphate, ethylene diamide tetraacetic acid (EDTA)) contains 3M sodium chloride, 0.2M sodium phosphate, and 0.025 M (EDTA). Other suitable moderate stringency and high stringency hybridization buffers and conditions are well known to those of skill in the art.

As used herein "polydispersity" is the quotient of weight-average molecular weight Mw and number-average molecular weight Mn. The polydispersity index is used as a measure of the broadness of a molecular weight distribution of a polymer. The larger the polydispersity index, the broader the molecular weight. The weight-average molecular weight can be determined by light scattering techniques.

It is understood that aspects and embodiments of the disclosure described herein include "consisting" and/or "consisting essentially of" aspects and embodiments.

Other objects, advantages and features will become apparent from the following specification.

Amylases

Embodiments disclosed herein provide polypeptides having amylase activities and their uses in paper production.

Some amylases have been described in WO2010088447, WO 2008092919, WO 2013044867, WO 2013034106, the contents of which are hereby incorporated by reference in their entireties.

In some embodiments, the amylase can be a thermostable alpha amylase, for example a thermostable alpha amylase from bacteria (e.g., *Bacillus*) or fungi, or any combination (mixture) thereof.

Further provided are isolated, synthetic or recombinant polypeptides having an amylase activity, (i) comprising an amino acid sequence having at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more, or has 100% (complete) sequence identity to any one of the exemplary polypeptide as described herein, over a region of at least about 10, 15, 20, 25, 30, 35, 40, 45, 50, 60, 70, 75, 100, 125, 150, 175, 200, 225 or 250 or more residues, wherein in one aspect (optionally) the sequence identities are determined by analysis with a sequence comparison algorithm or by a visual inspection, or, (ii) comprising an amino acid sequence encoded by a nucleic acid sequence having at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more, or has 100% (complete) sequence identity to any one of the disclosed nucleic acid sequences, over a region of at least about 10, 15, 20, 25, 30, 35, 40, 45, 50, 60, 70, 75, 100, 125, 150, 175, 200, 225, 250, 300, 400, 500, 600, 700, 800, 900, 1,000 or more nucleotides (including, e.g., exemplary sequences disclosed herein). Polypeptide or peptide sequences of the present disclosure include polypeptides or peptides specifically bound by an antibody of the disclosure (e.g., epitopes), or polypeptides or peptides that can generate an antibody of the disclosure (e.g., an immunogen).

Non-limiting examples of the amylases suitable for use in the methods and compositions disclosed herein include: LpHera® from Novozymes; a thermostable alpha amylase Gammalpha 120L described in Hypertext Transfer Protocol (HTTP)://World Wide Web (WWW).hussch.com.pl/Piwowarzy.html; fungal and bacterial amylases from Woellner GmbH & Co. KG (e.g., Warozym A 10, Warozym A 15, Warozym A 152, Warozym A 154, Warozym A 158, Warozym A 162, and Warozym A 164); α-amylase (GB-A-871,937) and CGT enzyme described in EP0690170A1; CGTase: cyclodextrin glucosyltransferase of *Bacillus circulans* 251 described in Lawson et al., J. Mol. Boil. 236:590-500 (1994); Amizyme (PMP Fermentation Products, Peoria, USA), Termamyl®, Fungamyl, BAN (Novozymes, Denmark), and α-amylase G9995 †(Enzyme Biosystems, USA) described in Gupta, R et al., B. (2003). Microbial -amylases: a biotechnological perspective. Process Biochem 38, 1599-1616; Fungamyl and its variants described in WO0134784; BAN 480 L, Fungamyl 800 L, and Duramyl 300 L from Novozyme and described in Vuuren and Wolfaardt, Evaluation of starch hydrolyzing enzymes to improve drainage of recycled pulp, International Convention Centre, Durban, Oct. 8-11, 2002.

In some embodiment, the polypeptides having amylase activity may be a commercial enzyme, for example, SPEZYME® XTRA, SPEZYME® CL, SPEZYME® Alpha, SPEZYME® RSL, SPEZYME® FRED, SPEZYME® LT 300, AmyS, AmyL, BAN® 480L, LIQUOZYME® Supra, LIQUOZYME® SCDS, MAX-LIFE™ P100, MALTOGENASE™ L, CLARASE® L, LIQUOZYME® SC, TERMAMYL® SC, VERETASE™, LIQUOZYME® SC4x, LIQUOZYME® Supra 2.8, LIQUOZYMEL® supra 2, LIQUOZYME® X, TERMAMYL® 120L, SPEZYME® ALPHA, CLEARFLOW® AA, OPTITHERM™ and TAKATHERM™, KEISTASE™, AVANTEC™. Non-limiting examples of commercial enzymes suitable for use in the methods and composition disclosed herein are described in Tables 1 and 2:

TABLE 1

Examples of commercial amylases

| Brand Name | Product Name | Enzyme Class | Enzyme Class | Company |
| --- | --- | --- | --- | --- |
| Spezyme ® | Spezyme ® AA | Alpha-Amylase | Alpha-Amylase | Genencor |
| Spezyme ® | Spezyme ® HPA | Alpha-Amylase | Alpha-Amylase | Genencor |
| Enzy-Size ® | Enzy-Size ® | Amylase | Amylase | Genencor |
| IndiAge ® | IndiAge ® Super | Beta-Glucanase | Beta-Glucanase | Genencor |
| Optimase ® | Optimase ® CA 400L | Catalase | Catalase | Solvay Enzymes |
| Genencor ® | Genencor ® Cellulase 250 P | Cellulase | Cellulase | Genencor |
| Multifect ® | Multifect ® A40 | Cellulase Hemicellulase | Cellulase Hemicellulase | |
| Pergalase ® | Pergalase ® | Cellulase Hemicellulase | Cellulase Hemicellulase | Genencor |
| Pergalase ® | Pergalase ® A40 | Cellulase Hemicellulase | Cellulase Hemicellulase | Genencor |
| Pergalase ® | Pergalase ® FL-60 | Cellulase Hemicellulase | Cellulase Hemicellulase | Genencor |
| Pergalase ® | Pergalase ® N20 | Cellulase Hemicellulase | Cellulase Hemicellulase | Genencor |
| Irgazyme ® | Irgazyme ® 10 | Xylanase | Xylanase | Genencor |
| Irgazyme ® | Irgazyme ® 40 | Xylanase | Xylanase | Genencor |
| Multifect ® | Multifect ® 720 | Xylanase | Xylanase | |
| Termamyl ® | Termamyl ® | Alpha-Amylase | High Alkaline and Temperature | Novo Industri |
| Thermamyl ® | Thermamyl ® | Alpha-Amylase | Thermostable | Novo Industri |

TABLE 1-continued

Examples of commercial amylases

| Brand Name | Product Name | Enzyme Class | Enzyme Class | Company |
|---|---|---|---|---|
| Celluclast ™ | Celluclast ™ | Beta-Xylosidase Xylanase | | Novo Industry |
| FiberCare ® | FiberCare ® R | Cellulase | Refining (Chemical/Recycled) | Novozymes |
| Novozym ® | Novozym ® 342 | Cellulase | Deinking | Novo Industri |
| Novozym ® | Novozym ® 476 | Cellulase | | Novo Industri |
| FiberCare ® | FiberCare ® D | Cellulase Beta-Glucanase | | Novozymes |
| Novozym ® | Novozym ® 613 | Glucanase Cellulase | Deinking | Novo Industri |
| Novozym ® | Novozym ® 51003 | Laccase | | Novo Industri |
| Novozym ® | Novozym ® 51054 | Lipase | Pitch Control | Novo Industri |
| Resinase ® | Resinase ® | Lipase | Resin Degradation | Novozymes |
| Resinase ® | Resinase ® HT | Lipase | Resin Degradation | Novozymes |
| Novozym ® | Novozym ® 51032 | Lipase Cutinase | Biofilm | Novo Industri |
| Pulpzyme ® | Pulpzyme ® HB | Xylanase | | Novo Nordisk |
| Pulpzyme ® | Pulpzyme ® HC | Xylanase | DP 4-5 or 6-7 | Novo Nordisk |
| Pulpzyme ® | Pulpzyme ® HA | Xylanase Cellulase | | Novo Nordisk |

TABLE 2

Non-limiting examples of amylases that can be used in the methods and compositions disclosed herein.

| SEQ ID NO: | Enzyme | Sequence |
|---|---|---|
| 1 | Spezyme FRED | AANLNGTLMQYFEWYTPNDGQHWKRLQNDSAYLAEHGITAVWIP PAYKGTSQADVGYGAYDLYDLGEFHQKGTVRTKYGTKGELQSAI KSLHSRDINVYGDVVINHKGGADATEDVTAVEVDPADRNRVISG EYLIKAWTHFHFPGRGSTYSDFKWHWYHFDGTDWDESRKLNRIY KFQGKAWDWEVSSENGNYDYLMYADIDYDHPDVVAEIKRWGTWY ANELQLDGFRLDAVKHIKFSFLRDWVNHVREKTGKEMFTVAEYW QNDLGALENYLNKTNFNHSVFDVPLHYQFHAASTQGGGYDMRKL LNGTVVSKHPLKSVTFVDNHDTQPGQSLESTVQTWFKPLAYAFI LTRESGYPQVFYGDMYGTKGDSQREIPALKHKIEPILKARKQYA YGAQHDYFDHHDIVGWTREGDSSVANSGLAALITDGPGGAKRMY VGRQNAGETWHDITGNRSEPVVINSEGWGEFHVNGGSVSIYVQR |
| 2 | Spezyme XTRA | AAPFNGTMMQYFEWYLPDDGTLWTKVANEANNLSSLGITALWLP PAYKGTSRSDVGYGVYDLYDLGEFNQKGTVRTKYGTKAQYLQAI QAAHAAGMQVYADVVFDHKGGADGTEWVDAVEVNPSDRNQEISG TYQIQAWTKFDFPGRGNTYSSFKWRWYHFDGVDWDESRKLSRIY KFRGIGKAWDWEVDTENGNYDYLMYADLDMDHPEVVTELKNWGK WYVNTTNIDGFRLDAVKHIKFSFFPDWLSYVRSQTGKPLFTVGE YWSYDINKLHNYITKTNGTMSLFDAPLHNKFYTASKSGGAFDMR TLMTNTLMKDQPTLAVTFVDNHDTEPGQALQSWVDPWFKPLAYA FILTRQEGYPCVFYGDYYGIPQYNIPSLKSKIDPLLIARRDYAY GTQHDYLDHSDIIGWTREGVTEKPGSGLAALITDGPGGSKWMYV GKQHAGKVFYDLTGNRSDTVTINSDGWGEFKVNGGSVSVWVPRK TT |
| 3 | Cytophaga (a variant) | AATNGTMMQYFEWYVPNDGQQWNRLRTDAPYLSSVGITAVWTPP AYKGTSQADVGYGPYDLYDLGEFNQKGTVRTKYGTKGELKSAVN TLHSNGIQVYGDVVMNHKAGADYTENVTAVEVNPSNRNQETSGE YNIQAWTGFNFPGRGTTYSNFKWQWFHFDGTDWDQSRSLSRIFK FRGTGKAWDWEVSSENGNYDYLMYADIDYDHPDVVNEMKKWGVW YANEVGLDGYRLDAVKHIKFSFLKDWVDNARAATGKEMFTVGEY WQNDLGALNNYLAKVNYNQSLFDAPLHYNFYAASTGGGYYDMRN ILNNTLVASNPTKAVTLVENHDTQPGQSLESTVQPWFKPLAYAF ILTRSGGYPSVFYGDMYGTKGTTTREIPALKSKIEPLLKARKDY AYGTQRDYIDNPDVIGWTREGDSTKAKSGLATVITDGPGGSKRM |

TABLE 2-continued

Non-limiting examples of amylases that can be used in the
methods and compositions disclosed herein.

| SEQ ID NO: | Enzyme | Sequence |
|---|---|---|
| | | YVGTSNAGEIWYDLTGNRTDKITIGSDGYATFPVNGGSVSVWVQQ |
| 4 | Paenibacillus | ADNGTIMQYFEWYLPNDGAHWNRLNNDAQNLKNVGITAVWIPPAYKGGSSADVGYGVYDTYDLGEFNQKGTVRTKYGTKSELISAVNNLHAKGIAVYGDVVLNHRMNADATELVDAVEVDPNNRNVETTSTYQIQAWTQYDFPGRGNTYSSFKWRWYHFDGVDWDQSRGLNRIYKLRGDGKDWDWEVDSEYGNYDYLMGADLDFNHPDVVNETKTWGKWFVNTVNLDGVRLDAVKHIKFDFMRDWVNNVRSTTGKNLFAVGEYWHYDVNKLNSYITKTNGTMSLFDVPLHFRFYDASNGGGGYDMRNLLNNTLMSSNPMKAVTFVENHDTQPTQALQSTVQSWFKPLAYATILTREQGYPCVFYGDYYGTSDGKISSYKPIMDKLLNARKVYAYGTQRDYFDHPDIVGWTREGDAAHAGSGLATLITDGPGGSKWMYVGTSKAGQVWTDKTGNRSGTVTIDANGWGNFWVNGGSVSVWAK |
| 5 | Aspergillus clavatus | MKLLALTTAFALLGKGVFGLTPAEWRGQSIYFLITDRFARTDGSTTAPCDLSQRAYCGGSWQGIIKQLDYIQGMGFTAIWITPITEQIPQDTAEGSAFHGYWQKDIYNVNSHFGTADDIRALSKALHDRGMYLMIDVVANHMGYNGPGASTDFSTFTPFNSASYFHSYCPINNYNDQSQVENCWLGDNTVALADLYTQHSDVRNIWYSWIKEIVGNYSADGLRIDTVKHVEKDFWTGYTQAAGVYTVGEVLDGDPAYTCPYQGYVDGVLNYPIYYPLLRAFESSSGSMGDLYNMINSVASDCKDPTVLGSFIENHDNPRFASYTKDMSQAKAVISYVILSDGIPIIYSGQEQHYSGGNDPYNREAIWLSGYSTTSELYKFIATTNKIRQLAISKDSSYLTSRNNPFYTDSNTIAMRKGSGGSQVITVLSNSGSNGGSYTLNLGNSGYSSGANLVEVYTCSSVTVGSDGKIPVPMASGLPRVLVPASWMSGSGLCGSSSTTTLVTATTTPTGSSSSTTLATAVTTPTGSCKTATTVPVVLEESVRTSYGENIFISGSIPQLGSWNPDKAVALSSSQYTSSNPLWAVTLDLPVGTSFEYKFLKKEQNGGVAWENDPNRSYTVPEACAGTSQKVDSSWR |
| 6 | GENESEQ_PROT\|BAY81185 Talaromyces stipitatus alpha-amylase protein | MKLSLLATTLPLFGKIVDALSAAEWRSQSIYFLLTDRFARTDGSTSAPCDLSQRAYCGGSWQGIIDHLDYIQGMGFTAVWITPITKQIPQATSEGSGYHGYWQQDIYSVNSNFGTADDIRALSKALHDKGMYLMIDVVANHMGYNGPGASTDFSVFTPFNSASYFHSYCPISNYDDQNQVENCWLGDDTVSLTDLYTQSNQVRNIWYSWVKDLVANYTVDGLRIDTVKHVEKDFWTGYREAAGVYTVGEVLHGDPAYTCPYQGYVDGVFNYPIYYPLLNAFKSSSGSISDLVNMINTVSSDCKDPSLLGSFIENHDNPRFPSYTSDMSQAKSVIAYVFFADGIPTIYSGQEQHYTGGNDPYNREAIWLSGYATDSELYKFITTANKIRNLAISKDSSYLTTRNNAFYTDSNTIAMRKGSSGSQVITVLSNSGSNGASYTLELANQGYNSGAQLIEVYTCSSVKVDSNGNIPVPMTSGLPRVLVPASWVTGSGLCGTSSGTPSSTTLTTTMSLASSTTSSCVSATSLPITFNELVTTSYGENIFIAGSIPQLGNWNSANAVPLASTQYTSTNPVWSVSLDLPVGSTFQYKFMKKEKDGSVVWESDPNRSYTVGNGCTGAKYTVNDSWR |
| 7 | GENESEQ_PROT\|BAY81186 Aspergillus nidulans FGSC A4 protein AN3402.2, | MRLLALTSALALLGKAVHGLDADGWRSQSIYFLLTDRFARTDGSTTAACDLAQRRYCGGSWQGIINQLDYIQDMGFTAIWITPITEQIPDVTAVGTGFHGYWQKNIYGVDTNLGTADDIRALSEALHDRGMYLMLDVVANHMSYGGPGGSTDFSIFTPFDSASYFHSYCAINNYDNQWQVENCFLGDDTVSLTDLNTQSSEVRDIWYDWIEDIVANYSVDGLRIDTVKHVEKDFWPGYIDAAGVYSVGEIFHGDPAYTCPYQGYMDGVMNYPIYYPLLNAFKSSSGSMSDLYNMINTVASNCRDPTLLGNFIENHDNPRFPNYTPDMSRAKNVLAFLFLTDGIPIVYAGQEQHYSGSNDPYNREPVWWSSYSTSSELYKFIATTNKIRKLAISKDSSYLTSRNTPFYSDSNYIAMRKGSGGSQVLTLLNNIGTSIGSYTFDLYDHGYNSGANLVELYTCSSVQVGSNGAISIPMTSGLPRVLVPAAWVSGSGLCGLTNPTSKTTTATTTSTTTCASATATAITVVFQERVQTAYGENVFLAGSISQLGNWDTTEAVALSAAQYTATDPLWTVAIELPVGTSFEFKFLKKRQDGSIVWESNPNRSAKVNEGCARTTQTISTSWR |
| 8 | GENESEQ_PROT\|BBF30084 Talaromyces emersonii alpha amylase mature protein | LTPAEWRKQSIYFLLTDRFGRADNSTTAACDVTERIYCGGSWQGIINHLDYIQGMGFTAIWISPVTEQLPQNTGEGEAYHGYWQQEIYTVNSNFGTSDDLLALSKALHDRGMYLMVDVVANHMGYDGDGDSVDYSVFNPFNSSSYFHPYCLITDYSNQTDVEDCWLGDTTVSLPDLNTTETVVRTIWYDWVADLVSNYSIDGLRIDTVKHVEKSFWPGYNSAAGVYCGEVLDGDPSYTCPYQDYLDGVLNYPIYYQLLYAFESSSGSISNLYNMINSVASECSDPTLLGNFIENHDNPRFASYTSDYSLAKNVIAFIFFSDGIPIVYAGQEQHYNGGNDPYNREATWLSGYSTTAELYTFIATTNAIRSLAISVDSEYLTYKNDPFYYDSNTLAMRKGSDGLQVITVLSNLGADGSSYTLTLSGSGYSSGTELVEAYTCTTVTVDSNGDIPVPMESGLPRVFLPASSFSGSSLCSSSPSPTTTTSTSTSTTTSTACTTATAVAVLFEELVTTTYGENVYLSGSISQLG |

TABLE 2-continued

Non-limiting examples of amylases that can be used in the
methods and compositions disclosed herein.

| SEQ ID NO: | Enzyme | Sequence |
|---|---|---|
| | | DWNTDDAVALSAANYTSSNPLWYVTVTLPVGTSFEYKFIKKEEN GDVEWESDPNRSYTVPTACTGATETIVDTWR |
| 9 | GENESEQ_PROT\| BBF92645 Penicillium sp. NN050730 alpha-amylase polypeptide, | MKALALAALCLAKAVAGLTAAEWRSQSIYFLLTDRFGRTDNSTT AACNVSDRVYCGGSWQGIINHLDYIQGMGFTAIWITPVTEQLSQ DTGDGEAYHGYWQQEIYNVNTNYGTAADLLALSKALHSRGMYLM VDVVANHMGYDGAGNTVDYSVFNPFDSSSYFHSYCEISDYSDQT NVEDCWLGDTTVSLPDLDTTLTSVQTIWYNWVTELVSNYSIDGL RIDTVKHVQKSFWPGYNSAAGVYCVGEVFDGDPAYTCPYQSYLD GVLNYPIYYQLLYAFESTSGSISGLYNMINSVASDCSDPTLLGN FIENHDNPRFASYTSDYSQAKNVISFIFFSDGIPIVYAGQEQHY SGGSDPANREATWLSGYDKTAQLYTYITTTNKIRALAISKDSAY ISSKNNAFYTDSNTIAMKKGSSGSQVITVLSNRGSSGSSYTLTL SGSGYSSGTKLMEMYTCTAVTVDSSGNIAVPMASGLPRVYMLAS SACSICSSACSATTTTSSTASTSTTTSTTLKTTTTTSTTSKTTT STTSTSCTQATALPVLFKEIVTTSYGQSIYISGSISQLGSWDTS SAVALSADQYTSSSHLWYVVVTIPVGTSFQYKFIEETSGSSTIT WESDPNRSYTVPTGCAGSTATVTATWR |
| 10 | Penicillium oxalicum WO2013044867 Novozymes | MKFLGLAALFLAQTVAGLTAAQWRSQSIYFLMTDRFGRTDKSVT APCNTNDRVYCGGTWQGIINQLDYIQGMGFTAIWITPVTEQLPQ DTGDGEAYHGYWQQEIYNVNNNYGTAADLKALSQALHSRGMYLM VDVVANHMGYAGAGNTVDYSVFKPFSSSSYFHPYCLISDYSNQT NVEDCWLGDTTVSLPDLDTTLSSVQTIWYNWVSDLVSNYSIDGL RIDTVKHVQKSFWPGYQSAAGVYCVGEVFSGDPAYTCPYQNYLD GVLNYPIYYQLLGAFKSTSGSISSLYNMINSVASDCADPTLLGN FIENHDNPRFASYTSDYSQAKNVISFIFLSDGIPIVYAGQEQHY SGGNDPANREATWLSGYSKNAQLYQHIASTNKIRSLAISKDANY ITSKNNAFYTDSNTIAMKKGSSGSQVVTVLSNRGSSGSSYTLSL SGSGYAAGTKLVEMYTCTAVTVDSNGNIAVSMTSGLPRVFMLAS SACSLCSSACSATATTLKTTTATATSCTQATALPVLFKDTVTTS YGQSVYLAGSISQLGNWNAANAVALSADKYTSSNPLWYATVTLP VGTSFQYKFIKKTSGSGSVTWESDPNRSYTVPTGCVGSTATVTA T |

The amylases disclosed herein further include all the isolated, synthetic or recombinant polypeptides with encoding sequences as disclosed or claimed by the U.S. Pat. Nos. 7,323,336, 9,062,295, or WO 2008/080093 as assigned to or applied by BASF (or Verenium), the contents of which are hereby expressly incorporated by reference in their entireties. For example, these include the amylases with sequences similar to SEQ ID NO:12 (SEQ ID NO:2 of U.S. Pat. No. 7,273,740 of Table 3), such as the amylases described in Example 10 in U.S. Pat. No. 7,407,677, the content of which is hereby expressly incorporated by reference in its entirety.

In some embodiments, the peptide having amylase activity may be Amylase BD5031, BD5063, BD5064 and BD5088 disclosed in Richardson et al., J. Biol. Chem. 277: 26501-26507 (2002), the content of which is hereby incorporated by reference in its entirety. In some preferred embodiments, the polypeptide having amylase activity may be a thermal stable amylase, such as the amylase described in Atichokudomchai et al., Carbohydrate Polymers 64:582-588 (2006), the content of which is hereby incorporated by reference in its entirety. In some other preferred embodiments, the polypeptide having amylase activity may be any of the amylase coded by the DNA sequences disclosed in Table 3 and 4 or having the protein sequences disclosed in Table 3 and 4.

TABLE 3

DNA coding sequences and protein sequences of non-limiting
examples of amylases that can be used in the methods and
compositions disclosed herein.

| SEQ ID NO: | Reference from Other Patents | Sequence |
|---|---|---|
| 1 | SEQ ID NO: 1 of U.S. Pat. No. 7273740 | ATGGCCAAGTACTCCGAGCTGGAAAAGGGCGGGGTCA TAATGCAGGCGTTCTACTGGGACGTGCCTTCAGGAGG AATATGGTGGGACACAATACGGCAGAAGATACCGGAG TGGTACGATGCCGGAATCTCCGCAATATGGATTCCCC CGGCGAGCAAGGGCATGGGCGGCGCCTATTCGATGGG CTACGACCCCTACGACTTCTTTGACCTCGGTGAGTAC GACCAGAAGGGAACGGTAGAGACGCGCTTTGGCTCCA AGCAGGAGCTCGTGAACATGATAAACACCGCCCACGC CTATGGCATGAAGGTAATAGCCGATATAGTCATCAAC CACCGCGCCGGCGGTGACCTGGAGTGGAACCCCTTCG TGAACGACTATACCTGGACCGACTTCTCAAAGGTCGC GTCGGGTAAATACACGGCCAACTACCTCGACTTCCAC |

TABLE 3-continued

DNA coding sequences and protein sequences of non-limiting examples of amylases that can be used in the methods and compositions disclosed herein.

| SEQ ID NO: | Reference from Other Patents | Sequence |
|---|---|---|
| | | CCGAACGAGCTCCATGCGGGCGATTCCGGAACATTTG GAGGCTATCCCGACATATGCCACGACAAGAGCTGGGA CCAGTACTGGCTCTGGGCCAGCCAGGAGAGCTACGCG GCATATCTCAGGAGCATCGGCATCGATGCCTGGCGCT TCGACTACGTCAAGGGCTATGCTCCCTGGGTCGTCAA GGACTGGCTGAACTGGTGGGGAGGCTGGGCGGTTGGA GAGTACTGGGACACCAACGTCGACGCTGTTCTCAACT GGGCATACTCGAGCGGTGCCAAGGTCTTTGACTTCGC CCTCTACTACAAGATGGATGAGGCCTTTGACAACAAA AACATTCCAGCGCTCGTCTCTGCCCTTCAGAACGGCC AGACTGTTGTCTCCCGCGACCCGTTCAAGGCCGTAAC CTTTGTAGCAAACCACGACACCGATATAATCTGGAAC AAGTATCCAGCCTACGCGTTCATCCTCACCTACGAGG GCCAGCCGACAATATTCTACCGCGACTACGAGGAGTG GCTCAACAAGGATAAGCTCAAGAACCTCATCTGGATA CATGAGAACCTCGCCGGAGGAAGCACCGACATAGTCT ACTACGATAACGATGAACTCATCTTCGTCAGGAACGG CTACGGGGACAAGCCGGGGCTTATAACCTACATCAAC CTAGGCTCGAGCAAGGCCGGAAGGTGGGTTTATGTGC CGAAGTTCGCGGGCGCGTGCATCCACGAGTATACTGG TAACCTCGGAGGCTGGGTAGACAAGTACGTCTACTCA AGCGGCTGGGTCTATCTCGAAGCTCCAGCTTACGACC CTGCCAACGGGCAGTATGGCTACTCCGTGTGGAGCTA CTGCGGGGTGGGCTGA |
| 12 | SEQ ID NO: 2 of U.S. Pat. No. 7273740 | MAKYSELEKGGVIMQAFYWDVPSGGIWWDTIRQKIPE WYDAGISAIWIPPASKGMGGAYSMGYDPYDFFDLGEY DQKGTVETRFGSKQELVNMINTAHAYGMKVIADIVIN HRAGGDLEWNPFVNDYTWTDFSKVASGKYTANYLDFH PNELHAGDSGTFGGYPDICHDKSWDQYWLWASQESYA AYLRSIGIDAWRFDYVKGYAPWVVKDWLNWWGGWAVG EYWDTNVDAVLNWAYSSGAKVFDPALYYKMDEAFDNK NIPALVSALQNGQTVVSRDPFKAVTFVANHDTDIIWN KYPAYAFILTYEGQPTIFYRDYEEWLNKDKLKNLIWI HENLAGGSTDIVYYDNDELIFVRNGYGDKPGLITYIN LGSSKAGRWVYVPKFAGACIHEYTGNLGGWVDKYVYS SGWVYLEAPAYDPANGQYGYSVWSYCGVG |
| 13 | SEQ ID NO: 6 of U.S. Pat. No. 7273740 | ATGAAGAAGTTTGTCGCCCTGTTCATAACCATGTTTT TCGTAGTGAGCATGGCAGTCGTTGCACAGCCAGCTAG CGCCGCAAAGTATTCCGAGCTCGAAGAAGGCGGCGTT ATAATGCAGGCCTTCTACTGGGACGTCCCAGGTGGAG GAATCTGGTGGGACACCATCAGGAGCAAGATACCGGA GTGGTACGAGGCGGGAATATCCGCCATTTGGATTCCG CCAGCCAGCAAGGGGATGAGCGGCGGTTACTCGATGG GCTACGATCCCTACGATTTCTTTGACCTCGGCGAGTA CAACCAGAAGGGAACCATCGAAACGCGCTTTGGCTCT AAACAGGAGCTCATCAATATGATAAACACGGCCCATG CCTACGGCATAAAGGTCATAGCGGACATCGTCATAAA CCACCGCGCAGGCGGAGACCTCGAGTGGAACCCGTTC GTTGGGGACTACACCTGGACGGACTTCTCAAAGGTGG CCTCGGGCAAATATACTGCCAACTACCTCGACTTCCA CCCCAACGAGGTCAAGTGCTGTGACGAGGGCACATTT GGAGGCTTCCCAGACATAGCCCACGAGAAGAGCTGGG ACCAGCACTGGCTCTGGGCGAGCGATGAGAGCTACGC CGCCTACCTAAGGAGCATCGGCGTTGATGCCTGGCGC TTTGACTACGTGAAGGGCTACGGAGCGTGGGTCGTCA AGGACTGGCTCAACTGGTGGGCGGCTGGGCCGTTGG CGAGTACTGGGACACCAACGTTGATGCACTCCTCAAC TGGGCCTACTCGAGCGGCGCCAAGGTCTTCGACTTCC CGCTCTACTACAAGATGGATGAGGCCTTTGACAACAA AAACATTCCAGCGCTCGTCTCTGCCCTTCAGAACGGC CAGACTGTTGTCTCCCGCGACCCGTTCAAGGCCGTAA CCTTTGTAGCAAACCACGACACCGATATAATCTGGAA CAAGTACCTTGCTTATGCTTTCATCCTCACCTACGAA GGCCAGCCCGTCATATTCTACCGCGACTACGAGGAGT GGCTCAACAAGGACAGGTTGAACAACCTCATATGGAT ACACGACCACCTCGCAGGTGGAAGCACCGAGCATAGTC TACTACGACAGCGACGAGATGATCTTCGTGAGGAACG GCTATGGAAGCAAGCCTGGCCTTATAACTTACATCAA CCTCGGCTCGAGCAAGGTTGGAAGGTGGGTTTATGTG CCGAAGTTCGCGGGCGCGTGCATCCACGAGTATACTG GTAACCTCGGAGGCTGGGTAGACAAGTACGTCTACTC |

TABLE 3-continued

DNA coding sequences and protein sequences of non-limiting
examples of amylases that can be used in the methods and
compositions disclosed herein.

| SEQ ID NO: | Reference from Other Patents | Sequence |
|---|---|---|
| | | AAGCGGCTGGGTCTATCTCGAAGCTCCAGCTTACGAC<br>CCTGCCAACGGGCAGTATGGCTACTCCGTGTGGAGCT<br>ATTGCGGTGTTGGGTGA |

TABLE 4

DNA coding sequences and protein sequences of non-limiting examples of amylases
that can be used in the methods and compositions disclosed herein.

| SEQ ID NO: | Reference from Other Patents | |
|---|---|---|
| 14 | SEQ ID NO: 1<br>of U.S. Pat. No. 7407677 | ATGGCAAAGTATTCCGAGCTCGAAGAGGGCGGGCTCATAATGCAGGCCT<br>TCTACTGGGACGTCCCCATGGGAGGAATCTGGTGGGACACGATAGCCCA<br>GAAGATACCCGACTGGGCAAGCGCCGGGATTTCGGCGATATGGATTCCC<br>CCGGCGAGCAAGGGCATGGGCGGCGCCTATTCGATGGGCTACGACCCCT<br>ACGACTTCTTTGACCTCGGTGAGTACGACCAGAAGGGAACGGTAGAGAC<br>GCGCTTTGGCTCCAAGCAGGAGCTCGTGAACATGATAAACACCGCCCAC<br>GCCTATGGCATGAAGGTAATAGCCGATATAGTCATCAACCACCGCGCCG<br>GCGGTGACCTGGAGTGGAACCCCTTCGTGAACGACTATACCTGGACCGA<br>CTTCTCAAAGGTCGCGTCGGGTAAATACACGGCCAACTACCTCGACTTC<br>CACCCGAACGAGCTCCATGCGGGCGATTCCGGAACATTTGGAGGCTATC<br>CCGACATATGCCACGACAAGAGCTGGGACCAGTACTGGCTCTGGGCCAG<br>CCAGGAGAGCTACGCGGCATATCTCAGGAGCATCGGCATCGATGCCTGG<br>CGCTTCGACTACGTCAAGGGCTACGGAGCGTGGGTCGTCAAGGACTGGC<br>TGGACTGGTGGGGAGGCTGGGCCGTCGGGGAGTACTGGGACACAAACGT<br>TGATGCACTGCTCAACTGGGCCTACTCGAGCGATGCAAAAGTCTTCGAC<br>TTCCCGCTCTACTACAAGATGGACGCGGCCTTTGACAACAAGAACATTC<br>CCGCACTCGTCGAGGCCCTCAAGAACGGGGGCACAGTCGTCAGCCGCGA<br>CCCGTTTAAGGCCGTAACCTTCGTTGCAAACCACGACACCGATATAATC<br>TGGAACAAGTATCCAGCCTACGCGTTCATCCTCACCTACGAGGGCCAGC<br>CGACAATATTCTACCGCGACTACGAGGAGTGGCTCAACAAGGATAAGCT<br>CAAGAACCTCATCTGGATACATGACAACCTCGCCGGAGGAAGCACTGAC<br>ATCGTTTACTACGACAACGACGAGCTGATATTCGTGAGAAACGGCTACG<br>GAAGCAAGCCGGGACTGATAACATACATCAACCTCGCCTCAAGCAAAGC<br>CGGAAGGTGGGTTTACGTTCCGAAGTTCGCAGGCTCGTGCATACACGAG<br>TACACCGGCAATCTCGGCGGCTGGGTGGACAAGTGGGTGGACTCAAGCG<br>GCTGGGTCTACCTCGAGGCTCCTGCCCACGACCCGGCCAACGGCCAGTA<br>CGGCTACTCCGTCTGGAGCTACTGCGGTGTTGGGTGA |
| 15 | SEQ ID NO: 2<br>of U.S. Pat. No. 7407677 | MAKYSELEEGGLIMQAFYWDVPMGGIWWDTIAQKIPDWASAGISAIWIP<br>PASKGMGGAYSMGYDPYDFFDLGEYDQKGTVETRFGSKQELVNMINTAH<br>AYGMKVIADIVINHRAGGDLEWNPFVNDYTWTDFSKVASGKYTANYLDF<br>HPNELHAGDSGTFGGYPDICHDKSWDQYWLWASQESYAAYLRSIGIDAW<br>RFDYVKGYGAWVVKDWLDWWGGWAVGEYWDTNVDALLNWAYSSDAKVFD<br>FPLYYKMDAAFDNKNIPALVEALKNGGTVVSRDPFKAVTFVANHDTDII<br>WNKYPAYAFILTYEGQPTIFYRDYEEWLNKDKLKNLIWIHDNLAGGSTD<br>IVYYDNDELIFVRNGYGSKPGLITYINLASSKAGRWVYVPKFAGSCIHE<br>YTGNLGGWVDKWVDSSGWVYLEAPAHDPANGQYGYSVWSYCGVG |
| 16 | SEQ ID NO: 11<br>of U.S. Pat. No. 7407677 | ATGGCCAAGTACCTGGAGCTCGAGGAGGGCGGGCTCATAATGCAGGCCT<br>TCTACTGGGACGTCCCCATGGGAGGAATCTGGTGGGACACGATAGCCCA<br>GAAGATACCCGACTGGGCAAGCGCCGGGATTTCGGCGATATGGATTCCC<br>CCGGCGAGCAAGGGCATGGGCGGCGCCTATTCGATGGGCTACGACCCCT<br>ACGACTTCTTTGACCTCGGTGAGTACGACCAGAAGGGAACGGTAGAGAC<br>GCGCTTTGGCTCCAAGCAGGAGCTCGTGAACATGATAAACACCGCCCAC<br>GCCTATGGCATGAAGGTAATAGCCGATATAGTCATCAACCACCGCGCCG<br>GCGGTGACCTGGAGTGGAACCCCTTCGTGAACGACTATACCTGGACCGA<br>CTTCTCAAAGGTCGCGTCGGGTAAATACACGGCCAACTACCTCGACTTC<br>CACCCGAACGAGCTCCATGCGGGCGATTCCGGAACATTTGGAGGCTATC<br>CCGACATATGCCACGACAAGAGCTGGGACCAGTACTGGCTCTGGGCCAG<br>CCAGGAGAGCTACGCGGCATATCTCAGGAGCATCGGCATCGATGCCTGG<br>CGCTTCGACTACGTCAAGGGCTATGCTCCTGGGTCGTCAAGGACTGGC<br>TGAACTGGTGGGGAGGCTGGGCGGTTGGAGAGTACTGGGACACCAACGT<br>CGACGCTGTTCTCAACTGGGCATACTCGAGCGGTGCCAAGGTCTTTGAC<br>TTCGCCCTCTACTACAAGATGGACGAGGCCTTCGATAACAACAACATTC<br>CCGCCCTGGTGGACGCCCTCAGATACGGTCAGACAGTGGTCAGCCGCGA<br>CCCGTTCAAGGCTGTGACGTTTGTAGCCAACCACGATACCGATATAATC<br>TGGAACAAGTATCCAGCCTACGCGTTCATCCTCACCTACGAGGGCCAGC<br>CGACAATATTCTACCGCGACTACGAGGAGTGGCTCAACAAGGATACGCT |

TABLE 4-continued

DNA coding sequences and protein sequences of non-limiting examples of amylases that can be used in the methods and compositions disclosed herein.

| SEQ ID NO: | Reference from Other Patents | |
|---|---|---|
| | | CAAGAACCTCATCTGGATACATGACAACCTCGCCGGAGGAAGCACGAGC<br>ATAGTTTACTACGACAGCGACGAGATGATCTTCGTGAGGAACGGCTATG<br>GAAGCAAGCCTGGCCTTATAACTTACATCAACCTCGGCTCGAGCAAGGT<br>TGGAAGGTGGGTCTACGTTCCGAAGTTCGCGGGAGCGTGCATCCACGAG<br>TACACCGGCAACCTCGGCGGCTGGGTGGACAAGTGGGTGGACTCAAGCG<br>GGTGGGTGTACCTCGAGGCCCCTGCCCACGACCCGGCCAACGGCTATTA<br>CGGCTACTCCGTCTGGAGCTACTGCGGTGTTGGCTGA |
| 17 | SEQ ID NO: 12<br>of U.S. Pat. No. 7407677 | MAKYLELEEGGLIMQAFYWDVPMGGIWWDTIAQKIPDWASAGISAIWIP<br>PASKGMGGAYSMGYDPYDFFDLGEYDQKGTVETRFGSKQELVNMINTAH<br>AYGMKVIADIVINHRAGGDLEWNPFVNDYTWTDFSKVASGKYTANYLDF<br>HPNELHAGDSGTFGGYPDICHDKSWDQYWLWASQESYAAYLRSIGIDAW<br>RFDYVKGYAPWVVKDWLNWWGGWAVGEYWDTNVDAVLNWAYSSGAKVFD<br>FALYYKMDEAFDNNNIPALVDALRYGQTVVSRDPFKAVTFVANHDTDII<br>WNKYPAYAFILTYEGQPTIFYRDYEEWLNKDTLKNLIWIHDNLAGGSTS<br>IVYYDSDEMIFVRNGYGSKPGLITYINLGSSKVGRWVYVPKFAGACIHE<br>YTGNLGGWVDKWVDSSGWVYLEAPAHDPANGYYGYSVWSYCGVG |
| 18 | SEQ ID NO: 13<br>of U.S. Pat. No. 7407677 | ATGGCCAAGTACCTGGAGCTCGAAGAGGGCGGGGTCATAATGCAGGCGT<br>TCTACTGGGACGTGCCTTCAGGAGGAATATGGTGGGACACAATACGGCA<br>GAAGATACCGGAGTGGTACGATGCCGGAATCTCCGCAATATGGATTCCC<br>CCGGCGAGCAAGGGCATGGGCGGCGCCTATTCGATGGGCTACGACCCCT<br>ACGACTTCTTTGACCTCGGTGAGTATGACCAGAAGGGAACGGTAGAGAC<br>GCGCTTTGGCTCCAAGCAGGAGCTCGTGAACATGATAAACACGGCACAT<br>GCCTACGGCATAAAGGTCATAGCGGACATCGTCATAAACCACCGCGCAG<br>GCGGAGACCTCGAGTGGAACCCGTTCGTTGGGGACTACACCTGGACGGA<br>CTTCTCAAAGGTGGCCTCGGGCAAATATACTGCCAACTACCTCGACTTC<br>CACCCCAACGAGGTCAAGTGCTGTGACGAGGGCACATTTGGAGGCTTCC<br>CAGACATAGCCCACGAGAAGAGCTGGGACCAGCACTGGCTCTGGGCGAG<br>CGATGAGAGCTACGCCGCCTACCTAAGGAGCATCGGCGTTGATGCCTGG<br>CGCTTCGACTACGTCAAGGGCTACGGAGCGTGGGTCGTCAAGGACTGGC<br>TGGACTGGTGGGGAGGCTGGGCCGTCGGGGAGTACTGGGACACAAACGT<br>TGATGCACTGCTCAACTGGGCCTACTCGAGCGATGCAAAAGTCTTCGAC<br>TTCCCGCTCTACTACAAGATGGATGAGGCCTTTGACAACAAAAACATTC<br>CAGCGCTCGTCTCTGCCCTTCAGAACGGCCAGACTGTTGTCTCCCGCGA<br>CCCGTTCAAGGCCGTAACCTTTGTAGCAAACCACGACACCGATATAATC<br>TGGAACAAGTATCCAGCCTACGCGTTCATCCTCACCTACGAGGGCCAGC<br>CGACAATATTCTACCGCGACTACGAGGAGTGGCTCAACAAGGATAAGCT<br>CAAGAACCTCATCTGGATACATGACAACCTCGCCGGAGGAAGCACTGAC<br>ATAGTCTACTACGATAACGATGAACTCATCTTCGTCAGGAACGGCTACG<br>GGGACAAGCCGGGGCTTATAACCTACATCAACCTAGGCTCGAGCAAGGC<br>CGGAAGGTGGGTTTATGTGCCGAAGTTCGCGGGCGCGTGCATCCACGAG<br>TATACTGGTAACCTCGGAGGCTGGGTAGACAAGTACGTCTACTCAAGCG<br>GCTGGGTCTATCTCGAAGCTCCAGCTTACGACCCTGCCAACGGGCAGTA<br>TGGCTACTCCGTGTGGAGCTACTGCGGTGTTGGCTGA |
| 19 | SEQ ID NO: 14<br>of U.S. Pat. No. 7407677 | MAKYLELEEGGVIMQAFYWDVPSGGIWWDTIRQKIPEWYDAGISAIWIP<br>PASKGMGGAYSMGYDPYDFFDLGEYDQKGTVETRFGSKQELVNMINTAH<br>AYGIKVIADIVINHRAGGDLEWNPFVGDYTWTDFSKVASGKYTANYLDF<br>HPNEVKCCDEGTFGGFPDIAHEKSWDQHWLWASDESYAAYLRSIGVDAW<br>RFDYVKGYGAWVVKDWLDWWGGWAVGEYWDTNVDALLNWAYSSDAKVFD<br>FPLYYKMDEAFDNKNIPALVSALQNGQTVVSRDPFKAVTFVANHDTDII<br>WNKYPAYAFILTYEGQPTIFYRDYEEWLNKDKLKNLIWIHDNLAGGSTD<br>IVYYDNDELIFVRNGYGDKPGLITYINLGSSKAGRWVYVPKFAGACIHE<br>YTGNLGGWVDKYVYSSGWVYLEAPAYDPANGQYGYSVWSYCGVG |
| 20 | SEQ ID NO: 15<br>of U.S. Pat. No. 7407677 | ATGGCCAAGTACTCCGAGCTGGAAGAGGGCGGGCTCATAATGCAGGCCT<br>TCTACTGGGACGTCCCCATGGGAGGAATCTGGTGGGACACGATAGCCCA<br>GAAGATACCCGACTGGGCAAGCGCCGGGATTTCGGCGATATGGATTCCC<br>CCGGCGAGCAAGGGCATGGGCGGCGCCTATTCGATGGGCTACGACCCCT<br>ACGACTTCTTTGACCTCGGTGAGTACGACCAGAAGGGGAACGGTAGAGAC<br>GCGCTTTGGCTCCAAGCAGGAGCTCGTGAACATGATAAACACGGCCCAT<br>GCCTACGGCATAAAGGTCATAGCGGACATCGTCATAAACCACCGCGCAG<br>GCGGAGACCTCGAGTGGAACCCGTTCGTTGGGGACTACACCTGGACGGA<br>CTTCTCAAAGGTGGCCTCGGGCAAATATACTGCCAACTACCTCGACTTC<br>CACCCGAACGAGCTCCATGCGGGCGATTCCGGAACATTTGGAGGCTATC<br>CCGACATATGCCACGACAAGAGCTGGGACCAGTACTGGCTCTGGGCCAG<br>CCAGGAGAGCTACGCGGCATATCTCAGGAGCATCGGCATCGATGCCTGG<br>CGCTTCGACTACGTCAAGGGCTACGGAGCGTGGGTCGTCAAGGACTGGC<br>TGGACTGGTGGGGAGGCTGGGCCGTCGGGGAGTACTGGGACACAAACGT<br>TGATGCACTGCTCAACTGGGCCTACTCGAGCGATGCAAAAGTCTTCGAC<br>TTCCCGCTCTACTACAAGATGGATGAGGCCTTTGACAACAAAAACATTC<br>CAGCGCTCGTCTCTGCCCTTCAGAACGGCCAGACTGTTGTCTCCCGCGA<br>CCCGTTCAAGGCCGTAACCTTTGTAGCAAACCACGACACCGATATAATT |

TABLE 4-continued

DNA coding sequences and protein sequences of non-limiting examples of amylases
that can be used in the methods and compositions disclosed herein.

| SEQ ID NO: | Reference from Other Patents | |
|---|---|---|
| | | TGGAACAAGTACCCGGCCTACGCCTTCATCCTCACCTACGAGGGCCAGC
CGACGATATTCTACCGCGACTACGAGGAGTGGCTCAACAAGGACAGGCT
CAAGAACCTCATCTGGATACACGACCACCTTGCCGGTGGAAGCACTGAC
ATCGTTTACTACGACAACGACGAGCTGATATTCGTGAGAAACGGCTACG
GAAGCAAGCCGGGACTGATAACATACATCAACCTCGCCTCAAGCAAAGC
CGGAAGGTGGGTTTATGTGCCGAAGTTCGCGGGCGCGTGCATCCACGAG
TATACTGGTAACCTCGGAGGCTGGGTAGACAAGTACGTCTACTCAAGCG
GCTGGGTCTATCTCGAAGCTCCAGCTTACGACCCTGCCAACGGGCAGTA
TGGCTACTCCGTGTGGAGCTATTGCGGTGTTGGGTGA |
| 21 | SEQ ID NO: 16
of U.S. Pat. No. 7407677 | MAKYSELEEGGLIMQAFYWDVPMGGIWWDTIAQKIPDWASAGISAIWIP
PASKGMGGAYSMGYDPYDFFDLGEYDQKGTVETRFGSKQELVNMINTAH
AYGIKVIADIVINHRAGGDLEWNPFVGDYTWTDFSKVASGKYTANYLDF
HPNELHAGDSGTFGGYPDICHDKSWDQYWLWASQESYAAYLRSIGIDAW
RFDYVKGYGAWVVKDWLDWWGGWAVGEYWDTNVDALLNWAYSSDAKVFD
FPLYYKMDEAFDNKNIPALVSALQNGQTVVSRDPFKAVTFVANHDTDII
WNKYPAYAFILTYEGQPTIFYRDYEEWLNKDRLKNLIWIHDHLAGGSTD
IVYYDNDELIFVRNGYGSKPGLITYINLASSKAGRWVYVPKFAGACIHE
YTGNLGGWVDKYVYSSGWVYLEAPAYDPANGQYGYSVWSYCGVG |
| 22 | SEQ ID NO: 17
of U.S. Pat. No. 7407677 | ATGGCCAAGTACTCCGAGCTGGAAGGGGCGGGCTCATAATGCAGGCCT
TCTACTGGGACGTCCCCATGGGAGGAATCTGGTGGGACACGATAGCCCA
GAAGATACCCGACTGGGCAAGCGCCGGGATTTCGGCGATATGGATTCCC
CCGGCGAGCAAGGGCATGGGCGGCGCCTATTCGATGGGCTACGACCCCT
ACGACTTCTTTGACCTCGGTGAGTACGACCAGGAGGGAACGGTAGAGAC
GCGCTTTGGCTCCAAGCAGGAGCTCGTGAACATGATAAACACGGCCCAT
GCCTACGGCATAAAGGTCATAGCGGACATCGTCATAAACCACCGCGCAG
GCGGAGACCTCGAGTGGAACCCGTTCGTTGGGGACTACACCTGGACGGA
CTTCTCAAAGGTGGCCTCGGGCAAATATACTGCCAACTACCTCGACTTC
CACCCCAACGAGGTCAAGTGCTGTGACGAGGGCACATTTGGAGGCTTCC
CAGACATAGCCCACGAGAAGAGCTGGGACCAGCACTGGCTCTGGGCGAG
CGATGAGAGCTACGCCGCCTACCTAAGGAGCATCGGCGTTGATGCCTGG
CGCTTCGACTACGTCAAGGGCTACGGAGCGTGGGTCGTCAAGGACTGGC
TGGACTGGTGGGGAGGCTGGGCCGTCGGGGAGTACTGGGACACAAACGT
TGATGCACTGCTCAACTGGGCCTACTCGAGCGATGCAAAGTCTTCGAC
TTCCCGCTCTACTACAAGATGGACGCGGCCTTTGACAACAAGAACATTC
CCGCACTCGTCGAGGCCCTCAAGAACGGGGGCACAGTCGTCAGCCGCGA
CCCGTTTAAGGCCGTAACCTTCGTTGCAAACCACGACACCGATATAATC
TGGAACAAGTATCCAGCCTACGCGTTCATCCTCACCTACGAGGGCCAGC
CGACAATATTCTACCGCGACTACGAGGAGTGGCTCAACAAGGATAAGCT
CAAGAACCTCATCTGGATACATGACAACCTCGCCGGAGGAAGCACGAGC
ATAGTTTACTACGACAGCGACGAGATGATCTTCGTGAGGAACGGCTATG
GAAGCAAGCCTGGCCTTATAACTTACATCAACCTCGGCTCGAGCAAGGT
TGGAAGGTGGGTTTACGTTCCGAAGTTCGCAGGCTCGTGCATACACGAG
TACACCGGCAATCTCGGCGGCTGGGTGGACAAGTGGGTGGACTCAAGCG
GCTGGGTCTACCTCGAGGCTCCTGCCCACGACCCGGCCAACGGCCAGTA
CGGCTACTCCGTCTGGAGCTACTGCGGTGTTGGGTGA |
| 23 | SEQ ID NO: 18
of U.S. Pat. No. 7407677 | MAKYSELEGGGLIMQAFYWDVPMGGIWWDTIAQKIPDWASAGISAIWIP
PASKGMGGAYSMGYDPYDFFDLGEYDQEGTVETRFGSKQELVNMINTAH
AYGIKVIADIVINHRAGGDLEWNPFVGDYTWTDFSKVASGKYTANYLDF
HPNEVKCCDEGTFGGFPDIAHEKSWDQHWLWASDESYAAYLRSIGVDAW
RFDYVKGYGAWVVKDWLDWWGGWAVGEYWDTNVDALLNWAYSSDAKVFD
FPLYYKMDAAFDNKNIPALVEALKNGGTVVSRDPFKAVTFVANHDTDII
WNKYPAYAFILTYEGQPTIFYRDYEEWLNKDKLKNLIWIHDNLAGGSTS
IVYYDSDEMIFVRNGYGSKPGLITYINLGSSKVGRWVYVPKFAGSCIHE
YTGNLGGWVDKWVDSSGWVYLEAPAHDPANGQYGYSVWSYCGVG |
| 24 | SEQ ID NO: 19
of U.S. Pat. No. 7407677 | ATGGCCAAGTACCTGGAGCTCGAAGAGGGCGGGCTCATAATGCAGGCCT
TCTACTGGGACGTCCCCATGGGAGGAATCTGGTGGGACACGATAGCCCA
GAAGATACCCGACTGGGCAAGCGCCGGGATTTCGGCGATATGGATTCCT
CCCGCGAGCAAGGGTATGAGCGGCGGCTATTCGATGGGCTACGACCCCT
ACGATTATTTTGACCTTGGTGAGTACTACCAGAAGGGAACGGTGGAAAC
GAGGTTCGGCTCAAAGCAGGAGCTCATAAACATGATAAACACGGCCCAT
GCCTACGGCATAAAGGTCATAGCGGACATCGTCATAAACCACCGCGCAG
GCGGAGACCTCGAGTGGAACCCGTTCGTTGGGGACTACACCTGGACGGA
CTTCTCAAAGGTGGCCTCGGGCAAATATACTGCCAACTACCTCGACTTC
CACCCGAACGAGCTCCATGCGGGCGATTCCGGAACATTTGGAGGCTATC
CCGACATATGCCACGACAAGAGCTGGGACCAGTACTGGCTCTGGGCCGA
CCAGGAGAGCTACGCGGCATATCTCAGGAGCATCGGCATCGATGCCTGG
CGCTTCGACTACGTCAAGGGCTATGCTCCCTGGGTCGTCAAGGACTGGC
TGAACTGGTGGGGGGCTGGGCGGTTGGAGAGTACTGGGACACCAACGT
CGACGCTGTTCTCAACTGGGCATACTCGAGCGGTGCCAAGGTCTTTGAC
TTCGCCCTCTACTACAAGATGGATGAGGCCTTTGACAACAAAAACATTC |

TABLE 4-continued

DNA coding sequences and protein sequences of non-limiting examples of amylases that can be used in the methods and compositions disclosed herein.

| SEQ ID NO: | Reference from Other Patents | |
|---|---|---|
| | | CAGCGCTCGTCTCTGCCCTTCAGAACGGCCAGACTGTTGTCTCCCGCGA<br>CCCGTTCAAGGCCGTAACCTTTGTAGCAAACCACGACACCGATATAATT<br>TGGAACAAGTACCCGGCCTACGCCTTCATCCTCACCTACGAGGGCCAGC<br>CGACGATATTCTACCGCGACTACGAGGAGTGGCTCAACAAGGACAGGCT<br>CAAGAACCTCATCTGGATACACGACCACCTCGCCGGTGGAAGCACTGAC<br>ATCGTTTACTACGACAACGACGAGCTGATATTCGTGAGAAACGGCTACG<br>GAAGCAAGCCGGGACTGATAACATACATCAACCTCGCCTCAAGCAAAGC<br>CGGAAGGTGGGTTTATGTGCCGAAGTTCGCGGGCGCGTGCATCCACGAG<br>CATACTGGTAACCTCGGAGGCTGGGTAGACAAGTACGTCTACTCAAGCG<br>GCTGGGTCTATCTCGAAGCTCCAGCTTACGACCCTGCCAACGGGCAGTA<br>TGGCTACTCCGTGTGGAGCTACTGCGGTGTTGGCTGA |
| 25 | SEQ ID NO: 20<br>of U.S. Pat. No. 7407677 | MAKYLELEEGGLIMQAFYWDVPMGGIWWDTIAQKIPDWASAGISAIWIP<br>PASKGMSGGYSMGYDPYDYFDLGEYYQKGTVETRFGSKQELINMINTAH<br>AYGIKVIADIVINHRAGGDLEWNPFVGDYTWTDFSKVASGKYTANYLDF<br>HPNELHAGDSGTFGGYPDICHDKSWDQYWLWASQESYAAYLRSIGIDAW<br>RFDYVKGYAPWVVKDWLNWWGGWAVGEYWDTNVDAVLNWAYSSGAKVFD<br>FALYYKMDEAFDNKNIPALVSALQNGQTVVSRDPFKAVTFVANHDTDII<br>WNKYPAYAFILTYEGQPTIFYRDYEEWLNKDRLKNLIWIHDHLAGGSTD<br>IVYYDNDELIFVRNGYGSKPGLITYINLASSKAGRWVYVPKFAGACIHE<br>HTGNLGGWVDKYVYSSGWVYLEAPAYDPANGQYGYSVWSYCGVG |
| 26 | SEQ ID NO: 21<br>of U.S. Pat. No. 7407677 | ATGGCCAAGTACTCCGAGCTGGAAGAGGGCGGCGTTATAATGCAGGCCT<br>TCTACTGGGACGTCCCAGGTGGAGGAATCTGGTGGGACACCATCAGGAG<br>CAAGATACCGGAGTGGTACGAGGCGGGAATATCCGCCATTTGGATTCCT<br>CCCGGGAGCAAGGGTATGAGCGGCGGCTATTCGATGGGCTACGACCCCT<br>ACGATGATTTGGACCTGGGTGAGTACTACCAGAAGGGAACGGTGGAAAC<br>GAGGTTCGGCTCAAAGCAGGAGCTCATAAACATGATAAACACGGCCCAT<br>GCCTACGGCATAAAGGTCATAGCGGACATCGTCATAAACCACCGCGCAG<br>GCGGAGACCTCGAGTGGAACCCGTTCGTTGGGGACTACACCTGGACGGA<br>CTTCTCAAAGGTGGCCTCGGGCAAATATACTGCCAACTACCTCGACTTC<br>CACCCGAACGAGCTCCATGCGGGCGATTCCGGAACATTTGGAGGCTATC<br>CGGACATATGCCACGACAAGAGCTGGGACCAGTACTGGCTCTGGGCCAG<br>CCAGGAGAGCTACGCGGTATATCTCAGGAGCATCGGCATCGATGCCTGG<br>CGCTTCGACTACGTCAAGGGCTACGGAGCGTGGGTCGTCAAGGACTGGC<br>TGGACTGGTGGGGAGGCTGGGCCGTCGGGGAGTACTGGGACACAAACGT<br>TGATGCACTGCTCAACTGGGCCTACTCGAGCGATGCAAAAGTCTTCGAC<br>TTCCCGCTCTACTACAAGATGGATGAGGCCTTTGACAACAAAAACATTC<br>CAGCGCTCGTCTCTGCCCTTCAGAACGGCCAGACTGTTGTCTCCCGCGA<br>CCCGTTCAAGGCCGTAACCTTTGTAGCAAACCACGACACCGATATAATT<br>TGGAACAAGTACCCGGCCTACGCCTTCATCCTCACCTACGAGGGCCAGC<br>CGACGATATTCTACCGCGACTACGAGGAGTGGCTCAACAAGGACAGGCT<br>CAAGAACCTCATCTGGATACACGACTACCTCGCCGGTGGAAGCACTGAC<br>ATCGTTTACTACGACAACGACGAGCTGATATTCGTGAGAAACGGCTACG<br>GAAGCAAGCCGGGACTGATAACATACATCAACCTCGCCTCAAGCAAAGC<br>CGGAAGGTGGGTTTATGTGCCGAAGTTCGCGGGCGCGTGCATCCACGAG<br>TATACTGGTAACCTCGGAGGCTGGGTAGACAAGTACGTCTACTCAAGCG<br>GCTGGGTCTATCTCGAAGCTCCAGCTTACGACCCTGCCAACGGGCAGTA<br>TGGCTACTCCGTGTGGAGCTATTGCGGTGTTGGCTGA |
| 27 | SEQ ID NO: 22<br>of U.S. Pat. No. 7407677 | MAKYSELEEGGVIMQAFYWDVPGGGIWWDTIRSKIPEWYEAGISAIWIP<br>PGSKGMSGGYSMGYDPYDDLDLGEYYQKGTVETRFGSKQELINMINTAH<br>AYGIKVIADIVINHRAGGDLEWNPFVGDYTWTDFSKVASGKYTANYLDF<br>HPNELHAGDSGTFGGYPDICHDKSWDQYWLWASQESYAVYLRSIGIDAW<br>RFDYVKGYGAWVVKDWLDWWGGWAVGEYWDTNVDALLNWAYSSDAKVFD<br>FPLYYKMDEAFDNKNIPALVSALQNGQTVVSRDPFKAVTFVANHDTDII<br>WNKYPAYAFILTYEGQPTIFYRDYEEWLNKDRLKNLIWIHDYLAGGSTD<br>IVYYDNDELIFVRNGYGSKPGLITYINLASSKAGRWVYVPKFAGACIHE<br>YTGNLGGWVDKYVYSSGWVYLEAPAYDPANGQYGYSVWSYCGVG |
| 28 | SEQ ID NO: 23<br>of U.S. Pat. No. 7407677 | ATGGCCAAGTACTCCGAGCTGGAAGAGGGCGGCGTTATAGTGCAGGCCT<br>TCTACTGGGACGTCCCAGGTGGAGGAATCTGGTGGGACACCATCAGGAG<br>CAAGATACCGGAGTGGTACGAGGCGGGAATATCCGCCATTTGGATTCCC<br>CCGGCGAGCAAGGGCATGGGCGGCGCCTATTCGATGGGCTACGACCCCT<br>ACGACTTCTTTGACCTCGGTGAGTACGACCAGAAGGGAACGGTAGAGAC<br>GCGCTTTGGCTCCAAGCAGGAGCTCGTGAACATGATAAACACGGCCCAT<br>GCCTACGGCATAAAGGTCATAGCGGACATCGTCATAAACCACCGCGCAG<br>GCGGAGACCTCGAGTGGAACCCGTTCGTTGGGGACTACACCTGGACGGA<br>CTTCTCAAAGGTGGCCTCGGGCAAATATACTGCCAACTACCTCGACTTC<br>CACCCGAACGAGCTCCATGCGGGCGATTCCGGAACATTTGGAGGCTATC<br>CGGACATATGCCACGACAAGAGCTGGGACCAGTACTGGCTCTGGGCCAG<br>CCAGGAGAGCTACGCGGCATATCTCAGGAGCATCGGCATCGATGCCTGG<br>CGCTTCGACTACGTCAAGGGCTACGGAGCGTGGGTCGTCAAGGACTGGC<br>TGGACTGGTGGGGAGGCTGGGCCGTCGGGGAGTACTGGGACACAAACGT |

TABLE 4-continued

DNA coding sequences and protein sequences of non-limiting examples of amylases that can be used in the methods and compositions disclosed herein.

| SEQ ID NO: | Reference from Other Patents | |
|---|---|---|
| | | TGATGCACTGCTCAACTGGGCCTACTCGAGCGATGCAAAAGTCTTCGAC<br>TTCCCGCTCTACTACAAGATGGATGAGGCCTTTGACAACAAAAACATTC<br>CAGCGCTCGTCTCTGCCCTTCAGAACGGCCAGACTGTTGTCTCCCGCGA<br>CCCGTTCAAGGCCGTAACCTTTGTAGCAAACCACGACACCGATATAATC<br>TGGAACAAGTATCCAGCCTACGCGTTCATCCTCACCTACGAGGGCCAGC<br>CGACAATATTCTACCGCGACTACGAGGAGTGGCTCAACAAGGATAAGCT<br>CAAGAACCTCATCTGGATACATGACAACCTCGCCGGAGGAAGCATGAGC<br>ATAGTTTACTACGACAGCGACGAGATGATCTTCGTGAGGAACGGCTATG<br>GAAGCAAGCCTGGCCTTATAACTTACATCAACCTCGGCTCGAGCAAGGT<br>TGGAAGGTGGGTCTACGTTCCGAAGTTCGCGGGAGCGTGCATCCACGAG<br>TACACCGGCAACCTCGGCGGCTGGGTGGACAAGTGGGTGGACTCAAGCG<br>GGTGGGTGTACCTCGAGGCCCCTGCCCACGACCCGGCCAACGGCTATTA<br>CGGCTACTCCGTCTGGAGCTATTGCGGTGTTGGCTGA |
| 29 | SEQ ID NO: 24<br>of U.S. Pat. No. 7407677 | MAKYSELEEGGVIVQAFYWDVPGGGIWWDTIRSKIPEWYEAGISAIWIP<br>PASKGMGGAYSMGYDPYDFFDLGEYDQKGTVETRFGSKQELVNMINTAH<br>AYGIKVIADIVINHRAGGDLEWNPFVGDYTWTDFSKVASGKYTANYLDF<br>HPNELHAGDSGTFGGYPDICHDKSWDQYWLWASQESYAAYLRSIGIDAW<br>RFDYVKGYGAWVVKDWLDWWGGWAVGEYWDTNVDALLNWAYSSDAKVFD<br>FPLYYKMDEAFDNKNIPALVSALQNGQTVVSRDPFKAVTFVANHDTDII<br>WNKYPAYAFILTYEGQPTIFYRDYEEWLNKDKLKNLIWIHDNLAGGSMS<br>IVYYDSDEMIFVRNGYGSKPGLITYINLGSSKVGRWVYVPKFAGACIHE<br>YTGNLGGWVDKWVDSSGWVYLEAPAHDPANGYYGYSVWSYCGVG |
| 30 | SEQ ID NO: 25<br>of U.S. Pat. No. 7407677 | ATGGCCAAGTACCTGGAGCTCGAAGAGGGCGGGCTCATAATGCAGGCCT<br>TCTACTGGGACGTCCCCATGGGAGGAATCTGGTGGGACACGATAGCCCA<br>GAAGATACCCGACTGGGCAAGCGCCGGGATTTCGGCGATATGGATTCCT<br>CCCGCGAGCAAGGGTATGAGCGGCGGCTATTCGATGGGCTACGACCCCT<br>ACGATTATTTTGACCTCGGTGAGTACTACCAGAAGGGAACGGTGGAAAC<br>GAGGTTCGGCTCAAAGCAGGAGCTCATAAACATGATAAACACCGCCCAC<br>GCCTATGGCATGAAGGTAATAGCCGATATAGTCATCAACCACCGCGCCG<br>GCGGTGACCTGGAGTGGAACCCCTTCGTGAACGACTATACCTGGACCGA<br>CTTCTCAAAGGTCGCGTCGGGTAAATACACGGCCAACTACCTCGACTTC<br>CACCCGAACGAGCTCCATGCGGGCGATTCCGGAACATTTGGAGGCTATC<br>CCGACATATGCCACGACAAGAGCTGGGACCAGTACTGGCTCTGGGCCAG<br>CCAGGAGAGCTACGCGGCATATCTCAGGAGCATCGGCATCGATGCCTGG<br>CGCTTCGACTACGTCAAGGGCTATGCTCCCTGGGTCGTCAAGGACTGGC<br>TGAACTGGTGGGGAGGCTGGGCGGTTGGAGAGTACTGGGACACCAACGT<br>CGACGCTGTTCTCAACTGGGCATACTCGAGCGGTGCCAAGGTCTTTGAC<br>TTCGCCCTCTACTACAAGATGGACGAGGCCTTCGATAACAACAACATTC<br>CCGCCCTGGTGGGCGCCCTCAGATACGGTCAGACAGTGGTCAGCCGCGA<br>CCCGTTCAAGGCTGTGACGTTTGTAGCCAACCACGATACCGATATAATC<br>TGGAACAAGTATCCAGCCTACGCGTTCATCCTCACCTACGAGGGCCAGC<br>CGACAATATTCTACCGCGACTACGAGGAGTGGCTCAACAAGGATAAGCT<br>CAAGAACCTCATCTGGATACATGACAACCTCGCCGGAGGAAGCACCGAC<br>ATAGTCTACTACGATAACGATGAACTCATCTTCGTCAGGCACGGCTACG<br>GGGACAAGCCGGGGCTTATAACCTACATCAACCTAGGCTCGAGCAAGGC<br>CGGAAGGTGGGTTTACGTTCCGAAGTTCGCAGGCTCGTGCATACACGAG<br>TACACCGGCAATCTCGGCGGCTGGGTGGACAAGTGGGTGGACTCAAGCG<br>GCTGGGTCTACCTCGAGGCTCCTGCCCACGACCCGGCCAACGGCCAGTA<br>CGGCTACTCCGTCTGGAGCTATTGCGGTGTTGGGTGA |
| 31 | SEQ ID NO: 26<br>of U.S. Pat. No. 7407677 | MAKYLELEEGGLIMQAFYWDVPMGGIWWDTIAQKIPDWASAGISAIWIP<br>PASKGMSGGYSMGYDPYDYFDLGEYYQKGTVETRFGSKQELINMINTAH<br>AYGMKVIADIVINHRAGGDLEWNPFVNDYTWTDFSKVASGKYTANYLDF<br>HPNELHAGDSGTFGGYPDICHDKSWDQYWLWASQESYAAYLRSIGIDAW<br>RFDYVKGYAPWVVKDWLNWWGGWAVGEYWDTNVDAVLNWAYSSGAKVFD<br>FALYYKMDEAFDNNNIPALVGALRYGQTVVSRDPFKAVTFVANHDTDII<br>WNKYPAYAFILTYEGQPTIFYRDYEEWLNKDKLKNLIWIHDNLAGGSTD<br>IVYYDNDELIFVRHGYGDKPGLITYINLGSSKAGRWVYVPKFAGSCIHE<br>YTGNLGGWVDKWVDSSGWVYLEAPAHDPANGQYGYSVWSYCGVG |
| 32 | SEQ ID NO: 27<br>of U.S. Pat. No. 7407677 | ATGGCAAAGTATTCCGAGCTCGAAGAGGGCGGCGTTATAATGCAGGCCT<br>TCTACTGGGACGTCCCAGGTGGAGGAATCTGGTGGGACACCATCAGGAG<br>CAAGATACCGGAGTGGTACGAGGCGGGAATATCCGCCATTTGGATTCCT<br>CCCGCGAGCAAGGGTATGAGCGGCGGCTATTCGATGGGCTACGACCCCT<br>ACGATTATTTTGACCTCGGTGAGTACTACCAGAAGGGAACGGTGGAAAC<br>GAGGTTCGGCTCAAAGCAGGAGCTCATAAACATGATAAACACCGCCCAT<br>GCCTACGGCATAAAGGTCATAGCGGACATCGTCATAAACCACCGCGCAG<br>GCGGAGACCTCGAGTGGAACCCGTTCGTTGGGGACTACACCTGGACGGA<br>CTTCTCAAAGGTGGCCTCGGGCAAATATACTGCCAACTACCTCGACTTC<br>CACCCGAACGAGCTCCATGCGGGCGATTCCGGAACATTTGGAGGCTATC<br>CCGACATATGCCACGACAAGAGCTGGGACCAGTACTGGCTCTGGGCCAG<br>CCAGGAGAGCTACGCGGCATATCTCAGGAGCATCGGCATCGATGCCTGG<br>CGCTTCGACTACGTCAAGGGCTATGCTCCCTGGGTCGTCAAGGACTGGC |

TABLE 4-continued

DNA coding sequences and protein sequences of non-limiting examples of amylases that can be used in the methods and compositions disclosed herein.

| SEQ ID NO: | Reference from Other Patents | |
|---|---|---|
| | | TGAACTGGTGGGGAGGCTGGGCGGTTGGAGAGTACTGGGACACCAACGT CGACGCTGTTCTCAACTGGGCATACTCGAGCGGTGCCAAGGTCTTTGAC TTCGCCCTCTACTACAAGATGGACGCGGCCTTTGACAACAAGAACATTC CCGCACTCGTCGAGGCCCTCAAGAACGGGGGCACAGTCGTCAGCCGCGA CCCGTTTAAGGCCGTAACCTTCGTTGCAAACCACGACACCGATATAATC TGGAACAAGTATCCAGCCTACGCCGTTCATCCTCACCTACGAGGGCCAGC CGACAATATTCTACCGCGACTACGAGGAGTGGCTCAACAAGGATAAGCT CAAGAACCTCATCTGGATACATGACAACCTCGCCGGAGGAAGCACTGAC ATCGTTTACTACGACAACGACGAGCTGATATTCGTGAGAAACGGCTACG GAAGCAAGCCGGGACTGATAACATACATCAACCTCGCGTCAAGCAAAGC CGGAAGGTGGGTTTACGTTCCGAAGTTCGCAGGCTCGTGCATACACGAG TACACCGGCAATCTCGGCGGCTGGGTGGACAAGTGGGTGGACTCAAGCG GCTGGGTCTACCTCGAGGCTCCTGCCCACGACCCGGCCAACGGCCAGTA CGGCTACTCCGTCTGGAGCTACTGCGGTGTTGGGTGA |
| 33 | SEQ ID NO: 28 of U.S. Pat. No. 7407677 | MAKYSELEEGGVIMQAFYWDVPGGGIWWDTIRSKIPEWYEAGISAIWIP PASKGMSGGYSMGYDPYDYFDLGEYYQKGTVETRFGSKQELINMINTAH AYGIKVIADIVINHRAGGDLEWNPFVGDYTWTDFSKVASGKYTANYLDF HPNELHAGDSGTFGGYPDICHDKSWDQYWLWASQESYAAYLRSIGIDAW RFDYVKGYAPWVVKDWLNWWGGWAVGEYWDTNVDAVLNWAYSSGAKVFD FALYYKMDAAFDNKNIPALVEALKNGGTVVSRDPFKAVTFVANHDTDII WNKYPAYAFILTYEGQPTIFYRDYEEWLNKDKLKNLIWIHDNLAGGSTD IVYYDNDELIFVRNGYGSKPGLITYINLASSKAGRWVYVPKFAGSCIHE YTGNLGGWVDKWVDSSGWVYLEAPAHDPANGQYGYSVWSYCGVG |
| 34 | SEQ ID NO: 29 of U.S. Pat. No. 7407677 | ATGGCCAAGTACCTGGAGCTCGAAGAGGGCGGGCTCATAATGCAGGCCT TCTACTGGGACGTCCCCATGGGAGGAATCTGGTGGGACACGGTAGCCCA GAAGATACCCGACTGGGCAAGCGCCGGGATTTCGGCGATATGGATTCCC CCGGCGAGCAAGGGCATGGGCGGCGCCTATTCGATGGGCTACGACCCCT ACGACTTCTTTGACCTCGGTGAGTACGACCAGAAGGGAACGGTAGAGAC GCGCTTTGGCTCCAAGCAGGAGCTCGTGAACATGATAAACACGGCCCAT GCCTACGGCATAAAGGTCATAGCGGACATCGTCATAAACCACCGCGCAG GCGGAGACCTCGAGTGGAACCCGTTCGTTGGGGACTACACCTGGACGGA CTTCTCAAAGGTGGTCTCGGGCAAATATACTGCCAACTACCTCGACTTC CACCCGAACGAGCTCCATGCGGGCGATTCCGGAACATTTGGAGGCTATC CCGACATATGCCACGACAAGAGCTGGGACCAGTACTGGCTCTGGGCCAG CCAGGAGAGCTACGCGGCATATCTCAGGAGCATCGGCATCGATGCCTGG CGCTTCGACTACGTCAAGGGCTATGCTCCCTGGGTCGTCAAGGACTGGC TGAACTGGTGGGGAGGCTGGGCGGTTGGAGAGTACTGGGACACCAACGT CGACGCTGTTCTCAACTGGGCATACTCGAGCGGTGCCAAGGTCTTTGAC TTCGCCCTCTACTACAAGATGGATGAGGCCTTTGACAACAAAAACATTC CAGCGCTCGTCTCTGCCCTTCAGAACGGCCAGACTGTTGTCTCCCGCGA CCCGTTCAAGGCCGTAACCTTTGTAGCAAACCACGACACCGATATAATC TGGAACAAGTACCTTGCTTATGCCTTCATCCTCACCTACGAAGGCCAGC CGTCATATTCTACCGCGACTACGAGGAGTGGCTCAACAAGGACAGGTT GAACAACCTCATATGGATACACGACCACCTCGCAGGGGGAAGCACCGAC ATAGTCTACTACGATAACGATGAACTCATCTTCGTCAGGAACGGCTACG GGGACAAGCCGGGGCTTATAACCTACATCAACCTAGGCTCGAGCAAGGC CGGAAGGTGGGTTTATGTGCCGAAGTTCGCGGGCGCGTGCATCCACGAG TATACTGGTAACCTCGGAGGCTGGGTAGACAAGTACGTCTACTCAAGCG GCTGGGTCTATCTCGAAGCTCCAGCTTACGACCCTGCCAACGGGCAGTA TGGCTACTCCGTGTGGAGCTACTGCGGTGTTGGGTGA |
| 35 | SEQ ID NO: 30 of U.S. Pat. No. 7407677 | MAKYLELEEGGLIMQAFYWDVPMGGIWWDTVAQKIPDWASAGISAIWIP PASKGMGGAYSMGYDPYDFFDLGEYDQKGTVETRFGSKQELVNMINTAH AYGIKVIADIVINHRAGGDLEWNPFVGDYTWTDFSKVVSGKYTANYLDF HPNELHAGDSGTFGGYPDICHDKSWDQYWLWASQESYAAYLRSIGIDAW RFDYVKGYAPWVVKDWLNWWGGWAVGEYWDTNVDAVLNWAYSSGAKVFD FALYYKMDEAFDNKNIPALVSALQNGQTVVSRDPFKAVTFVANHDTDII WNKYLAYAFILTYEGQPVIFYRDYEEWLNKDRLNNLIWIHDHLAGGSTD IVYYDNDELIFVRNGYGDKPGLITYINLGSSKAGRWVYVPKFAGACIHE YTGNLGGWVDKYVYSSGWVYLEAPAYDPANGQYGYSVWSYCGVG |
| 36 | SEQ ID NO: 3 of U.S. Pat. No. 7407677 | ATGGCCAAGTACCTGGAGCTCGAAGAGGGCGGGCTCATAATGCAGGCCT TCTACTGGGACGTCCCCATGGGAGGAATCTGGTGGGACACAGTAGCCCA GAAGATACCCGACTGGGCAAGCGCCGGGATTTCGGCGATATGGATTCCC CCGGCGAGCAAGGGCATGGGCGGCGCCTATTCGATGGGCTACGACCCCT ACGACTTCTTTGACCTCGGTGAGTACGACCAGAAGGGAACGGTAGAGAC GCGCTTTGGCTCCAAGCAGGAGCTCGTGAACATGATAAACACCGCCCAC GCCTACGGCATCAAGGTCATCGCAGACATAGTAATCAACCACCGCGCCG GAGGAGACCTTGAGTGGAACCCCTTCGTCAATGACTACACCTGGACGGA CTTCTCGAAGGTCGCTTCCGGCAAGTACACGGCCAATTACCTCGACTTC CACCCGAACGAGCTCCATGCGGGCGATTCCGGAACATTTGGAGGCTATC CCGACATATGCCACGACAAGAGCTGGGACCAGTACTGGCTCTGGGCCAG |

TABLE 4-continued

DNA coding sequences and protein sequences of non-limiting examples of amylases that can be used in the methods and compositions disclosed herein.

| SEQ ID NO: | Reference from Other Patents | |
|---|---|---|
| | | CCAGGAGAGCTACGCGGCATATCTCAGGAGCATCGGCATCGATGCCTGG<br>CGCTTCGACTACGTCAAGGGCTATGCTCCCTGGGTCGTCAAGGACTGGC<br>TGAACTGGTGGGGAGGCTGGGCGGTTGGAGAGTACTGGGACACCAACGT<br>CGACGCTGTTCTCAACTGGGCATACTCGAGCGGTGCCAAGGTCTTTGAC<br>TTCGCCCTCTACTACAAGATGGATGAGGCCTTTGACAACAAAAACATTC<br>CAGCGCTCGTCTCTGCCCTTCAGAACGGCCAGACTGTTGTCTCCCGCGA<br>CCCGTTCAAGGCCGTAACCTTTGTAGCAAACCACGACACCGATATAATC<br>TGGAACAAGTATCCAGCCTACGCGTTCATCCTCACCTACGAGGGCCAGC<br>CGACAATATTCTACCGCGACTACGAGGAGTGGCTCAACAAGGATAAGCT<br>CAAGAACCTCATCTGGATACATGACAACCTCGCCGGAGGAAGCACTGAC<br>ATCGTTTACTACGACAACGACGAGCTGATATTCGTGAGAAACGGCTACG<br>GAAGCAAGCCGGGACTGATAACATACATCAACCTCGCCTCAAGCGAAGC<br>CGGAAGGTGGGTCTACGTTCCGAAGTTCGCGGGAGCGTGCATCCACGAG<br>TACACCGGCAACCTCGGCGGCTGGGTGGACAAGTGGGTGGACTCAAGCG<br>GGTGGGTGTACCTCGAGGCCCCTGCCCACGACCCGGCCAACGGCTATTA<br>CGGCTACTCCGTCTGGAGCTATTGCGGTGTTGGGTGA |
| 37 | SEQ ID NO: 4<br>of U.S. Pat. No. 7407677 | MAKYLELEEGGLIMQAFYWDVPMGGIWWDTIAQKIPDWASAGISAIWIP<br>PASKGMGGAYSMGYDPYDFFDLGEYDQKGTVETRFGSKQELVNMINTAH<br>AYGIKVIADIVINHRAGGDLEWNPFVNDYTWTDFSKVASGKYTANYLDF<br>HPNELHAGDSGTFGGYPDICHDKSWDQYWLWASQESYAAYLRSIGIDAW<br>RFDYVKGYAPWVVKDWLNWWGGWAVGEYWDTNVDAVLNWAYSSGAKVFD<br>FALYYKMDEAFDNKNIPALVSALQNGQTVVSRDPPFKAVTFVANHDTDII<br>WNKYPAYAFILTYEGQPTIFYRDYEEWLNKDKLKNLIWIHDNLAGGSTD<br>IVYYDNDELIFVRNGYGSKPGLITYINLASSEAGRWYVPKFAGACIHE<br>YTGNLGGWVDKWVDSSGWVYLEAPAHDPANGYYGYSVWSYCGVG |
| 38 | SEQ ID NO: 31<br>of U.S. Pat. No. 7407677 | ATGGCAAAGTACTCCGAGCTGGAAGAGGGCGGCGTTATAATGCAGGCCT<br>TCTACTGGGACGTCCCAGGTGGAGGAATCTGGTGGGACACCATCAGGAG<br>CAGGATACCGGAGTGGTACGAGGCGGGAATATCCGCCATTTGGATTCCC<br>CCGGCGAGCAAGGGCATGGGCGGCGCCTATTCGATGGGCTACGACCCCT<br>ACGACTTCTTTGACCTCGGTGAGTACGACCAGAAGGGAACGGTAGAGAC<br>GCGCTTTGGCTCCAAGCAGGAGCTCGTGAACATGATAAACACGGCCCAT<br>GCCTACGGCATAAAGGTCATAGCGGACATCGTCATAAACCACCGCGCAG<br>GCGGAGACCTCGAGTGGAACCCGTTCGTTGGGGACTACACCTGGACGGA<br>CTTCTCAAAGGTGGCCTCGGGCAAATATACTGCCAACTACCTCGACTTC<br>CACCCGAACGAGCTCCATGCGGGCGATTCCGGAACATTTGGAGGCTATC<br>CCGACATATGCCACGACAAGAGCTGGGACCAGTACTGGCTCTGGGCCAG<br>CCAGGAGAGCTACGCGGCATATCTCAGGAGCATCGGCATCGATGCCTGG<br>CGCTTTGACTACGTGAAGGGCTACGGAGCGTGGGTCGTCAAGGACTGGC<br>TCAACTGGTGGGGCGGCTGGGCCGTTGGCGAGTACTGGGACACCAACGT<br>TGATGCACTCCTCAACTGGGCCTACTCGAGCGGCGCCAAGGTCTTCGAC<br>TTCCCGCTCTACTACAAGATGGACGAGGCCTTCGATAACAACAACATTC<br>CCGCCCTGGTGGACGCCCTCAGATACGGTCAGACAGTGGTCAGCCGCGA<br>CCCGTTCAAGGCTGTGACGTTTGTAGCCAACCACGATACCGATATAATC<br>TGGAACAAGTATCCAGCCTACGCGTTCATCCTCACCTACGAGGGCCAGC<br>CGACAATATTCTACCGCGACTACGAGGAGTGGCTCAACAAGGATAAGCT<br>CAAGAACCTCATCTGGATACATGACAACCTGGCCGGAGGAAGCACGAGC<br>ATAGTTTACTACGACAGCGACGAGATGATCTTCGTGAGGACCGGCTATG<br>GAAGCAAGCCTGGCCTTATAACTTACATCAACCTCGGCTCGAGCAAGGT<br>TGGAAGGTGGGTTTATGTGCCAAGTTCGCGGGCGCGTGCATCCACGAG<br>TATACTGGTAACCTCGGAGGCTGGGTAGACAAGTACGTCTACTCAAGCG<br>GCTGGGTCTATCTCGAAGCTCCAGCTTACGACCCTGCCAACGGGCAGTA<br>TGGCTACTCCGTGTGGAGCTATTGCGGTGTTGGCTGA |
| 39 | SEQ ID NO: 32<br>of U.S. Pat. No. 7407677 | MAKYSELEEGGVIMQAFYWDVPGGGIWWDTIRSRIPEWYEAGISAIWIP<br>PASKGMGGAYSMGYDPYDFFDLGEYDQKGTVETRFGSKQELVNMINTAH<br>AYGIKVIADIVINHRAGGDLEWNPFVGDYTWTDPSKVASGKYTANYLDF<br>HPNELHAGDSGTFGGYPDICHDKSWDQYWLWASQESYAAYLRSIGIDAW<br>RFDYVKGYGAWVVKDWLNWWGGWAVGEYWDTNVDALLNWAYSSGAKVFD<br>FPLYYKMDEAFDNNNIPALVDALRYGQTVVSRDPFKAVTFVANHDTDII<br>WNKYPAYAFILTYEGQPTIFYRDYEEWLNKDKLKNLIWIHDNLAGGSTS<br>IVYYDSDEMIFVRTGYGSKPGLITYINLGSSKVGRWVYVPKFAGACIHE<br>YTGNLGGWVDKVYSSGWVYLEAPAYDPANGQYGYSVWSYCGVG |
| 40 | SEQ ID NO: 33<br>of U.S. Pat. No. 7407677 | ATGGCCAAGTACTCCGAGCTGGAAGAGGGCGGGGTCATAATGCAGGCGT<br>TCTACTGGGACGTGCCTCAGGAGGAATATGGTGGGACACAATACGGCA<br>GAAGATACCGGAGTGGTACGATGCCGGAATCTCCGCAATATGGATTCCT<br>CCCGCGAGCAAGGGTATGAGCGGCGCTATTCGATGGGCTACGACCCCT<br>ACGATTATTTTGACCTCGGTGAGTACTACCAGAAGGGAACGGTGGAAAC<br>GAGGTTCGGCTCAAAGCAGGAGCTCATAAACATGATAAACACGGCCCAT<br>GCCTACGGCATAAAGGTCATAGCGGACATCGTCATAAACCACCGCGCAG<br>GCGGAGACCTCGAGTGGAACCCGTTCGTTGGGGACTACACCTGGACGGA<br>CTTCTCAAAGGTGGCCTCGGGCAAATATACTGCCAACTACCTCGACTTC |

TABLE 4-continued

DNA coding sequences and protein sequences of non-limiting examples of amylases that can be used in the methods and compositions disclosed herein.

| SEQ ID NO: | Reference from Other Patents | |
|---|---|---|
| | | CACCCGAACGAGCTCCATGCGGGCGATTCCGGAACATTTGGAGGCTATC<br>CCGACATATGCCACGACAAGAGCTGGGACCAGTACTGGCTCTGGGCCAG<br>CCAGGAGAGCTACGCGGCATATCTCAGGAGCATCGGCATCGATGCCTGG<br>CGCTTTGACTACGTGAAGGGCTACGAGCGTGGGTCGTCAAGGACTGGC<br>TCAACTGGTGGGGCGGCTGGGCCGTTGGCGAGTACTGGGACACCAACGT<br>TGATGCACTCCTCAACTGGGCCTACTCGAGCGGCGCCAAGGTCTTCGAC<br>TTTCCGCTCTACTACAAGATGGACGCGGCCTTTGACAACAAGAACATTC<br>CCGCACTCGTCGAGGCCCTCAAGAACGGGGGCACAGTCGTCAGCCGCGA<br>CCCGTTTAAGGCCGTAACCTTCGTTGCAAACCACGACACCGATATAATC<br>TGGACCAAGTACCTTGCTTATGCTTTCATCCTCACCTACGAAGGCCAGC<br>CCGTCATATTCTACCGCGACTACGAGGAGTGGCTCAACAAGGACAGGTT<br>GAACAACCTCATATGGATACACGACCACCTCGCAGGTGGAAGCACCGAC<br>ATAGTCTACTACGATAACGATGAACTCATCTTCGTCAGGAACGGCTACG<br>GGGACAAGCCGGGGCTTATAACCTACATCAACCTAGGCTCGAGCAAGGC<br>CGGAAGGTGGGTTTACGTTCCGAAGTTCGCAGGCTCGTGCATACACGAG<br>TACACCGGCAATCTCGGCGGCTGGGTGGACAAGTGGGTGGACTCAAGCG<br>GCTGGGTCTACCTCGAGGCTCCTGCCCACGACCCGGCCAACGGCCAGTA<br>CGGCTACTCCGTCTGGAGCTACTGCGGTGTTGGCTGA |
| 41 | SEQ ID NO: 34<br>of U.S. Pat. No. 7407677 | MAKYSELEEGGVIMQAFYWDVPSGGIWWDTIRQKIPEWYDAGISAIWIP<br>PASKGMSGGYSMGYDPYDYFDLGEYYQKGTVETRFGSKQELINMINTAH<br>AYGIKVIADIVINHRAGGDLEWNPFVGDYTWTDFSKVASGKYTANYLDF<br>HPNELHAGDSGTFGGYPDICHDKSWDQYWLWASQESYAAYLRSIGIDAW<br>RFDYVKGYGAWVVKDWLNWWGGWAVGEYWDTNVDALLNWAYSSGAKVFD<br>FPLYYKMDAAFDNKNIPALVEALKNGGTVVSRDPPFKAVTFVANHDTDII<br>WTKYLAYAFILTYEGQPVIFYRDYEEWLNKDRLNNLIWIHDHLAGGSTD<br>IVYYDNDELIFVRNGYGDKPGLITYINLGSSKAGRWVYVPKFAGSCIHE<br>YTGNLGGWVDKWVDSSGWVYLEAPAHDPANGQYGYSVWSYCGVG |
| 42 | SEQ ID NO: 35<br>of U.S. Pat. No. 7407677 | ATGGCCAAGTACTCCGAGCTGGAAGAGGGCGGCGTTATAATGCAGGCCT<br>TCTACTGGGACGTCCCAGGTGGAGGAATCTGGTGGGACACCATCAGGAG<br>CAAGATACCGGAGTGGTACGAGGCGGGAATATCCGCCATTTGGATTCCC<br>CCGGCGAGCAAGGGCATGGGCGGCGCCTATTCGATGGGCTACGACCCCT<br>ACGACTTCTTTGACCTCGGTGAGTACGACCAGAAGGGAACGGTAGAGAC<br>GCGCTTTGGCTCCAAGCAGGAGCTCGTGAACATGATAAACACCGCCCAC<br>GCCTACGGCATCAAGGTCATCGCAGACATAGTAATCAACCACCGCGCCG<br>GAGGAGACCTTGAGTGGAACCCCTTCGTCAATGACTACACCTGGACGGA<br>CTTCTCGAAGGTCGCTTCCGGCAAGTACACGGCCAACTACCTCGACTTC<br>CACCCCAACGAGGTCAAGTGCTGTGACGAGGGCACATTTGGAGGCTTCC<br>CAGACATAGCCCACGAGAAGAGCTGGGACCAGCACTGGCTCTGGGCGAG<br>CGATGAGAGCTACGCCGCCTACCTAAGGAGCATCGGCGTTGATGCCTGG<br>CGCTTCGACTACGTCAAGGGCTATGCTCCCTGGGTCGTCAAGGACTGGC<br>TGAACTGGTGGGGAGGCTGGGCGGTTGGAGAGTACTGGGACACCAACGT<br>CGACGCTGTTCTCAACTGGGCATACTCGAGCGGTGCCAAGGTCTTTGAC<br>TTCGCCCTCTACTACAAGATGGACGCGGCCTTTGACAACAAGAACATTC<br>CCGCACTCGTCGAGGCCCTCAAGAACGGGGGCACAGTCGTCAGCCGCGA<br>CCCGTTTAAGGCCGTAACCTTCGTTGCAAACCACGACACCGATATAATC<br>TGGAACAAGTATCCAGCCTACGCGTTCATCCTCACCTACGAGGGCCAGC<br>CGACAATATTCTACCGCGACTACGAGGAGTGGCTCAACAAGGATAAGCT<br>CAAGAACCTCATCTGGATACATGACAACGTCGCCGGAGGAAGCACCGAC<br>ATAGTCTACTACGATAACGATGAACTCATCTTCGTCAGGAACGGCTACG<br>GGGACAAGCCGGGGCTTATAACCTACATCAACCTAGGCTCGAGCAAGGC<br>CGGAAGGTGGGTTTACGTTCCGAAGTTCGCAGGCTCGTGCATACACGAG<br>TACACCGGCAATCTCGGCGGCTGGGTGGACAAGTGGGTGGACTCAAGCG<br>GCTGGGTCTACCTCGAGGCTCCTGCCCACGACCCGGCCAACGGCCAGTA<br>CGGCTACTCCGTCTGGAGCTACTGCGGTGTTGGGTGA |
| 43 | SEQ ID NO: 36<br>of U.S. Pat. No. 7407677 | MAKYSELEEGGVIMQAFYWDVPGGGIWWDTIRSKIPEWYEAGISAIWIP<br>PASKGMGGAYSMGYDPYDFFDLGEYDQKGTVETRFGSKQELVNMINTAH<br>AYGIKVIADIVINHRAGGDLEWNPFVNDYTWTDFSKVASGKYTANYLDF<br>HPNEVKCCDEGTFGGFPDIAHEKSWDQHWLWASDESYAAYLRSIGVDAW<br>RFDYVKGYAPWVVKDWLNWWGGWAVGEYWDTNVDAVLNWAYSSGAKVFD<br>FALYYKMDAAFDNKNIPALVEALKNGGTVVSRDPPFKAVTFVANHDTDII<br>WNKYPAYAFILTYEGQPTIFYRDYEEWLNKDKLKNLIWIHDNVAGGSTD<br>IVYYDNDELIFVRNGYGDKPGLITYINLGSSKAGRWVYVPKFAGSCIHE<br>YTGNLGGWVDKWVDSSGWVYLEAPAHDPANGQYGYSVWSYCGVG |
| 44 | SEQ ID NO: 37<br>of U.S. Pat. No. 7407677 | ATGGCCAAGTACCTGGAGCTCGAAGAGGGCGGGGTCATAATGCAGGCGT<br>TCTACTGGGACGTGCCCTTCAGGAGGAATATGGTGGGACACAATACGGA<br>GAAGATACCGGAGTGGTACGATGCCGGAATCTCCGCAATATGGATTCCC<br>CCGGCGAGCAAGGGCATGGGCGGCGCCTATTCGATGGGCTACGACCCCT<br>ACGACTTCTTTGACCTCGGTGAGTACGACCAGAAGGGAACGGTAGAGAC<br>GCGCTTTGGCTCCAAGCAGGAGCTCGTGAACATGATAAACACCGCCCAC<br>GCCTATGGCATGAAGGTAATAGCCGATATAGTCATCAACCACCGCGCCG |

TABLE 4-continued

DNA coding sequences and protein sequences of non-limiting examples of amylases that can be used in the methods and compositions disclosed herein.

| SEQ ID NO: | Reference from Other Patents | |
|---|---|---|
| | | GCGGTGACCTGGAGTGGAACCCCTTCGTGAACGACTATACCTGGACCGA CTTCTCAAAGGTCGCGTCGGGTAAATACACGGCCAACTACCTCGACTTC CACCCGAACGAGCTCCATGCGGGCGATTCCGGAACATTTGGAGGCTATC CCGACATATGCCACGACAAGAGCTGGGACCAGTACTGGCTCTGGGCCAG CCAGGAGAGCTACGCGGCATATCTCAGGAGCATCGGCATCGATGCCTGG CGCTTTGACTACGTGAAGGGCTACGGAGCGCGGGTCGTCAAGGACTGGC TCAACTGGTGGGGCGGCTGGGCCGTTGGCGAGTACTGGGACACCAACGT TGATGCACTCCTCAACTGGGCCTACTCGAGCGGCGCCAAGGTCTTCGAC TTCCCGCTCTACTACAAGATGGATGAGGCCTTTGACAACAAAAACATTC CAGCGCTCGTCTCTGCCCTTCAGAACGGCCAGACTGTTGTCTCCCGCGA CCCGTTCAAGGCCGTAACCTTTGTAGCAAACCACGACACCGATATAATC TGGAACAAGTATCCAGCCTACGCGTTCATCCTCACCTACGAGGGCCAGC CGACAATATTCTATCGCGACTACGAGGAGTGGCTCAACAAGGATAAGCT CAAGAACCTCATCTGGATACATGACAACCTCGCCGGAGGAAGCACTGAC ATCGTTTACTACGACAACGACGAGCTGATATTCGTGAGAAACGGCTACG GAAGCAAGCCGGGACTGATAACATACATCAACCTCGCCTCAAGCAAAGC CGGAAGGTGGGTTTACGTTCCGAAGTTCGCAGGCTCGTGCATACACGAG TACACCGGCAATCTCGGCGGCTGGGTGGACAAGTGGGTGGACTCAAGCG GCTGGGTCTACCTCGAGGCTCCTGCCCACGACCCGGCCAACGGCCAGTA CGGCTACTCCGTCTGGAGCTACTGCGGGGTGGGGTGA |
| 45 | SEQ ID NO: 38 of U.S. Pat. No. 7407677 | MAKYLELEEGGVIMQAFYWDVPSGGIWWDTIRQKIPEWYDAGISAIWIP PASKGMGGAYSMGYDPYDFFDLGEYDQKGTVETRFGSKQELVNMINTAH AYGMKVIADIVINHRAGGDLEWNPFVNDYTWTDFSKVASGKYTANYLDF HPNELHAGDSGTFGGYPDICHDKSWDQYWLWASQESYAAYLRSIGIDAW RFDYVKGYGARVVKDWLNWWGGWAVGEYWDTNVDALLNWAYSSGAKVFD FPLYYKMDEAFDNKNIPALVSALQNGQTVVSRDPFKAVTFVANHDTDII WNKYPAYAFILTYEGQPTIFYRDYEEWLNKDKLKNLIWIHDNLAGGSTD IVYYDNDELIFVRNGYGSKPGLITYINLASSKAGRWVYVPKFAGSCIHE YTGNLGGWVDKWVDSSGWVYLEAPAHDPANGQYGYSVWSYCGVG |
| 46 | SEQ ID NO: 39 of U.S. Pat. No. 7407677 | ATGGCCAAGTACCTGGAGCTCGAAGAGGGCGGGGTCATAATGCAGGCGT TCTACTGGGACGTGCCTTCAGGAGGAATATGGTGGGACACAATACGGCA GAAGATACCGGAGTGGTACGATGCCGGAATCTCCGCAATATGGATTCCT CCCGCGAGCAGGGGTATGAGCGGCGGCTATTCGATGGGCTACGACCCCT ACGATTATTTTGACCTCGGTGAGTACTACCAGAAGGGAACGGTGGAAAC GAGGTTCGGCTCAAAGCAGGAGCTCATAAACATGATAAACACCGCCCAC GCCTATGGCATGAAGGTAATAGCCGATATAGTCATCAACCACCGCGCCG GCGGTGACCTGGAGTGGAACCCCTTCGTGAACGACTATACCTGGACCGA CTTCTCAAAGGTCGCGTCGGGTAAATACACGGCCAACTACCTCGACTTC CACCCGAACGAGCTCCATGCGGGCGATTCCGGAACATTTGGAGGCTATC CCGACATATGCCACGACAAGAGCTGGGACCAGTACTGGCTCTGGGCCAG CCAGGAGAGCTACGCGGCATATCTCAGGAGCATCGGTATCGATGCCTGG CGCTTTGACTACGTGAAGGGCTACGGAGCGCGTGGGTCGTCAAGGACTGGC TCAACTGGTGGGGCGGCTGGGCCGTTGGCGAGTACTGGGACCCCAACGT TGATGCCCTCCTCCCCTGGGCCTACTCGAGCGGCGCCAAGGTCTTCGAC TTCCCGCTCTACTACAAGATGGATGAGGCCTTTGACAACAAAAACATTC CAGCGCTCGTCTCTGCCCTTCAGAACGGCCAGACTGTTGTCTCCCGCGA CCCGTTCAAGGCCGTAACCTTTGTAGCAACCACGATACCGATATAATC TGGAACAAGTATCCAGCCTACGCGTTCATCCTCACCTACGAGGGCCAGC CGACAATATTCTACCGCGACTACGAGGAGTGGCTCAACAAGGATAAGCT CAAGAACCTCATCTGGATACATGACAACCTCGCCGGAGGAAGCACCGAC ATAGTCTACTACGATAACGATGAACTCATCTTCGTCAGGAACGGCTACG GGGACAAGCCGGGCTTATAACCTACATCAACCTAGGCTCGAGCAAGGC CGGAAGGTGGGTCTACGTTCCGAAGTTCGCGGGAGCGTGCATCCACGAG TACACCGGCAACCTCGGCGGCTGGGTGGACAAGTGGGTGGACTCAAGCG GGTGGGTGTACCTCGAGGCCCTGCCCACGACCCGGCCAACGGCTATTA CGGCTACTCCGTCTGGAGCTACTGCGGGGTGGGCTGA |
| 47 | SEQ ID NO: 40 of U.S. Pat. No. 7407677 | MAKYLELEEGGVIMQAFYWDVPSGGIWWDTIRQKIPEWYDAGISAIWIP PASRGMSGGYSMGYDPYDYFDLGEYYQKGTVETRFGSKQELINMINTAH AYGMKVIADIVINHRAGGDLEWNPFVNDYTWTDFSKVASGKYTANYLDF HPNELHAGDSGTFGGYPDICHDKSWDQYWLWASQESYAAYLRSIGIDAW RFDYVKGYGAWVVKDWLNWWGGWAVGEYWDPNVDALLPWAYSSGAKVFD FPLYYKMDEAFDNKNIPALVSALQNGQTVVSRDPFKAVTFVANHDTDII WNKYPAYAFILTYEGQPTIFYRDYEEWLNKDKLKNLIWIHDNLAGGSTD IVYYDNDELIFVRNGYGDKPGLITYINLGSSKAGRWVYVPKFAGACIHE YTGNLGGWVDKWVDSSGWVYLEAPAHDPANGYYGYSVWSYCGVG |
| 48 | SEQ ID NO: 43 of U.S. Pat. No. 7407677 | ATGGCCAAGTACTCCGAGCTGGAAGAGGGCGGCGTTATAATGCAGGCCT TCTACTGGGACGTCCCAGGTGGAGGAATCTGGTGGGACACCATCAGGAG CAAGATACCGGAGTGGTACGAGGCGGGAATATCCGCCATTTGGATTCCC CCGGCGAGCAAGGGCATGGGCGGCGCCTATTCGATGGGCTACGACCCCT ACGACTTCTTTGACCTCGGTGAGTACGACCAGAAGGGAACGGTAGAGAC |

TABLE 4-continued

DNA coding sequences and protein sequences of non-limiting examples of amylases that can be used in the methods and compositions disclosed herein.

| SEQ ID NO: | Reference from Other Patents | |
|---|---|---|
| | | GCGCTTTGGCTCCAAGCAGGAGCTCGTGAACATGATAAACACGGCCCAT
GCCTACGGCATAAAGGTCATAGCGGACATCGTCATAAACCACCGCGCAG
GCGGAGACCTCGAGTGGAACCCGTTCGTTGGGGACTACACCTGGACGGA
CTTCTCAAAGGTGGCCTCGGGCAAATATACTGCCAACTACCTCGACTTC
CACCCCAACGAGGTCAAGTGCTGTGACGAGGGCACATTTGGAGGCTTCC
CAGACATAGCCCACGAGAAGAGCTGGGACCAGCACTGGCTCTGGGCGAG
CGATGAGAGCTACGCCGCCTACCTAAGGAGCATCGGCGTTGATGCCTGG
CGCTTCGACTACGTCAAGGGCTACGGAGCGTGGGTCGTCAAGGACTGGC
TGGACTGGTGGGGAGGCTGGGCCGTCGGGGAGTACTGGGACACAAACGT
TGATGCACTGCTCAACTGGGCCTACTCGAGCGATGCAAAAGTCTTCGAC
TTCCCGCTCTACTACAAGATGGATGAGGCCTTTGACAACAAAAACATTC
CAGCGCTCGTCTCTGCCCTTCAGAACGGCCAGACTGTTGTCTCCCGCGA
CCCCGTTCAAGGCCGTAACCTTTGTAGCAAACCACGACACCGATATAATC
TGGAACAAGTATCCAGCCTACGCGTTCATCCTCACCTACGAGGGCCAGC
CGACAATATTCTACCGCGACTACGAGGAGTGGCTCAACAAGGATAAGCT
CAAGAACCTCATCTGGATACATGACAACCTCGTCGGAGGAAGCACGAGC
ATAGTTTACTACGACAGCGACGAGATGATCTTCGTGAGGAACGGCTATG
GAAGCAAGCCTGGCCTTATAACTTACATCAACCTCGGCTCGAGCAAGGT
TGGAAGGTGGGTTTACGTTCCGAAGTTCGCAGGCTCGTGCATACACGAG
TACACCGGCAATCTCGGCGGCTGGGTGGACAAGTGGGTGGACTCAAGCG
GCTGGGTCTACCTCGAGGCTCCTGCCCACGACCCGGCCAACGGCCAGTA
CGGCTACTCCGTCTGGAGCTACTGCGGTGTTGGCTGA |
| 49 | SEQ ID NO: 44 of U.S. Pat. No. 7407677 | MAKYSELEEGGVIMQAFYWDVPGGGIWWDTIRSKIPEWYEAGISAIWIP
PASKGMGGAYSMGYDPYDFFDLGEYDQKGTVETRFGSKQELVNMINTAH
AYGIKVIADIVINHRAGGDLEWNPFVGDYTWTDFSKVASGKYTANYLDF
HPNEVKCCDEGTFGGFPDIAHEKSWDQHWLWASDESYAAYLRSIGVDAW
RFDYVKGYGAWVVKDWLDWWGGWAVGEYWDTNVDALLNWAYSSDAKVFD
FPLYYKMDEAFDNKNIPALVSALQNGQTVVSRDPFKAVTFVANHDTDII
WNKYPAYAFILTYEGQPTIFYRDYEEWLNKDKLKNLIWIHDNLVGGSTS
IVYYDSDEMIFVRNGYGSKPGLITYINLGSSKVGRWVYVPKFAGSCIHE
YTGNLGGWVDKWVDSSGWVYLEAPAHDPANGQYGYSVWSYCGVG |
| 50 | SEQ ID NO: 45 of U.S. Pat. No. 7407677 | ATGGCCAAGTACTCCGACCTGGAAGAGGGCGGCGTTATAATGCAGGCCT
TCTACTGGGACGTCCCAGGTGGAGGAATCTGGTGGGACACCATCAGGAG
CAAGATACCGGAGTGGTACGAGGCGGGAATATCCGCCATTTGGATTCCC
CCGGCGAGCAAGGGCATGGGCGGCGCCTATTCGATGGGCTACGACCCCT
ACGACTTCTTTGACCTCGGTGAGTACGACCAGAAGGGAACGGTAGAGAC
GCGCTTTGGCTCCAAGCAGGAGCTCGTGAACATGATAAACACGGCCCAT
GCCTACGGCATAAAGGTCATAGCGGACATCGTCATAAACCACCGCGCAG
GCGGAGACCTCGAGTGGAACCCGTTCGTTGGGGACTACACCTGGACGGA
CTTCTCAAAGGTGGCCTCGGGCAAATATACTGCCAACTACCTCGACTTC
CACCCCAACGAGGTCAAGTGCTGTGACGAGGGCACATTTGGAGGCTTCC
CAGACATAGCCCACGAGAAGAGCTGGGACCAGCACTGGCTCTGGGCGAG
CGATGAGAGCTACGCCGCCTACCTAAGGAGCATCGGCGTTGATGCCTGG
CGCTTTGACTACGTGAAGGGCTACGAGCGTGGGTCGTCAAGGACTGGC
TCAACTGGTGGGGCGGCTGGGCCGTTGGCGAGTACTGGGACACCAACGT
TGATGCACTCCTCAACTGGGCCTACTCGAGCGGCGCCAAGGTCTTCGAC
TTCCCGCTCTACTACAAGATGGATGAGGCCTTTGACAACAAAAACATTC
CAGCGCTCGTCTCTGCCCTTCAGAACGGCCAGACTGTTGTCTCCCGCGA
CCCCGTTCAAGGCCGTAACCTTTGTAGCAAACCACGACACCGATATAATC
TGGAACAAGTATCCAGCCTACGCGTTCATCCTCACCTACGAGGGCCAGC
CGACAATATTCTACCGCGACTACGAGGAGTGGCTCAACAAGGATAAGCT
CAAGAACCTCATCTGGATACATGACAACCTCGCCGGAGGAAGCACGGAC
ATAGTCTACTACGATAACGATGAACTCATCTTCGTCAGGAACGGCTACG
GGGACAAGCCGGGGCTTATAACCTACATCAACCTAGGCTCGAGCAAGGC
CGGAAGGTGGGTTTATGTGCCGAAGTTCGCGGGCGCGTGCATCCACGAG
TATACTGGTAACCTCGGAGGCTGGGTAGACAAGTACGTCTACTCAAGCG
GCTGGGTCTATCTCGAAGCTCCAGCTTACGACCCTGCCAACGGGCAGTA
TGGCTACTCCGTGTGGAGCTATTGCGGTGTTGGGTGA |
| 51 | SEQ ID NO: 46 of U.S. Pat. No. 7407677 | MAKYSDLEEGGVIMQAFYWDVPGGGIWWDTIRSKIPEWYEAGISAIWIP
PASKGMGGAYSMGYDPYDFFDLGEYDQKGTVETRFGSKQELVNMINTAH
AYGIKVIADIVINHRAGGDLEWNPFVGDYTWTDFSKVASGKYTANYLDF
HPNEVKCCDEGTFGGFPDIAHEKSWDQHWLWASDESYAAYLRSIGVDAW
RFDYVKGYGAWVVKDWLNWWGGWAVGEYWDTNVDALLNWAYSSGAKVFD
FPLYYKMDEAFDNKNIPALVSALQNGQTVVSRDPFKAVTFVANHDTDII
WNKYPAYAFILTYEGQPTIFYRDYEEWLNKDKLKNLIWIHDNLAGGSTD
IVYYDNDELIFVRNGYGDKPGLITYINLGSSKAGRWVYVPKFAGACIHE
YTGNLGGWVDKYVYSSGWVYLEAPAYDPANGQYGYSVWSYCGVG |
| 52 | SEQ ID NO: 47 of U.S. Pat. No. 7407677 | ATGGCCAAGTACACCGAGCTGGAAGAGGGCGGCGTTATAATGCAGGCCT
TCTACTGGGACGTCCCAGGTGGAGGAATCTGGTGGGACACCATCAGGAG
CAAGATACCGGAGTGGTACGAGGCGGGAATATCCGCCATTTGGATTCCC |

TABLE 4-continued

DNA coding sequences and protein sequences of non-limiting examples of amylases that can be used in the methods and compositions disclosed herein.

| SEQ ID NO: | Reference from Other Patents | |
|---|---|---|
| | | CCGGCGAGCAAGGGCATGGGCGGCGCCTATTCGATGGGCTACGACCCCT<br>ACGACTTCTTTGACCTCGGTGAGTACGACCAGAAGGGAACGGTAGAGAC<br>GCGCTTTGGCTCCAAGCAGGAGCTCGTGAACATGATAAACACCGCCCAC<br>GCCTATGGCATGAAGGTAATAGCCGATATAGTCATCAACCACCGCGCCG<br>GCGGTGACCTGGAGTGGAACCCCTTCGTGAACGACTATACCTGGACCGA<br>CTTCTCAAAGGTCGCGTCGGGTAAATACACGGCCAACTACCTCGACTTC<br>CACCCCAACGAGGTCAAGTGCTGTGACGAGGGCACATTTGGAGGCTTCC<br>CAGACATAGCCCACGAGAAGAGCTGGGACCAGCACTGGCTCTGGGCGAG<br>CGATGAGAGCTACGCCGCCTACCTAAGGAGCATCGGCGTTGATGCCTGG<br>CGCTTTGACTACGTGAAGGGCTACGGAGCGTGGGTCGTCAAGGACTGGC<br>TCAACTGGTGGGGCGGTTGGGCCGTTGGCGAGTACTGGGACACCAACGT<br>TGATGCACTCCTCAACTGGGCCTACTCGAGCGGCGCCAAGGTCTTCGAC<br>TTCCCGCTCTACTACAAGATGGATGAGGCCTTTGACAACAAAAACATTC<br>CAGCGCTCGTCTCTGCCCTTCAGAACGGCCAGACTGTTGTCTCCCGCGA<br>CCCGTTCAAGGCCGTAACCTTTGTAGCAAACCACGACACCGATATAATC<br>TGGAACAAGTACCTTGCTTATGCTTTCATCCTCACCTACGAAGGCCAGC<br>CCGTCATATTCTACCGCGACTACGAGGAGTGGCTCAACAAGGACAGGTT<br>GAACAACCTCATATGGATACACGACCACCTCGCAGGTGGAAGCACGAGC<br>ATAGTTTACTACGACAGCGACGAGATGATCTTCGTGAGGAACGGCTATG<br>GAAGCAAGCCTGGCCTTATAACTTACATCAACCTCGGCTCGAGCAAGGT<br>TGGAAGGTGGGTTTACGTTCCGAAGTTCGCAGGCCCGTGCATACACGAG<br>TACACCGGCAATCTCGGCGGCTGGGTGGACAAGTGGGTGGACTCAAGCG<br>GCTGGGTCTACCTCGAGGCTCCTGCCCACGACCCGGCCAACGGCCAGTA<br>CGGCTACTCCGTCTGGAGCTACTGCGGTGTTGGGTAG |
| 53 | SEQ ID NO: 48<br>of U.S. Pat. No. 7407677 | MAKYTELEEGGVIMQAFYWDVPGGGIWWDTIRSKIPEWYEAGISAIWIP<br>PASKGMGGAYSMGYDPYDFFDLGEYDQKGTVETRFGSKQELVNMINTAH<br>AYGMKVIADIVINHRAGGDLEWNPFVNDYTWTDFSKVASGKYTANYLDF<br>HPNEVKCCDEGTFGGFPDIAHEKSWDQHWLWASDESYAAYLRSIGVDAW<br>RFDYVKGYGAWVVKDWLNWWGGWAVGEYWDTNVDALLNWAYSSGAKVFD<br>FPLYYKMDEAFDNKNIPALVSALQNGQTVVSRDPPFKAVTFVANHDTDII<br>WNKYLAYAFILTYEGQPVIFYRDYEEWLNKDRLNNLIWIHDHLAGGSTS<br>IVYYDSDEMIFVRNGYGSKPGLITYINLGSSKVGRWVYVPKFAGPCIHE<br>YTGNLGGWVDKWVDSSGWVYLEAPAHDPANGQYGYSVWSYCGVG |
| 54 | SEQ ID NO: 5<br>of U.S. Pat. No. 7407677 | ATGGCCAAGTACTCCGAGCTGGAAGAGGGCGGCGTTATAATGCAGGCCT<br>TCTACTGGGACGTCCCAGGTGGAGGAATCTGGTGGGACACCATCAGGAG<br>CAAGATACCGGAGTGGTACGAGGCGGGAATATCCGCCATTTGGATTCCC<br>CCGGCAAGCAAGGGCATGGGCGGCGCCTATTCGATGGGCTACGACCCCT<br>ACGACTTCTTTGACCTCGGTGAGTACGACCAGAAGGGAACGGTAGAGAC<br>GCGCTTTGGCTCCAAGCAGGAGCTCGTGAACATGATAAACACCGCCCAC<br>GCCTATGGCATGAAGGTAATAGCCGATATAGTCATCAACCACCGCGCCG<br>GCGGTGACCTGGAGTGGAACCCCTTCGTGAACGACTATACCTGGACCGA<br>CTTCTCAAAGGTCGCGTCGGGTAAATACACGGCCAACTACCTCGACTTC<br>CACCCGAACGAGCTCCATGCGGGCGATTCCGGAACATTTGGAGGCTATC<br>CCGACATATGCCACGACAAGAGCTGGGACCAGTACTGGCTCTGGGCCAG<br>CCAGGAGAGCTACGCGGCATATCTCAGGAGCATCGGCATCGATGCCTGG<br>CGCTTCGACTACGTCAAGGGCTATGCTCCCTGGGTCGTCAAGGACTGGC<br>TGAACTGGTGGGGAGGCTGGGCGGTTGGAGAGTACTGGGACACCAACGT<br>CGACGCTGTTCTCAACTGGGCATACTCGAGCGGTGCCAAGGTCTTTGAC<br>TTCCCCCTCTACTACAAGATGGATGAGGCCTTTGACAACAAAAACATTC<br>CAGCGCTCGTCTCTGCCCTTCAGAACGGCCAGACTGTTGTCTCCCGCGA<br>CCCGTTCAAGGCCGTAACCTTTGTAGCAAACCACGACACCGATATAATC<br>TGGAACAAGTACCTTGCTTATGCTTTCATCCTCACCTACGAAGGCCAGC<br>CCGTCATATTCTACCGCGACCACGAGGAGTGGCTCAACAAGGACAGGTT<br>GAACAACCTCATATGGATACACGACCACCTCGCAGGTGGAAGCACCGAC<br>ATAGTCTACTACGATAACGATGAACTCATCTTCGTCAGGAACGGCTACG<br>GGGACAAGCCGGGCTTATAACCTACATCAACCTAGGCTCGAGCAAGGC<br>CGGAAGGTGGGTTTATGTGCCGAAGTTCGCGGGCGCGTGCATCCACGAG<br>TATACTGGTAACCTCGGAGGCTGGGTAGACAAGTACGTCTACTCAAGCG<br>GCTGGGTCTATCTCGAAGCTCCAGCTTACGACCCTGCCAACGGGCAGTA<br>TGGCTACTCCGTGTGGAGCTACTGCGGGGTGGGCTGA |
| 55 | SEQ ID NO: 6<br>of U.S. Pat. No. 7407677 | MAKYSELEEGGVIMQAFYWDVPGGGIWWDTIRSKIPEWYEAGISAIWIP<br>PASKGMGGAYSMGYDPYDFFDLGEYDQKGTVETRFGSKQELVNMINTAH<br>AYGMKVIADIVINHRAGGDLEWNPFVNDYTWTDFSKVASGKYTANYLDF<br>HPNELHAGDSGTFGGYPDICHDKSWDQYWLWASQESYAAYLRSIGIDAW<br>RFDYVKGYAPWVVKDWLNWWGGWAVGEYWDTNVDAVLNWAYSSGAKVFD<br>FALYYKMDEAFDNKNIPALVSALQNGQTVVSRDPPFKAVTFVANHDTDII<br>WNKYLAYAFILTYEGQPVIFYRDHEEWLNKDRLNNLIWIHDHLAGGSTD<br>IVYYDNDELIFVRNGYGDKPGLITYINLGSSKAGRWVYVPKFAGACIHE<br>YTGNLGGWVDKYVYSSGWVYLEAPAYDPANGQYGYSVWSYCGVG |

TABLE 4-continued

DNA coding sequences and protein sequences of non-limiting examples of amylases that can be used in the methods and compositions disclosed herein.

| SEQ ID NO: | Reference from Other Patents | |
|---|---|---|
| 56 | SEQ ID NO: 51 of U.S. Pat. No. 7407677 | ATGGCCAAGTACCTGGAGCTCGAAGAGGGCGGGGTCATAATGCAGGCGT<br>TCTACTGGGACGTGCCTTCAGGAGGAATATGGTGGGACACAATACGGCA<br>GAAGATACCGGAGTGGTACGATGCCGGAATCTCCGCAATATGGATTCCC<br>CCGGCGAGCAAGGGCATGGGCGGCGCCTATTCGATGGGCTACGACCCCT<br>ACGACTTCTTTGACCTCGGTGAGTACGACCAGAAGGGAACGGTAGAGAC<br>GCGCTTTGGCTCCAAGCAGGAGCTCGTGAACATGATAAACACCGCCCAC<br>GCCTATGGCATGAAGGTAATAGCCGATATAGTCATCAACCACCGCGCCG<br>GCGGTGACCTGGAGTGGAACCCCTTCGTGAACGACTATACCTGGACCGA<br>CTTCTCAAAGGTCGCGTCGGGTAAATACACGGCCAACTACCTCGACTTC<br>CACCCCAACGAGGTCAAGTGCTGTGACGAGGGCACATTTGGAGGCTTCC<br>CAGACATAGCCCACGAGAAGAGCTGGGACCAGCACTGGCTCTGGGCGAG<br>CGATGAGAGCTACGCCGCCTACCTAAGGAGCATCGGCGTTGATGCCTGG<br>CGCTTTGACTACGTGAAGGGCTACGGAGCGTGGGTCGTCAAGGACTGGC<br>TCAACTGGTGGGGCGGCTGGGCCGTTGGCGAGTACTGGGACACCAACGT<br>TGATGCACTCCTCAACTGGGCCTACTCGAGCGGCGCCAAGGTCTTCGAC<br>TTCCCGCTCTACTACAAGATGGATGAGGCCTTTGACAACAAAAACATTC<br>CAGCGCTCGTCTCTGCCCTTCAGAACGGCCAGACTGTTGTCTCCCGCGA<br>CCCGTTCAAGGCCGTAACCTTTGTAGCAAACCACGACACCGATATAATC<br>TGGAACAAGTATCCAGCCTACGCGTTCATCCTCACCTACGAGGGCCAGC<br>CGACAATATTCTACCGCGACTACGAGGAGTGGCTCAACAAGGATAAGCT<br>CAAGAACCTCATCTGGATACATGACAACCTCGCCGGAGGAAGCACTGAC<br>ATCGTTTACTACGACAACGACGAGCTGATATTCGTGAGAAACGGCTACG<br>GAAGCAAGCCGGGACTGATAACATACATCAACCTCGCCTCAAGCAAAGC<br>CGGAAGGTGGGTTTACGTTCCGAAGTTCGCAGGCTCGTGCATACACGAG<br>TACACCGGCAATCTCGGCGGCTGGGTGGACAAGTGGGTGGACTCAAGCG<br>GCTGGGTCTACCTCGAGGCTCCTGCCCACGACCCGGCCAACGGCCAGTA<br>CGGCTACTCCGTCTGGAGCTATTGCGGTGTTGGCTGA |
| 57 | SEQ ID NO: 52 of U.S. Pat. No. 7407677 | MAKYLELEEGGVIMQAFYWDVPSGGIWWDTIRQKIPEWYDAGISAIWIP<br>PASKGMGGAYSMGYDPYDFFDLGEYDQKGTVETRFGSKQELVNMINTAH<br>AYGMKVIADIVINHRAGGDLEWNPFVNDYTWTDFSKVASGKYTANYLDF<br>HPNEVKCCDEGTFGGFPDIAHEKSWDQHWLWASDESYAAYLRSIGVDAW<br>RFDYVKGYGAWVVKDWLNWWGGWAVGEYWDTNVDALLNWAYSSGAKVFD<br>FPLYYKMDEAFDNKNIPALVSALQNGQTVVSRDPFKAVTFVANHDTDII<br>WNKYPAYAFILTYEGQPTIFYRDYEEWLNKDKLKNLIWIHDNLAGGSTD<br>IVYYDNDELIFVRNGYGSKPGLITYINLASSKAGRWVYVPKFAGSCIHE<br>YTGNLGGWVDKWVDSSGWVYLEAPAHDPANGQYGYSVWSYCGVG |
| 58 | SEQ ID NO: 53 of U.S. Pat. No. 7407677 | ATGGCCAAGTACTCCGAGCTGGAAGAGGGCGGCGTTATAATGCAGGCCT<br>TCTACTGGGACGTCCCAGGTGGAGGAATCTGGTGGGACACCATCAGGAG<br>CAAGATACCGGAGTGGTACGAGGCGGGAATATCCGCCATTTGGATTCCC<br>CCGGCGAGCAAGGGCATGGGCGGCGCCTATTCGATGGGCTACGACCCCT<br>ACGACTTCTTTGACCTCGGTGAGTACGACCAGAAGGGAACGGTAGAGAC<br>GCGCTTTGGCTCCAAGCAGGAGCTCGTGAACATGATAAACACGGCCCAT<br>GCCTACGGCATAAAGGTCATAGCGGACATCGTCATAAACCACCGCACAG<br>GCGGAGACCTCGAGTGGAACCCGTTCGTTGGGGACTACACCTGGACGGA<br>CTTCTCAAAGGTGGCCTCGGGCAAATATACTGCCAACTACCTCGACTTC<br>CACCCCAACGAGGTCAAGTGCTGTGACGAGGGCACATTTGGAGGCTTCC<br>CAGACATAGCCCACGAGAAGAGCTGGGACCAGCACTGGCTCTGGGCGAG<br>CGATGAGAGCTACGCCGCCTACCTAAGGAGCATCGGCGTTGATGCCTGG<br>CGCTTCGACTACGTCAAGGGCTACGGAGCGTGGGTCGTCAAGGACTGGC<br>TGGACTGGTGGGGAGGCTGGGCCGTCGGGGAGTACTGGGACACAAACGT<br>TGATGCACTGCTCAACTGGGCCTACTCGAGCGATGCAAAAGTCTTCGAC<br>TTCCCGCTCTACTACAAGATGGATGAGGCCTTTGACAACAAAAACATTC<br>CAGCGCTCGTCTCTGCCCTTCAGAACGGCCAGACTGTTGTCTCCCGCGA<br>CCCGTTCAAGGCCGTAACCTTTGTAGCAAACCACGACACCGATATAATC<br>TGGAACAAGTATCCAGCCTACGCGTTCATCCTCACCTACGAGGGCCAGC<br>CGACAATATTCTACCGCGACTACGAGGAGTGGCTCAACAAGGATAAGCT<br>CAAGAACCTCATCTGGATACATGACAACCTCGCCGGAGGAAGCACTGAC<br>ATCGTTTACTACGACAACGACGAGCTGATATTCGTGAGAAACGGCTACG<br>GAAGCAAGCCGGGACTGATAACATACATCAACCTCGCCTCAAGCAAAGC<br>CGGAAGGTGGGTCTACGTTCCGAAGTTCGCGGGAGCGTGCATCCACGAG<br>TACACCGGCAACCTCGGCGGCTGGGTGGACAAGTGGGTGGACTCAAGCG<br>GGTGGGTGTACCTCGAGGCCCCTGCCCACGACCCGGCCAACGGCTATTA<br>CGGCTACTCCGTCTGGAGCTACTGCGGTGTTGGCTGA |
| 59 | SEQ ID NO: 54 of U.S. Pat. No. 7407677 | MAKYSELEEGGVIMQAFYWDVPGGGIWWDTIRSKIPEWYEAGISAIWIP<br>PASKGMGGAYSMGYDPYDFFDLGEYDQKGTVETRFGSKQELVNMINTAH<br>AYGIKVIADIVINHRTGGDLEWNPFVGDYTWTDFSKVASGKYTANYLDF<br>HPNEVKCCDEGTFGGFPDIAHEKSWDQHWLWASDESYAAYLRSIGVDAW<br>RFDYVKGYGAWVVKDWLDWWGGWAVGEYWDTNVDALLNWAYSSDAKVFD<br>FPLYYKMDEAFDNKNIPALVSALQNGQTVVSRDPFKAVTFVANHDTDII<br>WNKYPAYAFILTYEGQPTIFYRDYEEWLNKDKLKNLIWIHDNLAGGSTD |

TABLE 4-continued

DNA coding sequences and protein sequences of non-limiting examples of amylases that can be used in the methods and compositions disclosed herein.

| SEQ ID NO: | Reference from Other Patents | |
|---|---|---|
| | | IVYYDNDELIFVRNGYGSKPGLITYINLASSKAGRWVYVPKFAGACIHE YTGNLGGWVDKWVDSSGWVYLEAPAHDPANGYYGYSVWSYCGVG |
| 60 | SEQ ID NO: 55 of U.S. Pat. No. 7407677 | ATGGCCAAGTACCTGGAGCTCGAGGAGGGCGGGGTCATAATGCAGGCGT TCTACTGGGACGTGCCTTCAGGAGGAATATGGTGGGACACAATACGGCA GAAGATACCGGAGTGGTACGATGCCGGAATCTCCGCAATATGGATTCCC CCGGCGAGCAAGGGCATGGGCGGCGCCTATTCGATGGGCTACGACCCCT ACGACTTCTTTGACCTCGGTGAGTACGACCAGAAGGGAACGGTAGAGAC GCGCTTTGGCTCCAAGCAGGAGCTCGTGAACATGATAAACACCGCCCAC GCCTATGGCATGAAGGTAATAGCCGATATAGTCATCAACCACCGCGCCG GCGGTGACCTGGAGTGGAACCCCTTCGTGAACGACTATACCTGGACCGA CTTCTCAAAGGTCGCGTCGGGTAAATACACGGCCAACTACCTCGACTTC CACCCGAACGAGCTCCATGCGGGCGATTCCGGAACATTTGGAGGCTATC CCGACATATGCCACGACAAGAGCTGGGACCAGTACTGGCTCTGGGCCAG CCAGGAGAGCTACGCGGCATATCTCAGGAGCATCGGCATCGATGCCTGG CGCTTTGACTACGTGAAGGGCTACGGAGCGTGGGTCGTCAAGGACTGGC TCAACTGGTGGGGCGGCTGGGCCGTTGGCGAGTACTGGGACACCAACGT TGATGCACTCCTCAACTGGGCCTACTCGAGCGGCGCCAAGGTCTTCGAC TTCCCGCTCTACTACAAGATGGATGAGGCCTTTGACAACAAAAACATTC CAGCGCTCGTCTCTGCCCTTCAGAACGGCCAGACTGTTGTCTCCCGCGA CCCCGTTCAAGGCCGTAACCTTTGTAGCAAACCACGACACCGATATAATC TGGAACAAGTACCTTGCTTATGCTTTCATCCTCACCTACGAAGGCCAGC CCGTCATATTCTACCGCGACTACGAGGAGTGGCTCAACAAGGACAGGTT GAACAACCTCATATGGATACACGACCACCTCGCAGGTGGAAGCACGAGC ATAGTTTACTACGACAGCGACGAGATGATCTTCGTGAGGAACGGCTATG GAAGCAAGCCTGGCCTTATAACTTACATCAACCTCGGCTCGAGCAAGGT TGGAAGGTGGGTTTACGTTCCGAAGTTCGCAGGCTCGTGCATACACGAG TACACCGGCAATCTCGGCGGCTGGGTGGACAAGTGGGTGGACTCAAGCG GCTGGGTCTACCTCGAGGCTCCTGCCCACGACCCGGCCAACGGCCAGTA CGGCTACTCCGTCTGGAGCTATTGCGGTGTTGGCTGA |
| 61 | SEQ ID NO: 56 of U.S. Pat. No. 7407677 | MAKYLELEEGGVIMQAFYWDVPSGGIWWDTIRQKIPEWYDAGISAIWIP PASKGMGGAYSMGYDPYDFFDLGEYDQKGTVETRFGSKQELVNMINTAH AYGMKVIADIVINHRAGGDLEWNPFVNDYTWTDFSKVASGKYTANYLDF HPNELHAGDSGTFGGYPDICHDKSWDQYWLWASQESYAAYLRSIGIDAW RFDYVKGYGAWVVKDWLNWWGGWAVGEYWDTNVDALLNWAYSSGAKVFD FPLYYKMDEAFDNKNIPALVSALQNGQTVVSRDPFKAVTFVANHDTDII WNKYLAYAFILTYEGQPVIFYRDYEEWLNKDRLNNLIWIHDHLAGGSTS IVYYDSDEMIFVRNGYGSKPGLITYINLGSSKVGRWVYVPKFAGSCIHE YTGNLGGWVDKWVDSSGWVYLEAPAHDPANGQYGYSVWSYCGVG |
| 62 | SEQ ID NO: 57 of U.S. Pat. No. 7407677 | ATGGCCAAGTACCTGGAGCTCGAAGAGAGCGGGGTCATAATGCAGGCGT TCTACTGGGACGTGCCTTCAGGAGGAATATGGTGGGACACAATACGGCA GAAGATACCGGAGTGGTACGATGCCGGAATCTCCGCAATATGGATTCCT CCCGCGAGCAAGGGTATGAGCGGCGGCTATTCGATGGGCTACGACCCCT ACGATTATTTTGACCTCGGTGAGTACTACCAGAAGGGAACGGTGGAAAC GAGGTTCGGCTCAAAGCAGGAGCTCATAAACATGATAAACACCGCCCAC GCCTACGGCATCAAGGTCATCGCAGACATAGTAATCAACCACCGCGCCG GAGGAGACCTTGAGTGGAACCCCTTCGTCAATGACTACACCTGGACGGA CTTCTCGAAGGTCGCTTCCGGCAAGTACACGGCCAACTACCTCGACTTC CACCCCAACGAGGTCAAGTGCTGTGACGAGGGCACATTTGGAGGCTTCC CAGACATAGCCCACGAGAAGAGCTGGGACCAGCACTGGCTCTGGGCGAG CGATGAGAGCTACGCCGCCTACCTAAGGAGCATCGGCGTTGATGCCTGG CGCTTTGACTACGTGAAGGGCTACGAGCGTGGGTCGTCAAGGACTGGC TCAACTGGTGGGGTGGCTGGGCCGTCGGGGAGTACTGGGACACAAACGT TGATGCACTGCTCAACTGGGCCTACTCGAGCGATGCAAAAGTCTTCGAC TTCCCGCTCTACTACAAGATGGACGAGGCCTTCGATAACAACAACATTC CCGCCCTGGTGGACGCCCTCAGATACGGTCAGACAGTGGTCAGCCGCGA CCCCGTTCAAGGCTGTGACGTTTGTAGCCAACCACGATACCGATATAATC TGGAACAAGTACCTTGCTTATGCTTTCATCCTCACCTACGAAGGCCAGC CCGTCATATTCTACCGCGACTACGAGGAGTGGCTCAACAAGGACAGGTT GAACAACCTCATATGGATACACGACCACCTCGCAGGTGGAAGCACTGAC ATCGTTTACTACGACAACGACGAGCTGATATTCGTGAGAAACGGCTACG GAAGCAAGCCGGGACTGATAACATACATCAACCTCGCCTCAAGCAAAGC CGGAAGGTGGGTCTACGTTCCGAAGTTCGCGGGAGCGTGCATCCACGAG TACACCGGCAACCTCGGCGGCTGGGTGGACAAGTGGGTGGACTCAAGCG GCTGGGTGTACCTCGAGGCCCCTGCCCACGACCCGGCCAACGGCTATTA CGGCTACTCCGTCTGGAGCTATTGCGGTGTTGGCTGA |
| 63 | SEQ ID NO: 58 of U.S. Pat. No. 7407677 | MAKYLELEESGVIMQAFYWDVPSGGIWWDTIRQKIPEWYDAGISAIWIP PASKGMSGGYSMGYDPYDYFDLGEYYQKGTVETRFGSKQELINMINTAH AYGIKVIADIVINHRAGGDLEWNPFVNDYTWTDFSKVASGKYTANYLDF HPNEVKCCDEGTFGGFPDIAHEKSWDQHWLWASDESYAAYLRSIGVDAW RFDYVKGYGAWVVKDWLNWWGGWAVGEYWDTNVDALLNWAYSSDAKVFD |

TABLE 4-continued

DNA coding sequences and protein sequences of non-limiting examples of amylases that can be used in the methods and compositions disclosed herein.

| SEQ ID NO: | Reference from Other Patents | |
|---|---|---|
| | | FPLYYKMDEAFDNNNIPALVDALRYGQTVVSRDPFKAVTFVANHDTDII<br>WNKYLAYAFILTYEGQPVIFYRDYEEWLNKDRLNNLIWIHDHLAGGSTD<br>IVYYDNDELIFVRNGYGSKPGLITYINLASSKAGRWVYVPKFAGACIHE<br>YTGNLGGWVDKWVDSSGWVYLEAPAHDPANGYYGYSVWSYCGVG |
| 64 | SEQ ID NO: 59<br>of U.S. Pat. No. 7407677 | ATGGCCAAGTACCTGGAGCTCGAAGAGGGCGGGGTCATAATGCAGGCGT<br>TCTACTGGGACGTGCCTTCAGGAGGAATATGGTGGGACACAATACGGCA<br>GAAGATACCGGAGTGGTACGATGCCGGAATCTCCGCAATATGGATTCCT<br>CCCGCGAGCAAGGGTATGAGCGGCGGCTATTCGATGGGCTACGACCCCT<br>ACGATTATTTTGACCTCGGTGAGTACTACCAGAAGGGAACGGTGGAAAC<br>GAGGTTCGGCTCAAAGCAGGAGCTCATAAACATGATAAACACCGCCCAC<br>GCCTACGGCATCAAGGTCATCGCAGACATAGTAATCAACCACCGCGCCG<br>GAGGAGACCTTGAGTGGAACCCCTTCGTCAATGACTACACCTGGACGGA<br>CTTCTCGAAGGTCGCTTCCGGCAAGTACACGGCCAACTACCTCGACTTC<br>CACCCGAACGAGCTCCATGCGGGCGATTCCGGAACATTTGGAGGCTATC<br>CCGACATATGCCACGACAAGAGCTGGGACCAGTACTGGCTCTGGGCCAG<br>CCAGGAGAGCTACGCGGCATATCTCAGGAGCATCGGCATCGATGCCTGG<br>CGCTTCGACTACGTCAAGGGCTATGCTCCCTGGGTCGTCAAGGACTGGC<br>TGAACTGGTGGGGAGGCTGGGCGGTTGGAGAGTACTGGGACACCAACGT<br>CGACGCTGTTCTCAACTGGGCATACTCGAGCGGTGCCAAGGTCTTTGAC<br>TTCGCCCTCTACTACAAGATGGACGAGGCCTTCGATAACAACAACATTC<br>CCGCCCTGGTGGACGCCCTCAGATACGGTCAGACAGTGGTCAGCCGCGA<br>CCCGTTCAAGGCTGTGACGTTTGTAGCCAACCACGATACCGATATAATT<br>TGGAACAAGTACCCGGCCTACGCCTTCATCCTCACCTACGAGGGCCAGC<br>CGACGATATTCTACCGCGACTACGAGGAGTGGCTCAACAAGGACAGGCT<br>CAAGAACCTCATCTGGATACACGACCACCTCGCCGGTGGAAGCACTGAC<br>ATCGTTTACTACGACAACGACGAGCTGATATTCGTGAGAAACGGCTACG<br>GAAGCAAGCCGGGACTGATAACATACATCAACCTCGCGTCAAGCAAAGC<br>CGGAAGGTGGGTTTATGTGCCGAAGTTCGCGGGCGCGTGCATCCACGAG<br>TATACTGGTAACCTCGGAGGCTGGGTAGACAAGTACGTCTACTCAAGCG<br>GCTGGGTCTATCTCGAAGCTCCAGCTTACGACCCTGCCAACGGGCAGTA<br>TGGCTACTCCGTGTGGAGCTATTGCGGTGTTGGGTGA |
| 65 | SEQ ID NO: 60<br>of U.S. Pat. No. 7407677 | MAKYLELEEGGVIMQAFYWDVPSGGIWWDTIRQKIPEWYDAGISAIWIP<br>PASKGMSGGYSMGYDPYDYFDLGEYYQKGTVETRFGSKQELINMINTAH<br>AYGIKVIADIVINHRAGGDLEWNPFVNDYTWTDFSKVASGKYTANYLDF<br>HPNELHAGDSGTFGGYPDICHDKSWDQYWLWASQESYAAYLRSIGIDAW<br>RFDYVKGYAPWVVKDWLNWWGGWAVGEYWDTNVDAVLNWAYSSGAKVFD<br>FALYYKMDEAFDNNNIPALVDALRYGQTVVSRDPFKAVTFVANHDTDII<br>WNKYPAYAFILTYEGQPTIFYRDYEEWLNKDRLKNLIWIHDHLAGGSTD<br>IVYYDNDELIFVRNGYGSKPGLITYINLASSKAGRWVYVPKFAGACIHE<br>YTGNLGGWVDKYVYSSGWVYLEAPAYDPANGQYGYSVWSYCGVG |
| 66 | SEQ ID NO: 61<br>of U.S. Pat. No. 7407677 | ATGGCCAAGTACTCCGAGCTGAAAAAGGGCGGGGTCATAATGCAGGCGT<br>TCTACTGGGACGTGCCTTCAGGAGGAATATGGTGGGACACAATACGGCA<br>GAAGATACCGGAGTGGTACGAGGCGGGAATATCCGCCATTTGGATTCCT<br>CCCGCGAGCAAGGGTATGAGCGGCGGCTATTCGATGGGCTACGACCCCT<br>ACGATTATTTTGACCTCGGTGAGTACTACCAGAAGGGAACGGTGGAAAC<br>GAGGTTCGGCTCAAAGCAGGAGCTCATAAACATGATAAACACCGCCCAC<br>GCCTACGGCATCAAGGTCATCGCAGACATAGTAATCAACCACCGCGCCG<br>GAGGAGACCTTGAGTGGAACCCCTTCGTCAATGACTACACCTGGACGGA<br>CTTCTCGAAGGTCGCTTCCGGCAAGTACACGGCCAACTACCTCAACTTC<br>CACCCGAACGAGCTCCATGCGGGCGATTCCGGAACATTTGGAGGCTATC<br>CCGACATATGCCACGACAAGAGCTGGGACCAGTACTGGCTCTGGGCCAG<br>CCAGGAGAGCTACGCGGCATATCTCAGGAGCATCGGCATCGATGCCTGG<br>CGCTTCGACTACGTCAAGGGCTACGGAGCGTGGGTCGTCAAGGACTGGC<br>TGGACTGGTGGGGAGGCTGGGCCGTCGGGGAGTACTGGGACACAAACGT<br>TGATGCACTGCTCAACTGGGCCTACTCGAGCGATGCAAAAGTCTTCGAC<br>TTCCCGCTCTACTACAAGATGGATGAGGCCTTTGACAACAAAACATTC<br>CAGCGCTCGTCTCTGCCCTTCAGAACGGCCAGACTGTTGTCTCCCGCGA<br>CCCGTTCAAGGCCGTAACCTTTGTAGCAAACCATGACACCGATATAATT<br>TGGAACAAGTATCCAGCCTACGCGTTCATCCTCACCTACGAGGGCCAGC<br>CGACAATATTCTACCGCGACTACGAGGAGTGGCTCAACAAGGATAAGCT<br>CAAGAACCTCATCTGGATACATGACAACCTCGCCGGAGGAAGCACCGAC<br>ATAGTCTACTACGATAACGATGAACTCATCTTCGTCAGGAACGGCTACG<br>GGGACAAGCCGGGGCTTATAACCTACATCAACCTAGGCTCGAGCAAGGC<br>CGGAAGGTGGGTCTACGTTCCGAAGTTCGCGGGAGCGTGCATCCACGAG<br>TACACCGGCAACCTCGGCGGCTGGGTGGACAAGTGGGTGGACTCAAGCG<br>GGTGGGTGTACCTCGAGGCCCCTGCCCACGACCCGGCCAACGGCTATTA<br>CGGCTACTCCGTCTGGAGCTACTGCGGGGTGGGCTGA |
| 67 | SEQ ID NO: 62<br>of U.S. Pat. No. 7407677 | MAKYSELKKGGVIMQAFYWDVPSGGIWWDTIRQKIPEWYEAGISAIWIP<br>PASKGMSGGYSMGYDPYDYFDLGEYYQKGTVETRFGSKQELINMINTAH<br>AYGIKVIADIVINHRAGGDLEWNPFVNDYTWTDFSKVASGKYTANYLNF |

TABLE 4-continued

DNA coding sequences and protein sequences of non-limiting examples of amylases that can be used in the methods and compositions disclosed herein.

| SEQ ID NO: | Reference from Other Patents | |
|---|---|---|
| | | HPNELHAGDSGTFGGYPDICHDKSWDQYWLWASQESYAAYLRSIGIDAW RFDYVKGYGAWVVKDWLDWWGGWAVGEYWDTNVDALLNWAYSSDAKVFD FPLYYKMDEAFDNKNIPALVSALQNGQTVVSRDPFKAVTFVANHDTDII WNKYPAYAFILTYEGQPTIFYRDYEEWLNKDKLKNLIWIHDNLAGGSTD IVYYDNDELIFVRNGYGDKPGLITYINLGSSKAGRWVYVPKFAGACIHE YTGNLGGWVDKWVDSSGWVYLEAPAHDPANGYYGYSVWSYCGVG |
| 68 | SEQ ID NO: 63 of U.S. Pat. No. 7407677 | ATGGCCAAGTACCTGGAGCTCGAAGAGGGCGGGGTCATAATGCAGGCGT TCTACTGGGACGTGCCTTCAGGAGGAATATGGTGGGACACAATACGGCA GAAGATACCGGAGTGGTACGATGCCGGAATCTCCGCAATATGGATTCCC CCGGCGAGCAAGGGCATGGGCGGCGCCTATTCGATGGGCTACGACCCCT ACGACTTCTTTGACCTCGGTGAGTACGACCAGAAGGGAACGGTAGAGAC GCGCTTTGGCTCCAAGCAGGAGCTCGTGAACATGATAAACACGGCCCAT GCCTACGGCATAAAGGCCATAGCGGACATCGTCATAAACCACCGCGCAG GCGGAGACCTCGAGTGGAACCCGTTCGTTGGGGACTACACCTGGACGGA CTTCTCAAAGGTGGCCTCGGGCAAATATACTGCCAACTACCTCGACTTC CACCCCAACGAGGTCAAGTGCTGTGACGAGGGCACATTTGGAGGCTTCC CAGACATAGCCCACGAGAAGAGCTGGGACCAGCACTGGCTCTGGGCGAG CGATGAGAGCTACGCCGCCTACCTAAGGAGCATCGGCGTTGATGCCTGG CGCTTTGACTACGTGAAGGGCTACGGAGCGTGGGTCGTCAAGGACTGGC TCAACTGGTGGGGCGGCTGGGCCGTTGGCGAGTACTGGGACACCAACGT TGATGCACTCCTCAACTGGGCCTACTCGAGCGGCGCCAAGGTCTTCGAC TTCCCGCTCTACTACAAGATGGACGCGGCCTTTGACAACAAGAACATTC CCGCACTCGTCGAGGCCCTCAAGAACGGGGGCACAGTCGTCAGCCGCGA CCCGTTTAAGGCCGTAACCTTCGTTGCAAACCACGACACCGATATAATC TGGAACAAGTATCCAGCCTACGCGTTCATCCTCACCTACGAGGGCCAGC CGACAATATTCTACCGCGACTACGAGGAGTGGCTCAACAAGGATAAGCT CAAGAACCTCATCTGGATACATGACAACCTCGCCGGAGGAAGCACCGAC ATAGTCTACTACGATAACGATGAACTCATCTTCGTCAGGAACGGCTACG GGGACAAGCCGGGGCTTATAACCTACATCAACCTAGGCTGGAGCAAGGC CGGAAGGTGGGTTTATGTGCCGAAGTTCGCGGGCGCGTGCATCCACGAG TATACTGGTAACCTCGGAGGCTGGGTAGACAAGTACGTCTACTCAAGCG GCTGGGTCTATCTCGAAGCTCCAGCTTACGACCCTGCCAACGGGCAGTA TGGCTACTCCGTGTGGAGCTACTGCGGGGTGGGGTGA |
| 69 | SEQ ID NO: 64 of U.S. Pat. No. 7407677 | MAKYLELEEGGVIMQAFYWDVPSGGIWWDTIRQKIPEWYDAGISAIWIP PASKGMGGAYSMGYDPYDFFDLGEYDQKGTVTETRFGSKQELVNMINTAH AYGIKAIADIVINHRAGGDLEWNPFVGDYTWTDFSKVASGKYTANYLDF HPNEVKCCDEGTFGGFPDIAHEKSWDQHWLWASDESYAAYLRSIGVDAW RFDYVKGYGAWVVKDWLNWWGGWAVGEYWDTNVDALLNWAYSSGAKVFD FPLYYKMDAAFDNKNIPALVEALKNGGTVVSRDPFKAVTFVANHDTDII WNKYPAYAFILTYEGQPTIFYRDYEEWLNKDKLKNLIWIHDNLAGGSTD IVYYDNDELIFVRNGYGDKPGLITYINLGWSKAGRWVYVPKFAGACIHE YTGNLGGWVDKYVYSSGWVYLEAPAYDPANGQYGYSVWSYCGVG |
| 70 | SEQ ID NO: 65 of U.S. Pat. No. 7407677 | ATGGCCAAGTACTCCGAGCTGGAAGAAGGCGGCGTTATAATGCAGGCCT TCTACTGGGACGTCCCAGGTGGAGGAATCTGGTGGGGCACCATCAGGAG CAAGATACCGGAGTGGTACGAGGCGGGAATATCCGCCATTTGGATTCCT CCCGCGAGCAAGGGTATGAGCGGCGGCTATTCGATGGGCTACGACCCCT ACGATTATTTTGACCTCGGTGAGTACTACCAGAAGGGAACGGTGGAAAC GAGGTTCGGCTCAAAGCAGGAGCTCATAAACATGATAAACACGCCCAC GCCTATGGCATGAAGGTAATAGCCGATATAGTCATCAACCACCGCGCCG GCGGTGACCTGGAGTGGAACCCCTTCGTGAACGACTATACCTGGACCGA CTTCTCAAAGGTCGCGTCGGGTAAATACACGGCCAACTACCTCGACTTC CACCCGAACGAGCTCCATGCGGGCGATTCCGGAACATTTGGAGGCTATC CCGACATATGCCACGACAAGAGCTGGGACCAGTACTGGCTCTGGGCCAG CCAGGAGAGCTACGCGGCATATCTCAGGAGCATCGGCATCGATGCCTGG CGCTTCGACTACGTCAAGGGCTATGCTCCCTGGGTCGTCAAGGACTGGC TGAACTGGTGGGAGGCTGGGCGGTTGGAGAGTACTGGGACACCAACGT CGACGCTGTTCTCAACTGGGCATACTCGAGCGGTGCCAAGGTCTTTGAC TTCGCCCTCTACTACAAGATGGACGAGGCCTTCGATAACAACAACATTC CCGCCCTGGTGGACGCCCTCAGATACGGTCAGACAGTGGTCAGCCGCGA CCCGTTCAAGGCTGTGACGTTTGTAGCCAACCACGATACCGATATAATT TGGAACAAGTACCCGGCCTACGCCTTCATCCTCACCTACGAGGGCCAGC CGACGATATTCTACCGCGACTACGAGGAGTGGCTCAACAAGGACAGGCT CAAGAACCTCATCTGGATACACGACCACCTCGCCGGTGGAAGCACGAGC ATAGTTTACTACGACAGCGACGAGATGATCTTCGTGAGGAACGGCTATG GAAGCAAGCCTGGCCTTATAACTTACATCAACCTCGGCTCGAGCAAGGT TGGAAGGTGGGTTTACGTTCCGAAGTTCGCAGGCTCGTGCATACACGAG TACACCGGCAATCTCGGCGGCTGGGTGGACAAGTGGGTGGACTCAAGCG GCTGGGTCTACCTCGAGGCTCCTGCCCACGACCCGGCCAACGGCCAGTA CGGCTACTCCGTCTGGAGCTATTGCGGTGTTGGCTGA |

TABLE 4-continued

DNA coding sequences and protein sequences of non-limiting examples of amylases that can be used in the methods and compositions disclosed herein.

| SEQ ID NO: | Reference from Other Patents | |
|---|---|---|
| 71 | SEQ ID NO: 66 of U.S. Pat. No. 7407677 | MAKYSELEEGGVIMQAFYWDVPGGGIWWGTIRSKIPEWYEAGISAIWIP PASKGMSGGYSMGYDPYDYFDLGEYYQKGTVETRFGSKQELINMINTAH AYGMKVIADIVINHRAGGDLEWNPFVNDYTWTDFSKVASGKYTANYLDF HPNELHAGDSGTFGGYPDICHDKSWDQYWLWASQESYAAYLRSIGIDAW RFDYVKGYAPWVVKDWLNWWGGWAVGEYWDTNVDAVLNWAYSSGAKVFD FALYYKMDEAFDNNNIPALVDALRYGQTVVSRDPFKAVTFVANHDTDII WNKYPAYAFILTYEGQPTIFYRDYEEWLNKDRLKNLIWIHDHLAGGSTS IVYYDSDEMIFVRNGYGSKPGLITYINLGSSKVGRWVYVPKFAGSCIHE YTGNLGGWVDKWVDSSGWVYLEAPAHDPANGQYGYSVWSYCGVG |
| 72 | SEQ ID NO: 67 of U.S. Pat. No. 7407677 | ATGGCCAAGTACCTGGAGCTCGAAGAGGGCGGGGTCATAATGCAGGCGT TCTACTGGGACGTGCCTTCGGGAGGAATATGGTGGGACACAATACGGCA GAAGATACCGGAGTGGTACGATGCCGGAATCTCCGCAATATGGATTCCT CCCGCGAGCAAGGGTATGAGCGGCGGCTATTCGATGGGCTACGACCCCT ACGATTATTTTGACCTCGGTGAGTACTACCAGAAGGGAACGGTGGAAAC GAGGTTCGGCTCAAAGCAGGAGCTCATAAACATGATAAACACGGCCCAT GCCTACGGCATAAAGGTCATAGCGGACATCGTCATAAACCACCGCGCAG GCGGAGACCTCGAGTGGAACCCGTTCGTTGGGGACTACACCTGGACGGA CTTCTCAAAGGTGGCCTCGGGCAAATATACTGCCAACTACCTCGACTTC CACCCCAACGAGGTCAAGTGCTGTGACGAGGGCACATTTGGAGGCTTCC CAGACATAGCCCACGAGAAGAGCTGGGACCAGCACTGGCTCTGGGCGAG CGATGAGAGCTACGCCGCCTACCTAAGGAGCATCGGCGTTGATGCCTGG CGCTTCGACTACGTCAAGGGCTACGAGCGTGGGTCGTCAAGGACTGGC TGGACTGGTGGGGAGGCTGGGCCGTCGGGGAGTACTGGGACACAAACGT TGATGCACTGCTCAACTGGGCCTACTCGAGCGATGCAAAAGTCTTCGAC TTCCCGCTCTACTACAAGATGGACGAGGCCTTCGATAACAACAACATTC CCGCCCTGGTGGACGCCCTCAGATACGGTCAGACAGTGGTCAGCGCGA CCCGTTCAAGGCTGTGACGTTTGTAGCCAACCACGATACCGATATAATC TGGAACAAGTATCCAGCCTACGCGTTCATCCTCACCTACGAGGGCCAGC CGACAATATTCTACCGCGACTACGAGGAGTGGCTCAACAAGGATAAGCT CAAGAACCTCATCTGGATACATGACAACCTCGCCGGAGGAAGCACGAGC ATAGTTTACTACGACAGCGACGAGATGATCTTCGTGAGGAACGGCTATG GAAGCAAGCCTGGCCTTATAACTTACATCAACCTCGGCTCGAGCAAGGT TGGAAGGTGGGTCTACGTTCCGAAGTTCGCGGGAGCGTGCATCCACGAG TACACCGGCAACCTCGGCGGCTGGGTGGACAAGTGGGTGGACTCAAGCG GGTGGGTGTACCTCGAGGCCCCTGCCCACGACCCGGCCAACGGCTATTA CGGCTACTCCGTCTGGAGCTACTGCGTGGTGGGCTGA |
| 73 | SEQ ID NO: 68 of U.S. Pat. No. 7407677 | MAKYLELEEGGVIMQAFYWDVPSGGIWWDTIRQKIPEWYDAGISAIWIP PASKGMSGGYSMGYDPYDYFDLGEYYQKGTVETRFGSKQELINMINTAH AYGIKVIADIVINHRAGGDLEWNPFVGDYTWTDFSKVASGKYTANYLDF HPNEVKCCDEGTFGGFPDIAHEKSWDQHWLWASDESYAAYLRSIGVDAW RFDYVKGYGAWVVKDWLDWWGGWAVGEYWDT NVDALLNWAYSSDAKVFDFPLYYKMDEAFDNNNIPALVDALRYGQTVVS RDPFKAVTFVANHDTDIIWNKYPAYAFILTYEGQPTIFYRDYEEWLNKD KLKNLIWIHDNLAGGSTSIVYYDSDEMIFVRNGYGSKPGLITYINLGSS KVGRWVYVPKFAGACIHEYTGNLGGWVDKWVDSSGWVYLEAPAHDPANG YYGYSVWSYCVVG |
| 74 | SEQ ID NO: 71 of U.S. Pat. No. 7407677 | ATGGCCAAGTACCTGGAGCTCGAAGAGGGCGGGGTCATAATGCAGGCGT TCTACTGGGACGTGCCTTCAGGAGGAATATGGTGGGACACAATACGGCA GAAGATACCGGAGTGGTACGATGCCGGAATCTCCGCAATATGGATTCCC CCGGCGAGCAAGGGCATGGGCGGCGCCTATTCGATGGGCTACGACCCCT ACGACTTCTTTGACCTCGGTGAGTACGACCAGAAGGGAACGGTAGAGAC GCGCTTTGGCTCCAAGCAGGAGCTCGTGAACATGATAAACACGGCCCAT GCCTACGGCATAAAGGTCATAGCGGACATCGTCATAAACCACCGCGCAG GCGGAGACCTCGAGTGGAACCCGTTCGTTGGGGACTACACCTGGACGGA CTTCTCAAAGGTAGCCTCGGGCAAATATACTGCCAACTACCTCGACTTC CACCCGAACGAGCTCCATGCGGGCGATTCCGGAACATTTGGAGGCTATC CCGACATATGCCACGACAAGAGCTGGGACCAGTACTGGCTCTGGGCCAG CCAGGAGAGCTACGCGGCATATCTCAGGAGCATCGGCATCGATGCCTGG CGCTTCGACTACGTCAAGGGCTATGCTCCCTGGGTCGTCAAGGACTGGC TGAACTGGTGGGGAGGCTGGGCCGTTGGAGAGTACTGGGACACCAACGT CGACGCTGTTCTCAACTGGGCATACTCGAGCGGTGCCAAGGTCTTTGAC TTCCGCCCTCTACTACAAGATGGATGAGGCCTTTGACAACAAAAACATTC CAGCGCTCGTCTCTGCCCTTCAGAACGGCCAGACTGTTGTCTCCCGCGA CCCGTTCAAGGCCGTAACCTTTGTAGCAAACCACGACACCGATATAATC TGGAACAAGTATCCAGCCTACGCGTTCATCCTCACCTACGAGGGCCAGC CGACAATATTCTACCGCGACTACGAGGAGTGGCTCAACAAGGATAAGCT CAAGAACCTCATCTGGATACATGACAACCTCGCCGGAGGAAGCACTGAC ATCGTTTACTACGACAACGACGAGCTGATATTCGTGAGAAACGGCTACG GAAGCAAGCCGGGACTGATAACATACATCAACCTCGCCTCAAGCAAAGC CGGAAGGTGGGTTTATGTGCCGAAGTTCGCGGGCGCGTGCATCCACGAG TATACTGGTAACCTCGGAGGCTGGGTAGACAAGTACGTCTACTCAAGCG |

TABLE 4-continued

DNA coding sequences and protein sequences of non-limiting examples of amylases that can be used in the methods and compositions disclosed herein.

| SEQ ID NO: | Reference from Other Patents | |
|---|---|---|
| | | GCTGGGTCTATCTCGAAGCTCCAGCTTACGACCCTGCCAACGGGCAGTA<br>TGGCTACTCCGTGTGGAGCTACTGCGGGGTGGGCTGA |
| 75 | SEQ ID NO: 72<br>of U.S. Pat. No. 7407677 | MAKYLELEEGGVIMQAFYWDVPSGGIWWDTIRQKIPEWYDAGISAIWIP<br>PASKGMGGAYSMGYDPYDFFDLGEYDQKGTVETRFGSKQELVNMINTAH<br>AYGIKVIADIVINHRAGGDLEWNPFVGDYTWTDFSKVASGKYTANYLDF<br>HPNELHAGDSGTFGGYPDICHDKSWDQYWLWASQESYAAYLRSIGIDAW<br>RFDYVKGYAPWVVKDWLNWWGGWAVGEYWDTNVDAVLNWAYSSGAKVFD<br>FALYYKMDEAFDNKNIPALVSALQNGQTVVSRDPFKAVTFVANHDTDII<br>WNKYPAYAFILTYEGQPTIFYRDYEEWLNKDKLKNLIWIHDNLAGGSTD<br>IVYYDNDELIFVRNGYGSKPGLITYINLASSKAGRWVYVPKFAGACIHE<br>YTGNLGGWVDKYVYSSGWVYLEAPAYDPANGQYGYSVWSYCGVG |
| 76 | SEQ ID NO: 9<br>of U.S. Pat. No. 7407677 | ATGGCCAAGTACTCCGAGCTGGAAGAGGGCGGGCTCATAATGCAGGCCT<br>TCTACTGGGACGTCCCCATGGGAGGAATCTGGTGGGACACGATAGCCCA<br>GAAGATACCCGACTGGGCAAGCGCCGGGATTTCGGCGATATGGATTCCC<br>CCGGCGAGCAAGGGCATGGGCGGCGCCTATTCGATGGGCTACGACCCCT<br>ACGACTTCTTTGACCTCGGTGAGTACGACCAGAAGGGAACGGTAGAGAC<br>GCGCTTTGGCTCCAAGCAGGAGCTCGTGAACATGATAAACACGGCCCAT<br>GCCTACGGCATAAAGGTCATAGCGGACATCGTCATAAACCACCGCGCAG<br>GCGGAGACCTCGAGTGGAACCCGTTCGTTGGGGACTACACCTGGACGGA<br>CTTCTCAAAGGTGGCCTCGGGCAAATATACTGCCAACTACCTCGACTTC<br>CACCCGAACGAGCTCCATGCGGGCGATTCCGGAACATTTGGAGGCTATC<br>CCGACATATGCCACGACAAGAGCTGGGACCAGTACTGGCTCTGGGCCAG<br>CCAGGAGAGCTACGCGGCATATCTCAGGAGCATCGGCATCGATGCCTGG<br>CGCTTCGACTACGTCAAGGGCTATGCTCCCTGGGTCGTCAAGGACTGGC<br>TGAACTGGTGGGGAGGCTGGGCGGTTGGAGAGTACTGGGACACCAACGT<br>CGACGCTGTTCTCAACTGGGCATACTCGAGCGGTGCCAAGGTCTTTGAC<br>TTCGCCCTCTACTACAAGATGGACGAGGCCTTCGATAACAACAACATTC<br>CCGCCCTGGTGGACGCCCTCAGATACGGTCAGACAGTGGTCAGCCGCGA<br>CCCGTTCAAGGCTGTGACGTTTGTAGCCAACCACGATACCGATATAATC<br>TGGAACAAGTATCCAGCCTACGCGTTCATCCTCACCTACGAGGGCCAGC<br>CGACAATATTCTACCGCGACTACGAGGAGTGGCTCAACAAGGATAAGCT<br>CAAGAACCTCATCTGGATACATGACAACCTCGCCGGAGGAAGCACTGAC<br>ATCGTTTACTACGACAACGACGAGCTGATATTCGCGAGAAACGGCTACG<br>GAAGCAAGCCGGGACTGATAACATACATCAACCTCGCCTCAAGCAAAGC<br>CGGAAGGTGGGTTTACGTTCCGAAGTTCGCAGGCTCGTGCATACACGAG<br>TACACCGGCAATCTCGGCGGCTGGGTGGACAAGTGGGTGGACTCAAGCG<br>GCTGGGTCTACCTCGAGGCTCCTGCCCACGACCCGGCCAACGGCCAGTA<br>CGGCTACTCCGTCTGGAGCTACTGCGGTGTTGGGTGA |
| 77 | SEQ ID NO: 10<br>of U.S. Pat. No. 7407677 | MAKYSELEEGGLIMQAFYWDVPMGGIWWDTIAQKIPDWASAGISAIWIP<br>PASKGMGGAYSMGYDPYDFFDLGEYDQKGTVETRFGSKQELVNMINTAH<br>AYGIKVIADIVINHRAGGDLEWNPFVGDYTWTDFSKVASGKYTANYLDF<br>HPNELHAGDSGTFGGYPDICHDKSWDQYWLWASQESYAAYLRSIGIDAW<br>RFDYVKGYAPWVVKDWLNWWGGWAVGEYWDTNVDAVLNWAYSSGAKVFD<br>FALYYKMDEAFDNNNIPALVDALRYGQTVVSRDPFKAVTFVANHDTDII<br>WNKYPAYAFILTYEGQPTIFYRDYEEWLNKDKLKNLIWIHDNLAGGSTD<br>IVYYDNDELIFARNGYGSKPGLITYINLASSKAGRWVYVPKFAGSCIHE<br>YTGNLGGWVDKWVDSSGWVYLEAPAHDPANGQYGYSVWSYCGVG |
| 78 | SEQ ID NO: 77<br>of U.S. Pat. No. 7407677 | ATGGCTCTGGAAGAGGGCGGGCTCATAATGCAGGCCTTCTACTGGGACG<br>TCCCCATGGGAGGAATCTGGTGGGACACGATAGCCCAGAAGATACCCGA<br>CTGGGCAAGCGCCGGGATTTCGGCGATATGGATCCCTCCCGCGAGCAAG<br>GGTATGAGCGGCGGCTATTCGATGGGCTACGACCCCTACGATTATTTTG<br>ACCTCGGTGAGTACTACCAGAAGGGAACGGTGGAAACGAGGTTCGGCTC<br>AAAGCAGGAGCTCATAAACATGATAAACACCGCCCACGCCTATGGCATG<br>AAGGTAATAGCCGATATAGTCATCAACCACCGCGCCGGCGGTGACCTGG<br>AGTGGAACCCCTTCGTGAACGACTATACCTGGACCGACTTCTCAAAGGT<br>CGCCGTCGGGTAAATACACGGCCAACTACCTCGACTTCCACCCGAACGAG<br>CTCCATGCGGGCGATTCCGGAACATTTGGAGGCTATCCCGACATATGCC<br>ACGACAAGAGCTGGGACCAGTACTGGCTCTGGGCCAGCCAGGAGAGCTA<br>CGCGGCATATCTCAGGAGCATCGGCATCGATGCCTGGCGCTTCGACTAC<br>GTCAAGGGCTATGCTCCCTGGGTCGTCAAGGACTGGCTGAACTGGTGGG<br>GAGGCTGGGCGGTTGGAGAGTACTGGGACACCAACGTCGACGCTGTTCT<br>CAACTGGGCATACTCGAGCGGTGCCAAGGTCTTTGACTTCGCCCTCTAC<br>TACAAGATGGACGAGGCCTTCGATAACAACAACATTCCCGCCCTGGTGG<br>ACGCCCTCAGATACGGTCAGACAGTGGTCAGCCGCGACCCGTTCAAGGC<br>TGTGACGTTTGTAGCCAACCACGATACCGACATAATCTGGAACAAGTAT<br>CCAGCCTACGCGTTCATCCTCACCTACGAGGGCCAGCCGACAATATTCT<br>ACCGCGACTACGAGGAGTGGCTCAACAAGGATAAGCTCAAGAACCTCAT<br>CTGGATACATGACAACCTCGCCGGAGGGAGCACTGACATCGTTTACTAC<br>GACAACGACGAGCTGATATTCGTGAGAAACGGCTACGGAAGCAAGCCGG<br>GACTGATAACATACATCAACCTCGCCTCAAGCAAAGCCGGAAGGTGGGT |

TABLE 4-continued

DNA coding sequences and protein sequences of non-limiting examples of amylases that can be used in the methods and compositions disclosed herein.

| SEQ ID NO: | Reference from Other Patents | |
|---|---|---|
| | | TTACGTTCCGAAGTTCGCAGGCTCGTGCATACACGAGTACACCGGCAAT CTCGGCGGCTGGGTGGACAAGTGGGTGGACTCAAGCGGCTGGGTCTACC TCGAGGCTCCTGCCCACGACCCGGCCAACGGCCAGTACGGCTACTCCGT CTGGAGCTACTGCGGTGTTGGGTGA |
| 79 | SEQ ID NO: 78 of U.S. Pat. No. 7407677 | MALEEGGLIMQAFYWDVPMGGIWWDTIAQKIPDWASAGISAIWIPPASK GMSGGYSMGYDPYDYFDLGEYYQKGTVETRFGSKQELINMINTAHAYGM KVIADIVINHRAGGDLEWNPFVNDYTWTDFSKVASGKYTANYLDFHPNE LHAGDSGTFGGYPDICHDKSWDQYWLWASQESYAAYLRSIGIDAWRFDY VKGYAPWVVKDWLNWWGGWAVGEYWDTNVDAVLNWAYSSGAKVFDFALY YKMDEAFDNNNIPALVDALRYGQTVVSRDPFKAVTFVANHDTDIIWNKY PAYAFILTYEGQPTIFYRDYEEWLNKDKLKNLIWIHDNLAGGSTDIVYY DNDELIFVRNGYGSKPGLITYINLASSKAGRWVYVPKFAGSCIHEYTGN LGGWVDKWVDSSGWVYLEAPAHDPANGQYGYSVWSYCGVG |
| 80 | SEQ ID NO: 79 of U.S. Pat. No. 7407677 | ATGAAGCCTGCGAAACTCCTCGTCTTTGTGCTCGTAGTCTCTATCCTCG CGGGGGCTCTACGCCCAGCCCGCGGGGGCGGCCAAGTACCTGGAGCTCGA AGAGGGCGGCGTCATAATGCAGGCGTTCTACTGGGACGTGCCCTTCAGGA GGAATATGGTGGGACACAATACGGCAGAAGATACCGGAGTGGTACGATG CCGGAATCTCCGCAATATGGATTCCCCCGGCGAGCAAGGGCATGGGCGG CGCCTATTCGATGGGCTACGACCCCTACGACTTCTTTGACCTCGGTGAG TACGACCAGAAGGGAACGGTAGAGACGCGCTTTGGCTCCAAGCAGGAGC TCGTGAACATGATAAACACCGCCCACGCCTACGGCATCAAGGTCATCGC AGACATAGTAATCAACCACCGCGCCGGAGGAGACCTTGAGTGGAACCCC TTCGTCAATGACTACACCTGGACGGACTTCTCGAAGGTCGCTTCCGGCA AGTACACGGCCAACTACCTCGACTTCCACCCCAACGAGGTCAAGTGCTG CGACGAGGGCACCTTTGGAGGGTTCCCGGACATAGCCCACGAGAAGAGC TGGGACCAGTACTGGCTCTGGGCGAGCAACGAGAGCTACGCCGCCTACC TCAGGAGCATCGGCGTTGACGCATGGCGCTTCGACTACGTCAAGGGCTA CGGAGCGTGGGTCGTCAAGGACTGGCTGGACTGGTGGGGAGGCTGGGCC GTCGGGGAGTACTGGGACACAAACGTTGATGCACTGCTCAACTGGGCCT ACTCGAGCGATGCAAAAGTCTTCGACTTCCCGCTCTACTACAAGATGGA CGCGGCCTTTGACAACAAGAACATTCCCGCACTCGTCGAGGCCCTCAAG AACGGGGGCACAGTCGTCAGCCGCGACCCGTTTAAGGCCGTAACCTTCG TTGCAAACCACGACACGGACATAATTTGGAACAAGTACCCGGCCTACGC CTTCATCCTCACCTACGAGGGCCAGCCGACGATATTCTACCGCGACTAC GAGGAGTGGCTCAACAAGGACAGGCTCAAGAACCTCATCTGGATACACG ACCACCTCGCCGGTGGAAGCACCGACATAGTCTACTACGATAACGATGA ACTCATCTTCGTCAGGAACGGCTACGGGGACAAGCCGGGGCTTATAACC TACATCAACCTAGGCTCGAGCAAGGCCGGGAGGTGGGTCTACGTTCCGA AGTTCGCGGGAGCGTGCATCCACGAGTACACCGGCAACCTCGGCGGCTG GGTGGACAAGTGGGTGGACTCAAGCGGGTGGGTGTACCTCGAGGCCCCT GCCCACGACCCGGCCAACGGCTATTACGGCTACTCCGTCTGGAGCTACT GCGGGGTGGGCTGA |
| 81 | SEQ ID NO: 80 of U.S. Pat. No. 7407677 | MKPAKLLVFVLVVSILAGLYAQPAGAAKYLELEEGGVIMQAFYWDVPSG GIWWDTIRQKIPEWYDAGISAIWIPPASKGMGGAYSMGYDPYDFFDLGE YDQKGTVETRFGSKQELVNMINTAHAYGIKVIADIVINHRAGGDLEWNP FVNDYTWTDFSKVASGKYTANYLDFHPNEVKCCDEGTFGGFPDIAHEKS WDQYWLWASNESYAAYLRSIGVDAWRFDYVKGYGAWVVKDWLDWWGGWA VGEYWDTNVDALLNWAYSSDAKVFDFPLYYKMDAAFDNKNIPALVEALK NGGTVVSRDPFKAVTFVANHDTDIIWNKYPAYAFILTYEGQPTIFYRDY EEWLNKDRLKNLIWIHDHLAGGSTDIVYYDNDELIFVRNGYGDKPGLIT YINLGSSKAGRWVYVPKFAGACIHEYTGNLGGWVDKWVDSSGWVYLEAP AHDPANGYYGYSVWSYCGVG |
| 82 | SEQ ID NO: 81 of U.S. Pat. No. 7407677 | ATGAAGAAGTTTGTCGCCCTGTTCATAACCATGTTTTTCGTAGTGAGCA TGGCAGTCGTTGCACAGCCAGCTAGCGCCGCAAAGTATTCCGAGCTCGA AGAGGGCGGCGTTATAATGCAGGCCTTCTACTGGGACGTCCCAGGTGGA GGAATCTGGTGGGACACCATCAGGAGCAAGATACCGGAGTGGTACGAGG CGGGAATATCCGCCATTTGGATTCCGCCAGCCAGCAAGGGGATGAGCGG CGGTTACTCGATGGGCTACGATCCCTACGATTTCTTTGACCTCGGCGAG TACAACCAGAAGGGAACCATCGAAACGCGCTTTGGCTCTAAACAGGAGC TCATCAATATGATAAACACGGCCCATGCCTACGGCATAAAGGTCATAGC GGACATCGTCATAAACCACCGCGCAGGCGGAGACCTCGAGTGGAACCCG TTCGTTGGGGACTACACCTGGACGGACTTCTCAAAGGTGGCCTCGGGCA AATATACTGCCAACTACCTCGACTTCCACCCCAACGAGGTCAAGTGCTG TGACGAGGGCACATTTGGAGGCTTCCCAGACATAGCCCACGAGAAGAGC TGGGACCAGTACTGGCTCTGGGCGAGCGATGAGAGCTACGCCGCCTACC TAAGGAGCATCGGCGTTGATGCCTGGCGCTTTGACTACGTGAAGGGCTA CGGAGCGTGGGTCGTCAAGGACTGGCTCAACTGGTGGGCGGCTGGGCC GTTGGCGAGTACTGGGACACCAACGTTGATGCACTCCTCAACTGGGCCT ACTCGAGCGGCGCCAAGGTCTTCGACTTCCCGCTCTACTACAAGATGGA TGAGGCCTTTGACAACAAAAACATTCCAGCGCTCGTCTCTGCCCTTCAG |

TABLE 4-continued

DNA coding sequences and protein sequences of non-limiting examples of amylases that can be used in the methods and compositions disclosed herein.

| SEQ ID NO: | Reference from Other Patents | |
|---|---|---|
| | | AACGGCCAGACTGTTGTCTCCCGCGACCCGTTCAAGGCCGTAACCTTTG<br>TAGCAAACCACGACACCGATATAATCTGGAACAAGTACCTTGCTTATGC<br>TTTCATCCTCACCTACGAAGGCCAGCCCGTCATATTCTACCGCGACTAC<br>GAGGAGTGGCTCAACAAGGACAGGTTGAACAACCTCATATGGATACACG<br>ACCACCTCGCAGGTGGAAGCACGAGCATAGTCTACTACGACAGCGACGA<br>GATGATCTTCGTGAGGAACGGCTATGGAAGCAAGCCTGGCCTTATAACT<br>TACATCAACCTCGGCTCGAGCAAGGTTGGAAGGTGGGTTTATGTGCCGA<br>AGTTCGCGGGCGCGTGCATCCACGAGTATACTGGTAACCTCGGAGGCTG<br>GGTAGACAAGTACGTCTACTCAAGCGGCTGGGTCTATCTCGAAGCTCCA<br>GCTTACGACCCTGCCAACGGGCAGTATGGCTACTCCGTGTGGAGCTATT<br>GCGGTGTTGGGTGA |
| 83 | SEQ ID NO: 82<br>of U.S. Pat. No. 7407677 | MKKFVALFITMFFVVSMAVVAQPASAAKYSELEEGGVIMQAFYWDVPGG<br>GIWWDTIRSKIPEWYEAGISAIWIPPASKGMSGGYSMGYDPYDFFDLGE<br>YNQKGTIETRFGSKQELINMINTAHAYGIKVIADIVINHRAGGDLEWNP<br>FVGDYTWTDFSKVASGKYTANYLDFHPNEVKCCDEGTFGGFPDIAHEKS<br>WDQHWLWASDESYAAYLRSIGVDAWRFDYVKGYGAWVVKDWLNWWGGWA<br>VGEYWDTNVDALLNWAYSSGAKVFDFPLYYKMDEAFDNKNIPALVSALQ<br>NGQTVVSRDPFKAVTFVANHDTDIIWNKYLAYAFILTYEGQPVIFYRDY<br>EEWLNKDRLNNLIWIHDHLAGGSTSIVYYDSDEMIFVRNGYGSKPGLIT<br>YINLGSSKVGRWVYVPKFAGACIHEYTGNLGGWVDKYVYSSGWVYLEAP<br>AYDPANGQYGYSVWSYCGVG |

In a broad sense, the alpha amylases isolated from, derived from, or recombined with any origins are implied, including bacterium, fungi, animal, and plant origins. Examples of the origins may include, for example, *Bacillus, Aspergillus, Pseudomonas fluorescens, Pseudomonas sarccharophilla*, etc.

Low Dose Enzymatic Formulations for Producing a Paper Product

Embodiments disclosed herein provide low dose enzymatic formulations for producing a paper product. In some embodiments, the low dose enzymatic formulations may comprise a polypeptide having an amylase activity. In some embodiments, the polypeptide having the amylase activity is applied to a starch at 0.01 ppm to 1000 ppm based on the weight of the starch.

In the present disclosure, the amount of the aforementioned alpha amylase for surface starch treatment is about 0.0001 wt % (5 ppm) market product (the polypeptide of SEQ ID NO: 12, i.e. SEQ ID NO:2 of U.S. Pat. No. 7,273,740 of Table 3) to 10 wt %, preferable 0.0005 wt % to 0.5 wt % based on the weight of starch, preferably from 0.001% to 0.1%, more preferably from 0.001% to 0.01% based on the weight of the starch.

In some embodiments, the enzyme formulation may comprise 1% to 50% amylase. In some preferred embodiments, the enzyme formation may comprise less than 3%, for example, 1%, amylase. In some embodiments, the enzyme formulation is provided to a starch at 0.001% to 1% by weight.

In some embodiments, the amylase may be a mixture or cocktail of commercial alpha amylase enzyme/enzymes (including for example amylases from BASF, Novozymes), with at least one de-branching enzyme. Any glycohydrolases with de-branching functions can be used. One non-limiting example is a gamma amylase, an exo-amylase, pullunanase, or mixtures containing beta amylase, and gamma amylase.

The amount of the aforementioned alpha amylase for surface starch treatment is about 0.0005% (5 ppm) to 0.5% based on the weight of starch, preferably between 0.001% and 0.1%, more preferably between 0.001% and 0.01% based on the weight of the starch. The temperature of the starch (surface) modification can range from 70 C to 110 C, preferably 85 C to 100 C. Optionally, the enzymatic starching modification can be carried out in the pre-heating step of the starch cooking, prior to jet-cooking. Optionally, it can be conducted at starch cooker stage at temperatures below 114 C. The pH of enzyme treatment may first be treated between pH 3 to pH 8, preferably between pH 5 to pH7.5. Optionally, the starch is enzymatically treated between pH 5-7, and then adjusting pH to alkaline range by Ca(OH)$_2$ or CaO, where alkaline starch surface composition is formed.

Debranching Enzymes

In some embodiments, the enzyme formulations disclosed herein may be used in combination with a debranching enzyme. In some alternative embodiments, the enzyme formulations disclosed herein may be used in the absence of a debranching enzyme. In some embodiments, the debranching enzyme is a hemicellulase, an isoamylase, a beta amylase, a gamma amylase, an exo-amylase, a pullulanase, a xylanase, a mannanase, an alpha gluconase, an endocellulase, an exocellulase, or any combination thereof.

Compositions for Producing a Paper Product

Embodiments disclosed herein further provide compositions for producing a paper product comprising an enzymatic formulation disclosed herein and a paper or a paper pulp or a biomass material.

Starch Modification

Embodiments disclosed herein provide use of an enzyme formulation for producing a paper or board surface treatment composition, comprising: (a) providing an enzymatic formulation comprising a polypeptide having an amylase activity; (b) providing a starch; and (c) contacting the enzymatic formulation with the starch, thereby hydrolyzing the starch to produce a paper surface treatment composition comprising modified degraded starch having a weight-average molecular weight (Mw) in the range from 10,000 to 12,000,000 and with a polydispersity index (Mw/Mn) of 1.3 to 49.

The surface starch used in accordance with the present compositions and methods can be starches from any sources from the plant kingdom. Common sources are corn/maize, potato, wheat, cereals, rice, legumes, tapioca, tubers, roots, nuts, seeds, kernels. The starches could also be any biomass-containing starch components from plants or agricultural residues. The starches may be present with other hemicelluloses or polysaccharides, such as but not limited to galactomannans, xylans, arabinoxylans, glucuronoxylans, glucomannans, xyloglucans (such as Tamarind seed flour), pectins/pectate, galactans, arabinogalactans. In the case where starch used contains other polysaccharides, it is optional that hemicellulase enzymes or polysaccharide enzymes may be used in combination with the amylase for the preparations of the surface starch composition. In one option, xylanases (Luminase, PB-100, PB-200) from BASF can be used. In fact hemicellulses, xylanases, and cellulases from any supply is implied, including from Novozymes, Dyadic, Dupont, and BASF. If the starchy materials contain proteins and fats, protease and lipases may optionally be used in combination with the aformentioned enzymes comprising amylase.

Preferably the temperature of the starch (surface) modification can range from 70° C. to 110° C., preferably 85° C. to 100° C. Optionally, the enzymatic starching modification can be carried out in the pre-heating step of the starch cooking, prior to jet-cooking. Optionally, it can be conducted at starch cooker stage at temperatures below 114° C. The pH of enzyme treatment may first be treated between in the range from pH 3 to pH 8, preferably from pH 5 to pH 7.5. Optionally, the starch is enzymatically treated in the range from pH 5 to 7, and then adjusting pH to alkaline range by $Ca(OH)_2$ or CaO, where alkaline starch surface composition is formed.

The amylase enzymatic modification of starch, may be conducted at the starch manufacturing facility, and therein supplied to the paper mills for use in the surface starch preparations such as in a jet cooker.

Alternatively, the amylase enzymatic treatment of starch may be conducted on-site of a paper mill, wherein the on-site enzyme-modified starch is further cooked in a jet cooker.

Methods of applying the surface starch composition are also facilitated by the highly effective amylase enzymes disclosed herein. For instance, in the traditional puddled size-press, the starch solids is very much limited by the viscosity of the starch solution, making it very uneconomical in terms of water evaporation load, as well as reduced paper properties due to less starch mass staying on the surface layers. The highly effective starch modification of the present amylase allows the use of higher solids of starches in puddled size-press because of the substantially reduced and uniformly generated viscosities. This effect can also be applied to the metering size-press, and even in pigmented coating (starch) binders, further improving starch solids in surface treatment.

In another embodiment, the highly effective and economically low dosage of amylase starch (surface treatment) modification disclosed herein, enables the use of native starches in spray coating, or curtain coating, wherein very low viscosity and consistently uniform rheology is required. One version of the curtain application is the use of shower boxes on top of the wet end forming section of the Fourdrinier paper machines, as is manufactured by Black Clawson (Kadant). Another application enabled by the highly effective amylase is to apply sufficient quantity of starch into the paper machine headboxes, preferably in the top layers of the multi-layer headboxes, without negatively affecting the forming and drainage in papermaking.

The enzyme inactivation can be achieved by pressurized heating or jet-cooking above 114° C. A non-limiting example of the Jet-Cooking process is described in EP 1109927. The inactivation can also be made by chemical means, or combinations of thermal-chemical means. Examples of the chemical inactivation include the use of alkali chemicals, such as NaOH, KOH, $Ca(OH)_2$ (slaked lime), ammonium hydroxide, sodium or potassium hypochlorite, sodium carbonate (soda ash), magnesium hydroxide, sodium silicate solutions, alkali salts of peroxides such as sodium percarbonate, sodium perborate, sodium persulfate, sodium/potassium permonosulfate (Oxone), quaternary amines, polyvinylamines, cross-linking agents (which is described in the following paragraphes), borax, glyoxal, Kymene, G-PAM, sodium azide, AKD sizing chemicals, alkaline hydrogen peroxide, catalytic peroxide, UV-peroxide, alkaline peroxyformic acid, alkaline peracetic acid, sodium phosphates, sodium or potassium acetate, ionic liquids (either imidazolium based or not), MMNO, etc. In another option, the starch solution may be cooled indirectly or directly and then treated with protease enzymes.

In one option, the amylase contained in the starch composition may be inactivated first by ammonium hydroxide, then $CO_2$ is added to neutralize the solution, wherein the ammonium carbonate generated can be easily decomposed into gaseous products (NH3 and CO2) and removed during heating and/or drying.

In some embodiment, the enzyme modification process of the surface treatment composition may contain stabilizers or activators for the amylase enzymes. For instance, calcium salts, preferably soluble or partially soluble calcium salts, can be applied during the amylase enzyme modifications. Non-limiting examples of stabilizers or activators include calcium chloride, phosphates, sulfates, carbonates, calcium salts of mono-organic acids or multi-carboxylic acids. Examples include calcium acetate, oxalates, propriate, gluconate, malonate, tartarate, citrate, lactate, sorbate, Calcium-EDTA, DTPA, Calcium stearate, Calcium oleate/palmitate, sulfamate, sulfonates, or any combination thereof. Other stabilizers include PEG or PEG derivatives, glycols, glycol ethers, glycerols, TWEEN, carboxymethyl cellulose, PVOH, or any combination thereof.

Degraded Starch Composition

Embodiments disclosed herein provide compositions comprising a starch having a weight-average molecular weight (Mw) in the range from 10,000 to 12,000,000 and a polydispersity index (Mw/Mn) of 1.3 to 49.

The degraded starch has preferable a weight-average molecular weight Mw of in the range from 500 000 to 12 000 000 and a polydispersity of 10 to 49, for example a degraded starch with weight-average molecular weight Mw of in the range from 500 000 to 12 000 000 and a polydispersity of 20 to 45. The degraded starch may have a weight-average molecular weight Mw that is, is about, is less than, is more than, 10,000, 20,000, 30,000, 40,000, 50,000, 100,000, 200,000, 300,000, 400,000, 500,000, 1,000,000, 2,000,000, 3,000,000, 4,000,000, 5,000,000, 10,000,000, 12,000,000, or a range between any two of the abovementioned values, for example, 10,000 to 12,000,000, 400,000 to 1,000,000, etc.

The width of the molar mass distribution is characterized by a value for the polydispersity (quotient of weight-average molecular weight Mw and number-average molecular weight Mn) and is in the range of 10 to 49, preferably at least 15 to 45, in particular at least 20 to 42.

In some embodiments, the enzyme modified starch composition can be modified with borax or glyoxal cross-linking, and sometimes used for adhesives and gluing applications.

Many of the aforementioned cross-liking agents in paper surface treatment composition can also serve to inactivate the amylase enzymes chemically.

In some embodiments, the enzymatically modified starch compositions can be combined with any papermaking or surface sizing/treatment minerals, inorganic pigments, including various types of clays, kaolin, PCC, GCC, calcium silicates, silica, plastic spheres pigments including hollow sphere pigments, expandable plastic spheres, microcrystalline celluloses, nanocrystalline cellulose, nano-frillated cellulose, colloidal MCC, TiO2, talc, alumina, etc.

In some preferred embodiments, the average molecular weight (Mw) of the starch is in the range from 400,000 to 5,000,000 and a polydispersity of 10 to 49 for film-press application technique.

In some preferred embodiments, the average molecular weight (Mw) of the starch is in the range from 400,000 to 12,000,000 and a polydispersity of 10 to 49 for size press application technique.

In some embodiments, the amylases and enzymatic formulations disclosed herein can be used in the compositions, processes and applications described in WO2006124869, WO2006124871, WO2007055911, WO2007055912, WO2010003054, WO2012076163, the contents of which are hereby expressly incorporated by reference in their entireties. In some embodiments, a polypeptide having amylase activity of SEQ ID NO: 12, i.e., SEQ ID NO:2 of Table 3 can be used in these compositions, processes and applications.

Aqueous Surface Treatment Composition

Further disclosed is a surface treatment composition comprising enzymatically modified starch or starchy materials. The surface treatment composition is mainly targeted for applications onto web materials, such as, but not limited to paper webs, nonwoven webs, fabric surface, or any web surfaces made of synthetic polymers, plastics, biopolymers, or biodegradable polymers. One particularly application, is related to the surface composition used for paper surface treatment by any means, including surface sizing, coating, pre-coat, and various paper machine wet end and dry end applications. The present disclosure further relates to the methods of paper surface treatment and the enzymatic modifications of the surface treatment compositions.

Embodiments disclosed herein provide paper or board surface treatment compositions comprising degraded starch. In some embodiments, the paper or board surface treatment compositions are obtained by a method comprising: (a) providing an enzymatic formulation comprising a polypeptide having an amylase activity; (b) providing a starch; and (c) contacting the enzymatic formulation with the starch, thereby hydrolyzing the starch to produce a paper surface treatment composition comprising modified degraded starch having a weight-average molecular weight (Mw) in the range from 10,000 to 12,000,000 and with a polydispersity index (Mw/Mn) of 1.3 to 49.

Preference is given to an aqueous surface treatment composition for paper and board comprising 2 to 30 wt %, especially 3 to 25 wt % of the degraded starch.

The aqueous surface treatment composition described herein may further comprise a surface sizing agent based on an aqueous dispersion. The aqueous dispersions may possess anionic or cationic charge and they have a particle size of between 50 and 500 nm.

Examples of suitable dispersions are those obtainable by copolymerizing ethylenically unsaturated monomers, especially acrylonitrile and (meth)acrylates, and also, optionally, up to 10 wt % of further monomers such as styrene, by means of radically initiated emulsion polymerization in the presence of degraded starch. It is possible here for chain transfer agents to be used. Aqueous dispersions of this kind are described in EP 0 273 770, EP 0 257 412, WO 99/42490, WO 2002/14393, WO 2007/000419, WO 2007/000420, and WO 2011/039185, the disclosure content of which is expressly referenced.

In some embodiments, the surface treatment composition may contain any types of papermaking dyes or colorants, including organic dyes, and pigment dyes.

In some embodiments, the surface treatment composition contains optical brightening agents (OBAs). Any conventional or non-conventional OBA can be used to brighten mechanical or Kraft pulp based papers can be used. Any brighteners cited, for example, in Ullmann's Encyclopedia of Industrial Chemistry, Sixth Edition, 2000 Electronic Release, OPTICAL BRIGHTENERS—Chemistry of Technical Products which is incorporated here by reference. Other useful optical brighteners are described in U.S. Pat. Nos. 5,902,454; 6,723,846; 6,890,454; 5,482,514; 6,893,473; 6,723,846; 6,890,454; 6,426,382; 4,169,810; and 5,902,454 and references cited are all included. Useful examples of optical brighteners are 4,4'-bis-(triazinylamino)-stilbene-2,2'-disulfonic acids, 4,4'-bis-(triazol-2-yl)stilbene-2,2'-disulfonic acids, 4,4'-dibenzofuranyl-biphenyls, 4,4'-(diphenyl)-stilbenes, 4,4'-distyryl-biphenyls, 4-phenyl-4'-benzoxazolyl-stilbenes, stilbenyl-naphthotriazoles, 4-styryl-stilbenes, bis-(benzoxazol-2-yl) derivatives, bis-(benzimidazol-2-yl) derivatives, coumarins, pyrazolines, naphthalimides, triazinyl-pyrenes, 2-styryl-benzoxazole or -naphthoxazoles, benzimidazole-benzofurans or oxanilides.

Commercially available optical brightening agents based on stilbene, coumarin and pyrazoline structures are included. Some preferred optical brighteners include 1,3,5-triazinyl derivatives of 4,4'-diaminostilbene-2,2'-disulfonic acid and salts thereof, which may carry additional sulfo groups, as for example at the 2, 4 and/or 6 positions. Commercially available stilbene derivatives from Ciba Geigy under the tradename "Tinopal", from Clariant under the tradename "Leucophor", from Lanxess under the tradename "Blankophor", from 3V under the tradename "Optiblanc" such as disulfonate, tetrasulfonate and hexasulfonate stilbene based optical brightening agents are all included. The commercially available disulfonate and tetra sulfonate stilbene based optical brightening agents are more preferred in some embodiments.

Cross linking agents can optionally be applied to the surface treatment composition after enzymatic starch modifications. Multi-functional carboxylic acids, such as 1,2,3,4-Butanetetracarboxylic acid (BTCA), Poly (maleic acid), (PMA), poly(itaconic acid), and citric acid may be used for cross-linking reaction, preferably with catalysts. Crosslinking may also be achieved with a water-dispersible or water-soluble bi-, multifunctional carbodiimide and/or polycarbodiimide such as 1,6-hexamethylene bis(ethylcarbodiimide); 1,8-octamethylene bis(ethylcarbodiimide); 1,10 decamethylene bis(ethylcarbodiimide); 1,12 dodecamethylene bis (ethylcarbodiimide); PEG-bis(propyl(ethylcarbodiimide)); 2,2'-dithioethyl bis(ethylcarbodiimde); 1,1'-dithio-p-phenylene bis(ethylcarbodiimide); and 1,1'-dithio-m-phenylene bis(ethylcarbodiimide).

In some embodiments, the starch surface treatment composition may contain non-reactive sizing agents, for instance, without limitation, BASOPLAST® 335D non-reactive polymeric surface size emulsion from BASF, FLEXBOND® 325 emulsion of a co-polymer of vinyl acetate and butyl acrylate from Air Products and Chemicals, and PENTAPRINT® non-reactive sizing agents as disclosed in WO97/45590 from Ashland (Hercules, Solenis).

The amylase enzyme modification disclosed herein creates fresh hydroxyl groups from starch molecules in the surface composition, which can be interacted with cationic treatment, dry strength agents, wet strength agents, or cross-linking, after the enzymatic modifications. Any wet strength agents and dry strength agents common used in paper industry is incorporated. Dry strength agents based on polyacrylamide in included. Wet strength agents such as polyaminoamide-epichlorohydrin (PAE), or Kymene, are included, as well as dialdehyde starches. One particular example is the G-PAM (glyoxalated polyacrylamide) chemistry of BASF, which is an excellent dry strength agent as well as a temporary wet strength agent.

The cationization can be achieved either reactively, or non-reactively by associations. For instance, the cationic agents include 1-ethyl-3-(3-dimethylaminopropyl)-carbodiimide hydrochloride (EDC), hexadimethrine bromide, polyethyleneimines (both linear and branched), copolymers of diallyldimethyl ammonium chloride (DADMAC), copolymers of vinyl pyrrolidone (VP) with quaternized diethylaminoethylmethacrylate (DEAMEMA), polyamides, cationic polyurethane latex, cationic polyvinyl alcohol, polyalkylamines, dicyandiamide copolymers, amine glycidyl addition polymers, poly[oxyethylene (dimethyliminio) ethylene (dimethyliminio) ethylene] dichlorides, polyallylamine (PAH), poly (hexamethylene biguanide hydrochloride) (i.e. PHMB), polyamidoamine (or polyethylenimine); cationic metal ions, such as water-soluble aluminum salts, calcium salts, and zirconium salts; cationic dendrimers including PAMAM (polyamidoamine) dendrimers with amino surface groups, and polypropylenimine dendrimers with amino surface groups. One particular cationic agent is the high charge density polyvinylamine (PVAM) from BASF.

Extracted wood hemicellulose or extracted lignin particles may be blended into the starch surface treatment composition disclosed herein, for paper, board, or packaging applications. In this case, optionally, hemicellulose enzymes, glycyl transferase enzymes, oxidoreductase enzymes (laccase, peroxidases, etc.), endo-cellulase and/or exo-cellulase enzymes may be applied, in addition to the aforementioned amylase enzymes.

In some embodiments, the aqueous surface treatment composition of the disclosure preferably has a viscosity in the range from 1 to 200 mPas (12% solids content and Brookfield spindle 2 at 100 rpm at which solids content (Brookfield LV viscosity, spindle 4, 6 rpm, RT).

The surface treatment composition disclosed herein is suitable for treatment of base paper. The paper obtained accordingly is distinguished by high strengths.

The surface treatment compositions disclosed herein may be processed by all of the methods suitable in a surface sizing context. Application with the surface treatment composition of the disclosure takes place in a film and/or size press or by a contactless application technique with a spraying bar or curtain treatment process. Treatment may be accomplished by means of a doctor blade or a nozzle. Preferred in some embodiments is film-press application technique. Further preferred is size-press application technique.

In some embodiments, the aqueous surface treatment composition obtained by a method comprising the steps:
a) preparing a suspension of water and starch;
b) addition of 0,0001 to 1% of a polypeptide having at least 80% identity to SEQ ID NO:2; and
c) heating the mixture comprising starch and enzyme to a temperature of 60 to 100° C. for 5 to 60 Minutes.

Methods of Producing a Paper Product

Embodiments disclosed herein further provide methods of producing a paper product. In some embodiments, the methods of producing a paper product comprises: (a) providing a paper surface treatment composition comprising degraded modified starch with a polydispersity index (Mw/Mn) of 1.3 to 49; (b) providing a web material; and (c) applying the paper surface treatment composition to the web material whereby a paper product having improved surface quality is produced.

Application is made in the quantities customary in each case. For use, the surface treatment composition is normally added to the size press liquor in an amount of 0.05 to 3 7 wt %, based on solids, guided by the desired degree of sizing of the papers to be furnished.

The present disclosure further relates to a method for producing paper and board, comprising the steps of
a) treating paper stock with paper auxiliary and/or filler,
b) draining the paper stock treated by a), with sheet formation, and
c) treating the paper web obtained by b) with the surface treatment composition disclosed herein,
d) and drying the paper web coated by c).

Fibrous material used in accordance with aspects of the disclosure may comprise virgin and/or recovered fibers. Any softwood or hardwood fiber typically used in the paper industry may be employed, examples being unbleached chemical pulp, and also fibrous materials from any annual plants. Mechanical pulp includes, for example, groundwood, thermomechanical pulp (TMP), chemithermomechanical pulp (CTMP), pressure groundwood, semichemical pulp, high-yield pulp, and refiner mechanical pulp (RMP). Sulfate, sulfite, and soda chemical pulps are contemplated, for example. Suitable annual plants for producing fibrous materials include, for example, rice, wheat, sugarcane, and kenaf.

The pulp furnishes are preferably produced using waste paper, which is used either alone or in a mixture with other fibrous materials.

One method for producing paper and board comprises the steps of
a) treating paper stock with paper auxiliary and/or filler,
b) draining the paper stock treated by a), with sheet formation, and
c) treating the paper web obtained by b) with the surface treatment composition disclosed herein,
d) and drying the paper web coated by c),
with the proviso that no polyvinyl alcohol fibers are part of the pulp.

In the case of waste paper it is possible to use a fibrous material having a freeness of 20 to 50 SR. In general a fibrous material with a freeness of about 40 SR is used, which is ground during the production of the pulp furnish. Preference is given to using fibrous material having a freeness of ≤40 SR.

The disclosed method may serve for producing filler-containing paper. The filler content of the paper is generally 1-20 wt %, preferably 5 to 20 wt %, more particularly 10-15 wt %, based on dry total paper stock or on paper stock. Filler here, as is usual in papermaking, means inorganic pigment.

As well as the filler, generally at a fibrous material concentration of 5 to 15 g/l, it is possible optionally for customary paper auxiliaries to be admixed to the paper stock. Examples of conventional paper auxiliaries are sizing agents, wet strength agents, cationic or anionic retention agents based on synthetic polymers, and also dual systems, dewatering agents, optical brighteners, defoamers, biocides, and paper dyes. These conventional paper additives may be used in the customary amounts.

Stock sizing agents include alkylketene dimers (AKDs), alkenylsuccinic anhydrides (ASAs), and rosin size.

Wet strength agents are synthetic dry strengtheners such as polyvinylamine, or natural dry strengtheners such as starch.

Retention aids suitable include, for example, anionic microparticles (colloidal silica, bentonite), anionic polyacrylamides, cationic polyacrylamides, cationic starch, cationic polyethyleneimine, or cationic polyvinylamine. Further conceivable are any desired combinations thereof, examples being dual systems consisting of a cationic polymer with an anionic microparticle or of an anionic polymer with a cationic microparticle. To achieve high filler retention, it is advisable to add such retention aids as may be added, for example, to thin stuff as well as to thick stuff.

Drainage takes place on the wire of the paper machine, with sheet formation. The paper web obtained accordingly then passes through the press section, in which the paper web is generally dried to a solids content of <40 wt %. This is followed by further dewatering by drying.

The treating step takes place during the drying phase. Depending on the paper machine, there may already be a drying unit upstream of the coating apparatus, preferably a size press.

The present disclosure relates further to the paper treated with the disclosed surface coating composition. Corrugated boards produced using this paper exhibit enhanced strength properties.

The surface treatment composition from the enzymatic starch modification disclosed herein, also facilitates the improved methods of surface treatment strategies. For instance, this extend the solids range and operability of traditional size-press of starches, and coating applications. It also enable the use of this type of enzymatically modified starches for spray surface treatment or spray coating formulations. The disclosed enzymatically modified starches, due to reduced viscosity or manageable higher solids, may also be used on "shower coating" or "curtain coating" on the wet end former or on the dry end. Other enabled applications include addition on the top layers (or target layers) of multi-layer paper machine headboxes; in the "water-boxes" of calendars, and as adhesive component for paper packaging, to name a few.

Coating and Surface Seizing

It is possible, generally speaking, to coat base paper in a separate film press and/or size press. The film press and/or size press is preferably arranged inline in the paper machine. Generally it is incubated into the drying unit. At the time of application, the paper sheet preferably has a water content of <60 wt %.

The disclosed surface treatment composition may be applied to base paper.

The amount of treatment composition is applied with a coatweight of preferably 0.1 to 10 g/m2.

The surface treatment composition disclosed herein can be applied to any web materials, and particularly paper web materials. The paper web materials include any paper grades, uncoated or coated, unbleached, semi-bleached, or fully bleached paper grades, printing and writing papers of any sorts, uncoated free sheet, surface sized papers, high yield papers (containing mechanical or chemi-mechanical pulps), newsprint, LWC, film coated mechanical grades, surface treated mechanical grades, paper boards of any types, uncoated board, coated board, white board, brown boards, SUS, SBS, multi-layered boards, linerboards, kraft papers, sulfite papers, medium papers, and corrugated boards, tissues, towels, napkins, wipes, nonwovens, paper web containing glass fibers, plastic fibers, and certain textile fabrics used as printing or digital printing media.

Typically the starch cooking process for surface application in the paper making customer is conducted in 3 process steps. Firstly a suspension of starch with solid contents of 20-35% is prepared at room temperature. To this slurry the enzyme are added in typical concentrations of and the suspension is transferred to starch cooker vessel. In the transfer pipe the slurry is optionally heated up in a jet stream in order to achieve gelatinize starch granules. In the starch cooker the starch suspension and enzyme are heated to 60 to 90° C. in order to get fast enzymatic degradation of the starch to achieve lower molecular weight of the starch. The residence time in starch cooker is typically between 5 to 60 minutes, more preferably 20 to 30 min. The solids content of the slurry is diluted by the steam used to heat up the slurry. Typically the solids content is in the range from 10-30 wt % more preferably in the range from 20 to 25 wt %. The targeted viscosities are typically 100-300 mPas (Sp. 2) at 85° C. However shorter and longer residence times and starch cooking temperatures are also feasible but commercially not to so common. In order to inactive the starch the cooked starch solution is heated to 120 to 130 C by feeding the solution through a steam jet. The residence time in the steam jet can be very short i.e. 1 to 60 seconds. Afterwards the starch solution is stored at elevated temperature 60-90° C. Prior to application the starch are diluted to 6 to 12% with a viscosity of 20 to 90 mPas Sp II at 80° C.

WO2014 003556 discloses coating paper using highly branched starch produced by a debranching enzyme, e.g., isoamylase, the content of which is hereby incorporated by reference in its entirety. EP1214442 discloses of using a maltogenic amylase for coating/seizing of paper, the content of which is hereby incorporated by reference in its entirety.

One aspect of the present disclosure is directed to paper surface treatment using an enzymatically modified starch containing formulations, wherein a unique amylase enzyme enables:

Substantially improved dose effectiveness and economical advantage of the enzymatic starch modifications vs. current commercial amylase enzymes.

Improved pick up of starch-containing surface treatment at same solids or at higher and manageable solids due to effectively reduced viscosities.

This will therefore allow the most efficient use of many of the surface treatment strategies, for delivering the utmost amount or efficiency of target paper chemicals on the paper surface. For instance, this will allow more Optical Brightener Agents (OBAs) or Dye/Colorants on the surface. It may also deliver higher amount of starch on the surface, among other effects, for strength or bending stiffness (i.e. the I-Beam effect).

Without being bound by the theory, we believe, these surprising benefits in surface treatment composition may be also partially due to the unique mode of random and uniform actions on starch molecules by this type of amylase enzyme or enzymes. For instance, in the starch liquefaction for syrups or for biofuels/bio-product conversions, this amylase is known to have substantially improved thermo-stability, pH stability, fast and more effective actions. It is also shown to have a unique mode of attacking the starch molecules, more random and more uniform than the comparative other enzymes derived from bacterium, as demonstrated by the much narrower polydispersity of starch hydrolysis from members of this unique amylase groups as measured by size exclusion chromatography. Richardson et al., supra; Atichokudomchai et al., supra. The significant difference of the amylase disclosed in these references from commercial enzymes such as Termamyl® LC and Termamyl® SC was clearly demonstrated.

The surface treatment composition from the enzymatic starch modification, also facilitates the improved methods of surface treatment strategies. For instance, this extends the solids range and operability of traditional size-press of starches, and coating applications. It also enables the use of this type of enzymatically modified starches for spray surface treatment or spray coating formulations. The disclosed enzymatically modified starches, due to reduced viscosity or manageable higher solids, may also be used on "shower coating" or "curtain coating" on the wet end former or on the dry end. Other enabled applications include addition on the top layers (or target layers) of multi-layer paper machine headboxes; in the "water-box" of calendars, and as adhesive component for paper packaging, to name a few.

Furthermore, the disclosed starch surface treatment composition provides good compatibility (or sometimes synergy) with other paper chemical systems, such as but not limited to, optical brighteners, color/dyes, cross-linking agents, strength agents, fillers, pigments, non-traditional surface treatment binders, latex, dispersants, surface property (charge, friction, barriers, gloss, smoothness) agents, and other enzyme systems.

Paper Products with Improved Surface Quality

Embodiments disclosed herein further provide paper products having improved surface quality. In some embodiments, the paper products having improved surface quality are produced using a paper surface treatment composition disclosed herein. In some embodiments, the paper surface treatment composition comprises modified degraded starch having a weight-average molecular weight (Mw) in the range from 10,000 to 12,000,000 and with a polydispersity index (Mw/Mn) of 1.3 to 49.

In some embodiments, the paper products have improved surface quality selected from the group consisting of water resistance, a barrier property for moisture, vapor, oxygen, oil, or grease, resistance to fuzz, reduced abrasiveness, a printing property, a surface charge property, ink/color/dye fixation, and bonding or surface strength. In some embodiments, the paper products have enhanced starch pick-up due to higher solids with reduced viscosities. In some embodiments, the pick-up of the paper products ranges from 0.2 grams per square meter up to 50 grams per square meter. In some embodiments, the optical brightener pick-up of the paper products is enhanced by 5% compared to the untreated paper. In some embodiments, the liner board compression strength of the paper products is enhanced by 3 Kilo newton per meter (SCT(CD) compared to the untreated paper.

With being limited to any particular theory, it is believed that many of the amylase enzyme stabilizers can contribute synergistically to paper properties, such as color enhancement, OBA enhancement, printing or ink improvement, surface charge development, etc.

Paper Products Comprising Degraded Starch

Embodiments disclosed herein further provide paper or board products comprising a degraded starch. In some embodiments, the degraded starch has a weight-average molecular weight (Mw) in the range from 10,000 to 12,000,000 and with a polydispersity index (Mw/Mn) of 1.3 to 49.

EXAMPLES

The examples which follow illustrate aspects of the present disclosure. The percentages in the examples are by weight, unless otherwise stated.

The solids content was ascertained by temperature-conditioning a sample of the product (approximately 3 g)—that is, drying it to constant weight—in a preheated forced air drying cabinet at 120° C.

Polymers used in the inventive and comparative examples were as follows.

General Experimental Procedures

Procedure of Alpha Amylase Treatment on Starch

Starch was made into slurry at target solids concentrations, usually from 40 g/L to 100 g/L.

The starch slurry was heated to warm temperature of 88° C., and specified doses of alpha amylase enzymes were added under stirring. The system was then heated at 88° C. temperature of 40 minutes to carry out the enzyme modification reactions, after which the system was further heated to 130° C. to inactivate the enzyme.

Preparation of Starch Solution:

Merizet® 120 maize starch (from Tate & Lyle) was used, and was enzymatically degraded as follows: a 12% slurry of Merizet 120 was prepared in hot water at 65° C. under agitation in a 1000 L vessel, and 0.012% of PL 120 enzyme from Novozyme was added. After 20 minutes, 100 ml of acetic acid were metered into the starch solution to terminate the process of starch degradation. The starch solution had a viscosity of 55 mPas at 100 rpm (spindle 2).

Determination of the weight-average molecular weight (Mw) and number-average molecular weight (Mn) of the starch solution The aqueous starch solutions were diluted with DMSO and thereby stabilized. The molar mass distribution was determined by GPC-MALLS (gel chromatography with multiangle laser light scattering). The GPC-MALLS consists of a Waters 515 pump module, devotalilizer, Waters 717 Autosampler, GPC column heating (Jet Stream). The MALLS detector is a Dawn-Heleos (Wyatt Technology, Santa Barbara, USA) equipped with a K5 flow cell and a He—Ne laser m from 10 to 658 nm and equipped with 16 detectors with an angle of 15 to 162°. The following GPC columns were used in series: Suprema S 30000, S 1000, and S 10 (PSS, Mainz, Germany). The samples were eluted with a DMSO-containing 0.09 M NaNO3 solution with a flow rate of 0.5 ml/min and a temperature of 70° C. in the GPC columns. For software analysis, ASTRA 5.3.0.18 was used.

Paper Coating and Paper Testing

In following examples and comparative examples standard uncoated testliner from Thur Papier (120 g/m2) were coated using a lab size press (Company Mattis, Type SP). The coated papers were subsequently contact dried using heated (120 C) cylinders for 5 minutes to achieve a moisture content of 5% for the coated paper sheets. In order to achieve sufficient pick up the papers were run through the size press twice prior to drying.

Paper Testing

Prior to paper testing the papers were stored for 24 h and 50% humidity and following strength parameters were tested
- Berst according to DIN ISO 2758 (up to 600 kPa) and DIN ISO 2759 (above 600 kPa)
- SCT according to DIN 54518 (Shortspan compression test)
- CMT according to DIN EN 23035 (Corona medium test)

Example 1 Dose Effectiveness of Amylase on Wheat Starch Modification

An industrial wheat starch obtained from Propapier (Germany) was dispersed into slurry at 100 g/L, and treated with enzymes with the procedure as in described in the Experimental session. In this example, enzymatic formulation comprising SEQ. ID NO: 12, i.e., SEQ ID NO:2 of U.S. Pat. No. 7,273,740 of Table 3 was used at doses of 0.01%, 0.02%, 0.03%, and 0.06% based on the weight of the starch. In comparison, a commercial amylase enzyme, Gammalpha 120L was used at dose of 0.06%.

The results are summarized in the table below. The viscosity was determined with a Brookfield Viscosimeter (Sp I, 20 RPM)

TABLE I

| Example | 100 g/L wheat starch | Viscosity, mPas at 80 C., 100 rpm | Viscosity, mPas at 50 C., at 100 rpm |
|---|---|---|---|
| Comparative example C1 | Treatment with 0.06% Gammalpha 120L | 30.0 | 33.6 |
| 1a | Treatment with 0.06% enzymatic formulation comprising polypeptide of SEQ ID NO: 12 (SEQ ID NO: 2 of U.S. Pat. No. 7,273,740 of Table 3) | 14.5 | 15.5 |
| 1b | Treatment with 0.03% enzymatic formulation comprising polypeptide of SEQ ID NO: 12 (SEQ ID NO: 2 of U.S. Pat. No. 7,273,740 of Table 3) | 14.5 | — |
| 1c | Treatment with 0.02% enzymatic formulation comprising polypeptide of SEQ ID NO: 12 (SEQ ID NO: 2 of U.S. Pat. No. 7,273,740 of Table 3) | 18.4 | — |
| 1d | Treatment with 0.01% enzymatic formulation comprising polypeptide of SEQ ID NO: 12 (SEQ ID NO: 2 of U.S. Pat. No. 7,273,740 of Table 3) | 32.5 | 35.5 |

TABLE II

| Example | 100 g/L wheat starch | Mw g/mol | Mn g/mol | Polydispersity Index |
|---|---|---|---|---|
| C1 | Treatment with 0.06% Gammalpha 120L | 4300000 | 45000 | 96 |
| 1a | Treatment with 0.06% enzymatic formulation comprising polypeptide of SEQ ID NO: 12 (SEQ ID NO: 2 of U.S. Pat. No. 7,273,740 of Table 3) | 3200000 | 128000 | 25 |
| 1b | Treatment with 0.03% enzymatic formulation comprising polypeptide of SEQ ID NO: 12 (SEQ ID NO: 2 of U.S. Pat. No. 7,273,740 of Table 3) | 3700000 | 123333, 333 | 30 |
| 1c | Treatment with 0.02% enzymatic formulation comprising polypeptide of SEQ ID NO: 12 (SEQ ID NO: 2 of U.S. Pat. No. 7,273,740 of Table 3) | 4300000 | 95555, 5556 | 45 |
| 1d | Treatment with 0.01% enzymatic formulation comprising polypeptide of SEQ ID NO: 12 (SEQ ID NO: 2 of U.S. Pat. No. 7,273,740 of Table 3) | 5600000 | 116666, 667 | 48 |

It is obvious that, the enzymatic formulation comprising polypeptide of SEQ ID NO:12 (SEQ ID NO: 2 of U.S. Pat. No. 7,273,740 of Table 3) is much more effective than the commercial amylase G, in reducing the starch viscosity, as measured at both 50° C. and 80° C. This represents substantial economic advantages.

Example 2 Size Press Application on the Surface Treatment Composition: Viscosity and Starch Pick-Up A size-press application experiment was conducted using the starch surface compositions modified by the amylase enzymes as described above in Example 1, 0.06% enzymatic formulation comprising the polypeptide of SEQ ID NO:12 (SEQ ID NO:2 of U.S. Pat. No. 7,273,740 of Table 3) vs. the Reference 0.06% Gammalpha 120L. The size press solution was maintained at 55° C., and the size press was run at a speed of 2 m/min, 2 application cycles, with a nip pressure of 1 bar. A liner grade of paper of basis weight 131.2 and 133.7 g/m² were used as base paper, and the size press was run at the same starch solids of 100 g/L. The wet pick-up and starch pick up were measured, summarized below.

TABLE III

| Surface sizing starch solution 100 g/L | Reference 0.06% Gammalpha | enzymatic formulation comprising 0.06% of the polypeptide of SEQ ID NO: 12 (SEQ ID NO: 2 of U.S. Pat. No. 7,273,740 of Table 3) |
|---|---|---|
| Viscosity 80 C., 20 rpm | 12.5 | 5.5 |
| Viscosity 50 C., 20 rpm | 17.5 | 7.5 |
| Viscosity 80 C., 100 rpm | 30.0 | 14.5 |
| Viscosity 50 C., 100 rpm | 33.6 | 15.5 |

TABLE III-continued

| Surface sizing starch solution 100 g/L | Reference 0.06% Gammalpha | enzymatic formulation comprising 0.06% of the polypeptide of SEQ ID NO: 12 (SEQ ID NO: 2 of U.S. Pat. No. 7,273,740 of Table 3) |
|---|---|---|
| Pick-up % | 48.7 | 54.9 |
| Starch pick-up, kg/ton | 48.7 | 54.9 |

It may be interesting to note that, the substantially reduced viscosity of starch surface treatment solutions may make it feasible to apply by spraying, shower, or curtain applications.

Example 3 Strategies to Replace Commercial Amylase with the Polypeptide of SEQ ID NO:12 (SEQ ID NO:2 of U.S. Pat. No. 7,273,740 of Table 3) at Substantially Reduced Enzyme Dose in Starch Surface Sizing while Maintaining Substantially the Same Properties This strategy is to replace the currently used commercial amylase enzymes in starch surface sizing, with the more effective polypeptide of SEQ ID NO:12 (SEQ ID NO:2 of U.S. Pat. No. 7,273,740 of Table 3) at substantially reduced doses for economics, runnability and reduced protein carry-over. A Merizet 120 (native corn starch from Tate and Lyle) was used in this example, where we compare 0.005% enzymatic formulation comprising polypeptide of SEQ ID NO:12 (SEQ ID NO:2 of U.S. Pat. No. 7,273,740 of Table 3) with 0.1% of Gammalpha amylase. The viscosity of the starch surface sizing solution and pick-up were maintained as close as possible. The results are shown below.

It is obvious that, despite the 20 times less dosage of the polypeptide of SEQ ID NO:12 (SEQ ID NO:2 of U.S. Pat. No. 7,273,740 of Table 3) as compared to the current commercial amylase (Gammalpha), the starch viscosity as well as paper strength properties were maintained in the quite similar range.

TABLE IV

| Merizet 120 Corn Starch from Tate Lyle | 0 g/L starch (base paper) | 80 g/L starch | 100 g/L starch |
|---|---|---|---|
| Reference 0.1% Gammalpha Amylase Viscosity at 80 C., 100 rpm, viscosity 34.5 mPas | | | |
| Basis Weight | 133.5 g/m2 | 140.7 g/m2 | 142.9 g/m2 |
| Short Span Compressive Strength, SCT(CD) linerboard | 2.49 kN/m | 3.31 kN/m | 3.50 kN/m |
| SCT (CD) Index | 1.87 kNm/g | 2.35 kNm/g | 2.45 kNm/g |
| Polypeptide of SEQ ID NO: 12 (SEQ ID NO: 2 of U.S. Pat. No. 7,273,740 of Table 3) 0.005% enzymatic formulation comprising Polypeptide of SEQ ID NO: 12 (SEQ ID NO: 2 of U.S. Pat. No. 7,273,740 of Table 3) Treatment Viscosity at 80 C., 100 rpm, viscosity 36.5 mPas | | | |
| Basis Weight, g/m2 | 133.3 g/m2 | 137.8 g/m2 | 140.4 g/m2 |
| Linerboard Compressive Strength, SCT(CD) | 2.55 kN/m | 3.34 kN/m | 3.53 kN/m |
| SCT (CD) Index | 1.91 kNm/g | 2.42 kNm/g | 2.51 kNm/g |

Example 4: Surface Sizing Composition of Potato Starch Modified by 0.01% Enzymatic Formulation with Polypeptide of SEQ ID NO:12, i.e., SEQ ID NO:2 of U.S. Pat. No. 7,273,740 of Table 3

Native potato starch was modified with 0.01% of the enzymatic formulation comprising polypeptide of SEQ ID NO:12, i.e., SEQ ID NO:2 of U.S. Pat. No. 7,273,740 of Table 3 for use as the surface sizing compositions. The starch viscosities were effectively reduced for surface size handling. In contrast, a commercial amylase Warozym A10 was much less effective to modify the native starch for surface sizing handling. In fact, even at a dose of 0.26% Warozym A10, the starch viscosity at 100 g/L is 66.6 mPas, which is still twice as high as the starch solutions modified by 0.01% of the enzymatic formulation comprising polypeptide of SEQ ID NO:12 (SEQ ID NO:2 of U.S. Pat. No. 7,273,740 of Table 3).

A surface size treatment experiment was conducted with the 0.01% of the enzymatic formulation comprising polypeptide of SEQ ID NO:12 (SEQ ID NO:2 of U.S. Pat. No. 7,273,740 of Table 3) treated potato starch on a linerboard, to illustrate the viability of the surface treatment composition disclosed herein. The results are shown below.

TABLE V

| Potato Starch 0.01% of the enzymatic formulation comprising Polypeptide of SEQ ID NO: 12 (SEQ ID NO: 2 of U.S. Pat. No. 7,273,740 of Table 3) | 0 g/L Starch (base paper) | 60 g/L starch | 80 g/L starch | 100 g/L starch |
|---|---|---|---|---|
| Viscosity at 80 C., 100 rpm | | 14.5 mPas | — | 31.8 mPas |
| Basis Weight, g/m2 | 132.9 | 139.4 | 139.7 | 139.9 |
| Linerboard compressive strength SCT (CD), kN/m | 2.25 | 3.02 | 3.28 | 3.34 |
| SCT (CD) Index, kN m/g | 1.69 | 2.17 | 2.35 | 2.39 |

The following Clauses 1 to 106 illustrate different aspects of the present technical teaching.

1. Use of an enzymatic formulation for producing surface treatment composition for paper and board, comprising:
   (a) providing an enzymatic formulation comprising a polypeptide having an amylase activity;
   (b) providing a starch; and
   (c) contacting the enzymatic formulation with the starch, thereby hydrolyzing the starch to produce a paper surface treatment composition comprising degraded starch having a weight-average molecular weight (Mw) in the range from 10,000 to 12,000,000 and a polydispersity index (Mw/Mn) of 1.3 to 49.

2. The use of Clause 1, for the production of a paper product.

3. The use of Clause 1, for the production of a paper product having improved surface quality.

4. The use of any one of Clauses 1-3, wherein the enzymatic formulation comprises a glucoamylase and/or a debranching enzyme.

5. The use of any one of Clauses 1-3, wherein the enzymatic formulation does not comprise a glucoamylase and/or a debranching enzyme.

6. The use of any one of Clauses 1-5, wherein the enzymatic formulation further comprises a protease, a lipase, a peroxidase, a laccase, a tyrosinase, a cellubiohydrolase, a glucose oxidase, a transferase, a glycosyl transferase, a pectinase, an esterase, a cellobiose oxidoreductase, a glyoxal oxidase, an epimerase, an invertase, a chlorophyllase, or any combination thereof.

7. The use of any one of Clauses 1-6, wherein the paper surface treatment composition comprises 1 to 40 wt % of the degraded starch.

8. The use of any one of Clauses 1-7, wherein the paper surface treatment composition comprises 2 to 30 wt % of the degraded starch.

9. The use of any one of Clauses 1-21, wherein the polypeptide having an amylase activity has at least 80% identity to SEQ ID NO:12 (SEQ ID NO:2 of U.S. Pat. No. 7,273,740 of Table 3).

10. The use of any one of Clauses 1-8, wherein the polypeptide having an amylase activity has at least 80% identity to any one of amino acid sequences disclosed in Table 3 and 4.

11. The use of any one of Clauses 1-8, wherein the polypeptide having an amylase activity is any one of those set forth in Tables 1 & 2.

12. A method for producing a surface treatment composition for paper or board, comprising:
   (a) providing a polypeptide having an amylase activity;
   (b) providing a starch; and
   (c) contacting the polypeptide of (a) with the starch of (b), thereby hydrolyzing the starch to produce a paper surface treatment composition comprising 1 to 40 wt % degraded starch having a weight-average molecular weight (Mw) in the range from 10,000 to 12,000,000 and a polydispersity index (Mw/Mn) of 1.3 to 49.

13. The method of Clause 12, wherein the paper surface treatment composition comprises 2 to 30 wt % of the degraded starch.

14. The method of any one of Clauses 12-13, wherein the degraded starch has a weight-average molecular weight Mw of in the range from 400,000 to 5,000,000 and a polydispersity index (Mw/Mn) of 10 to 49.

15. The method of any one of Clauses 12-14, wherein the polypeptide having an amylase activity has at least 80% identity to SEQ ID NO:12.

16. The method of any one of Clauses 12-14, wherein the polypeptide having an amylase activity has at least 80% identity to any one of amino acid sequences disclosed in Table 3 and 4.

17. The method of any one of Clauses 12-14, wherein the polypeptide having an amylase activity is any one of those set forth in Tables 1 & 2.

18. The method of any one of Clauses 12-17, wherein the polypeptide having amylase activity is provided at 0.01 ppm to 1000 ppm based on the weight of the starch.

19. The method of any one of Clauses 12-18, wherein the method further comprises use of a protease, a lipase, a peroxidase, a laccase, a tyrosinase, a cellubiohydrolase, a glucose oxidase, a transferase, a glycosyl transferase, a pectinase, an esterase, a cellobiose oxidoreductase, a glyoxal oxidase, an epimerase, an invertase, a chlorophyllase, or any combination thereof.

20. The method of any one of Clauses 12-18, wherein the method further comprises use of a glucoamylase and/or a debranching enzyme.

21. The method of Clause 20, wherein the debranching enzyme is a hemicellulase, an isoamylase, a beta amylase, a gamma amylase, an exo-amylase, a pullulanase, a xylanase, a mannanase, an alpha gluconase, an endocellulase, an exocellulase, or any combination thereof.

22. The method of any one of Clauses 12-21 wherein the starch is from rice, corn, barley, wheat, legumes, potato, Tapioca, soybean oat, rye, beet or sugar cane.

23. The method of any one of Clauses 12-22, wherein the starch is treated by chemical treatment, mechanical treatment, thermal treatment, acid treatment, oxidation, derivatization, or enzymatic treatment.

24. The method of any one of Clauses 12-23, comprising inactivating the polypeptide having an amylase activity.

25. A paper or board surface treatment composition, comprising degraded starch obtained by a method comprising:
   (a) providing an enzymatic formulation comprising a polypeptide having an amylase activity;
   (b) providing a starch; and
   (c) contacting the enzymatic formulation with the starch, thereby hydrolyzing the starch to produce a paper surface treatment composition comprising 1 to 40 wt % degraded starch having a weight-average molecular weight (Mw) in the range from 10,000 to 12,000,000 and a polydispersity index (Mw/Mn) of 1.3 to 49.

26. The paper surface treatment composition of Clause 25, wherein the paper surface treatment composition is for treating photocopy paper, computer printer paper, notebook paper, notepad paper, typewriter paper, newspaper, magazine, cardboard, corrugated board, or paper-based packaging material.

27. The paper surface treatment composition of any one of Clauses 25-26, wherein the paper surface treatment composition comprises 2 to 30 wt % of the degraded starch.

28. The paper surface treatment composition of any one of Clauses 25-27, wherein the degraded starch has a weight-average molecular weight Mw of in the range from 400,000 to 5,000,000 and a polydispersity index (Mw/Mn) of 10 to 49.

29. The paper surface treatment composition of any one of Clauses 25-28, comprising degraded starch with a viscosity of 3 to 2,000 mPas at 80° C., 100 rpm.

30. The paper surface treatment composition of any one of Clauses 25-29, modified with a cross-linking agent.

31. The paper surface treatment composition of any one of Clauses 25-30, comprising a mineral, an inorganic pigment, clays, kaolin, PCC, GCC, calcium silicates, silica, plastic spheres pigments including hollow sphere pigments, expandable plastic spheres, microcrystalline celluloses, nanocrystalline cellulose, nano-frillated cellulose, colloidal MCC, TiO2, talc, alumina, or any combination thereof.

32. The paper surface treatment composition of any one of Clauses 25-31, comprising a hemicellulose or a lignin.

33. The paper surface treatment composition of any one of Clauses 25-31, wherein the polypeptide having an amylase activity has at least 80% identity to SEQ ID NO:12.

34. The paper surface treatment composition of any one of Clauses 25-31, wherein the polypeptide having an amylase activity has at least 80% identity to any one of amino acid sequences disclosed in Table 3 and 4.

35. The paper surface treatment composition of any one of Clauses 25-31, wherein the polypeptide having an amylase activity is any one of those set forth in Tables 1 & 2.

36. The paper surface treatment composition of any one of Clauses 25-31, wherein (a) further comprises a glucoamylase and/or a debranching enzyme.

37. The paper surface treatment composition of Clause 36, wherein the debranching enzyme is a hemicellulase, an isoamylase, a beta amylase, a gamma amylase, an exo-amylase, a pullulanase, a xylanase, a mannanase, an alpha gluconase, an endocellulase, an exocellulase, or any combination thereof.

38. The paper surface treatment composition of any one of Clauses 25-37, wherein the method further comprises use of a protease, a lipase, a peroxidase, a laccase, a tyrosinase, a cellubiohydrolase, a glucose oxidase, a transferase, a glycosyl transferase, a pectinase, an esterase, a cellobiose oxidoreductase, a glyoxal oxidase, an epimerase, an invertase, a chlorophyllase, or any combination thereof.

39. A method of producing a paper product, comprising:
   (a) providing a paper surface treatment composition comprising 1 to 40 wt % degraded starch with a polydispersity index (Mw/Mn) of 1.3 to 49;
   (b) providing a web material; and
   (c) applying the paper surface treatment composition to the web material whereby a paper product having improved surface quality is produced.

40. The method of Clause 39, wherein the paper product is a photocopy paper, computer printer paper, notebook paper, notepad paper, typewriter paper, newspaper, magazine, board, cardboard, corrugated board, paper-based packaging material, or paper-based printing and writing material.

41. The method of any one of Clauses 39-40, wherein the paper surface treatment composition comprises 2 to 30 wt % of the degraded starch.

42. The method of any one of Clauses 39-41, wherein the degraded starch has a weight-average molecular weight Mw of in the range from 400,000 to 5,000,000 and a polydispersity index (Mw/Mn) of 10 to 49.

43. The method of any one of Clauses 39-42, wherein the degraded starch has a viscosity of 3 to 2,000 mPas at 80° C., 100 rpm.

44. The method of any one of Clauses 39-43, wherein the web material is made of synthetic polymers, plastics, biopolymers, or biodegradable polymers.

45. The method of any one of Clauses 39-44, wherein the surface quality of the paper product is selected from the group consisting of water resistance, a barrier property for moisture, vapor, oxygen, oil, or grease, resistance to fuzz, reduced abrasiveness, a printing property, a surface charge property, ink/color/dye fixation, and bonding or surface strength.

46. The method of any one of Clauses 39-45, wherein the web material is a paper web.

47. The method of any one of Clauses 39-46, wherein the paper surface treatment composition is applied to the paper web as a sizing agent, a wet end application, a coating binder/carrier, or an adhesive agent.

48. The method of any one of Clauses 39-47, wherein the paper surface treatment composition is applied to the paper web via size-press, metered size-press, film-press, roll coating, blade coating, rod coating, cast coating, spray coating, curtain coating, shower coatings, injections, transfer coating, water-box pick-up, or headbox.

49. The method of Clause 48, wherein the sizing agent is applied to the paper web via the wet end section of a paper machine.

50. A paper product having improved surface quality produced using a paper surface treatment composition comprising 1 to 40 wt % degraded starch having a weight-average molecular weight (Mw) in the range from 10,000 to 12,000,000 and a polydispersity index (Mw/Mn) of 1.3 to 49.

51. The paper product of Clause 50, wherein the paper surface treatment composition comprises 2 to 30 wt % of the degraded starch.

52. The paper product of any one of Clauses 50-51, wherein the degraded starch has a weight-average molecular weight Mw of in the range from 400,000 to 5,000,000 and a polydispersity index (Mw/Mn) of 10 to 49.

53. The paper product of any one of Clauses 50-52, wherein the degraded starch has a viscosity of 3 to 2,000 mPas at 80° C., 100 rpm.

54. The paper product of any one of Clauses 50-53, wherein the surface quality of the paper product is selected from the group consisting of water resistance, a barrier property for moisture, vapor, oxygen, oil, or grease, resistance to fuzz, reduced abrasiveness, a printing property, a surface charge property, ink/color/dye fixation, and bonding or surface strength.

55. A paper or board product comprising a degraded starch having a weight-average molecular weight (Mw) in the range from 10,000 to 12,000,000 and a polydispersity index (Mw/Mn) of 1.3 to 49.

56. The paper product of Clause 55, comprising at least 10%-90% disaccharides.

57. The paper product of any one of Clauses 55-56, comprising at least 10%-90% trisaccharides.

58. A low dose enzymatic formulation for producing a paper product comprising a polypeptide having an amylase activity, wherein the polypeptide having the amylase activity is applied to a starch at 0.01 ppm to 1000 ppm based on the weight of the starch.

59. The low dose enzymatic formulation of Clause 58, wherein the paper product is a photocopy paper, computer printer paper, notebook paper, notepad paper, typewriter paper, newspaper, magazine, board, cardboard, corrugated board, paper-based packaging material, or paper-based printing and writing material.

60. The low dose enzymatic formulation of any one of Clauses 58-59, wherein the enzymatic formulation comprises a glucoamylase and/or a debranching enzyme.

61. The low dose enzymatic formulation of Clause 60, wherein the debranching enzyme is a hemicellulase, an isoamylase, a beta amylase, a gamma amylase, an exo-amylase, a pullulanase, a xylanase, a mannanase, an alpha gluconase, an endocellulase, an exocellulase, or any combination thereof.

62. The low dose enzymatic formulation of any one of Clauses 58-61, wherein the enzymatic formulation further comprises a protease, a lipase, a peroxidase, a laccase, a tyrosinase, a cellubiohydrolase, a glucose oxidase, a transferase, a glycosyl transferase, a pectinase, an esterase, a cellobiose oxidoreductase, a glyoxal oxidase, an epimerase, an invertase, a chlorophyllase, or any combination thereof.

63. The low dose enzymatic formulation of any one of Clauses 58-62, wherein the polypeptide having an amylase activity has at least 80% identity to SEQ ID NO:12.

64. The low dose enzymatic formulation of any one of Clauses 58-62, wherein the polypeptide having an amylase activity has at least 80% identity to any one of amino acid sequences disclosed in Table 3.

65. The low dose enzymatic formulation of any one of Clauses 58-62, wherein the polypeptide having an amylase activity is any one of those set forth in Tables 1 & 2.

66. A composition for producing a paper product, comprising:
 (a) an enzymatic formulation comprising a polypeptide having an amylase, a glucoamylase and/or a debranching enzyme activity; and
 (b) a paper or a paper pulp or a biomass material.

67. The composition of any one of Clause 66, wherein the polypeptide having an amylase activity has at least 80% identity to SEQ ID NO:12.

68. The composition of any one of Clauses 66-67, wherein the polypeptide having an amylase activity has at least 80% identity to any one of amino acid sequences disclosed in Table 3.

69. The composition of any one of Clauses 66-68, wherein the polypeptide having an amylase activity is any one of those set forth in Tables 1 & 2.

70. The composition of any one of Clauses 66-69, wherein the debranching enzyme is a hemicellulase, an isoamylase, a beta amylase, a gamma amylase, an exo-amylase, a pullulanase, a xylanase, a mannanase, an alpha gluconase, an endocellulase, an exocellulase, or any combination thereof.

71. The composition of any one of Clauses 66-70, wherein the enzymatic formulation further comprises a protease, a lipase, a peroxidase, a laccase, a tyrosinase, a cellubiohydrolase, a glucose oxidase, a transferase, a glycosyl transferase, a pectinase, an esterase, a cellobiose oxidoreductase, a glyoxal oxidase, an epimerase, an invertase, a chlorophyllase, or any combination thereof.

72. The composition of any one of Clauses 66-71, wherein the biomass material comprises or is derived from an agricultural crop, a byproduct of a food or a feed production, a lignocellulosic waste product, a plant residue, a waste paper, or waste paper product.

73. The method of Clause 72, wherein the plant residue comprise stems, leaves, hulls, husks, cobs, wood, wood chips, wood pulp or sawdust, or, the paper waste comprises discarded or used photocopy paper, computer printer paper, notebook paper, notepad paper, typewriter paper, newspapers, magazines, cardboard or paper-based packaging materials.

74. A method for producing a paper product, the method comprising:
 (a) treating a paper stock with paper auxiliary and/or filler;
 (b) draining the paper stock treated in (a) with sheet formation to obtain a paper web;
 (c) providing a paper surface treatment composition comprising a 1 to 40 wt % degraded starch having a weight-average molecular weight (Mw) in the range from 10,000 to 12,000,000 and a polydispersity index (Mw/Mn) of 1.3 to 49;
 (d) contacting the paper web with the paper surface treatment composition of (c); and
 (e) drying the paper web contacted in (d),
 whereby a paper product is produced.

75. The method of Clause 74, wherein the paper surface treatment composition comprises 2 to 30 wt % of the degraded starch.

76. The method of any one of Clauses 74-75, wherein the degraded starch has a weight-average molecular weight Mw of in the range from 400,000 to 5,000,000 and a polydispersity index (Mw/Mn) of 10 to 49.

77. The method of any one of Clauses 74-76, wherein the paper stock contains no polyvinyl alcohol fiber.

78. The method of any one of Clauses 74-77, wherein the paper surface treatment composition is modified with a cross-linking agent.

79. The method of any one of Clauses 74-78, wherein the paper surface treatment composition comprises a mineral, an inorganic pigment, clays, kaolin, PCC, GCC, calcium silicates, silica, plastic spheres pigments including hollow sphere pigments, expandable plastic spheres, microcrystalline celluloses, nanocrystalline cellulose, nano-frillated cellulose, colloidal MCC, TiO2, talc, alumina, or a combination thereof.

80. The method of any one of Clauses 74-79, wherein the paper surface treatment composition comprises a hemicellulose or a lignin.

81. The method of any one of Clauses 74-80, wherein the method further comprises a filtration process, and optionally a filtrate is generated.

82. The method of Clause 81, wherein the method further comprises recycling of the filtrate, and optionally fines are collected from the filtrate.

83. The method of any one of Clauses 74-82, wherein the method further comprises a mixing process.

84. The method of any one of Clauses 74-83, wherein the method further comprises a bleaching process.

85. The method of any one of Clauses 74-84, wherein optionally the method further comprises addition of additional enzymes, and optionally the additional enzymes are added at multiple time points or step-wise in the method.

86. The method of any one of Clauses 74-85, wherein the method further comprises a pre-washing or a pretreatment process.

87. The method of any one of Clauses 74-86, wherein the paper surface treatment composition is applied to the paper web as a sizing agent, a wet end application, a coating binder/carrier, or an adhesive agent.

88. The method any one of Clauses 74-87, wherein the paper surface treatment composition is applied to the paper web via size-press, metered size-press, film-press, roll coating, blade coating, rod coating, cast coating, spray coating, curtain coating, shower coatings, injections, transfer coating, water-box pick-up, or headbox.

89. A paper product obtainable by the method according to any one of Clauses 1-88, in particular according to any one of Clauses 39-49 or 74-88.

90. A composition comprising a starch having a weight-average molecular weight (Mw) in the range from 10,000 to 12,000,000 and a polydispersity index (Mw/Mn) of 1.3 to 49.

91. An aqueous surface treatment composition for paper and board comprising 1 to 40 wt % of a degraded starch with a weight-average molecular weight Mw of in the range from 400 000 to 12 000 000 and a polydispersity index of 1.3 to 49.

92. The aqueous surface treatment composition according to Clause 91, wherein 0.0001 wt % to 1 wt % of the polypeptide of SEQ ID NO:12 based on the weight of starch are used to obtain the degraded starch.

93. The aqueous surface treatment composition according to any of Clauses 91-92, wherein the enzymatic formulation comprises a glucoamylase and/or a debranching enzyme.

94. The aqueous surface treatment composition according to any of Clauses 91-93, wherein the debranching enzyme is a hemicellulase, an isoamylase, a beta amylase, a gamma amylase, an exo-amylase, a pullulanase, a xylanase, a mannanase, an alpha gluconase, an endocellulase, an exocellulase, or any combination thereof.

95. The aqueous surface treatment composition according to any of Clauses 91-94, wherein the enzymatic formulation further comprises a protease, a lipase, a peroxidase, a laccase, a tyrosinase, a cellubiohydrolase, a glucose oxidase, a transferase, a glycosyl transferase, a pectinase, an esterase, a cellobiose oxidoreductase, a glyoxal oxidase, an epimerase, an invertase, a chlorophyllase, or any combination thereof.

96. The aqueous surface treatment composition according to any of Clauses 91-95, wherein the polypeptide having an amylase activity has at least 80% identity to SEQ ID NO:12.

97. The aqueous surface treatment composition according to any of Clauses 91-96, wherein the polypeptide having an amylase activity has at least 80% identity to any one of amino acid sequences disclosed in Table 3.

98. The aqueous surface treatment composition according to any of Clauses 91-97, wherein the polypeptide having an amylase activity is any one of those set forth in Tables 1 & 2.

99. The aqueous surface treatment composition according to any of Clauses 91-98, wherein the degraded starch is obtained by a method comprising the steps
   a) preparing a suspension of water and starch;
   b) addition of 0,0001 to 1% a polypeptide having an amylase activity which has at least 80% identity to SEQ ID NO:12; and
   c) heating the mixture comprising starch and enzyme to a temperature of 60 to 100° C. for 5 to 60 Minutes.

100. The aqueous surface treatment composition according to any of Clauses 91-99, comprising 2 to 30 wt % of a degraded starch.

101. The aqueous surface treatment composition according to any of Clauses 91-100, wherein the degraded starch has a weight-average molecular weight Mw of in the range from 400 000 to 5 000 000 and a polydispersity index of 10 to 49.

102. A method for producing paper and board comprising the steps of
   a) treating paper stock with paper auxiliary and/or filler,
   b) draining the paper stock treated by a), with sheet formation, and
   c) treating the paper web obtained by b) with the surface treatment composition according to any of Clauses 91-101,
   d) and drying the paper web coated by c).

103. The method according to Clause 102, wherein the degraded starch has a weight-average molecular weight Mw in the range from 400 000 to 12 000 000 and a polydispersity of index 10 to 49 and the surface treatment composition is applied by size press application technique.

104. The method according to Clause 102, wherein the degraded starch has a weight-average molecular weight Mw in the range from 400 000 to 5 000 000 and a polydispersity of index 10 to 49 and the surface treatment composition is applied by film-press application technique.

105. A paper and board obtainable by the method according to any of Clauses 91-104, in particular according to Clauses 102-104.

106. A use of a paper and board according to Clause 105 for producing corrugated board.

The following clauses 1'. to 47'. illustrate still further aspects of the present technical teaching.

1'. An aqueous surface treatment composition for paper and board comprising 1 to 40 wt % of a degraded starch with a weight-average molecular weight Mw of in the range from 10,000 to 12,000,000 and a polydispersity index (Mw/Mn) of 1.3 to 49.

2'. An aqueous surface treatment composition according to clause 1', wherein the degraded starch has a weight-average molecular weight Mw of in the range from 400 000 to 12 000 000 and a polydispersity index (Mw/Mn) of 10 to 49.

3'. An aqueous surface treatment composition according to clause 1' or 2', wherein the degraded starch is obtained by treating starch with an enzymatic formulation comprising a polypeptide having an amylase activity.

4'. The aqueous surface treatment composition according to clause 3', wherein the enzymatic formulation comprises a glucoamylase and/or a debranching enzyme.

5'. The aqueous surface treatment according to clause 4', wherein the debranching enzyme is a hemicellulase, an isoamylase, a beta amylase, a gamma amylase, an exo-amylase, a pullulanase, a xylanase, a mannanase, an alpha gluconase, an endocellulase, an exocellulase, or any combination thereof.

6'. The aqueous surface treatment composition according to clause 3', wherein the enzymatic formulation further comprises a protease, a lipase, a peroxidase, a laccase, a tyrosinase, a cellubiohydrolase, a glucose oxidase, a transferase, a glycocyl transferase, a pectinase, an esterase, a cellobiose oxidoreductase, a glyoxal oxidase, an epimerase, an invertase, a chlorophyllase, or any combination thereof.

7'. The aqueous surface treatment composition according to any of clauses 1'-6', wherein 0.0001 wt % to 1 wt % of the polypeptide having an amylase activity, based on the weight of the starch, are used to obtain the degraded starch.

8'. The aqueous surface treatment composition according to any of clauses 1'-7', wherein the polypeptide having an amylase activity has at least 80% identity to SEQ ID NO:12 (SEQ ID No:2 of U.S. Pat. No. 7,273,740 of Table 3).

9'. The aqueous surface treatment composition according to any of clauses 1'-8', wherein the polypeptide having an amylase activity has at least 80% identity to any one of amino acid sequences disclosed in Table 3 and 4.

10'. The aqueous surface treatment composition according to any of clauses 1'-7', wherein the polypeptide having an amylase activity is any one of those set forth in Tables 1 & 2.

11'. The aqueous surface treatment composition according to any of clauses 1'-9', wherein the polypeptide having an amylase activity is the polypeptide of SEQ ID NO:12.

12'. The aqueous surface treatment composition according to any of clauses 1'-9', wherein the degraded starch is obtained by a method comprising the steps
a) preparing a suspension of water and starch;
b) addition of 0,0001 to 1% a polypeptide having an amylase activity which has at least 80% identity to SEQ ID NO:12; and
c) heating the mixture comprising starch and enzyme to a temperature of 60 to 100° C. for 5 to 60 Minutes.

13'. The aqueous surface treatment composition according to any of clauses 1'-12', comprising 2 to 30 wt % of a degraded starch.

14'. The aqueous surface treatment composition according to any of clauses 1'-13', wherein the degraded starch has a weight-average molecular weight Mw of in the range from 400 000 to 5 000 000 and a polydispersity index (Mw/Mn) of 10 to 49.

15'. A method for producing paper and board comprising the steps of
a) treating paper stock with paper auxiliary and/or filler,
b) draining the paper stock treated by a), with sheet formation, and
c) treating the paper web obtained by b) with the surface treatment composition according to any of clauses 1'-14',
d) and drying the paper web coated by c).

16'. The method according to clause 15', wherein the degraded starch has a weight-average molecular weight Mw in the range from 400 000 to 12 000 000 and a polydispersity index (Mw/Mn) of 10 to 49 and the surface treatment composition is applied by size press application technique.

17'. The method according to clause 16', wherein the degraded starch has a weight-average molecular weight Mw in the range from 400 000 to 5 000 000 and a polydispersity index (Mw/Mn) of 10 to 49 and the surface treatment composition is applied by film-press application technique.

18'. A paper and board obtainable by the method according to any of clauses 15'-17'.

19'. A use of a paper and board according to clause 18' for producing corrugated board.

20'. A method for producing a surface treatment composition for paper or board, comprising:
(a) providing a polypeptide having an amylase activity;
(b) providing a starch; and
(c) contacting the polypeptide of (a) with the starch of (b), thereby hydrolyzing the starch to produce a paper surface treatment composition comprising 1 to 40 wt % degraded starch having a weight-average molecular weight (Mw) in the range from 10,000 to 12,000,000 and a polydispersity index (Mw/Mn) of 1.3 to 49.

21'. The method according to clause 20', wherein the paper surface treatment composition comprises 2 to 30 wt % of the degraded starch.

22'. The method according to any of clauses 20'-21', wherein the degraded starch has a weight-average molecular weight Mw of in the range from 400,000 to 5,000,000 and a polydispersity index (Mw/Mn) of 10 to 49.

23'. The method according to any of clauses 20'-22', wherein the polypeptide having an amylase activity has at least 80% identity to SEQ ID NO:12.

24'. The method according to any of clauses 20'-23', wherein the polypeptide having an amylase activity has at least 80% identity to any one of amino acid sequences disclosed in Table 3 and 4.

25'. The method according to any of clauses 20'-22', wherein the polypeptide having an amylase activity is any one of those set forth in Tables 1 & 2.

26'. The method according to any of clauses 20'-25', wherein the polypeptide having amylase activity is provided at 0.01 ppm to 1000 ppm based on the weight of the starch.

27'. The method according to any of clauses 20'-26', wherein the method further comprises use of a protease, a lipase, a peroxidase, a laccase, a tyrosinase, a cellubiohydrolase, a glucose oxidase, a transferase, a glycocyl transferase, a pectinase, an esterase, a cellobiose oxidoreductase, a glyoxal oxidase, an epimerase, an invertase, a chlorophyllase, or any combination thereof.

28'. The method according to any of clauses 20'-26', wherein the method further comprises use of a glucoamylase and/or a debranching enzyme.

29'. The method according to clause 28', wherein the debranching enzyme is a hemicellulase, an isoamylase, a beta amylase, a gamma amylase, an exo-amylase, a pullulanase, a xylanase, a mannanase, an alpha gluconase, an endocellulase, an exocellulase, or any combination thereof.

30'. The method according to any of clauses 20'-29', wherein the starch is from rice, corn, barley, wheat, legumes, potato, Tapioca, soybean oat, rye, beet or sugar cane.

31'. The method according to any of clauses 20'-30', wherein the starch is treated by chemical treatment, mechanical treatment, thermal treatment, acid treatment, oxidation, derivatization, or enzymatic treatment.

32'. The method according to any of clauses 20'-31', comprising inactivating the polypeptide having an amylase activity.

33'. A paper product having improved surface quality produced using a paper surface treatment composition comprising 1 to 40 wt % degraded starch having a weight-average molecular weight (Mw) in the range from 10,000 to 12,000,000 and a polydispersity index (Mw/Mn) of 1.3 to 49.

34'. The paper product according to clause 33', wherein the paper surface treatment composition comprises 2 to 30 wt % of the degraded starch.

35'. The paper product according to any of clauses 33'-34', wherein the degraded starch has a weight-average molecular weight Mw of in the range from 400,000 to 5,000,000 and a polydispersity index (Mw/Mn) of 10 to 49.

36'. The paper product according to any of clauses 33'-35', wherein the degraded starch has a viscosity of 3 to 2,000 mPas at 80° C., 100 rpm.

37'. The paper product according to any of clauses 33'-36', wherein the surface quality of the paper product is selected from the group consisting of water resistance, a barrier property for moisture, vapor, oxygen, oil, or grease, resistance to fuzz, reduced abrasiveness, a printing property, a surface charge property, ink/color/dye fixation, and bonding or surface strength.

38'. The paper product according to any of clauses 33'-37', comprising at least 10%-90% disaccharides.

39'. The paper product according to any of clauses 33'-38', comprising at least 10%-90% trisaccharides.

40'. A low dose enzymatic formulation for producing a paper product comprising a polypeptide having an amylase activity, wherein the polypeptide having the amylase activity is applied to a starch at 0.01 ppm to 1000 ppm based on the weight of the starch.

41'. The low dose enzymatic formulation according to clause 40', wherein the paper product is a photocopy paper, computer printer paper, notebook paper, notepad paper, typewriter paper, newspaper, magazine, board, cardboard, corrugated board, paper-based packaging material, or paper-based printing and writing material.

42'. The low dose enzymatic formulation according to clause 40' or 41', wherein the enzymatic formulation comprises a glucoamylase and/or a debranching enzyme.

43'. The low dose enzymatic formulation according to clause 42', wherein the debranching enzyme is a hemicellulase, an isoamylase, a beta amylase, a gamma amylase, an exo-amylase, a pullulanase, a xylanase, a mannanase, an alpha gluconase, an endocellulase, an exocellulase, or any combination thereof 44'. The low dose enzymatic formulation according to any of clauses 40'-43', wherein the enzymatic formulation further comprises a protease, a lipase, a peroxidase, a laccase, a tyrosinase, a cellubiohydrolase, a glucose oxidase, a transferase, a glycocyl transferase, a pectinase, an esterase, a cellobiose oxidoreductase, a glyoxal oxidase, an epimerase, an invertase, a chlorophyllase, or any combination thereof.

45'. The low dose enzymatic formulation according to any of clauses 40'-44', wherein the polypeptide having an amylase activity has at least 80% identity to SEQ ID NO:12.

46'. The low dose enzymatic formulation of any of clauses 40'-45', wherein the polypeptide having an amylase activity has at least 80% identity to any one of amino acid sequences disclosed in Table 3 and 4.

47'. The low dose enzymatic formulation according to any of clauses 40'-46', wherein the polypeptide having an amylase activity is any one of those set forth in Tables 1 & 2.

The following clauses I. to XVI. illustrate still other aspects of the present technical teaching.

I. An aqueous surface treatment composition for paper and board comprising 1 to 40 wt % of a degraded starch with a weight-average molecular weight Mw of in the range from 10,000 to 12,000,000 and a polydispersity index (Mw/Mn) of 1.3 to 49.

II. An aqueous surface treatment composition according to clause I, wherein the degraded starch has a weight-average molecular weight Mw of in the range from 400 000 to 12 000 000 and a polydispersity index (Mw/Mn) of 10 to 49.

III. An aqueous surface treatment composition according to clause I or II, wherein the degraded starch is obtained by treating starch with an enzymatic formulation comprising a polypeptide having an amylase activity.

IV. The aqueous surface treatment composition according to clause III, wherein the enzymatic formulation comprises a glucoamylase and/or a debranching enzyme.

V. The aqueous surface treatment composition according to any of clauses I to IV, wherein 0.0001 wt % to 1 wt % of the polypeptide having an amylase activity, based on the weight of the starch, are used to obtain the degraded starch, and wherein the polypeptide having an amylase activity has at least 80% identity to SEQ ID NO:12 (SEQ ID No:2 of U.S. Pat. No. 7,273,740 of Table 3).

VI. The aqueous surface treatment composition according to any of clauses I to V, wherein the polypeptide having an amylase activity has at least 80% identity to any one of amino acid sequences disclosed in Table 3 and 4.

VII. The aqueous surface treatment composition according to any of clauses I to VI, wherein the polypeptide having an amylase activity is any one of those set forth in Tables 1 & 2.

VIII. The aqueous surface treatment composition according to any of clauses I to VII, wherein the polypeptide having an amylase activity is the polypeptide of SEQ ID NO:12.

IX. The aqueous surface treatment composition according to any of clauses I to VIII, wherein the degraded starch is obtained by a method comprising the steps
  a) preparing a suspension of water and starch;
  b) addition of 0,0001 to 1% a polypeptide having an amylase activity which has at least 80% identity to SEQ ID NO:12; and
  c) heating the mixture comprising starch and enzyme to a temperature of 60 to 100° C. for 5 to 60 Minutes.

X. The aqueous surface treatment composition according to any of clauses I to IX, comprising 2 to 30 wt % of a degraded starch.

XI. The aqueous surface treatment composition according to any of clauses I to X, wherein the degraded starch has a weight-average molecular weight Mw of in the range from 400 000 to 5 000 000 and a polydispersity index (Mw/Mn) of 10 to 49.

XII. A method for producing paper and board comprising the steps of
  a) treating paper stock with paper auxiliary and/or filler,
  b) draining the paper stock treated by a), with sheet formation, and
  c) treating the paper web obtained by b) with the surface treatment composition according to any of clauses I to XI,
  d) and drying the paper web coated by c).

XIII. The method according to clause XII, wherein the degraded starch has a weight-average molecular weight Mw in the range from 400 000 to 12 000 000 and a polydispersity index (Mw/Mn) of 10 to 49 and the surface treatment composition is applied by size press application technique.

XIV. The method according to clause XIII, wherein the degraded starch has a weight-average molecular weight Mw in the range from 400 000 to 5 000 000 and a polydispersity index (Mw/Mn) of 10 to 49 and the surface treatment composition is applied by film-press application technique.

XV. A paper and board obtainable by the method according to any of clauses XII to XIV.

XVI. A use of a paper and board according to clause XV for producing corrugated board.

The invention claimed is:

1. An aqueous surface treatment composition for paper and board, the composition comprising from 1 to 40 wt % of a degraded starch having a weight-average molecular weight Mw of from 10,000 to 12,000,000 and a polydispersity index (Mw/Mn) of from 1.3 to 49 wherein Mn is a number averaged molecular weight and Mw is a weight-average molecular weight,
wherein the degraded starch is obtained by a method comprising:
a) preparing a suspension of water and starch,
b) adding an enzymatic formulation comprising from 0.0001 wt % to 1 wt % of a polypeptide having an amylase activity, based on the total weight of the starch, hereby obtaining a mixture, and
c) heating the mixture to a temperature of from 60 to 100° C. for from 5 to 60 minutes, thereby obtaining the degraded starch which is enzymatically and thermally treated starch, and
wherein the polypeptide having an amylase activity comprises the amino acid sequence of SEQ ID NO:12.

2. The aqueous surface treatment composition of claim 1, wherein the degraded starch has a weight-average molecular weight Mw of from 400,000 to 12,000,000 and a polydispersity index (Mw/Mn) of from 10 to 49.

3. The aqueous surface treatment composition of claim 1, wherein the enzymatic formulation further comprises at least one selected from the group consisting of a glucoamylase and a debranching enzyme.

4. The aqueous surface treatment according to of claim 3, wherein:
the enzymatic formulation further comprises a debranching enzyme; and
the debranching enzyme is a hemicellulase, an isoamylase, a beta amylase, a gamma amylase, an exo-amylase, a pullulanase, a xylanase, a mannanase, an alpha gluconase, an endocellulase, an exocellulase, or a combination thereof.

5. The aqueous surface treatment composition of claim 1, wherein the enzymatic formulation further comprises a protease, a lipase, a peroxidase, a laccase, a tyrosinase, a cellubiohydrolase, a glucose oxidase; a transferase, a glycosyl transferase, a pectinase, an esterase, a cellobiose oxidoreductase, a glyoxal oxidase, an epimerase, an invertase, a chlorophyllase, or a combination thereof.

6. The aqueous surface treatment composition of claim 1, comprising from 2 to 30 wt % of the degraded starch.

7. The aqueous surface treatment composition of claim 1, wherein the degraded starch has a weight-average molecular weight Mw of from 400,000 to 5,000,000 and a polydispersity index (Mw/Mn) of from 10 to 49.

8. The aqueous surface treatment composition of claim 1, wherein the composition comprises the degraded starch in an amount in a range of 3 to 25 wt%.

9. The aqueous surface treatment composition of claim 1, wherein the composition comprises the degraded starch in an amount in a range of 6 to 12 wt%.

10. The aqueous surface treatment composition of claim 9, wherein the composition has a viscosity of 3 to 90 mPas at 80° C., 100 rpm.

11. A method for producing paper and board, the method comprising:
a) treating a paper stock with a paper auxiliary, a filler, or a combination thereof,
b) draining the paper stock treated by a), with a sheet formation, thereby obtaining a paper web, and
c) treating the paper web obtained by b) with the surface treatment composition of claim 1, and
d) drying the paper web treated in c), thereby producing paper and board.

12. The method according to claim 11, wherein the degraded starch of the surface treatment composition has a weight-average molecular weight Mw of from 400,000 to 12,000,000 and a polydispersity index (Mw/Mn) of from 10 to 49 and the surface treatment composition is applied by size press application technique.

13. The method according to claim 12, wherein the degraded starch of the surface treatment composition has a weight-average molecular weight Mw of from 400,000 to 500,000 and a polydispersity index (Mw/Mn) of from 10 to 49 and the surface treatment composition is applied by film-press application technique.

14. A paper and board obtained by the method according to claim 11.

15. A corrugated board produced from the paper and board of claim 14.

16. A method for producing the aqueous surface treatment composition of claim 1 for paper or board, the method comprising: (a) providing a polypeptide having an amylase activity, wherein the polypeptide comprises the amino acid sequence of SEP ID NO: 12;
(b) preparing a suspension of water and a starch:
(c) adding an enzymatic formulation comprising from 0,0001 wt % to 1 wt % of the polypeptide, based on the total weight of the starch, hereby obtaining a mixture, and
(d) heating the mixture to a temperature of from 60 to 100° C. for from 5 to 60 minutes to hydrolyzing the starch and to obtain a degraded starch winch is enzymatically and thermally treated, thereby producing the aqueous paper surface treatment composition of claim 1, the composition comprising from 1 to 40 wt % of the degraded starch having a weight-average molecular weight (Mw) of from 10,000 to 12,000,000 and a polydispersity index (Mw/Mn) of from 1.3 to 49, wherein Mn is a number averaged molecular weight and Mw is a weight-average molecular weight.

17. The method according to claim 16, wherein the paper surface treatment composition comprises from 2 to 30 wt % of the degraded starch.

18. The method according to claim 16, wherein the degraded starch has a weight-average molecular weight Mw of from 400,000 to 5,000,000 and a polydispersity index (Mw/Mn) of from 10 to 49.

19. The method according to claim 16, wherein the enzymatic formulation comprises from 0.01 ppm to 1000 ppm of the polypeptide, based on the weight of the starch.

20. The method according to claim 13, further comprising providing a protease, a lipase, a peroxidase, a laccase, a tyrosinase, a cellobiohydrolase, a glucose oxidase, a transferase, a glycosyl transferase, a pectinase, an esterase, a cellobiose oxidoreductase, a glyoxal oxidase, an epimerase, an invertase, a chlorophyllase, or any combination thereof.

21. The method according to claim 16, further comprising providing a glucoamylase, a debranching enzyme, or a combination thereof.

22. The method according to claim 21, wherein the debranching enzyme is contained and is a hemicellulase, an isoamylase, a beta amylase, a gamma amylase, an exo-amylase, a pullulanase, a xylanase, a mannanase, an alpha gluconase, an endocellulase, an exocellulase, or a combination thereof.

23. The method according to claim 16, wherein the starch is from rice, corn, barley, wheat, legumes, potato, Tapioca, soybean oat, rye, beet or sugar cane.

24. The method according to claim 16, comprising inactivating the polypeptide having an amylase activity.

\* \* \* \* \*

SEQUENCE LISTING

```
<160> NUMBER OF SEQ ID NOS: 83

<210> SEQ ID NO 1
<211> LENGTH: 484
<212> TYPE: PRT
<213> ORGANISM: Unknown
<220> FEATURE:
<223> OTHER INFORMATION: commercial amylase

<400> SEQUENCE: 1

Ala Ala Asn Leu Asn Gly Thr Leu Met Gln Tyr Phe Glu Trp Tyr Thr
1               5                   10                  15

Pro Asn Asp Gly Gln His Trp Lys Arg Leu Gln Asn Asp Ser Ala Tyr
            20                  25                  30

Leu Ala Glu His Gly Ile Thr Ala Val Trp Ile Pro Pro Ala Tyr Lys
        35                  40                  45

Gly Thr Ser Gln Ala Asp Val Gly Tyr Gly Ala Tyr Asp Leu Tyr Asp
    50                  55                  60

Leu Gly Glu Phe His Gln Lys Gly Thr Val Arg Thr Lys Tyr Gly Thr
65                  70                  75                  80

Lys Gly Glu Leu Gln Ser Ala Ile Lys Ser Leu His Ser Arg Asp Ile
                85                  90                  95

Asn Val Tyr Gly Asp Val Val Ile Asn His Lys Gly Gly Ala Asp Ala
            100                 105                 110

Thr Glu Asp Val Thr Ala Val Glu Val Asp Pro Ala Asp Arg Asn Arg
        115                 120                 125

Val Ile Ser Gly Glu Tyr Leu Ile Lys Ala Trp Thr His Phe His Phe
    130                 135                 140

Pro Gly Arg Gly Ser Thr Tyr Ser Asp Phe Lys Trp His Trp Tyr His
145                 150                 155                 160

Phe Asp Gly Thr Asp Trp Asp Glu Ser Arg Lys Leu Asn Arg Ile Tyr
                165                 170                 175

Lys Phe Gln Gly Lys Ala Trp Asp Trp Glu Val Ser Ser Glu Asn Gly
            180                 185                 190

Asn Tyr Asp Tyr Leu Met Tyr Ala Asp Ile Asp Tyr Asp His Pro Asp
        195                 200                 205

Val Val Ala Glu Ile Lys Arg Trp Gly Thr Trp Tyr Ala Asn Glu Leu
    210                 215                 220

Gln Leu Asp Gly Phe Arg Leu Asp Ala Val Lys His Ile Lys Phe Ser
225                 230                 235                 240

Phe Leu Arg Asp Trp Val Asn His Val Arg Glu Lys Thr Gly Lys Glu
                245                 250                 255

Met Phe Thr Val Ala Glu Tyr Trp Gln Asn Asp Leu Gly Ala Leu Glu
            260                 265                 270

Asn Tyr Leu Asn Lys Thr Asn Phe Asn His Ser Val Phe Asp Val Pro
        275                 280                 285

Leu His Tyr Gln Phe His Ala Ala Ser Thr Gln Gly Gly Gly Tyr Asp
    290                 295                 300
```

-continued

Met Arg Lys Leu Leu Asn Gly Thr Val Val Ser Lys His Pro Leu Lys
305                 310                 315                 320

Ser Val Thr Phe Val Asp Asn His Asp Thr Gln Pro Gly Gln Ser Leu
            325                 330                 335

Glu Ser Thr Val Gln Thr Trp Phe Lys Pro Leu Ala Tyr Ala Phe Ile
        340                 345                 350

Leu Thr Arg Glu Ser Gly Tyr Pro Gln Val Phe Tyr Gly Asp Met Tyr
    355                 360                 365

Gly Thr Lys Gly Asp Ser Gln Arg Glu Ile Pro Ala Leu Lys His Lys
370                 375                 380

Ile Glu Pro Ile Leu Lys Ala Arg Lys Gln Tyr Ala Tyr Gly Ala Gln
385                 390                 395                 400

His Asp Tyr Phe Asp His His Asp Ile Val Gly Trp Thr Arg Glu Gly
            405                 410                 415

Asp Ser Ser Val Ala Asn Ser Gly Leu Ala Ala Leu Ile Thr Asp Gly
        420                 425                 430

Pro Gly Gly Ala Lys Arg Met Tyr Val Gly Arg Gln Asn Ala Gly Glu
    435                 440                 445

Thr Trp His Asp Ile Thr Gly Asn Arg Ser Glu Pro Val Val Ile Asn
450                 455                 460

Ser Glu Gly Trp Gly Glu Phe His Val Asn Gly Gly Ser Val Ser Ile
465                 470                 475                 480

Tyr Val Gln Arg

<210> SEQ ID NO 2
<211> LENGTH: 486
<212> TYPE: PRT
<213> ORGANISM: Unknown
<220> FEATURE:
<223> OTHER INFORMATION: commercial amylase

<400> SEQUENCE: 2

Ala Ala Pro Phe Asn Gly Thr Met Met Gln Tyr Phe Glu Trp Tyr Leu
1               5                   10                  15

Pro Asp Asp Gly Thr Leu Trp Thr Lys Val Ala Asn Glu Ala Asn Asn
            20                  25                  30

Leu Ser Ser Leu Gly Ile Thr Ala Leu Trp Leu Pro Pro Ala Tyr Lys
        35                  40                  45

Gly Thr Ser Arg Ser Asp Val Gly Tyr Gly Val Tyr Asp Leu Tyr Asp
    50                  55                  60

Leu Gly Glu Phe Asn Gln Lys Gly Thr Val Arg Thr Lys Tyr Gly Thr
65                  70                  75                  80

Lys Ala Gln Tyr Leu Gln Ala Ile Gln Ala Ala His Ala Ala Gly Met
                85                  90                  95

Gln Val Tyr Ala Asp Val Val Phe Asp His Lys Gly Gly Ala Asp Gly
            100                 105                 110

Thr Glu Trp Val Asp Ala Val Glu Val Asn Pro Ser Asp Arg Asn Gln
        115                 120                 125

Glu Ile Ser Gly Thr Tyr Gln Ile Gln Ala Trp Thr Lys Phe Asp Phe
    130                 135                 140

Pro Gly Arg Gly Asn Thr Tyr Ser Ser Phe Lys Trp Arg Trp Tyr His
145                 150                 155                 160

Phe Asp Gly Val Asp Trp Asp Glu Ser Arg Lys Leu Ser Arg Ile Tyr
                165                 170                 175

```
Lys Phe Arg Gly Ile Gly Lys Ala Trp Asp Trp Glu Val Asp Thr Glu
                180                 185                 190

Asn Gly Asn Tyr Asp Tyr Leu Met Tyr Ala Asp Leu Asp Met Asp His
            195                 200                 205

Pro Glu Val Val Thr Glu Leu Lys Asn Trp Gly Lys Trp Tyr Val Asn
        210                 215                 220

Thr Thr Asn Ile Asp Gly Phe Arg Leu Asp Ala Val Lys His Ile Lys
225                 230                 235                 240

Phe Ser Phe Phe Pro Asp Trp Leu Ser Tyr Val Arg Ser Gln Thr Gly
                245                 250                 255

Lys Pro Leu Phe Thr Val Gly Glu Tyr Trp Ser Tyr Asp Ile Asn Lys
            260                 265                 270

Leu His Asn Tyr Ile Thr Lys Thr Asn Gly Thr Met Ser Leu Phe Asp
        275                 280                 285

Ala Pro Leu His Asn Lys Phe Tyr Thr Ala Ser Lys Ser Gly Gly Ala
290                 295                 300

Phe Asp Met Arg Thr Leu Met Thr Asn Thr Leu Met Lys Asp Gln Pro
                305                 310                 315                 320

Thr Leu Ala Val Thr Phe Val Asp Asn His Asp Thr Glu Pro Gly Gln
            325                 330                 335

Ala Leu Gln Ser Trp Val Asp Pro Trp Phe Lys Pro Leu Ala Tyr Ala
        340                 345                 350

Phe Ile Leu Thr Arg Gln Glu Gly Tyr Pro Cys Val Phe Tyr Gly Asp
        355                 360                 365

Tyr Tyr Gly Ile Pro Gln Tyr Asn Ile Pro Ser Leu Lys Ser Lys Ile
    370                 375                 380

Asp Pro Leu Leu Ile Ala Arg Arg Asp Tyr Ala Tyr Gly Thr Gln His
385                 390                 395                 400

Asp Tyr Leu Asp His Ser Asp Ile Ile Gly Trp Thr Arg Glu Gly Val
                405                 410                 415

Thr Glu Lys Pro Gly Ser Gly Leu Ala Ala Leu Ile Thr Asp Gly Pro
            420                 425                 430

Gly Gly Ser Lys Trp Met Tyr Val Gly Lys Gln His Ala Gly Lys Val
        435                 440                 445

Phe Tyr Asp Leu Thr Gly Asn Arg Ser Asp Thr Val Thr Ile Asn Ser
    450                 455                 460

Asp Gly Trp Gly Glu Phe Lys Val Asn Gly Gly Ser Val Ser Val Trp
465                 470                 475                 480

Val Pro Arg Lys Thr Thr
                485

<210> SEQ ID NO 3
<211> LENGTH: 485
<212> TYPE: PRT
<213> ORGANISM: Unknown
<220> FEATURE:
<223> OTHER INFORMATION: commercial amylase

<400> SEQUENCE: 3

Ala Ala Thr Asn Gly Thr Met Met Gln Tyr Phe Glu Trp Tyr Val Pro
1               5                   10                  15

Asn Asp Gly Gln Gln Trp Asn Arg Leu Arg Thr Asp Ala Pro Tyr Leu
                20                  25                  30

Ser Ser Val Gly Ile Thr Ala Val Trp Thr Pro Pro Ala Tyr Lys Gly
            35                  40                  45
```

```
Thr Ser Gln Ala Asp Val Gly Tyr Gly Pro Tyr Asp Leu Tyr Asp Leu
    50              55                  60

Gly Glu Phe Asn Gln Lys Gly Thr Val Arg Thr Lys Tyr Gly Thr Lys
65              70                  75                  80

Gly Glu Leu Lys Ser Ala Val Asn Thr Leu His Ser Asn Gly Ile Gln
                85                  90                  95

Val Tyr Gly Asp Val Val Met Asn His Lys Ala Gly Ala Asp Tyr Thr
            100                 105                 110

Glu Asn Val Thr Ala Val Glu Val Asn Pro Ser Asn Arg Asn Gln Glu
            115                 120                 125

Thr Ser Gly Glu Tyr Asn Ile Gln Ala Trp Thr Gly Phe Asn Phe Pro
    130                 135                 140

Gly Arg Gly Thr Thr Tyr Ser Asn Phe Lys Trp Gln Trp Phe His Phe
145                 150                 155                 160

Asp Gly Thr Asp Trp Asp Gln Ser Arg Ser Leu Ser Arg Ile Phe Lys
                165                 170                 175

Phe Arg Gly Thr Gly Lys Ala Trp Asp Trp Glu Val Ser Ser Glu Asn
                180                 185                 190

Gly Asn Tyr Asp Tyr Leu Met Tyr Ala Asp Ile Asp Tyr Asp His Pro
            195                 200                 205

Asp Val Val Asn Glu Met Lys Lys Trp Gly Val Trp Tyr Ala Asn Glu
    210                 215                 220

Val Gly Leu Asp Gly Tyr Arg Leu Asp Ala Val Lys His Ile Lys Phe
225                 230                 235                 240

Ser Phe Leu Lys Asp Trp Val Asp Asn Ala Arg Ala Ala Thr Gly Lys
                245                 250                 255

Glu Met Phe Thr Val Gly Glu Tyr Trp Gln Asn Asp Leu Gly Ala Leu
            260                 265                 270

Asn Asn Tyr Leu Ala Lys Val Asn Tyr Asn Gln Ser Leu Phe Asp Ala
            275                 280                 285

Pro Leu His Tyr Asn Phe Tyr Ala Ala Ser Thr Gly Gly Gly Tyr Tyr
    290                 295                 300

Asp Met Arg Asn Ile Leu Asn Asn Thr Leu Val Ala Ser Asn Pro Thr
305                 310                 315                 320

Lys Ala Val Thr Leu Val Glu Asn His Asp Thr Gln Pro Gly Gln Ser
                325                 330                 335

Leu Glu Ser Thr Val Gln Pro Trp Phe Lys Pro Leu Ala Tyr Ala Phe
            340                 345                 350

Ile Leu Thr Arg Ser Gly Gly Tyr Pro Ser Val Phe Tyr Gly Asp Met
            355                 360                 365

Tyr Gly Thr Lys Gly Thr Thr Thr Arg Glu Ile Pro Ala Leu Lys Ser
    370                 375                 380

Lys Ile Glu Pro Leu Leu Lys Ala Arg Lys Asp Tyr Ala Tyr Gly Thr
385                 390                 395                 400

Gln Arg Asp Tyr Ile Asp Asn Pro Asp Val Ile Gly Trp Thr Arg Glu
                405                 410                 415

Gly Asp Ser Thr Lys Ala Lys Ser Gly Leu Ala Thr Val Ile Thr Asp
            420                 425                 430

Gly Pro Gly Gly Ser Lys Arg Met Tyr Val Gly Thr Ser Asn Ala Gly
    435                 440                 445

Glu Ile Trp Tyr Asp Leu Thr Gly Asn Arg Thr Asp Lys Ile Thr Ile
450                 455                 460
```

Gly Ser Asp Gly Tyr Ala Thr Phe Pro Val Asn Gly Ser Val Ser
465                 470                 475                 480

Val Trp Val Gln Gln
            485

<210> SEQ ID NO 4
<211> LENGTH: 480
<212> TYPE: PRT
<213> ORGANISM: Paenibacillus

<400> SEQUENCE: 4

Ala Asp Asn Gly Thr Ile Met Gln Tyr Phe Glu Trp Tyr Leu Pro Asn
1               5                   10                  15

Asp Gly Ala His Trp Asn Arg Leu Asn Asn Asp Ala Gln Asn Leu Lys
            20                  25                  30

Asn Val Gly Ile Thr Ala Val Trp Ile Pro Pro Ala Tyr Lys Gly Gly
        35                  40                  45

Ser Ser Ala Asp Val Gly Tyr Gly Val Tyr Asp Thr Tyr Asp Leu Gly
    50                  55                  60

Glu Phe Asn Gln Lys Gly Thr Val Arg Thr Lys Tyr Gly Thr Lys Ser
65                  70                  75                  80

Glu Leu Ile Ser Ala Val Asn Asn Leu His Ala Lys Gly Ile Ala Val
                85                  90                  95

Tyr Gly Asp Val Val Leu Asn His Arg Met Asn Ala Asp Ala Thr Glu
            100                 105                 110

Leu Val Asp Ala Val Glu Val Asp Pro Asn Asn Arg Asn Val Glu Thr
        115                 120                 125

Thr Ser Thr Tyr Gln Ile Gln Ala Trp Thr Gln Tyr Asp Phe Pro Gly
130                 135                 140

Arg Gly Asn Thr Tyr Ser Ser Phe Lys Trp Arg Trp Tyr His Phe Asp
145                 150                 155                 160

Gly Val Asp Trp Asp Gln Ser Arg Gly Leu Asn Arg Ile Tyr Lys Leu
                165                 170                 175

Arg Gly Asp Gly Lys Asp Trp Asp Trp Glu Val Asp Ser Glu Tyr Gly
            180                 185                 190

Asn Tyr Asp Tyr Leu Met Gly Ala Asp Leu Asp Phe Asn His Pro Asp
        195                 200                 205

Val Val Asn Glu Thr Lys Thr Trp Gly Lys Trp Phe Val Asn Thr Val
    210                 215                 220

Asn Leu Asp Gly Val Arg Leu Asp Ala Val Lys His Ile Lys Phe Asp
225                 230                 235                 240

Phe Met Arg Asp Trp Val Asn Asn Val Arg Ser Thr Thr Gly Lys Asn
                245                 250                 255

Leu Phe Ala Val Gly Glu Tyr Trp His Tyr Asp Val Asn Lys Leu Asn
            260                 265                 270

Ser Tyr Ile Thr Lys Thr Asn Gly Thr Met Ser Leu Phe Asp Val Pro
        275                 280                 285

Leu His Phe Arg Phe Tyr Asp Ala Ser Asn Gly Gly Gly Tyr Asp
    290                 295                 300

Met Arg Asn Leu Leu Asn Asn Thr Leu Met Ser Ser Asn Pro Met Lys
305                 310                 315                 320

Ala Val Thr Phe Val Glu Asn His Asp Thr Gln Pro Thr Gln Ala Leu
                325                 330                 335

Gln Ser Thr Val Gln Ser Trp Phe Lys Pro Leu Ala Tyr Ala Thr Ile
            340                 345                 350

```
Leu Thr Arg Glu Gln Gly Tyr Pro Cys Val Phe Tyr Gly Asp Tyr Tyr
            355                 360                 365

Gly Thr Ser Asp Gly Lys Ile Ser Ser Tyr Lys Pro Ile Met Asp Lys
    370                 375                 380

Leu Leu Asn Ala Arg Lys Val Tyr Ala Tyr Gly Thr Gln Arg Asp Tyr
385                 390                 395                 400

Phe Asp His Pro Asp Ile Val Gly Trp Thr Arg Glu Gly Asp Ala Ala
                405                 410                 415

His Ala Gly Ser Gly Leu Ala Thr Leu Ile Thr Asp Gly Pro Gly Gly
            420                 425                 430

Ser Lys Trp Met Tyr Val Gly Thr Ser Lys Ala Gly Gln Val Trp Thr
            435                 440                 445

Asp Lys Thr Gly Asn Arg Ser Gly Thr Val Thr Ile Asp Ala Asn Gly
    450                 455                 460

Trp Gly Asn Phe Trp Val Asn Gly Gly Ser Val Ser Val Trp Ala Lys
465                 470                 475                 480

<210> SEQ ID NO 5
<211> LENGTH: 636
<212> TYPE: PRT
<213> ORGANISM: Aspergillus clavatus

<400> SEQUENCE: 5

Met Lys Leu Leu Ala Leu Thr Thr Ala Phe Ala Leu Leu Gly Lys Gly
1               5                   10                  15

Val Phe Gly Leu Thr Pro Ala Glu Trp Arg Gly Gln Ser Ile Tyr Phe
            20                  25                  30

Leu Ile Thr Asp Arg Phe Ala Arg Thr Asp Gly Ser Thr Thr Ala Pro
        35                  40                  45

Cys Asp Leu Ser Gln Arg Ala Tyr Cys Gly Gly Ser Trp Gln Gly Ile
    50                  55                  60

Ile Lys Gln Leu Asp Tyr Ile Gln Gly Met Gly Phe Thr Ala Ile Trp
65                  70                  75                  80

Ile Thr Pro Ile Thr Glu Gln Ile Pro Gln Asp Thr Ala Glu Gly Ser
                85                  90                  95

Ala Phe His Gly Tyr Trp Gln Lys Asp Ile Tyr Asn Val Asn Ser His
            100                 105                 110

Phe Gly Thr Ala Asp Asp Ile Arg Ala Leu Ser Lys Ala Leu His Asp
        115                 120                 125

Arg Gly Met Tyr Leu Met Ile Asp Val Val Ala Asn His Met Gly Tyr
    130                 135                 140

Asn Gly Pro Gly Ala Ser Thr Asp Phe Ser Thr Phe Thr Pro Phe Asn
145                 150                 155                 160

Ser Ala Ser Tyr Phe His Ser Tyr Cys Pro Ile Asn Asn Tyr Asn Asp
                165                 170                 175

Gln Ser Gln Val Glu Asn Cys Trp Leu Gly Asp Asn Thr Val Ala Leu
            180                 185                 190

Ala Asp Leu Tyr Thr Gln His Ser Asp Val Arg Asn Ile Trp Tyr Ser
        195                 200                 205

Trp Ile Lys Glu Ile Val Gly Asn Tyr Ser Ala Asp Gly Leu Arg Ile
    210                 215                 220

Asp Thr Val Lys His Val Glu Lys Asp Phe Trp Thr Gly Tyr Thr Gln
225                 230                 235                 240

Ala Ala Gly Val Tyr Thr Val Gly Glu Val Leu Asp Gly Asp Pro Ala
                245                 250                 255
```

```
Tyr Thr Cys Pro Tyr Gln Gly Tyr Val Asp Gly Val Leu Asn Tyr Pro
                260                 265                 270

Ile Tyr Tyr Pro Leu Leu Arg Ala Phe Glu Ser Ser Ser Gly Ser Met
            275                 280                 285

Gly Asp Leu Tyr Asn Met Ile Asn Ser Val Ala Ser Asp Cys Lys Asp
        290                 295                 300

Pro Thr Val Leu Gly Ser Phe Ile Glu Asn His Asp Asn Pro Arg Phe
305                 310                 315                 320

Ala Ser Tyr Thr Lys Asp Met Ser Gln Ala Lys Ala Val Ile Ser Tyr
                325                 330                 335

Val Ile Leu Ser Asp Gly Ile Pro Ile Ile Tyr Ser Gly Gln Glu Gln
            340                 345                 350

His Tyr Ser Gly Gly Asn Asp Pro Tyr Asn Arg Glu Ala Ile Trp Leu
        355                 360                 365

Ser Gly Tyr Ser Thr Thr Ser Glu Leu Tyr Lys Phe Ile Ala Thr Thr
        370                 375                 380

Asn Lys Ile Arg Gln Leu Ala Ile Ser Lys Asp Ser Ser Tyr Leu Thr
385                 390                 395                 400

Ser Arg Asn Asn Pro Phe Tyr Thr Asp Ser Asn Thr Ile Ala Met Arg
                405                 410                 415

Lys Gly Ser Gly Gly Ser Gln Val Ile Thr Val Leu Ser Asn Ser Gly
            420                 425                 430

Ser Asn Gly Gly Ser Tyr Thr Leu Asn Leu Gly Asn Ser Gly Tyr Ser
        435                 440                 445

Ser Gly Ala Asn Leu Val Glu Val Tyr Thr Cys Ser Ser Val Thr Val
450                 455                 460

Gly Ser Asp Gly Lys Ile Pro Val Pro Met Ala Ser Gly Leu Pro Arg
465                 470                 475                 480

Val Leu Val Pro Ala Ser Trp Met Ser Gly Gly Leu Cys Gly Ser
                485                 490                 495

Ser Ser Thr Thr Thr Leu Val Thr Ala Thr Thr Pro Thr Gly Ser
            500                 505                 510

Ser Ser Ser Thr Thr Leu Ala Thr Ala Val Thr Thr Pro Thr Gly Ser
        515                 520                 525

Cys Lys Thr Ala Thr Thr Val Pro Val Val Leu Glu Glu Ser Val Arg
530                 535                 540

Thr Ser Tyr Gly Glu Asn Ile Phe Ile Ser Gly Ser Ile Pro Gln Leu
545                 550                 555                 560

Gly Ser Trp Asn Pro Asp Lys Ala Val Ala Leu Ser Ser Ser Gln Tyr
                565                 570                 575

Thr Ser Asn Pro Leu Trp Ala Val Thr Leu Asp Leu Pro Val Gly
            580                 585                 590

Thr Ser Phe Glu Tyr Lys Phe Leu Lys Lys Glu Gln Asn Gly Gly Val
        595                 600                 605

Ala Trp Glu Asn Asp Pro Asn Arg Ser Tyr Thr Val Pro Glu Ala Cys
        610                 615                 620

Ala Gly Thr Ser Gln Lys Val Asp Ser Ser Trp Arg
625                 630                 635

<210> SEQ ID NO 6
<211> LENGTH: 627
<212> TYPE: PRT
<213> ORGANISM: Talaromyces stipitatus
```

<400> SEQUENCE: 6

```
Met Lys Leu Ser Leu Leu Ala Thr Thr Leu Pro Leu Phe Gly Lys Ile
1               5                   10                  15

Val Asp Ala Leu Ser Ala Ala Glu Trp Arg Ser Gln Ser Ile Tyr Phe
            20                  25                  30

Leu Leu Thr Asp Arg Phe Ala Arg Thr Asp Gly Ser Thr Ser Ala Pro
        35                  40                  45

Cys Asp Leu Ser Gln Arg Ala Tyr Cys Gly Gly Ser Trp Gln Gly Ile
    50                  55                  60

Ile Asp His Leu Asp Tyr Ile Gln Gly Met Gly Phe Thr Ala Val Trp
65                  70                  75                  80

Ile Thr Pro Ile Thr Lys Gln Ile Pro Gln Ala Thr Ser Glu Gly Ser
                85                  90                  95

Gly Tyr His Gly Tyr Trp Gln Gln Asp Ile Tyr Ser Val Asn Ser Asn
            100                 105                 110

Phe Gly Thr Ala Asp Asp Ile Arg Ala Leu Ser Lys Ala Leu His Asp
        115                 120                 125

Lys Gly Met Tyr Leu Met Ile Asp Val Val Ala Asn His Met Gly Tyr
130                 135                 140

Asn Gly Pro Gly Ala Ser Thr Asp Phe Ser Val Phe Thr Pro Phe Asn
145                 150                 155                 160

Ser Ala Ser Tyr Phe His Ser Tyr Cys Pro Ile Ser Asn Tyr Asp Asp
                165                 170                 175

Gln Asn Gln Val Glu Asn Cys Trp Leu Gly Asp Asp Thr Val Ser Leu
            180                 185                 190

Thr Asp Leu Tyr Thr Gln Ser Asn Gln Val Arg Asn Ile Trp Tyr Ser
        195                 200                 205

Trp Val Lys Asp Leu Val Ala Asn Tyr Thr Val Asp Gly Leu Arg Ile
210                 215                 220

Asp Thr Val Lys His Val Glu Lys Asp Phe Trp Thr Gly Tyr Arg Glu
225                 230                 235                 240

Ala Ala Gly Val Tyr Thr Val Gly Glu Val Leu His Gly Asp Pro Ala
                245                 250                 255

Tyr Thr Cys Pro Tyr Gln Gly Tyr Val Asp Gly Val Phe Asn Tyr Pro
            260                 265                 270

Ile Tyr Tyr Pro Leu Leu Asn Ala Phe Lys Ser Ser Gly Ser Ile
        275                 280                 285

Ser Asp Leu Val Asn Met Ile Asn Thr Val Ser Ser Asp Cys Lys Asp
290                 295                 300

Pro Ser Leu Leu Gly Ser Phe Ile Glu Asn His Asp Asn Pro Arg Phe
305                 310                 315                 320

Pro Ser Tyr Thr Ser Asp Met Ser Gln Ala Lys Ser Val Ile Ala Tyr
                325                 330                 335

Val Phe Phe Ala Asp Gly Ile Pro Thr Ile Tyr Ser Gly Gln Glu Gln
            340                 345                 350

His Tyr Thr Gly Gly Asn Asp Pro Tyr Asn Arg Glu Ala Ile Trp Leu
        355                 360                 365

Ser Gly Tyr Ala Thr Asp Ser Glu Leu Tyr Lys Phe Ile Thr Thr Ala
370                 375                 380

Asn Lys Ile Arg Asn Leu Ala Ile Ser Lys Asp Ser Ser Tyr Leu Thr
385                 390                 395                 400

Thr Arg Asn Asn Ala Phe Tyr Thr Asp Ser Asn Thr Ile Ala Met Arg
                405                 410                 415
```

```
Lys Gly Ser Ser Gly Ser Gln Val Ile Thr Val Leu Ser Asn Ser Gly
            420                 425                 430

Ser Asn Gly Ala Ser Tyr Thr Leu Glu Leu Ala Asn Gln Gly Tyr Asn
        435                 440                 445

Ser Gly Ala Gln Leu Ile Glu Val Tyr Thr Cys Ser Ser Val Lys Val
    450                 455                 460

Asp Ser Asn Gly Asn Ile Pro Val Pro Met Thr Ser Gly Leu Pro Arg
465                 470                 475                 480

Val Leu Val Pro Ala Ser Trp Val Thr Gly Ser Gly Leu Cys Gly Thr
                485                 490                 495

Ser Ser Gly Thr Pro Ser Ser Thr Thr Leu Thr Thr Thr Met Ser Leu
            500                 505                 510

Ala Ser Ser Thr Thr Ser Ser Cys Val Ser Ala Thr Ser Leu Pro Ile
        515                 520                 525

Thr Phe Asn Glu Leu Val Thr Thr Ser Tyr Gly Glu Asn Ile Phe Ile
    530                 535                 540

Ala Gly Ser Ile Pro Gln Leu Gly Asn Trp Asn Ser Ala Asn Ala Val
545                 550                 555                 560

Pro Leu Ala Ser Thr Gln Tyr Thr Ser Thr Asn Pro Val Trp Ser Val
                565                 570                 575

Ser Leu Asp Leu Pro Val Gly Ser Thr Phe Gln Tyr Lys Phe Met Lys
            580                 585                 590

Lys Glu Lys Asp Gly Ser Val Val Trp Glu Ser Asp Pro Asn Arg Ser
        595                 600                 605

Tyr Thr Val Gly Asn Gly Cys Thr Gly Ala Lys Tyr Thr Val Asn Asp
    610                 615                 620

Ser Trp Arg
625

<210> SEQ ID NO 7
<211> LENGTH: 623
<212> TYPE: PRT
<213> ORGANISM: Aspergillus nidulans

<400> SEQUENCE: 7

Met Arg Leu Leu Ala Leu Thr Ser Ala Leu Ala Leu Leu Gly Lys Ala
1               5                   10                  15

Val His Gly Leu Asp Ala Asp Gly Trp Arg Ser Gln Ser Ile Tyr Phe
            20                  25                  30

Leu Leu Thr Asp Arg Phe Ala Arg Thr Asp Gly Ser Thr Thr Ala Ala
        35                  40                  45

Cys Asp Leu Ala Gln Arg Arg Tyr Cys Gly Gly Ser Trp Gln Gly Ile
    50                  55                  60

Ile Asn Gln Leu Asp Tyr Ile Gln Asp Met Gly Phe Thr Ala Ile Trp
65                  70                  75                  80

Ile Thr Pro Ile Thr Glu Gln Ile Pro Asp Val Thr Ala Val Gly Thr
                85                  90                  95

Gly Phe His Gly Tyr Trp Gln Lys Asn Ile Tyr Gly Val Asp Thr Asn
            100                 105                 110

Leu Gly Thr Ala Asp Asp Ile Arg Ala Leu Ser Glu Ala Leu His Asp
        115                 120                 125

Arg Gly Met Tyr Leu Met Leu Asp Val Val Ala Asn His Met Ser Tyr
    130                 135                 140

Gly Gly Pro Gly Gly Ser Thr Asp Phe Ser Ile Phe Thr Pro Phe Asp
145                 150                 155                 160
```

-continued

```
Ser Ala Ser Tyr Phe His Ser Tyr Cys Ala Ile Asn Asn Tyr Asp Asn
                165                 170                 175

Gln Trp Gln Val Glu Asn Cys Phe Leu Gly Asp Asp Thr Val Ser Leu
            180                 185                 190

Thr Asp Leu Asn Thr Gln Ser Ser Glu Val Arg Asp Ile Trp Tyr Asp
        195                 200                 205

Trp Ile Glu Asp Ile Val Ala Asn Tyr Ser Val Asp Gly Leu Arg Ile
210                 215                 220

Asp Thr Val Lys His Val Glu Lys Asp Phe Trp Pro Gly Tyr Ile Asp
225                 230                 235                 240

Ala Ala Gly Val Tyr Ser Val Gly Glu Ile Phe His Gly Asp Pro Ala
                245                 250                 255

Tyr Thr Cys Pro Tyr Gln Asp Tyr Met Asp Gly Val Met Asn Tyr Pro
            260                 265                 270

Ile Tyr Tyr Pro Leu Leu Asn Ala Phe Lys Ser Ser Gly Ser Met
        275                 280                 285

Ser Asp Leu Tyr Asn Met Ile Asn Thr Val Ala Ser Asn Cys Arg Asp
        290                 295                 300

Pro Thr Leu Leu Gly Asn Phe Ile Glu Asn His Asp Asn Pro Arg Phe
305                 310                 315                 320

Pro Asn Tyr Thr Pro Asp Met Ser Arg Ala Lys Asn Val Leu Ala Phe
                325                 330                 335

Leu Phe Leu Thr Asp Gly Ile Pro Ile Val Tyr Ala Gly Gln Glu Gln
            340                 345                 350

His Tyr Ser Gly Ser Asn Asp Pro Tyr Asn Arg Glu Pro Val Trp Trp
        355                 360                 365

Ser Ser Tyr Ser Thr Ser Ser Glu Leu Tyr Lys Phe Ile Ala Thr Thr
370                 375                 380

Asn Lys Ile Arg Lys Leu Ala Ile Ser Lys Asp Ser Ser Tyr Leu Thr
385                 390                 395                 400

Ser Arg Asn Thr Pro Phe Tyr Ser Asp Ser Asn Tyr Ile Ala Met Arg
                405                 410                 415

Lys Gly Ser Gly Gly Ser Gln Val Leu Thr Leu Leu Asn Asn Ile Gly
            420                 425                 430

Thr Ser Ile Gly Ser Tyr Thr Phe Asp Leu Tyr Asp His Gly Tyr Asn
        435                 440                 445

Ser Gly Ala Asn Leu Val Glu Leu Tyr Thr Cys Ser Ser Val Gln Val
        450                 455                 460

Gly Ser Asn Gly Ala Ile Ser Ile Pro Met Thr Ser Gly Leu Pro Arg
465                 470                 475                 480

Val Leu Val Pro Ala Ala Trp Val Ser Gly Ser Gly Leu Cys Gly Leu
                485                 490                 495

Thr Asn Pro Thr Ser Lys Thr Thr Thr Ala Thr Thr Thr Ser Thr Thr
            500                 505                 510

Thr Cys Ala Ser Ala Thr Ala Thr Ala Ile Thr Val Val Phe Gln Glu
        515                 520                 525

Arg Val Gln Thr Ala Tyr Gly Glu Asn Val Phe Leu Ala Gly Ser Ile
        530                 535                 540

Ser Gln Leu Gly Asn Trp Asp Thr Thr Glu Ala Val Ala Leu Ser Ala
545                 550                 555                 560

Ala Gln Tyr Thr Ala Thr Asp Pro Leu Trp Thr Val Ala Ile Glu Leu
                565                 570                 575
```

-continued

```
Pro Val Gly Thr Ser Phe Glu Phe Lys Phe Leu Lys Lys Arg Gln Asp
                580                 585                 590

Gly Ser Ile Val Trp Glu Ser Asn Pro Asn Arg Ser Ala Lys Val Asn
            595                 600                 605

Glu Gly Cys Ala Arg Thr Thr Gln Thr Ile Ser Thr Ser Trp Arg
610                 615                 620

<210> SEQ ID NO 8
<211> LENGTH: 603
<212> TYPE: PRT
<213> ORGANISM: Talaromyces emersonii

<400> SEQUENCE: 8

Leu Thr Pro Ala Glu Trp Arg Lys Gln Ser Ile Tyr Phe Leu Leu Thr
1               5                   10                  15

Asp Arg Phe Gly Arg Ala Asp Asn Ser Thr Thr Ala Ala Cys Asp Val
                20                  25                  30

Thr Glu Arg Ile Tyr Cys Gly Gly Ser Trp Gln Gly Ile Ile Asn His
            35                  40                  45

Leu Asp Tyr Ile Gln Gly Met Gly Phe Thr Ala Ile Trp Ile Ser Pro
50                  55                  60

Val Thr Glu Gln Leu Pro Gln Asn Thr Gly Glu Gly Glu Ala Tyr His
65                  70                  75                  80

Gly Tyr Trp Gln Gln Glu Ile Tyr Thr Val Asn Ser Asn Phe Gly Thr
                85                  90                  95

Ser Asp Asp Leu Leu Ala Leu Ser Lys Ala Leu His Asp Arg Gly Met
            100                 105                 110

Tyr Leu Met Val Asp Val Val Ala Asn His Met Gly Tyr Asp Gly Asp
            115                 120                 125

Gly Asp Ser Val Asp Tyr Ser Val Phe Asn Pro Phe Asn Ser Ser Ser
130                 135                 140

Tyr Phe His Pro Tyr Cys Leu Ile Thr Asp Tyr Ser Asn Gln Thr Asp
145                 150                 155                 160

Val Glu Asp Cys Trp Leu Gly Asp Thr Thr Val Ser Leu Pro Asp Leu
                165                 170                 175

Asn Thr Thr Glu Thr Val Val Arg Thr Ile Trp Tyr Asp Trp Val Ala
            180                 185                 190

Asp Leu Val Ser Asn Tyr Ser Ile Asp Gly Leu Arg Ile Asp Thr Val
            195                 200                 205

Lys His Val Glu Lys Ser Phe Trp Pro Gly Tyr Asn Ser Ala Ala Gly
210                 215                 220

Val Tyr Cys Val Gly Glu Val Leu Asp Gly Asp Pro Ser Tyr Thr Cys
225                 230                 235                 240

Pro Tyr Gln Asp Tyr Leu Asp Gly Val Leu Asn Tyr Pro Ile Tyr Tyr
                245                 250                 255

Gln Leu Leu Tyr Ala Phe Glu Ser Ser Gly Ser Ile Ser Asn Leu
            260                 265                 270

Tyr Asn Met Ile Asn Ser Val Ala Ser Glu Cys Ser Asp Pro Thr Leu
            275                 280                 285

Leu Gly Asn Phe Ile Glu Asn His Asp Asn Pro Arg Phe Ala Ser Tyr
            290                 295                 300

Thr Ser Asp Tyr Ser Leu Ala Lys Asn Val Ile Ala Phe Ile Phe Phe
305                 310                 315                 320

Ser Asp Gly Ile Pro Ile Val Tyr Ala Gly Gln Glu Gln His Tyr Asn
                325                 330                 335
```

Gly Gly Asn Asp Pro Tyr Asn Arg Glu Ala Thr Trp Leu Ser Gly Tyr
            340                 345                 350

Ser Thr Thr Ala Glu Leu Tyr Thr Phe Ile Ala Thr Asn Ala Ile
    355                 360                 365

Arg Ser Leu Ala Ile Ser Val Asp Ser Glu Tyr Leu Thr Tyr Lys Asn
370                 375                 380

Asp Pro Phe Tyr Tyr Asp Ser Asn Thr Leu Ala Met Arg Lys Gly Ser
385                 390                 395                 400

Asp Gly Leu Gln Val Ile Thr Val Leu Ser Asn Leu Gly Ala Asp Gly
                405                 410                 415

Ser Ser Tyr Thr Leu Thr Leu Ser Gly Ser Gly Tyr Ser Ser Gly Thr
                420                 425                 430

Glu Leu Val Glu Ala Tyr Thr Cys Thr Thr Val Thr Val Asp Ser Asn
            435                 440                 445

Gly Asp Ile Pro Val Pro Met Glu Ser Gly Leu Pro Arg Val Phe Leu
            450                 455                 460

Pro Ala Ser Ser Phe Ser Gly Ser Ser Leu Cys Ser Ser Ser Pro Ser
465                 470                 475                 480

Pro Thr Thr Thr Thr Ser Thr Ser Thr Ser Thr Thr Ser Thr Ala Cys
                485                 490                 495

Thr Thr Ala Thr Ala Val Ala Val Leu Phe Glu Glu Leu Val Thr Thr
            500                 505                 510

Thr Tyr Gly Glu Asn Val Tyr Leu Ser Gly Ser Ile Ser Gln Leu Gly
            515                 520                 525

Asp Trp Asn Thr Asp Ala Val Ala Leu Ser Ala Ala Asn Tyr Thr
            530                 535                 540

Ser Ser Asn Pro Leu Trp Tyr Val Thr Val Thr Leu Pro Val Gly Thr
545                 550                 555                 560

Ser Phe Glu Tyr Lys Phe Ile Lys Lys Glu Asn Gly Asp Val Glu
                565                 570                 575

Trp Glu Ser Asp Pro Asn Arg Ser Tyr Thr Val Pro Thr Ala Cys Thr
                580                 585                 590

Gly Ala Thr Glu Thr Ile Val Asp Thr Trp Arg
            595                 600

<210> SEQ ID NO 9
<211> LENGTH: 643
<212> TYPE: PRT
<213> ORGANISM: Penicillium sp

<400> SEQUENCE: 9

Met Lys Ala Leu Ala Leu Ala Ala Leu Cys Leu Ala Lys Ala Val Ala
1               5                   10                  15

Gly Leu Thr Ala Ala Glu Trp Arg Ser Gln Ser Ile Tyr Phe Leu Leu
            20                  25                  30

Thr Asp Arg Phe Gly Arg Thr Asp Asn Ser Thr Thr Ala Ala Cys Asn
        35                  40                  45

Val Ser Asp Arg Val Tyr Cys Gly Gly Ser Trp Gln Gly Ile Ile Asn
    50                  55                  60

His Leu Asp Tyr Ile Gln Gly Met Gly Phe Thr Ala Ile Trp Ile Thr
65                  70                  75                  80

Pro Val Thr Glu Gln Leu Ser Gln Asp Thr Gly Asp Gly Glu Ala Tyr
                85                  90                  95

```
His Gly Tyr Trp Gln Gln Glu Ile Tyr Asn Val Asn Thr Asn Tyr Gly
                100                 105                 110

Thr Ala Ala Asp Leu Leu Ala Leu Ser Lys Ala Leu His Ser Arg Gly
            115                 120                 125

Met Tyr Leu Met Val Asp Val Ala Asn His Met Gly Tyr Asp Gly
        130                 135                 140

Ala Gly Asn Thr Val Asp Tyr Ser Val Phe Asn Pro Phe Asp Ser Ser
145                 150                 155                 160

Ser Tyr Phe His Ser Tyr Cys Glu Ile Ser Asp Tyr Ser Asp Gln Thr
                165                 170                 175

Asn Val Glu Asp Cys Trp Leu Gly Asp Thr Thr Val Ser Leu Pro Asp
            180                 185                 190

Leu Asp Thr Thr Leu Thr Ser Val Gln Thr Ile Trp Tyr Asn Trp Val
        195                 200                 205

Thr Glu Leu Val Ser Asn Tyr Ser Ile Asp Gly Leu Arg Ile Asp Thr
    210                 215                 220

Val Lys His Val Gln Lys Ser Phe Trp Pro Gly Tyr Asn Ser Ala Ala
225                 230                 235                 240

Gly Val Tyr Cys Val Gly Glu Val Phe Asp Gly Asp Pro Ala Tyr Thr
                245                 250                 255

Cys Pro Tyr Gln Ser Tyr Leu Asp Gly Val Leu Asn Tyr Pro Ile Tyr
            260                 265                 270

Tyr Gln Leu Leu Tyr Ala Phe Glu Ser Thr Ser Gly Ser Ile Ser Gly
        275                 280                 285

Leu Tyr Asn Met Ile Asn Ser Val Ala Ser Asp Cys Ser Asp Pro Thr
    290                 295                 300

Leu Leu Gly Asn Phe Ile Glu Asn His Asp Asn Pro Arg Phe Ala Ser
305                 310                 315                 320

Tyr Thr Ser Asp Tyr Ser Gln Ala Lys Asn Val Ile Ser Phe Ile Phe
                325                 330                 335

Phe Ser Asp Gly Ile Pro Ile Val Tyr Ala Gly Gln Glu Gln His Tyr
            340                 345                 350

Ser Gly Gly Ser Asp Pro Ala Asn Arg Glu Ala Thr Trp Leu Ser Gly
        355                 360                 365

Tyr Asp Lys Thr Ala Gln Leu Tyr Thr Tyr Ile Thr Thr Asn Lys
    370                 375                 380

Ile Arg Ala Leu Ala Ile Ser Lys Asp Ser Ala Tyr Ile Ser Ser Lys
385                 390                 395                 400

Asn Asn Ala Phe Tyr Thr Asp Ser Asn Thr Ile Ala Met Lys Lys Gly
                405                 410                 415

Ser Ser Gly Ser Gln Val Ile Thr Val Leu Ser Asn Arg Gly Ser Ser
            420                 425                 430

Gly Ser Ser Tyr Thr Leu Thr Leu Ser Gly Ser Gly Tyr Ser Ser Gly
        435                 440                 445

Thr Lys Leu Met Glu Met Tyr Thr Cys Thr Ala Val Thr Val Asp Ser
    450                 455                 460

Ser Gly Asn Ile Ala Val Pro Met Ala Ser Gly Leu Pro Arg Val Tyr
465                 470                 475                 480

Met Leu Ala Ser Ser Ala Cys Ser Ile Cys Ser Ser Ala Cys Ser Ala
                485                 490                 495

Thr Thr Thr Thr Ser Ser Thr Ala Ser Thr Ser Thr Thr Thr Ser Thr
            500                 505                 510
```

```
Thr Leu Lys Thr Thr Thr Thr Thr Ser Thr Thr Ser Lys Thr Thr Thr
        515                 520                 525

Ser Thr Thr Ser Thr Ser Cys Thr Gln Ala Thr Ala Leu Pro Val Leu
    530                 535                 540

Phe Lys Glu Ile Val Thr Thr Ser Tyr Gly Gln Ser Ile Tyr Ile Ser
545                 550                 555                 560

Gly Ser Ile Ser Gln Leu Gly Ser Trp Asp Thr Ser Ser Ala Val Ala
                565                 570                 575

Leu Ser Ala Asp Gln Tyr Thr Ser Ser Ser His Leu Trp Tyr Val Val
            580                 585                 590

Val Thr Ile Pro Val Gly Thr Ser Phe Gln Tyr Lys Phe Ile Glu Glu
        595                 600                 605

Thr Ser Gly Ser Ser Thr Ile Thr Trp Glu Ser Asp Pro Asn Arg Ser
    610                 615                 620

Tyr Thr Val Pro Thr Gly Cys Ala Gly Ser Thr Ala Thr Val Thr Ala
625                 630                 635                 640

Thr Trp Arg

<210> SEQ ID NO 10
<211> LENGTH: 617
<212> TYPE: PRT
<213> ORGANISM: Penicillium oxalicum

<400> SEQUENCE: 10

Met Lys Phe Leu Gly Leu Ala Ala Leu Phe Leu Ala Gln Thr Val Ala
1               5                   10                  15

Gly Leu Thr Ala Ala Gln Trp Arg Ser Gln Ser Ile Tyr Phe Leu Met
                20                  25                  30

Thr Asp Arg Phe Gly Arg Thr Asp Lys Ser Val Thr Ala Pro Cys Asn
            35                  40                  45

Thr Asn Asp Arg Val Tyr Cys Gly Gly Thr Trp Gln Gly Ile Ile Asn
        50                  55                  60

Gln Leu Asp Tyr Ile Gln Gly Met Gly Phe Thr Ala Ile Trp Ile Thr
65                  70                  75                  80

Pro Val Thr Glu Gln Leu Pro Gln Asp Thr Gly Asp Gly Glu Ala Tyr
                85                  90                  95

His Gly Tyr Trp Gln Gln Glu Ile Tyr Asn Val Asn Asn Asn Tyr Gly
            100                 105                 110

Thr Ala Ala Asp Leu Lys Ala Leu Ser Gln Ala Leu His Ser Arg Gly
        115                 120                 125

Met Tyr Leu Met Val Asp Val Val Ala Asn His Met Gly Tyr Ala Gly
    130                 135                 140

Ala Gly Asn Thr Val Asp Tyr Ser Val Phe Lys Pro Phe Ser Ser Ser
145                 150                 155                 160

Ser Tyr Phe His Pro Tyr Cys Leu Ile Ser Asp Tyr Ser Asn Gln Thr
                165                 170                 175

Asn Val Glu Asp Cys Trp Leu Gly Asp Thr Val Ser Leu Pro Asp
            180                 185                 190

Leu Asp Thr Thr Leu Ser Ser Val Gln Thr Ile Trp Tyr Asn Trp Val
        195                 200                 205

Ser Asp Leu Val Ser Asn Tyr Ser Ile Asp Gly Leu Arg Ile Asp Thr
    210                 215                 220

Val Lys His Val Gln Lys Ser Phe Trp Pro Gly Tyr Gln Ser Ala Ala
225                 230                 235                 240
```

```
Gly Val Tyr Cys Val Gly Glu Val Phe Ser Gly Asp Pro Ala Tyr Thr
            245                 250                 255
Cys Pro Tyr Gln Asn Tyr Leu Asp Gly Val Leu Asn Tyr Pro Ile Tyr
        260                 265                 270
Tyr Gln Leu Leu Gly Ala Phe Lys Ser Thr Ser Gly Ser Ile Ser Ser
    275                 280                 285
Leu Tyr Asn Met Ile Asn Ser Val Ala Ser Asp Cys Ala Asp Pro Thr
290                 295                 300
Leu Leu Gly Asn Phe Ile Glu Asn His Asp Asn Pro Arg Phe Ala Ser
305                 310                 315                 320
Tyr Thr Ser Asp Tyr Ser Gln Ala Lys Asn Val Ile Ser Phe Ile Phe
                325                 330                 335
Leu Ser Asp Gly Ile Pro Ile Val Tyr Ala Gly Gln Glu Gln His Tyr
            340                 345                 350
Ser Gly Gly Asn Asp Pro Ala Asn Arg Glu Ala Thr Trp Leu Ser Gly
        355                 360                 365
Tyr Ser Lys Asn Ala Gln Leu Tyr Gln His Ile Ala Ser Thr Asn Lys
    370                 375                 380
Ile Arg Ser Leu Ala Ile Ser Lys Asp Ala Asn Tyr Ile Thr Ser Lys
385                 390                 395                 400
Asn Asn Ala Phe Tyr Thr Asp Ser Asn Thr Ile Ala Met Lys Lys Gly
                405                 410                 415
Ser Ser Gly Ser Gln Val Val Thr Val Leu Ser Asn Arg Gly Ser Ser
            420                 425                 430
Gly Ser Ser Tyr Thr Leu Ser Leu Ser Gly Ser Gly Tyr Ala Ala Gly
        435                 440                 445
Thr Lys Leu Val Glu Met Tyr Thr Cys Thr Ala Val Thr Val Asp Ser
    450                 455                 460
Asn Gly Asn Ile Ala Val Ser Met Thr Ser Gly Leu Pro Arg Val Phe
465                 470                 475                 480
Met Leu Ala Ser Ser Ala Cys Ser Leu Cys Ser Ser Ala Cys Ser Ala
                485                 490                 495
Thr Ala Thr Thr Leu Lys Thr Thr Thr Ala Thr Ala Thr Ser Cys Thr
            500                 505                 510
Gln Ala Thr Ala Leu Pro Val Leu Phe Lys Asp Thr Val Thr Thr Ser
        515                 520                 525
Tyr Gly Gln Ser Val Tyr Leu Ala Gly Ser Ile Ser Gln Leu Gly Asn
    530                 535                 540
Trp Asn Ala Ala Asn Ala Val Ala Leu Ser Ala Asp Lys Tyr Thr Ser
545                 550                 555                 560
Ser Asn Pro Leu Trp Tyr Ala Thr Val Thr Leu Pro Val Gly Thr Ser
                565                 570                 575
Phe Gln Tyr Lys Phe Ile Lys Lys Thr Ser Gly Ser Gly Ser Val Thr
            580                 585                 590
Trp Glu Ser Asp Pro Asn Arg Ser Tyr Thr Val Pro Thr Gly Cys Val
        595                 600                 605
Gly Ser Thr Ala Thr Val Thr Ala Thr
    610                 615

<210> SEQ ID NO 11
<211> LENGTH: 1311
<212> TYPE: DNA
<213> ORGANISM: Artificial Sequence
<220> FEATURE:
<223> OTHER INFORMATION: DNA sequence coding for an amylase
```

<400> SEQUENCE: 11

```
atggccaagt actccgagct ggaaaagggc ggggtcataa tgcaggcgtt ctactgggac      60
gtgccttcag gaggaatatg gtgggacaca atacggcaga agataccgga gtggtacgat     120
gccggaatct ccgcaatatg gattcccccg gcgagcaagg gcatgggcgg cgcctattcg     180
atgggctacg accctacga cttctttgac ctcggtgagt acgaccagaa gggaacggta     240
gagacgcgct ttggctccaa gcaggagctc gtgaacatga taaacaccgc ccacgcctat     300
ggcatgaagg taatagccga tatagtcatc aaccaccgcg ccggcggtga cctggagtgg     360
aaccccttcg tgaacgacta tacctggacc gacttctcaa aggtcgcgtc gggtaaatac     420
acggccaact acctcgactt ccacccgaac gagctccatg cgggcgattc cggaacattt     480
ggaggctatc ccgacatatg ccacgacaag agctgggacc agtactggct ctgggccagc     540
caggagagct acgcggcata tctcaggagc atcggcatcg atgcctggcg cttcgactac     600
gtcaagggct atgctccctg gtcgtcaag gactggctga actggtgggg aggctgggcg     660
gttggagagt actgggacac caacgtcgac gctgttctca actgggcata ctcgagcggt     720
gccaaggtct ttgacttcgc cctctactac aagatggatg aggcctttga caacaaaaac     780
attccagcgc tcgtctctgc ccttcagaac ggccagactg ttgtctcccg cgacccgttc     840
aaggccgtaa cctttgtagc aaaccacgac accgatataa tctggaacaa gtatccagcc     900
tacgcgttca tcctcaccta cgagggccag ccgacaatat tctaccgcga ctacgaggag     960
tggctcaaca aggataagct caagaacctc atctggatac atgagaacct cgccggagga    1020
agcaccgaca tagtctacta cgataacgat gaactcatct tcgtcaggaa cggctacggg    1080
gacaagccgg ggcttataac ctacatcaac ctaggctcga gcaaggccgg aaggtgggtt    1140
tatgtgccga agttcgcggg cgcgtgcatc cacgagtata ctggtaacct cggaggctgg    1200
gtagacaagt acgtctactc aagcggctgg gtctatctcg aagctccagc ttacgaccct    1260
gccaacgggc agtatggcta ctccgtgtgg agctactgcg gggtgggctg a             1311
```

<210> SEQ ID NO 12
<211> LENGTH: 436
<212> TYPE: PRT
<213> ORGANISM: Artificial Sequence
<220> FEATURE:
<223> OTHER INFORMATION: protein sequence of an amylase

<400> SEQUENCE: 12

```
Met Ala Lys Tyr Ser Glu Leu Glu Lys Gly Gly Val Ile Met Gln Ala
1               5                   10                  15

Phe Tyr Trp Asp Val Pro Ser Gly Gly Ile Trp Trp Asp Thr Ile Arg
            20                  25                  30

Gln Lys Ile Pro Glu Trp Tyr Asp Ala Gly Ile Ser Ala Ile Trp Ile
        35                  40                  45

Pro Pro Ala Ser Lys Gly Met Gly Gly Ala Tyr Ser Met Gly Tyr Asp
    50                  55                  60

Pro Tyr Asp Phe Phe Asp Leu Gly Glu Tyr Asp Gln Lys Gly Thr Val
65                  70                  75                  80

Glu Thr Arg Phe Gly Ser Lys Gln Glu Leu Val Asn Met Ile Asn Thr
                85                  90                  95

Ala His Ala Tyr Gly Met Lys Val Ile Ala Asp Ile Val Ile Asn His
            100                 105                 110

Arg Ala Gly Gly Asp Leu Glu Trp Asn Pro Phe Val Asn Asp Tyr Thr
        115                 120                 125
```

Trp Thr Asp Phe Ser Lys Val Ala Ser Gly Lys Tyr Thr Ala Asn Tyr
    130                 135                 140

Leu Asp Phe His Pro Asn Glu Leu His Ala Gly Asp Ser Gly Thr Phe
145                 150                 155                 160

Gly Gly Tyr Pro Asp Ile Cys His Asp Lys Ser Trp Asp Gln Tyr Trp
                165                 170                 175

Leu Trp Ala Ser Gln Glu Ser Tyr Ala Ala Tyr Leu Arg Ser Ile Gly
            180                 185                 190

Ile Asp Ala Trp Arg Phe Asp Tyr Val Lys Gly Tyr Ala Pro Trp Val
        195                 200                 205

Val Lys Asp Trp Leu Asn Trp Trp Gly Gly Trp Ala Val Gly Glu Tyr
210                 215                 220

Trp Asp Thr Asn Val Asp Ala Val Leu Asn Trp Ala Tyr Ser Ser Gly
225                 230                 235                 240

Ala Lys Val Phe Asp Phe Ala Leu Tyr Tyr Lys Met Asp Glu Ala Phe
                245                 250                 255

Asp Asn Lys Asn Ile Pro Ala Leu Val Ser Ala Leu Gln Asn Gly Gln
            260                 265                 270

Thr Val Val Ser Arg Asp Pro Phe Lys Ala Val Thr Phe Val Ala Asn
        275                 280                 285

His Asp Thr Asp Ile Ile Trp Asn Lys Tyr Pro Ala Tyr Ala Phe Ile
290                 295                 300

Leu Thr Tyr Glu Gly Gln Pro Thr Ile Phe Tyr Arg Asp Tyr Glu Glu
305                 310                 315                 320

Trp Leu Asn Lys Asp Lys Leu Lys Asn Leu Ile Trp Ile His Glu Asn
                325                 330                 335

Leu Ala Gly Gly Ser Thr Asp Ile Val Tyr Tyr Asp Asn Asp Glu Leu
            340                 345                 350

Ile Phe Val Arg Asn Gly Tyr Gly Asp Lys Pro Gly Leu Ile Thr Tyr
        355                 360                 365

Ile Asn Leu Gly Ser Ser Lys Ala Gly Arg Trp Val Tyr Val Pro Lys
370                 375                 380

Phe Ala Gly Ala Cys Ile His Glu Tyr Thr Gly Asn Leu Gly Gly Trp
385                 390                 395                 400

Val Asp Lys Tyr Val Tyr Ser Ser Gly Trp Val Tyr Leu Glu Ala Pro
                405                 410                 415

Ala Tyr Asp Pro Ala Asn Gly Gln Tyr Gly Tyr Ser Val Trp Ser Tyr
            420                 425                 430

Cys Gly Val Gly
        435

<210> SEQ ID NO 13
<211> LENGTH: 1386
<212> TYPE: DNA
<213> ORGANISM: Unknown
<220> FEATURE:
<223> OTHER INFORMATION: DNA sequence coding for an amylase

<400> SEQUENCE: 13
atgaagaagt tgtcgccct gttcataacc atgttttttcg tagtgagcat ggcagtcgtt      60
gcacagccag ctagcgccgc aaagtattcc gagctcgaag aaggcggcgt tataatgcag     120
gccttctact gggacgtccc aggtggagga tctggtgggg acaccatcag gagcaagata     180
ccggagtggt acgaggcggg aatatccgcc atttggattc cgccagccag caaggggatg     240
agcggcggtt actcgatggg ctacgatccc tacgatttct ttgacctcgg cgagtacaac     300

```
cagaagggaa ccatcgaaac gcgctttggc tctaaacagg agctcatcaa tatgataaac      360
acggcccatg cctacggcat aaaggtcata gcggacatcg tcataaacca ccgcgcaggc      420
ggagacctcg agtggaaccc gttcgttggg gactacacct ggacggactt ctcaaaggtg      480
gcctcgggca aatatactgc caactacctc gacttccacc ccaacgaggt caagtgctgt      540
gacgagggca catttggagg cttcccagac atagcccacg agaagagctg ggaccagcac      600
tggctctggg cgagcgatga gagctacgcc gcctacctaa ggagcatcgg cgttgatgcc      660
tggcgctttg actacgtgaa gggctacgga gcgtgggtcg tcaaggactg gctcaactgg      720
tggggcggct gggccgttgg cgagtactgg gacaccaacg ttgatgcact cctcaactgg      780
gcctactcga gcggcgccaa ggtcttcgac ttcccgctct actacaagat ggatgaggcc      840
tttgacaaca aaacattcc agcgctcgtc tctgcccttc agaacggcca gactgttgtc      900
tcccgcgacc cgttcaaggc cgtaaccttt gtagcaaacc acgacaccga tataatctgg      960
aacaagtacc ttgcttatgc tttcatcctc acctacgaag ccagcccgt catattctac     1020
cgcgactacg aggagtggct caacaaggac aggttgaaca acctcatatg gatacacgac     1080
cacctcgcag gtggaagcac gagcatagtc tactacgaca gcgacgagat gatcttcgtg     1140
aggaacggct atggaagcaa gcctggcctt ataacttaca tcaacctcgg ctcgagcaag     1200
gttggaaggt gggtttatgt gccgaagttc gcgggcgcgt gcatccacga gtatactggt     1260
aacctcggag gctgggtaga caagtacgtc tactcaagcg gctgggtcta tctcgaagct     1320
ccagcttacg accctgccaa cgggcagtat ggctactccg tgtggagcta ttgcggtgtt     1380
gggtga                                                               1386

<210> SEQ ID NO 14
<211> LENGTH: 1311
<212> TYPE: DNA
<213> ORGANISM: Artificial Sequence
<220> FEATURE:
<223> OTHER INFORMATION: DNA sequence coding for an amylase

<400> SEQUENCE: 14
atggcaaagt attccgagct cgaagagggc gggctcataa tgcaggcctt ctactgggac       60
gtccccatgg gaggaatctg gtgggacacg atagcccaga agatacccga ctgggcaagc      120
gccgggattt cggcgatatg gattcccccg gcgagcaagg gcatgggcgg cgcctattcg      180
atgggctacg accctacga cttctttgac ctcggtgagt acgaccagaa gggaacggta      240
gagacgcgct ttggctccaa gcaggagctc gtgaacatga taaacaccgc ccacgcctat      300
ggcatgaagg taatagccga tatagtcatc aaccaccgcg ccggcggtga cctggagtgg      360
aaccccttcg tgaacgacta tacctggacc gacttctcaa aggtcgcgtc gggtaaatac      420
acggccaact acctcgactt ccacccgaac gagctccatg cggcgattc cggaacattt      480
ggaggctatc ccgacatatg ccacgacaag agctgggacc agtactgct ctgggccagc      540
caggagagct acgcggcata tctcaggagc atcggcatcg atgcctggcg cttcgactac      600
gtcaagggct acggagcgtg ggtcgtcaag gactggctgg actggtgggg aggctgggcc      660
gtcgggagt actgggacac aaacgttgat gcactgctca ctgggcctaa ctcgagcgat      720
gcaaaagtct tcgacttccc gctctactac aagatggacg cggcctttga caacaagaac      780
attcccgcac tcgtcgaggc cctcaagaac gggggcacag tcgtcagccg cgacccgttt      840
aaggccgtaa ccttcgttgc aaaccacgac accgatataa tctggaacaa gtatccagcc      900
tacgcgttca tcctcaccta cgagggccag ccgacaatat tctaccgcga ctacgaggag      960
```

-continued

```
tggctcaaca aggataagct caagaacctc atctggatac atgacaacct cgccggagga    1020
agcactgaca tcgtttacta cgacaacgac gagctgatat tcgtgagaaa cggctacgga    1080
agcaagccgg gactgataac atacatcaac ctcgcctcaa gcaaagccgg aaggtgggtt    1140
tacgttccga agttcgcagg ctcgtgcata cacgagtaca ccggcaatct cggcggctgg    1200
gtggacaagt gggtggactc aagcggctgg gtctacctcg aggctcctgc ccacgacccg    1260
gccaacggcc agtacggcta ctccgtctgg agctactgcg gtgttgggtg a             1311
```

<210> SEQ ID NO 15
<211> LENGTH: 436
<212> TYPE: PRT
<213> ORGANISM: Artificial Sequence
<220> FEATURE:
<223> OTHER INFORMATION: protein sequence of an amylase

<400> SEQUENCE: 15

```
Met Ala Lys Tyr Ser Glu Leu Glu Glu Gly Gly Leu Ile Met Gln Ala
1               5                   10                  15

Phe Tyr Trp Asp Val Pro Met Gly Gly Ile Trp Trp Asp Thr Ile Ala
            20                  25                  30

Gln Lys Ile Pro Asp Trp Ala Ser Ala Gly Ile Ser Ala Ile Trp Ile
        35                  40                  45

Pro Pro Ala Ser Lys Gly Met Gly Gly Ala Tyr Ser Met Gly Tyr Asp
    50                  55                  60

Pro Tyr Asp Phe Phe Asp Leu Gly Glu Tyr Asp Gln Lys Gly Thr Val
65                  70                  75                  80

Glu Thr Arg Phe Gly Ser Lys Gln Glu Leu Val Asn Met Ile Asn Thr
                85                  90                  95

Ala His Ala Tyr Gly Met Lys Val Ile Ala Asp Ile Val Ile Asn His
            100                 105                 110

Arg Ala Gly Gly Asp Leu Glu Trp Asn Pro Phe Val Asn Asp Tyr Thr
        115                 120                 125

Trp Thr Asp Phe Ser Lys Val Ala Ser Gly Lys Tyr Thr Ala Asn Tyr
    130                 135                 140

Leu Asp Phe His Pro Asn Glu Leu His Ala Gly Asp Ser Gly Thr Phe
145                 150                 155                 160

Gly Gly Tyr Pro Asp Ile Cys His Asp Lys Ser Trp Asp Gln Tyr Trp
                165                 170                 175

Leu Trp Ala Ser Gln Glu Ser Tyr Ala Ala Tyr Leu Arg Ser Ile Gly
            180                 185                 190

Ile Asp Ala Trp Arg Phe Asp Tyr Val Lys Gly Tyr Gly Ala Trp Val
        195                 200                 205

Val Lys Asp Trp Leu Asp Trp Trp Gly Gly Trp Ala Val Gly Glu Tyr
    210                 215                 220

Trp Asp Thr Asn Val Asp Ala Leu Leu Asn Trp Ala Tyr Ser Ser Asp
225                 230                 235                 240

Ala Lys Val Phe Asp Phe Pro Leu Tyr Tyr Lys Met Asp Ala Ala Phe
                245                 250                 255

Asp Asn Lys Asn Ile Pro Ala Leu Val Glu Ala Leu Lys Asn Gly Gly
            260                 265                 270

Thr Val Val Ser Arg Asp Pro Phe Lys Ala Val Thr Phe Val Ala Asn
        275                 280                 285

His Asp Thr Asp Ile Ile Trp Asn Lys Tyr Pro Ala Tyr Ala Phe Ile
    290                 295                 300
```

```
Leu Thr Tyr Glu Gly Gln Pro Thr Ile Phe Tyr Arg Asp Tyr Glu Glu
305                 310                 315                 320

Trp Leu Asn Lys Asp Lys Leu Lys Asn Leu Ile Trp Ile His Asp Asn
            325                 330                 335

Leu Ala Gly Gly Ser Thr Asp Ile Val Tyr Tyr Asp Asn Asp Glu Leu
            340                 345                 350

Ile Phe Val Arg Asn Gly Tyr Gly Ser Lys Pro Gly Leu Ile Thr Tyr
            355                 360                 365

Ile Asn Leu Ala Ser Ser Lys Ala Gly Arg Trp Val Tyr Val Pro Lys
            370                 375                 380

Phe Ala Gly Ser Cys Ile His Glu Tyr Thr Gly Asn Leu Gly Gly Trp
385                 390                 395                 400

Val Asp Lys Trp Val Asp Ser Ser Gly Trp Val Tyr Leu Glu Ala Pro
            405                 410                 415

Ala His Asp Pro Ala Asn Gly Gln Tyr Gly Tyr Ser Val Trp Ser Tyr
            420                 425                 430

Cys Gly Val Gly
        435
```

<210> SEQ ID NO 16
<211> LENGTH: 1311
<212> TYPE: DNA
<213> ORGANISM: Artificial Sequence
<220> FEATURE:
<223> OTHER INFORMATION: DNA sequence coding for an amylase

<400> SEQUENCE: 16

```
atggccaagt acctggagct cgaggagggc gggctcataa tgcaggcctt ctactgggac      60
gtccccatgg aggaatctg  gtgggacacg atagcccaga agatacccga ctgggcaagc     120
gccgggattt cggcgatatg gattcccccg gcgagcaagg gcatgggcgg cgcctattcg     180
atgggctacg accctacga cttctttgac ctcggtgagt acgaccagaa gggaacggta     240
gagacgcgct ttggctccaa gcaggagctc gtgaacatga taaacaccgc ccacgcctat     300
ggcatgaagg taatagccga tatagtcatc aaccaccgcg ccggcggtga cctggagtgg     360 aacccctttcg tgaacgacta tacctggacc gacttctcaa aggtcgcgtc gggtaaatac     420
acggccaact acctcgactt ccacccgaac gagctccatg cgggcgattc cggaacattt     480
ggaggctatc ccgacatatg ccacgacaag agctgggacc agtactggct ctgggccagc     540
caggagagct acgcggcata tctcaggagc atcggcatcg atgcctggcg cttcgactac     600
gtcaagggct atgctccctg gtcgtcaag  gactggctga actggtgggg aggctgggcg     660
gttggagagt actgggacac caacgtcgac gctgttctca actgggcata ctcgagcggt     720
gccaaggtct ttgacttcgc cctctactac aagatggacg aggccttcga taacaacaac     780
attcccgccc tggtggacgc cctcagatac ggtcagacag tggtcagccg cgaccgttc      840 aaggctgtga cgtttgtagc caaccacgat accgatataa tctggaacaa gtatccagcc     900
tacgcgttca tcctcaccta cgagggccag ccgacaatat tctaccgcga ctacgaggag     960
tggctcaaca aggatacgct caagaacctc atctggatac atgacaacct cgccggagga    1020
agcacgagca tgtttactca cgacagcgac gagatgatct tcgtgaggaa cggctatgga    1080
agcaagcctg gccttataac ttacatcaac ctcggctcga gcaaggttgg aaggtgggtc    1140
tacgttccga agttcgcggg gagcgtgcatc cacgagtaca ccggcaacct cggcggctgg    1200
```

```
gtggacaagt gggtggactc aagcgggtgg gtgtacctcg aggcccctgc ccacgacccg    1260
gccaacggct attacggcta ctccgtctgg agctactgcg gtgttggctg a             1311
```

<210> SEQ ID NO 17
<211> LENGTH: 436
<212> TYPE: PRT
<213> ORGANISM: Artificial Sequence
<220> FEATURE:
<223> OTHER INFORMATION: protein sequence of an amylase

<400> SEQUENCE: 17

```
Met Ala Lys Tyr Leu Glu Leu Glu Glu Gly Gly Leu Ile Met Gln Ala
1               5                   10                  15

Phe Tyr Trp Asp Val Pro Met Gly Gly Ile Trp Trp Asp Thr Ile Ala
            20                  25                  30

Gln Lys Ile Pro Asp Trp Ala Ser Ala Gly Ile Ser Ala Ile Trp Ile
        35                  40                  45

Pro Pro Ala Ser Lys Gly Met Gly Gly Ala Tyr Ser Met Gly Tyr Asp
    50                  55                  60

Pro Tyr Asp Phe Phe Asp Leu Gly Glu Tyr Asp Gln Lys Gly Thr Val
65                  70                  75                  80

Glu Thr Arg Phe Gly Ser Lys Gln Glu Leu Val Asn Met Ile Asn Thr
                85                  90                  95

Ala His Ala Tyr Gly Met Lys Val Ile Ala Asp Ile Val Ile Asn His
            100                 105                 110

Arg Ala Gly Gly Asp Leu Glu Trp Asn Pro Phe Val Asn Asp Tyr Thr
        115                 120                 125

Trp Thr Asp Phe Ser Lys Val Ala Ser Gly Lys Tyr Thr Ala Asn Tyr
    130                 135                 140

Leu Asp Phe His Pro Asn Glu Leu His Ala Gly Asp Ser Gly Thr Phe
145                 150                 155                 160

Gly Gly Tyr Pro Asp Ile Cys His Asp Lys Ser Trp Asp Gln Tyr Trp
                165                 170                 175

Leu Trp Ala Ser Gln Glu Ser Tyr Ala Ala Tyr Leu Arg Ser Ile Gly
            180                 185                 190

Ile Asp Ala Trp Arg Phe Asp Tyr Val Lys Gly Tyr Ala Pro Trp Val
        195                 200                 205

Val Lys Asp Trp Leu Asn Trp Trp Gly Gly Trp Ala Val Gly Glu Tyr
    210                 215                 220

Trp Asp Thr Asn Val Asp Ala Val Leu Asn Trp Ala Tyr Ser Ser Gly
225                 230                 235                 240

Ala Lys Val Phe Asp Phe Ala Leu Tyr Tyr Lys Met Asp Glu Ala Phe
                245                 250                 255

Asp Asn Asn Asn Ile Pro Ala Leu Val Asp Ala Leu Arg Tyr Gly Gln
            260                 265                 270

Thr Val Val Ser Arg Asp Pro Phe Lys Ala Val Thr Phe Val Ala Asn
        275                 280                 285

His Asp Thr Asp Ile Ile Trp Asn Lys Tyr Pro Ala Tyr Ala Phe Ile
    290                 295                 300

Leu Thr Tyr Glu Gly Gln Pro Thr Ile Phe Tyr Arg Asp Tyr Glu Glu
305                 310                 315                 320

Trp Leu Asn Lys Asp Thr Leu Lys Asn Leu Ile Trp Ile His Asp Asn
                325                 330                 335

Leu Ala Gly Gly Ser Thr Ser Ile Val Tyr Tyr Asp Ser Asp Glu Met
            340                 345                 350
```

```
Ile Phe Val Arg Asn Gly Tyr Gly Ser Lys Pro Gly Leu Ile Thr Tyr
            355                 360                 365
Ile Asn Leu Gly Ser Ser Lys Val Gly Arg Trp Val Tyr Val Pro Lys
        370                 375                 380
Phe Ala Gly Ala Cys Ile His Glu Tyr Thr Gly Asn Leu Gly Gly Trp
385                 390                 395                 400
Val Asp Lys Trp Val Asp Ser Ser Gly Trp Val Tyr Leu Glu Ala Pro
                405                 410                 415
Ala His Asp Pro Ala Asn Gly Tyr Tyr Gly Tyr Ser Val Trp Ser Tyr
            420                 425                 430
Cys Gly Val Gly
        435
```

<210> SEQ ID NO 18
<211> LENGTH: 1311
<212> TYPE: DNA
<213> ORGANISM: Artificial Sequence
<220> FEATURE:
<223> OTHER INFORMATION: DNA sequence coding for an amylase

<400> SEQUENCE: 18

```
atggccaagt acctggagct cgaagagggc ggggtcataa tgcaggcgtt ctactgggac      60
gtgccttcag gaggaatatg gtgggacaca atacggcaga agataccgga gtggtacgat     120
gccggaatct ccgcaatatg gattcccccg gcgagcaagg gcatgggcgg cgcctattcg     180
atgggctacg accccctacga cttctttgac ctcggtgagt atgaccagaa gggaacggta     240
gagacgcgct ttggctccaa gcaggagctc gtgaacatga taaacacggc acatgcctac     300
ggcataaagg tcatagcgga catcgtcata aaccaccgcg caggcggaga cctcgagtgg     360
aacccgttcg ttggggacta cacctggacg gacttctcaa aggtggcctc gggcaaatat     420
actgccaact acctcgactt ccaccccaac gaggtcaagt gctgtgacga gggcacattt     480
ggaggcttcc cagacatagc ccacgagaag agctgggacc agcactggct ctgggcgagc     540
gatgagagct acgccgccta cctaaggagc atcgcgttg atgcctggcg cttcgactac     600
gtcaagggct acggagcgtg ggtcgtcaag gactggctgg actggtgggg aggctgggcc     660
gtcggggagt actgggacac aaacgttgat gcactgctca actgggccta ctcgagcgat     720
gcaaaagtct tcgacttccc gctctactac aagatggatg aggcctttga caacaaaaac     780
attccagcgc tcgtctctgc ccttcagaac ggccagactg ttgtctcccg cgacccgttc     840
aaggccgtaa cctttgtagc aaaccacgac accgatataa tctggaacaa gtatccagcc     900
tacgcgttca tcctcaccta cgagggccag ccgacaatat tctaccgcga ctacgaggag     960
tggctcaaca aggataagct caagaaccta tctggataca tgacaaccta cgccggagga    1020
agcactgaca tagtctacta cgataacgat gaactcatct tcgtcaggaa cggctacggg    1080
gacaagccgg ggcttataac ctacatcaac ctaggctcga gcaaggccgg aaggtgggtt    1140
tatgtgccga gttcgcgggg cgcgtgcatc cacgagtata ctggtaacct cggaggctgg    1200
gtagacaagt acgtctactc aagcggctgg gtctatctcg aagctccagc ttacgaccct    1260
gccaacgggc agtatggcta ctccgtgtgg agctactgcg gtgttggctg a             1311
```

<210> SEQ ID NO 19
<211> LENGTH: 436
<212> TYPE: PRT
<213> ORGANISM: Artificial Sequence
<220> FEATURE:
<223> OTHER INFORMATION: protein sequence of an amylase -continued

```
<400> SEQUENCE: 19

Met Ala Lys Tyr Leu Glu Leu Glu Glu Gly Gly Val Ile Met Gln Ala
1               5                   10                  15

Phe Tyr Trp Asp Val Pro Ser Gly Gly Ile Trp Trp Asp Thr Ile Arg
            20                  25                  30

Gln Lys Ile Pro Glu Trp Tyr Asp Ala Gly Ile Ser Ala Ile Trp Ile
        35                  40                  45

Pro Pro Ala Ser Lys Gly Met Gly Gly Ala Tyr Ser Met Gly Tyr Asp
    50                  55                  60

Pro Tyr Asp Phe Phe Asp Leu Gly Glu Tyr Asp Gln Lys Gly Thr Val
65                  70                  75                  80

Glu Thr Arg Phe Gly Ser Lys Gln Glu Leu Val Asn Met Ile Asn Thr
                85                  90                  95

Ala His Ala Tyr Gly Ile Lys Val Ile Ala Asp Ile Val Ile Asn His
            100                 105                 110

Arg Ala Gly Gly Asp Leu Glu Trp Asn Pro Phe Val Gly Asp Tyr Thr
        115                 120                 125

Trp Thr Asp Phe Ser Lys Val Ala Ser Gly Lys Tyr Thr Ala Asn Tyr
    130                 135                 140

Leu Asp Phe His Pro Asn Glu Val Lys Cys Cys Asp Glu Gly Thr Phe
145                 150                 155                 160

Gly Gly Phe Pro Asp Ile Ala His Glu Lys Ser Trp Asp Gln His Trp
                165                 170                 175

Leu Trp Ala Ser Asp Glu Ser Tyr Ala Ala Tyr Leu Arg Ser Ile Gly
            180                 185                 190

Val Asp Ala Trp Arg Phe Asp Tyr Val Lys Gly Tyr Gly Ala Trp Val
        195                 200                 205

Val Lys Asp Trp Leu Asp Trp Trp Gly Gly Trp Ala Val Gly Glu Tyr
    210                 215                 220

Trp Asp Thr Asn Val Asp Ala Leu Leu Asn Trp Ala Tyr Ser Ser Asp
225                 230                 235                 240

Ala Lys Val Phe Asp Phe Pro Leu Tyr Tyr Lys Met Asp Glu Ala Phe
                245                 250                 255

Asp Asn Lys Asn Ile Pro Ala Leu Val Ser Ala Leu Gln Asn Gly Gln
            260                 265                 270

Thr Val Val Ser Arg Asp Pro Phe Lys Ala Val Thr Phe Val Ala Asn
        275                 280                 285

His Asp Thr Asp Ile Ile Trp Asn Lys Tyr Pro Ala Tyr Ala Phe Ile
    290                 295                 300

Leu Thr Tyr Glu Gly Gln Pro Thr Ile Phe Tyr Arg Asp Tyr Glu Glu
305                 310                 315                 320

Trp Leu Asn Lys Asp Lys Leu Lys Asn Leu Ile Trp Ile His Asp Asn
                325                 330                 335

Leu Ala Gly Gly Ser Thr Asp Ile Val Tyr Tyr Asp Asn Asp Glu Leu
            340                 345                 350

Ile Phe Val Arg Asn Gly Tyr Gly Asp Lys Pro Gly Leu Ile Thr Tyr
        355                 360                 365

Ile Asn Leu Gly Ser Ser Lys Ala Gly Arg Trp Val Tyr Val Pro Lys
    370                 375                 380

Phe Ala Gly Ala Cys Ile His Glu Tyr Thr Gly Asn Leu Gly Gly Trp
385                 390                 395                 400

Val Asp Lys Tyr Val Tyr Ser Ser Gly Trp Val Tyr Leu Glu Ala Pro
                405                 410                 415
```

Ala Tyr Asp Pro Ala Asn Gly Gln Tyr Gly Tyr Ser Val Trp Ser Tyr
            420                 425                 430

Cys Gly Val Gly
    435

<210> SEQ ID NO 20
<211> LENGTH: 1311
<212> TYPE: DNA
<213> ORGANISM: Artificial Sequence
<220> FEATURE:
<223> OTHER INFORMATION: DNA sequence coding for an amylase

<400> SEQUENCE: 20

| | | | | | |
|---|---|---|---|---|---|
| atggccaagt | actccgagct | ggaagagggc | gggctcataa | tgcaggcctt | ctactgggac | 60 |
| gtccccatgg | gaggaatctg | gtgggacacg | atagcccaga | agatacccga | ctgggcaagc | 120 |
| gccgggattt | cggcgatatg | gattccccccg | gcgagcaagg | gcatgggcgg | cgcctattcg | 180 |
| atgggctacg | accccctacga | cttctttgac | ctcggtgagt | acgaccagaa | gggaacggta | 240 |
| gagacgcgct | ttggctccaa | gcaggagctc | gtgaacatga | taaacacggc | ccatgcctac | 300 |
| ggcataaagg | tcatagcgga | catcgtcata | aaccaccgcg | caggcggaga | cctcgagtgg | 360 |
| aacccgttcg | ttggggacta | cacctggacg | gacttctcaa | aggtggcctc | gggcaaatat | 420 |
| actgccaact | acctcgactt | ccaccccgaac | gagctccatg | cgggcgattc | cggaacattt | 480 |
| ggaggctatc | ccgacatatg | ccacgacaag | agctgggacc | agtactggct | ctgggccagc | 540 |
| caggagagct | acgcggcata | tctcaggagc | atcggcatcg | atgcctggcg | cttcgactac | 600 |
| gtcaagggct | acgagcgtg | gtcgtcaag | gactggctgg | actggtgggg | aggctgggcc | 660 |
| gtcggggagt | actgggacac | aaacgttgat | gcactgctca | actgggccta | ctcgagcgat | 720 |
| gcaaaagtct | tcgacttccc | gctctactac | aagatggatg | aggcctttga | caacaaaaac | 780 |
| attccagcgc | tcgtctctgc | ccttcagaac | ggccagactg | ttgtctcccg | cgacccgttc | 840 |
| aaggccgtaa | cctttgtagc | aaaccacgac | accgatataa | tttggaacaa | gtacccggcc | 900 |
| tacgccttca | tcctcaccta | cgagggccag | ccgacgatat | tctaccgcga | ctacgaggag | 960 |
| tggctcaaca | aggacaggct | caagaacctc | atctggatac | acgaccacct | tgccggtgga | 1020 |
| agcactgaca | tcgtttacta | cgacaacgac | gagctgatat | tcgtgagaaa | cggctacgga | 1080 |
| agcaagccgg | gactgataac | atacatcaac | ctcgcctcaa | gcaaagccgg | aaggtgggtt | 1140 |
| tatgtgccga | agttcgcggg | cgcgtgcatc | cacgagtata | ctggtaacct | cggaggctgg | 1200 |
| gtagacaagt | acgtctactc | aagcggctgg | gtctatctcg | aagctccagc | ttacgaccct | 1260 |
| gccaacgggc | agtatggcta | ctccgtgtgg | agctattgcg | gtgttgggtg | a | 1311 |

<210> SEQ ID NO 21
<211> LENGTH: 436
<212> TYPE: PRT
<213> ORGANISM: Artificial Sequence
<220> FEATURE:
<223> OTHER INFORMATION: protein sequence of an amylase

<400> SEQUENCE: 21

Met Ala Lys Tyr Ser Glu Leu Glu Glu Gly Gly Leu Ile Met Gln Ala
1               5                   10                  15

Phe Tyr Trp Asp Val Pro Met Gly Gly Ile Trp Trp Asp Thr Ile Ala
                20                  25                  30

Gln Lys Ile Pro Asp Trp Ala Ser Ala Gly Ile Ser Ala Ile Trp Ile
            35                  40                  45

```
Pro Pro Ala Ser Lys Gly Met Gly Gly Ala Tyr Ser Met Gly Tyr Asp
    50                  55                  60
Pro Tyr Asp Phe Phe Asp Leu Gly Glu Tyr Asp Gln Lys Gly Thr Val
65                  70                  75                  80
Glu Thr Arg Phe Gly Ser Lys Gln Glu Leu Val Asn Met Ile Asn Thr
                85                  90                  95
Ala His Ala Tyr Gly Ile Lys Val Ile Ala Asp Ile Val Ile Asn His
                    100                 105                 110
Arg Ala Gly Gly Asp Leu Glu Trp Asn Pro Phe Val Gly Asp Tyr Thr
                115                 120                 125
Trp Thr Asp Phe Ser Lys Val Ala Ser Gly Lys Tyr Thr Ala Asn Tyr
    130                 135                 140
Leu Asp Phe His Pro Asn Glu Leu His Ala Gly Asp Ser Gly Thr Phe
145                 150                 155                 160
Gly Gly Tyr Pro Asp Ile Cys His Asp Lys Ser Trp Asp Gln Tyr Trp
                165                 170                 175
Leu Trp Ala Ser Gln Glu Ser Tyr Ala Ala Tyr Leu Arg Ser Ile Gly
                180                 185                 190
Ile Asp Ala Trp Arg Phe Asp Tyr Val Lys Gly Tyr Gly Ala Trp Val
            195                 200                 205
Val Lys Asp Trp Leu Asp Trp Trp Gly Gly Trp Ala Val Gly Glu Tyr
    210                 215                 220
Trp Asp Thr Asn Val Asp Ala Leu Leu Asn Trp Ala Tyr Ser Ser Asp
225                 230                 235                 240
Ala Lys Val Phe Asp Phe Pro Leu Tyr Tyr Lys Met Asp Glu Ala Phe
                245                 250                 255
Asp Asn Lys Asn Ile Pro Ala Leu Val Ser Ala Leu Gln Asn Gly Gln
                260                 265                 270
Thr Val Val Ser Arg Asp Pro Phe Lys Ala Val Thr Phe Val Ala Asn
            275                 280                 285
His Asp Thr Asp Ile Ile Trp Asn Lys Tyr Pro Ala Tyr Ala Phe Ile
    290                 295                 300
Leu Thr Tyr Glu Gly Gln Pro Thr Ile Phe Tyr Arg Asp Tyr Glu Glu
305                 310                 315                 320
Trp Leu Asn Lys Asp Arg Leu Lys Asn Leu Ile Trp Ile His Asp His
                325                 330                 335
Leu Ala Gly Gly Ser Thr Asp Ile Val Tyr Tyr Asp Asn Asp Glu Leu
                340                 345                 350
Ile Phe Val Arg Asn Gly Tyr Gly Ser Lys Pro Gly Leu Ile Thr Tyr
            355                 360                 365
Ile Asn Leu Ala Ser Ser Lys Ala Gly Arg Trp Val Tyr Val Pro Lys
    370                 375                 380
Phe Ala Gly Ala Cys Ile His Glu Tyr Thr Gly Asn Leu Gly Gly Trp
385                 390                 395                 400
Val Asp Lys Tyr Val Tyr Ser Ser Gly Trp Val Tyr Leu Glu Ala Pro
                405                 410                 415
Ala Tyr Asp Pro Ala Asn Gly Gln Tyr Gly Tyr Ser Val Trp Ser Tyr
                420                 425                 430
Cys Gly Val Gly
            435
```

<210> SEQ ID NO 22
<211> LENGTH: 1311
<212> TYPE: DNA
<213> ORGANISM: Artificial Sequence
<220> FEATURE:
<223> OTHER INFORMATION: DNA sequence coding for an amylase

<400> SEQUENCE: 22

```
atggccaagt actccgagct ggaaggggc gggctcataa tgcaggcctt ctactgggac      60
gtccccatgg gaggaatctg gtgggacacg atagcccaga agatacccga ctgggcaagc     120
gccgggattt cggcgatatg gattccccg gcgagcaagg gcatgggcgg cgcctattcg      180
atgggctacg accctacga cttctttgac ctcggtgagt acgaccagga gggaacggta      240
gagacgcgct ttggctccaa gcaggagctc gtgaacatga taaacacggc ccatgcctac     300
ggcataaagg tcatagcgga catcgtcata aaccaccgcg caggcggaga cctcgagtgg     360
aacccgttcg ttggggacta cacctggacg gacttctcaa aggtggcctc gggcaaatat     420
actgccaact acctcgactt ccaccccaac gaggtcaagt gctgtgacga gggcacattt     480
ggaggcttcc cagacatagc ccacgagaag agctgggacc agcactggct ctgggcgagc     540
gatgagagct acgccgccta cctaaggagc atcggcgttg atgcctggcg cttcgactac     600
gtcaagggct acggagcgtg ggtcgtcaag gactggctgg actggtgggg aggctgggcc     660
gtcggggagt actgggacac aaacgttgat gcactgctca ctgggcccta ctcgagcgat     720
gcaaaagtct tcgacttccc gctctactac aagatggacg cggcctttga caacaagaac     780
attcccgcac tcgtcgaggc cctcaagaac ggggcacag tcgtcagccg cgacccgttt      840
aaggccgtaa cctcgttgc aaaccacgac accgatataa tctggaacaa gtatccagcc     900
tacgcgttca tcctcaccta cgagggccag ccgacaatat tctaccgcga ctacgaggag     960
tggctcaaca aggataagct caagaaccte atctggatac atgacaacct cgccggagga    1020
agcacgagca tagtttacta cgacagcgac gagatgatct tcgtgaggaa cggctatgga    1080
agcaagcctg gccttataac ttacatcaac ctcggctcga gcaaggttgg aaggtgggtt    1140
tacgttccga agttcgcagg ctcgtgcata cacgagtaca ccggcaatct cggcggctgg    1200
gtggacaagt gggtggactc aagcggctgg gtctacctcg aggctcctgc ccacgacccg    1260
gccaacggcc agtacggcta ctccgtctgg agctactgcg gtgttgggtg a             1311
```

<210> SEQ ID NO 23
<211> LENGTH: 436
<212> TYPE: PRT
<213> ORGANISM: Artificial Sequence
<220> FEATURE:
<223> OTHER INFORMATION: protein sequence of an amylase

<400> SEQUENCE: 23

```
Met Ala Lys Tyr Ser Glu Leu Glu Gly Gly Gly Leu Ile Met Gln Ala
1               5                   10                  15

Phe Tyr Trp Asp Val Pro Met Gly Gly Ile Trp Trp Asp Thr Ile Ala
            20                  25                  30

Gln Lys Ile Pro Asp Trp Ala Ser Ala Gly Ile Ser Ala Ile Trp Ile
        35                  40                  45

Pro Pro Ala Ser Lys Gly Met Gly Gly Ala Tyr Ser Met Gly Tyr Asp
    50                  55                  60

Pro Tyr Asp Phe Phe Asp Leu Gly Glu Tyr Asp Gln Glu Gly Thr Val
65                  70                  75                  80
```

```
Glu Thr Arg Phe Gly Ser Lys Gln Glu Leu Val Asn Met Ile Asn Thr
                    85                  90                  95

Ala His Ala Tyr Gly Ile Lys Val Ile Ala Asp Ile Val Ile Asn His
            100                 105                 110

Arg Ala Gly Gly Asp Leu Glu Trp Asn Pro Phe Val Gly Asp Tyr Thr
        115                 120                 125

Trp Thr Asp Phe Ser Lys Val Ala Ser Gly Lys Tyr Thr Ala Asn Tyr
130                 135                 140

Leu Asp Phe His Pro Asn Glu Val Lys Cys Cys Asp Glu Gly Thr Phe
145                 150                 155                 160

Gly Gly Phe Pro Asp Ile Ala His Glu Lys Ser Trp Asp Gln His Trp
                165                 170                 175

Leu Trp Ala Ser Asp Glu Ser Tyr Ala Ala Tyr Leu Arg Ser Ile Gly
            180                 185                 190

Val Asp Ala Trp Arg Phe Asp Tyr Val Lys Gly Tyr Gly Ala Trp Val
        195                 200                 205

Val Lys Asp Trp Leu Asp Trp Trp Gly Gly Trp Ala Val Gly Glu Tyr
210                 215                 220

Trp Asp Thr Asn Val Asp Ala Leu Leu Asn Trp Ala Tyr Ser Ser Asp
225                 230                 235                 240

Ala Lys Val Phe Asp Phe Pro Leu Tyr Tyr Lys Met Asp Ala Ala Phe
                245                 250                 255

Asp Asn Lys Asn Ile Pro Ala Leu Val Glu Ala Leu Lys Asn Gly Gly
            260                 265                 270

Thr Val Val Ser Arg Asp Pro Phe Lys Ala Val Thr Phe Val Ala Asn
        275                 280                 285

His Asp Thr Asp Ile Ile Trp Asn Lys Tyr Pro Ala Tyr Ala Phe Ile
290                 295                 300

Leu Thr Tyr Glu Gly Gln Pro Thr Ile Phe Tyr Arg Asp Tyr Glu Glu
305                 310                 315                 320

Trp Leu Asn Lys Asp Lys Leu Lys Asn Leu Ile Trp Ile His Asp Asn
                325                 330                 335

Leu Ala Gly Gly Ser Thr Ser Ile Val Tyr Tyr Asp Ser Asp Glu Met
            340                 345                 350

Ile Phe Val Arg Asn Gly Tyr Gly Ser Lys Pro Gly Leu Ile Thr Tyr
        355                 360                 365

Ile Asn Leu Gly Ser Ser Lys Val Gly Arg Trp Val Tyr Val Pro Lys
370                 375                 380

Phe Ala Gly Ser Cys Ile His Glu Tyr Thr Gly Asn Leu Gly Gly Trp
385                 390                 395                 400

Val Asp Lys Trp Val Asp Ser Ser Gly Trp Val Tyr Leu Glu Ala Pro
                405                 410                 415

Ala His Asp Pro Ala Asn Gly Gln Tyr Gly Tyr Ser Val Trp Ser Tyr
            420                 425                 430

Cys Gly Val Gly
        435

<210> SEQ ID NO 24
<211> LENGTH: 1311
<212> TYPE: DNA
<213> ORGANISM: Artificial Sequence
<220> FEATURE:
<223> OTHER INFORMATION: DNA sequence coding for an amylase
```

<400> SEQUENCE: 24

```
atggccaagt acctggagct cgaagagggc gggctcataa tgcaggcctt ctactgggac    60
gtccccatgg aggaatctg gtgggacacg atagcccaga agatacccga ctgggcaagc   120
gccgggattt cggcgatatg gattcctccc gcgagcaagg gtatgagcgg cggctattcg   180
atgggctacg accctacga ttattttgac cttggtgagt actaccagaa gggaacggtg   240
gaaacgaggt tcggctcaaa gcaggagctc ataaacatga taaacacggc ccatgcctac   300
ggcataaagg tcatagcgga catcgtcata aaccaccgcg caggcggaga cctcgagtgg   360
aacccgttcg ttggggacta cacctggacg gacttctcaa aggtggcctc gggcaaatat   420
actgccaact acctcgactt ccacccgaac gagctccatg cgggcgattc cggaacattt   480
ggaggctatc ccgacatatg ccacgacaag agctgggacc agtactgct ctgggccagc   540
caggagagct acgcggcata tctcaggagc atcggcatcg atgcctggcg cttcgactac   600
gtcaagggct atgctccctg gtcgtcaag gactggctga actggtgggg gggctgggcg   660
gttggagagt actgggacac caacgtcgac gctgttctca actgggcata ctcgagcggt   720
gccaaggtct ttgacttcgc cctctactac aagatggatg aggcctttga caacaaaaac   780
attccagcgc tcgtctctgc ccttcagaac ggccagactg ttgtctcccg cgacccgttc   840
aaggccgtaa cctttgtagc aaaccacgac accgatataa tttggaacaa gtacccggcc   900
tacgccttca tcctcaccta cgagggccag ccgacgatat tctaccgcga ctacgaggag   960
tggctcaaca aggacaggct caagaacctc atctggatac acgaccacct cgccggtgga  1020
agcactgaca tcgtttacta cgacaacgac gagctgatat tcgtgagaaa cggctacgga  1080
agcaagccgg gactgataac atacatcaac ctcgcctcaa gcaaagccgg aaggtgggtt  1140
tatgtgccga agttcgcggg gcgtgcatc acgagcata ctggtaacct cggaggctgg  1200
gtagacaagt acgtctactc aagcggctgg gtctatctcg aagctccagc ttacgaccct  1260
gccaacgggc agtatggcta ctccgtgtgg agctactgcg gtgttggctg a           1311
```

<210> SEQ ID NO 25
<211> LENGTH: 436
<212> TYPE: PRT
<213> ORGANISM: Artificial Sequence
<220> FEATURE:
<223> OTHER INFORMATION: protein sequence of an amylase

<400> SEQUENCE: 25

```
Met Ala Lys Tyr Leu Glu Leu Glu Glu Gly Gly Leu Ile Met Gln Ala
1               5                   10                  15

Phe Tyr Trp Asp Val Pro Met Gly Gly Ile Trp Trp Asp Thr Ile Ala
                20                  25                  30

Gln Lys Ile Pro Asp Trp Ala Ser Ala Gly Ile Ser Ile Trp Ile
            35                  40                  45

Pro Pro Ala Ser Lys Gly Met Ser Gly Gly Tyr Ser Met Gly Tyr Asp
        50                  55                  60

Pro Tyr Asp Tyr Phe Asp Leu Gly Glu Tyr Tyr Gln Lys Gly Thr Val
65                  70                  75                  80

Glu Thr Arg Phe Gly Ser Lys Gln Glu Leu Ile Asn Met Ile Asn Thr
                85                  90                  95

Ala His Ala Tyr Gly Ile Lys Val Ile Ala Asp Ile Val Ile Asn His
                100                 105                 110

Arg Ala Gly Gly Asp Leu Glu Trp Asn Pro Phe Val Gly Asp Tyr Thr
            115                 120                 125
```

```
Trp Thr Asp Phe Ser Lys Val Ala Ser Gly Lys Tyr Thr Ala Asn Tyr
    130                 135                 140

Leu Asp Phe His Pro Asn Glu Leu His Ala Gly Asp Ser Gly Thr Phe
145                 150                 155                 160

Gly Gly Tyr Pro Asp Ile Cys His Asp Lys Ser Trp Asp Gln Tyr Trp
                165                 170                 175

Leu Trp Ala Ser Gln Glu Ser Tyr Ala Ala Tyr Leu Arg Ser Ile Gly
                180                 185                 190

Ile Asp Ala Trp Arg Phe Asp Tyr Val Lys Gly Tyr Ala Pro Trp Val
                195                 200                 205

Val Lys Asp Trp Leu Asn Trp Trp Gly Gly Trp Ala Val Gly Glu Tyr
210                 215                 220

Trp Asp Thr Asn Val Asp Ala Val Leu Asn Trp Ala Tyr Ser Ser Gly
225                 230                 235                 240

Ala Lys Val Phe Asp Phe Ala Leu Tyr Tyr Lys Met Asp Glu Ala Phe
                245                 250                 255

Asp Asn Lys Asn Ile Pro Ala Leu Val Ser Ala Leu Gln Asn Gly Gln
                260                 265                 270

Thr Val Val Ser Arg Asp Pro Phe Lys Ala Val Thr Phe Val Ala Asn
                275                 280                 285

His Asp Thr Asp Ile Ile Trp Asn Lys Tyr Pro Ala Tyr Ala Phe Ile
                290                 295                 300

Leu Thr Tyr Glu Gly Gln Pro Thr Ile Phe Tyr Arg Asp Tyr Glu Glu
305                 310                 315                 320

Trp Leu Asn Lys Asp Arg Leu Lys Asn Leu Ile Trp Ile His Asp His
                325                 330                 335

Leu Ala Gly Gly Ser Thr Asp Ile Val Tyr Tyr Asp Asn Asp Glu Leu
                340                 345                 350

Ile Phe Val Arg Asn Gly Tyr Gly Ser Lys Pro Gly Leu Ile Thr Tyr
                355                 360                 365

Ile Asn Leu Ala Ser Ser Lys Ala Gly Arg Trp Val Tyr Val Pro Lys
                370                 375                 380

Phe Ala Gly Ala Cys Ile His Glu His Thr Gly Asn Leu Gly Gly Trp
385                 390                 395                 400

Val Asp Lys Tyr Val Tyr Ser Ser Gly Trp Val Tyr Leu Glu Ala Pro
                405                 410                 415

Ala Tyr Asp Pro Ala Asn Gly Gln Tyr Gly Tyr Ser Val Trp Ser Tyr
                420                 425                 430

Cys Gly Val Gly
        435

<210> SEQ ID NO 26
<211> LENGTH: 1311
<212> TYPE: DNA
<213> ORGANISM: Artificial Sequence
<220> FEATURE:
<223> OTHER INFORMATION: DNA sequence coding for an amylase

<400> SEQUENCE: 26
atggccaagt actccgagct ggaagagggc ggcgttataa tgcaggcctt ctactgggac      60
gtcccaggtg gaggaatctg gtgggacacc atcaggagca agataccgga gtggtacgag     120
gcgggaatat ccgccatttg gattcctccc gggagcaagg gtatgagcgg cggctattcg     180
atgggctacg accctacga tgatttggac ctgggtgagt actaccagaa gggaacggtg     240
gaaacgaggt tcggctcaaa gcaggagctc ataaacatga taaacacggc ccatgcctac     300
```

```
ggcataaagg tcatagcgga catcgtcata aaccaccgcg caggcggaga cctcgagtgg      360
aacccgttcg ttggggacta cacctggacg gacttctcaa aggtggcctc gggcaaatat      420
actgccaact acctcgactt ccacccgaac gagctccatg cgggcgattc cggaacattt      480
ggaggctatc ccgacatatg ccacgacaag agctgggacc agtactggct ctgggccagc      540
caggagagct acgcggtata tctcaggagc atcggcatcg atgcctggcg cttcgactac      600
gtcaagggct acgagcgtg gtcgtcaag gactggctgg actggtgggg aggctgggcc        660
gtcggggagt actgggacac aaacgttgat gcactgctca actgggccta ctcgagcgat      720
gcaaaagtct tcgacttccc gctctactac aagatggatg aggcctttga caacaaaaac      780
attccagcgc tcgtctctgc ccttcagaac ggccagactg ttgtctcccg cgacccgttc      840
aaggccgtaa cctttgtagc aaaccacgac accgatataa tttggaacaa gtacccggcc      900
tacgccttca tcctcaccta cgagggccag ccgacgatat tctaccgcga ctacgaggag      960
tggctcaaca aggacaggct caagaacctc atctggatac acgactacct cgccggtgga     1020
agcactgaca tcgtttacta cgacaacgac gagctgtatt tcgtgagaaa cggctacgga     1080
agcaagccgg gactgataac atacatcaac ctcgcctcaa gcaaagccgg aaggtgggtt     1140
tatgtgccga agttcgcggg cgcgtgcatc cacgagtata ctggtaacct cggaggctgg     1200
gtagacaagt acgtctactc aagcggctgg gtctatctcg aagctccagc ttacgaccct     1260
gccaacgggc agtatggcta ctccgtgtgg agctattgcg gtgttggctg a              1311
```

<210> SEQ ID NO 27
<211> LENGTH: 436
<212> TYPE: PRT
<213> ORGANISM: Artificial Sequence
<220> FEATURE:
<223> OTHER INFORMATION: protein sequence of an amylase

<400> SEQUENCE: 27

```
Met Ala Lys Tyr Ser Glu Leu Glu Gly Gly Val Ile Met Gln Ala
1               5                   10                  15

Phe Tyr Trp Asp Val Pro Gly Gly Ile Trp Trp Asp Thr Ile Arg
                20                  25                  30

Ser Lys Ile Pro Glu Trp Tyr Glu Ala Gly Ile Ser Ala Ile Trp Ile
            35                  40                  45

Pro Pro Gly Ser Lys Gly Met Ser Gly Gly Tyr Ser Met Gly Tyr Asp
        50                  55                  60

Pro Tyr Asp Asp Leu Asp Leu Gly Glu Tyr Tyr Gln Lys Gly Thr Val
65                  70                  75                  80

Glu Thr Arg Phe Gly Ser Lys Gln Glu Leu Ile Asn Met Ile Asn Thr
                85                  90                  95

Ala His Ala Tyr Gly Ile Lys Val Ile Ala Asp Ile Val Ile Asn His
            100                 105                 110

Arg Ala Gly Gly Asp Leu Glu Trp Asn Pro Phe Val Gly Asp Tyr Thr
        115                 120                 125

Trp Thr Asp Phe Ser Lys Val Ala Ser Gly Lys Tyr Thr Ala Asn Tyr
    130                 135                 140

Leu Asp Phe His Pro Asn Glu Leu His Ala Gly Asp Ser Gly Thr Phe
145                 150                 155                 160

Gly Gly Tyr Pro Asp Ile Cys His Asp Lys Ser Trp Asp Gln Tyr Trp
                165                 170                 175

Leu Trp Ala Ser Gln Glu Ser Tyr Ala Val Tyr Leu Arg Ser Ile Gly
            180                 185                 190
```

```
Ile Asp Ala Trp Arg Phe Asp Tyr Val Lys Gly Tyr Gly Ala Trp Val
            195                 200                 205

Val Lys Asp Trp Leu Asp Trp Trp Gly Gly Trp Ala Val Gly Glu Tyr
210                 215                 220

Trp Asp Thr Asn Val Asp Ala Leu Leu Asn Trp Ala Tyr Ser Ser Asp
225                 230                 235                 240

Ala Lys Val Phe Asp Phe Pro Leu Tyr Tyr Lys Met Asp Glu Ala Phe
            245                 250                 255

Asp Asn Lys Asn Ile Pro Ala Leu Val Ser Ala Leu Gln Asn Gly Gln
            260                 265                 270

Thr Val Val Ser Arg Asp Pro Phe Lys Ala Val Thr Phe Val Ala Asn
            275                 280                 285

His Asp Thr Asp Ile Ile Trp Asn Lys Tyr Pro Ala Tyr Ala Phe Ile
            290                 295                 300

Leu Thr Tyr Glu Gly Gln Pro Thr Ile Phe Tyr Arg Asp Tyr Glu Glu
305                 310                 315                 320

Trp Leu Asn Lys Asp Arg Leu Lys Asn Leu Ile Trp Ile His Asp Tyr
            325                 330                 335

Leu Ala Gly Gly Ser Thr Asp Ile Val Tyr Tyr Asp Asn Asp Glu Leu
            340                 345                 350

Ile Phe Val Arg Asn Gly Tyr Gly Ser Lys Pro Gly Leu Ile Thr Tyr
            355                 360                 365

Ile Asn Leu Ala Ser Ser Lys Ala Gly Arg Trp Val Tyr Val Pro Lys
            370                 375                 380

Phe Ala Gly Ala Cys Ile His Glu Tyr Thr Gly Asn Leu Gly Gly Trp
385                 390                 395                 400

Val Asp Lys Tyr Val Tyr Ser Ser Gly Trp Val Tyr Leu Glu Ala Pro
            405                 410                 415

Ala Tyr Asp Pro Ala Asn Gly Gln Tyr Gly Tyr Ser Val Trp Ser Tyr
            420                 425                 430

Cys Gly Val Gly
            435

<210> SEQ ID NO 28
<211> LENGTH: 1311
<212> TYPE: DNA
<213> ORGANISM: Artificial Sequence
<220> FEATURE:
<223> OTHER INFORMATION: DNA sequence coding for an amylase

<400> SEQUENCE: 28
atggccaagt actccgagct ggaagagggc ggcgttatag tgcaggcctt ctactgggac      60
gtcccaggtg aggaatctg  tgggacacc  atcaggagca agataccgga gtggtacgag     120
gcgggaatat ccgccatttg gattccccg  gcgagcaagg gcatgggcgg cgcctattcg     180
atgggctacg accctacga cttctttgac ctcggtgagt acgaccagaa gggaacggta     240
gagacgcgct ttggctccaa gcaggagctc gtgaacatga taaacacggc ccatgcctac     300
ggcataaagg tcatagcgga catcgtcata aaccaccgcg caggcggaga cctcgagtgg     360
aacccgttcg ttggggacta cacctggacg gacttctcaa aggtggcctc gggcaaatat     420
actgccaact acctcgactt ccacccgaac gagctccatg cgggcgattc cggaacattt     480
ggaggctatc ccgacatatg ccacgacaag agctgggacc agtactggct ctgggccagc     540
caggagagct acgcggcata tctcaggagc atcggcatcg atgcctggcg cttcgactac     600
gtcaagggct acggagcgtg ggtcgtcaag gactggctgg actggtgggg aggctgggcc     660
```

-continued

```
gtcggggagt actgggacac aaacgttgat gcactgctca actgggccta ctcgagcgat    720
gcaaaagtct tcgacttccc gctctactac aagatggatg aggcctttga caacaaaaac    780
attccagcgc tcgtctctgc ccttcagaac ggccagactg ttgtctcccg cgacccgttc    840
aaggccgtaa cctttgtagc aaaccacgac accgatataa tctggaacaa gtatccagcc    900
tacgcgttca tcctcaccta cgagggccag ccgacaatat tctaccgcga ctacgaggag    960
tggctcaaca aggataagct caagaacctc atctggatac atgacaacct cgccggagga   1020
agcatgagca tagtttacta cgacagcgac gagatgatct tcgtgaggaa cggctatgga   1080
agcaagcctg gccttataac ttacatcaac ctcggctcga gcaaggttgg aaggtgggtc   1140
tacgttccga agttcgcggg agcgtgcatc cacgagtaca ccggcaacct cggcggctgg   1200
gtggacaagt gggtggactc aagcgggtgg gtgtacctcg aggcccctgc ccacgacccg   1260
gccaacggct attacggcta ctccgtctgg agctattgcg gtgttggctg a            1311
```

<210> SEQ ID NO 29
<211> LENGTH: 436
<212> TYPE: PRT
<213> ORGANISM: Artificial Sequence
<220> FEATURE:
<223> OTHER INFORMATION: protein sequence of an amylase

<400> SEQUENCE: 29

```
Met Ala Lys Tyr Ser Glu Leu Glu Glu Gly Gly Val Ile Val Gln Ala
1               5                   10                  15

Phe Tyr Trp Asp Val Pro Gly Gly Ile Trp Trp Asp Thr Ile Arg
            20                  25                  30

Ser Lys Ile Pro Glu Trp Tyr Glu Ala Gly Ile Ser Ala Ile Trp Ile
        35                  40                  45

Pro Pro Ala Ser Lys Gly Met Gly Gly Ala Tyr Ser Met Gly Tyr Asp
    50                  55                  60

Pro Tyr Asp Phe Phe Asp Leu Gly Glu Tyr Asp Gln Lys Gly Thr Val
65                  70                  75                  80

Glu Thr Arg Phe Gly Ser Lys Gln Glu Leu Val Asn Met Ile Asn Thr
                85                  90                  95

Ala His Ala Tyr Gly Ile Lys Val Ile Ala Asp Ile Val Ile Asn His
            100                 105                 110

Arg Ala Gly Gly Asp Leu Glu Trp Asn Pro Phe Val Gly Asp Tyr Thr
        115                 120                 125

Trp Thr Asp Phe Ser Lys Val Ala Ser Gly Lys Tyr Thr Ala Asn Tyr
    130                 135                 140

Leu Asp Phe His Pro Asn Glu Leu His Ala Gly Asp Ser Gly Thr Phe
145                 150                 155                 160

Gly Gly Tyr Pro Asp Ile Cys His Asp Lys Ser Trp Asp Gln Tyr Trp
                165                 170                 175

Leu Trp Ala Ser Gln Glu Ser Tyr Ala Ala Tyr Leu Arg Ser Ile Gly
            180                 185                 190

Ile Asp Ala Trp Arg Phe Asp Tyr Val Lys Gly Tyr Gly Ala Trp Val
        195                 200                 205

Val Lys Asp Trp Leu Asp Trp Trp Gly Gly Trp Ala Val Gly Glu Tyr
    210                 215                 220

Trp Asp Thr Asn Val Asp Ala Leu Leu Asn Trp Ala Tyr Ser Ser Asp
225                 230                 235                 240

Ala Lys Val Phe Asp Phe Pro Leu Tyr Tyr Lys Met Asp Glu Ala Phe
                245                 250                 255
```

```
Asp Asn Lys Asn Ile Pro Ala Leu Val Ser Ala Leu Gln Asn Gly Gln
            260                 265                 270

Thr Val Val Ser Arg Asp Pro Phe Lys Ala Val Thr Phe Val Ala Asn
        275                 280                 285

His Asp Thr Asp Ile Ile Trp Asn Lys Tyr Pro Ala Tyr Ala Phe Ile
    290                 295                 300

Leu Thr Tyr Glu Gly Gln Pro Thr Ile Phe Tyr Arg Asp Tyr Glu Glu
305                 310                 315                 320

Trp Leu Asn Lys Asp Lys Leu Lys Asn Leu Ile Trp Ile His Asp Asn
            325                 330                 335

Leu Ala Gly Gly Ser Met Ser Ile Val Tyr Tyr Asp Ser Asp Glu Met
        340                 345                 350

Ile Phe Val Arg Asn Gly Tyr Gly Ser Lys Pro Gly Leu Ile Thr Tyr
    355                 360                 365

Ile Asn Leu Gly Ser Ser Lys Val Gly Arg Trp Val Tyr Val Pro Lys
370                 375                 380

Phe Ala Gly Ala Cys Ile His Glu Tyr Thr Gly Asn Leu Gly Gly Trp
385                 390                 395                 400

Val Asp Lys Trp Val Asp Ser Ser Gly Trp Val Tyr Leu Glu Ala Pro
            405                 410                 415

Ala His Asp Pro Ala Asn Gly Tyr Tyr Gly Tyr Ser Val Trp Ser Tyr
        420                 425                 430

Cys Gly Val Gly
        435

<210> SEQ ID NO 30
<211> LENGTH: 1311
<212> TYPE: DNA
<213> ORGANISM: Artificial Sequence
<220> FEATURE:
<223> OTHER INFORMATION: DNA sequence coding for an amylase

<400> SEQUENCE: 30
atggccaagt acctggagct cgaagagggc gggctcataa tgcaggcctt ctactgggac      60
gtccccatgg aggaatctg tgggacacg atagcccaga agatacccga ctgggcaagc      120
gccgggattt cggcgatatg gattcctccc gcgagcaagg gtatgagcgg cggctattcg      180
atgggctacg accctacga ttattttgac ctcggtgagt actaccagaa gggaacggtg      240
gaaacgaggt tcggctcaaa gcaggagctc ataaacatga taaacaccgc ccacgcctat      300
ggcatgaagg taatagccga tatagtcatc aaccaccgcg ccggcggtga cctggagtgg      360
aaccccttcg tgaacgacta tacctggacc gacttctcaa aggtcgcgtc gggtaaatac      420
acggccaact acctcgactt ccacccgaac gagctccatg cgggcgattc cggaacattt      480
ggaggctatc ccgacatatg ccacgacaag agctgggacc agtactggct ctgggccagc      540
caggagagct acgcggcata tctcaggagc atcggcatcg atgcctggcg cttcgactac      600
gtcaagggct atgctccctg gtcgtcaag gactggctga ctggtgggg aggctgggcg      660 gttggagagt actgggacac caacgtcgac gctgttctca actgggcata ctcgagcggt      720
gccaaggtct ttgacttcgc cctctactac aagatggacg aggccttcga taacaacaac      780
attcccgccc tggtgggcgc cctcagatac ggtcagacag tggtcagccg cgaccgttc      840 aaggctgtga cgtttgtagc caaccacgat accgatataa tctggaacaa gtatccagcc      900
tacgcgttca tcctcaccta cgagggccag ccgacaatat tctaccgcga ctacgaggag      960
tggctcaaca aggataagct caagaacctc atctggatac atgacaacct cgccggagga     1020
```

-continued

```
agcaccgaca tagtctacta cgataacgat gaactcatct tcgtcaggca cggctacggg    1080
gacaagccgg ggcttataac ctacatcaac ctaggctcga gcaaggccgg aaggtgggtt    1140
tacgttccga agttcgcagg ctcgtgcata cacgagtaca ccggcaatct cggcggctgg    1200
gtggacaagt gggtggactc aagcggctgg gtctacctcg aggctcctgc ccacgacccg    1260
gccaacggcc agtacggcta ctccgtctgg agctattgcg gtgttgggtg a             1311
```

```
<210> SEQ ID NO 31
<211> LENGTH: 436
<212> TYPE: PRT
<213> ORGANISM: Artificial Sequence
<220> FEATURE:
<223> OTHER INFORMATION: protein sequence of an amylase

<400> SEQUENCE: 31
```

| | | | | | | | | | | | | | | | |
|---|---|---|---|---|---|---|---|---|---|---|---|---|---|---|---|
| Met | Ala | Lys | Tyr | Leu | Glu | Leu | Glu | Glu | Gly | Gly | Leu | Ile | Met | Gln | Ala |
| 1 | | | | 5 | | | | | 10 | | | | | 15 | |
| Phe | Tyr | Trp | Asp | Val | Pro | Met | Gly | Gly | Ile | Trp | Trp | Asp | Thr | Ile | Ala |
| | | | 20 | | | | | 25 | | | | | 30 | | |
| Gln | Lys | Ile | Pro | Asp | Trp | Ala | Ser | Ala | Gly | Ile | Ser | Ala | Ile | Trp | Ile |
| | | | 35 | | | | | 40 | | | | | 45 | | |
| Pro | Pro | Ala | Ser | Lys | Gly | Met | Ser | Gly | Gly | Tyr | Ser | Met | Gly | Tyr | Asp |
| | 50 | | | | | 55 | | | | | 60 | | | | |
| Pro | Tyr | Asp | Tyr | Phe | Asp | Leu | Gly | Glu | Tyr | Tyr | Gln | Lys | Gly | Thr | Val |
| 65 | | | | | 70 | | | | | 75 | | | | | 80 |
| Glu | Thr | Arg | Phe | Gly | Ser | Lys | Gln | Glu | Leu | Ile | Asn | Met | Ile | Asn | Thr |
| | | | | 85 | | | | | 90 | | | | | 95 | |
| Ala | His | Ala | Tyr | Gly | Met | Lys | Val | Ile | Ala | Asp | Ile | Val | Ile | Asn | His |
| | | | 100 | | | | | 105 | | | | | 110 | | |
| Arg | Ala | Gly | Gly | Asp | Leu | Glu | Trp | Asn | Pro | Phe | Val | Asn | Asp | Tyr | Thr |
| | | | 115 | | | | | 120 | | | | | 125 | | |
| Trp | Thr | Asp | Phe | Ser | Lys | Val | Ala | Ser | Gly | Lys | Tyr | Thr | Ala | Asn | Tyr |
| | | | 130 | | | | | 135 | | | | | 140 | | |
| Leu | Asp | Phe | His | Pro | Asn | Glu | Leu | His | Ala | Gly | Asp | Ser | Gly | Thr | Phe |
| 145 | | | | | 150 | | | | | 155 | | | | | 160 |
| Gly | Gly | Tyr | Pro | Asp | Ile | Cys | His | Asp | Lys | Ser | Trp | Asp | Gln | Tyr | Trp |
| | | | | 165 | | | | | 170 | | | | | 175 | |
| Leu | Trp | Ala | Ser | Gln | Glu | Ser | Tyr | Ala | Ala | Tyr | Leu | Arg | Ser | Ile | Gly |
| | | | 180 | | | | | 185 | | | | | 190 | | |
| Ile | Asp | Ala | Trp | Arg | Phe | Asp | Tyr | Val | Lys | Gly | Tyr | Ala | Pro | Trp | Val |
| | | | 195 | | | | | 200 | | | | | 205 | | |
| Val | Lys | Asp | Trp | Leu | Asn | Trp | Trp | Gly | Gly | Trp | Ala | Val | Gly | Glu | Tyr |
| | | | 210 | | | | | 215 | | | | | 220 | | |
| Trp | Asp | Thr | Asn | Val | Asp | Ala | Val | Leu | Asn | Trp | Ala | Tyr | Ser | Ser | Gly |
| 225 | | | | | 230 | | | | | 235 | | | | | 240 |
| Ala | Lys | Val | Phe | Asp | Phe | Ala | Leu | Tyr | Tyr | Lys | Met | Asp | Glu | Ala | Phe |
| | | | | 245 | | | | | 250 | | | | | 255 | |
| Asp | Asn | Asn | Asn | Ile | Pro | Ala | Leu | Val | Gly | Ala | Leu | Arg | Tyr | Gly | Gln |
| | | | 260 | | | | | 265 | | | | | 270 | | |
| Thr | Val | Val | Ser | Arg | Asp | Pro | Phe | Lys | Ala | Val | Thr | Phe | Val | Ala | Asn |
| | | | 275 | | | | | 280 | | | | | 285 | | |
| His | Asp | Thr | Asp | Ile | Ile | Trp | Asn | Lys | Tyr | Pro | Ala | Tyr | Ala | Phe | Ile |
| | | 290 | | | | | 295 | | | | | 300 | | | |
| Leu | Thr | Tyr | Glu | Gly | Gln | Pro | Thr | Ile | Phe | Tyr | Arg | Asp | Tyr | Glu | Glu |
| 305 | | | | | 310 | | | | | 315 | | | | | 320 |

```
Trp Leu Asn Lys Asp Lys Leu Lys Asn Leu Ile Trp Ile His Asp Asn
            325                 330                 335

Leu Ala Gly Gly Ser Thr Asp Ile Val Tyr Tyr Asp Asn Asp Glu Leu
        340                 345                 350

Ile Phe Val Arg His Gly Tyr Gly Asp Lys Pro Gly Leu Ile Thr Tyr
            355                 360                 365

Ile Asn Leu Gly Ser Ser Lys Ala Gly Arg Trp Val Tyr Val Pro Lys
        370                 375                 380

Phe Ala Gly Ser Cys Ile His Glu Tyr Thr Gly Asn Leu Gly Gly Trp
385                 390                 395                 400

Val Asp Lys Trp Val Asp Ser Ser Gly Trp Val Tyr Leu Glu Ala Pro
            405                 410                 415

Ala His Asp Pro Ala Asn Gly Gln Tyr Gly Tyr Ser Val Trp Ser Tyr
        420                 425                 430

Cys Gly Val Gly
        435

<210> SEQ ID NO 32
<211> LENGTH: 1311
<212> TYPE: DNA
<213> ORGANISM: Artificial Sequence
<220> FEATURE:
<223> OTHER INFORMATION: DNA sequence coding for an amylase

<400> SEQUENCE: 32
atggcaaagt attccgagct cgaagagggc ggcgttataa tgcaggcctt ctactgggac      60
gtcccaggtg aggaatctg gtgggacacc atcaggagca agataccgga gtggtacgag     120
gcgggaatat ccgccatttg gattcctccc gcgagcaagg gtatgagcgg cggctattcg     180
atgggctacg accctacga ttattttgac ctcggtgagt actaccagaa gggaacggtg      240
gaaacgaggt tcggctcaaa gcaggagctc ataaacatga taaacacggc ccatgcctac      300
ggcataaagg tcatagcgga catcgtcata aaccaccgcg caggcggaga cctcgagtgg      360
aacccgttcg ttggggacta cacctggacg gacttctcaa aggtggcctc gggcaaatat      420
actgccaact acctcgactt ccacccgaac gagctccatg cgggcgattc cggaacattt      480
ggaggctatc ccgacatatg ccacgacaag agctgggacc agtactggct ctgggccagc      540
caggagagct acgcggcata tctcaggagc atcggcatcg atgcctggcg cttcgactac      600
gtcaagggct atgctccctg gtcgtcaag gactggctga actggtgggg aggctgggcg      660
gttggagagt actgggacac caacgtcgac gctgttctca actgggcata ctcgagcggt      720
gccaaggtct ttgacttcgc cctctactac aagatggacg cggcctttga acaagaac       780 attcccgcac tcgtcgaggc cctcaagaac ggggggcacag tcgtcagccg cgacccgttt      840
aaggccgtaa ccttcgttgc aaaccacgac accgatataa tctggaacaa gtatccagcc      900
tacgcgttca tcctcaccta cgagggccag ccgacaatat tctaccgcga ctacgaggag      960
tggctcaaca aggataagct caagaacctc atctggatac atgacaacct cgccggagga     1020
agcactgaca tcgtttacta cgacaacgac gagctgatat cgtgagaaaa cggctacgga     1080
agcaagccgg gactgataac atacatcaac ctcgcgtcaa gcaaagccgg aagtgggtt     1140 tacgttccga agttcgcagg ctcgtgcata cacgagtaca ccggcaatct cggcggctgg     1200
gtggacaagt gggtgactc aagcggctgg gtctacctcg aggctcctgc ccacgacccg     1260
gccaacggcc agtacggcta ctccgtctgg agctactgcg gtgttgggtg a             1311
```

```
<210> SEQ ID NO 33
<211> LENGTH: 436
<212> TYPE: PRT
<213> ORGANISM: Artificial Sequence
<220> FEATURE:
<223> OTHER INFORMATION: protein sequence of an amylase

<400> SEQUENCE: 33
```

Met Ala Lys Tyr Ser Glu Leu Glu Glu Gly Val Ile Met Gln Ala
1               5                   10                  15

Phe Tyr Trp Asp Val Pro Gly Gly Ile Trp Trp Asp Thr Ile Arg
                20                  25                  30

Ser Lys Ile Pro Glu Trp Tyr Glu Ala Gly Ile Ser Ala Ile Trp Ile
            35                  40                  45

Pro Pro Ala Ser Lys Gly Met Ser Gly Gly Tyr Ser Met Gly Tyr Asp
50                  55                  60

Pro Tyr Asp Tyr Phe Asp Leu Gly Glu Tyr Tyr Gln Lys Gly Thr Val
65                  70                  75                  80

Glu Thr Arg Phe Gly Ser Lys Gln Glu Leu Ile Asn Met Ile Asn Thr
                85                  90                  95

Ala His Ala Tyr Gly Ile Lys Val Ile Ala Asp Ile Val Ile Asn His
            100                 105                 110

Arg Ala Gly Gly Asp Leu Glu Trp Asn Pro Phe Val Gly Asp Tyr Thr
        115                 120                 125

Trp Thr Asp Phe Ser Lys Val Ala Ser Gly Lys Tyr Thr Ala Asn Tyr
    130                 135                 140

Leu Asp Phe His Pro Asn Glu Leu His Ala Gly Asp Ser Gly Thr Phe
145                 150                 155                 160

Gly Gly Tyr Pro Asp Ile Cys His Asp Lys Ser Trp Asp Gln Tyr Trp
                165                 170                 175

Leu Trp Ala Ser Gln Glu Ser Tyr Ala Ala Tyr Leu Arg Ser Ile Gly
            180                 185                 190

Ile Asp Ala Trp Arg Phe Asp Tyr Val Lys Gly Tyr Ala Pro Trp Val
        195                 200                 205

Val Lys Asp Trp Leu Asn Trp Trp Gly Gly Trp Ala Val Gly Glu Tyr
    210                 215                 220

Trp Asp Thr Asn Val Asp Ala Val Leu Asn Trp Ala Tyr Ser Ser Gly
225                 230                 235                 240

Ala Lys Val Phe Asp Phe Ala Leu Tyr Tyr Lys Met Asp Ala Ala Phe
                245                 250                 255

Asp Asn Lys Asn Ile Pro Ala Leu Val Glu Ala Leu Lys Asn Gly Gly
            260                 265                 270

Thr Val Val Ser Arg Asp Pro Phe Lys Ala Val Thr Phe Val Ala Asn
        275                 280                 285

His Asp Thr Asp Ile Ile Trp Asn Lys Tyr Pro Ala Tyr Ala Phe Ile
    290                 295                 300

Leu Thr Tyr Glu Gly Gln Pro Thr Ile Phe Tyr Arg Asp Tyr Glu Glu
305                 310                 315                 320

Trp Leu Asn Lys Asp Lys Leu Lys Asn Leu Ile Trp Ile His Asp Asn
                325                 330                 335

Leu Ala Gly Gly Ser Thr Asp Ile Val Tyr Tyr Asp Asn Asp Glu Leu
            340                 345                 350

Ile Phe Val Arg Asn Gly Tyr Gly Ser Lys Pro Gly Leu Ile Thr Tyr
        355                 360                 365

Ile Asn Leu Ala Ser Ser Lys Ala Gly Arg Trp Val Tyr Val Pro Lys
370             375                 380

Phe Ala Gly Ser Cys Ile His Glu Tyr Thr Gly Asn Leu Gly Gly Trp
385             390                 395                 400

Val Asp Lys Trp Val Asp Ser Ser Gly Trp Val Tyr Leu Glu Ala Pro
            405                 410                 415

Ala His Asp Pro Ala Asn Gly Gln Tyr Gly Tyr Ser Val Trp Ser Tyr
                420                 425                 430

Cys Gly Val Gly
        435

<210> SEQ ID NO 34
<211> LENGTH: 1311
<212> TYPE: DNA
<213> ORGANISM: Artificial Sequence
<220> FEATURE:
<223> OTHER INFORMATION: DNA sequence coding for an amylase

<400> SEQUENCE: 34

```
atggccaagt acctggagct cgaagagggc gggctcataa tgcaggcctt ctactgggac      60
gtccccatgg gaggaatctg gtgggacacg gtagcccaga agatacccga ctgggcaagc     120
gccgggattt cggcgatatg gattcccccg gcgagcaagg gcatgggcgg cgcctattcg     180
atgggctacg accctacga cttctttgac ctcggtgagt acgaccagaa gggaacggta     240
gagacgcgct ttggctccaa gcaggagctc gtgaacatga taaacacggc ccatgcctac     300
ggcataaagg tcatagcgga catcgtcata aaccaccgcg caggcggaga cctcgagtgg     360
aacccgttcg ttggggacta cacctggacg gacttctcaa aggtggtctc gggcaaatat     420
actgccaact acctcgactt ccacccgaac gagctccatg cgggcgattc cggaacattt     480
ggaggctatc ccgacatatg ccacgacaag agctgggacc agtactggct ctgggccagc     540
caggagagct acgcggcata tctcaggagc atcggcatcg atgcctggcg cttcgactac     600
gtcaagggct atgctccctg ggtcgtcaag gactggctga actggtgggg aggctgggcg     660
gttggagagt actgggacac caacgtcgac gctgttctca actgggcata ctcgagcggt     720
gccaaggtct ttgacttcgc cctctactac aagatggatg aggcctttga acaaaaaac     780
attccagcgc tcgtctctgc ccttcagaac ggccagactg ttgtctcccg cgacccgttc     840
aaggccgtaa cctttgtagc aaaccacgac accgatataa tctggaacaa gtaccttgct     900
tatgccttca tcctcaccta cgaaggccag cccgtcatat tctaccgcga ctacgaggag     960
tggctcaaca aggacaggtt gaacaacctc atatggatac acgaccacct cgcagggga    1020
agcaccgaca tagtctacta cgataacgat gaactcatct tcgtcaggaa cggctacggg    1080
gacaagccgg ggcttataac ctacatcaac ctaggctcga gcaaggccgg aaggtgggtt    1140
tatgtgccga agttcgcggg cgcgtgcatc cacgagtata ctggtaacct cggaggctgg    1200
gtagacaagt acgtctactc aagcggctgg gtctatctcg aagctccagc ttacgaccct    1260
gccaacgggc agtatggcta ctccgtgtgg agctactgcg gtgttgggtg a             1311
```

<210> SEQ ID NO 35
<211> LENGTH: 436
<212> TYPE: PRT
<213> ORGANISM: Artificial Sequence
<220> FEATURE:
<223> OTHER INFORMATION: protein sequence of an amylase

<400> SEQUENCE: 35

```
Met Ala Lys Tyr Leu Glu Leu Glu Glu Gly Leu Ile Met Gln Ala
1               5                   10                  15

Phe Tyr Trp Asp Val Pro Met Gly Gly Ile Trp Trp Asp Thr Val Ala
            20                  25                  30

Gln Lys Ile Pro Asp Trp Ala Ser Ala Gly Ile Ser Ala Ile Trp Ile
            35                  40                  45

Pro Pro Ala Ser Lys Gly Met Gly Gly Ala Tyr Ser Met Gly Tyr Asp
50                  55                  60

Pro Tyr Asp Phe Phe Asp Leu Gly Glu Tyr Asp Gln Lys Gly Thr Val
65                  70                  75                  80

Glu Thr Arg Phe Gly Ser Lys Gln Glu Leu Val Asn Met Ile Asn Thr
                85                  90                  95

Ala His Ala Tyr Gly Ile Lys Val Ile Ala Asp Ile Val Ile Asn His
            100                 105                 110

Arg Ala Gly Gly Asp Leu Glu Trp Asn Pro Phe Val Gly Asp Tyr Thr
            115                 120                 125

Trp Thr Asp Phe Ser Lys Val Val Ser Gly Lys Tyr Thr Ala Asn Tyr
130                 135                 140

Leu Asp Phe His Pro Asn Glu Leu His Ala Gly Asp Ser Gly Thr Phe
145                 150                 155                 160

Gly Gly Tyr Pro Asp Ile Cys His Asp Lys Ser Trp Asp Gln Tyr Trp
                165                 170                 175

Leu Trp Ala Ser Gln Glu Ser Tyr Ala Ala Tyr Leu Arg Ser Ile Gly
            180                 185                 190

Ile Asp Ala Trp Arg Phe Asp Tyr Val Lys Gly Tyr Ala Pro Trp Val
            195                 200                 205

Val Lys Asp Trp Leu Asn Trp Trp Gly Gly Trp Ala Val Gly Glu Tyr
            210                 215                 220

Trp Asp Thr Asn Val Asp Ala Val Leu Asn Trp Ala Tyr Ser Ser Gly
225                 230                 235                 240

Ala Lys Val Phe Asp Phe Ala Leu Tyr Tyr Lys Met Asp Glu Ala Phe
                245                 250                 255

Asp Asn Lys Asn Ile Pro Ala Leu Val Ser Ala Leu Gln Asn Gly Gln
            260                 265                 270

Thr Val Val Ser Arg Asp Pro Phe Lys Ala Val Thr Phe Val Ala Asn
            275                 280                 285

His Asp Thr Asp Ile Ile Trp Asn Lys Tyr Leu Ala Tyr Ala Phe Ile
290                 295                 300

Leu Thr Tyr Glu Gly Gln Pro Val Ile Phe Tyr Arg Asp Tyr Glu Glu
305                 310                 315                 320

Trp Leu Asn Lys Asp Arg Leu Asn Asn Leu Ile Trp Ile His Asp His
                325                 330                 335

Leu Ala Gly Gly Ser Thr Asp Ile Val Tyr Tyr Asp Asn Asp Glu Leu
            340                 345                 350

Ile Phe Val Arg Asn Gly Tyr Gly Asp Lys Pro Gly Leu Ile Thr Tyr
            355                 360                 365

Ile Asn Leu Gly Ser Ser Lys Ala Gly Arg Trp Val Tyr Val Pro Lys
370                 375                 380

Phe Ala Gly Ala Cys Ile His Glu Tyr Thr Gly Asn Leu Gly Gly Trp
385                 390                 395                 400

Val Asp Lys Tyr Val Tyr Ser Ser Gly Trp Val Tyr Leu Glu Ala Pro
                405                 410                 415
```

Ala Tyr Asp Pro Ala Asn Gly Gln Tyr Gly Tyr Ser Val Trp Ser Tyr
            420                 425                 430

Cys Gly Val Gly
        435

<210> SEQ ID NO 36
<211> LENGTH: 1311
<212> TYPE: DNA
<213> ORGANISM: Artificial Sequence
<220> FEATURE:
<223> OTHER INFORMATION: DNA sequence coding for an amylase

<400> SEQUENCE: 36

```
atggccaagt acctggagct cgaagagggc gggctcataa tgcaggcctt ctactgggac      60
gtccccatgg gaggaatctg gtgggacacg atagcccaga agatacccga ctgggcaagc     120
gccgggattt cggcgatatg gattcccccg gcgagcaagg gcatgggcgg cgcctattcg     180
atgggctacg accctacga cttctttgac ctcggtgagt acgaccagaa gggaacggta     240
gagacgcgct ttggctccaa gcaggagctc gtgaacatga taaacaccgc ccacgcctac     300
ggcatcaagg tcatcgcaga catagtaatc aaccaccgcg ccggaggaga ccttgagtgg     360
aaccccttcg tcaatgacta cacctggacg gacttctcga aggtcgcttc cggcaagtac     420
acggccaatt acctcgactt ccacccgaac gagctccatg cgggcgattc cggaacattt     480
ggaggctatc ccgacatatg ccacgacaag agctgggacc agtactggct ctgggccagc     540
caggagagct acgcggcata tctcaggagc atcggcatcg atgcctggcg cttcgactac     600
gtcaagggct atgctccctg gtcgtcaag actggctga actggtgggg aggctgggcg     660
gttggagagt actgggacac caacgtcgac gctgttctca actgggcata ctcgagcggt     720
gccaaggtct ttgacttcgc cctctactac aagatggatg aggcctttga caacaaaaac     780
attccagcgc tcgtctctgc ccttcagaac ggccagactg ttgtctcccg gacccgttc     840
aaggccgtaa cctttgtagc aaaccacgac accgatataa tctggaacaa gtatccagcc     900
tacgcgttca tcctcaccta cgagggccag ccgacaatat tctaccgcga ctacgaggag     960
tggctcaaca aggataagct caagaacctc atctggatac atgacaacct cgccggagga    1020
agcactgaca tcgtttacta cgacaacgac gagctgatat tcgtgagaaa cggctacgga    1080
agcaagccgg gactgataac atacatcaac ctcgcctcaa gcgaagccgg aaggtgggtc    1140
tacgttccga agttcgcggg agcgtgcatc cacgagtaca ccggcaacct cggcggctgg    1200
gtggacaagt gggtggactc aagcgggtgg gtgtacctcg aggcccctgc ccacgacccg    1260
gccaacggct attacggcta ctccgtctgg agctattgcg gtgttgggtg a              1311
```

<210> SEQ ID NO 37
<211> LENGTH: 436
<212> TYPE: PRT
<213> ORGANISM: Artificial Sequence
<220> FEATURE:
<223> OTHER INFORMATION: protein sequence of an amylase

<400> SEQUENCE: 37

Met Ala Lys Tyr Leu Glu Leu Glu Glu Gly Gly Leu Ile Met Gln Ala
1               5                   10                  15

Phe Tyr Trp Asp Val Pro Met Gly Gly Ile Trp Trp Asp Thr Ile Ala
            20                  25                  30

Gln Lys Ile Pro Asp Trp Ala Ser Ala Gly Ile Ser Ala Ile Trp Ile
        35                  40                  45

```
Pro Pro Ala Ser Lys Gly Met Gly Gly Ala Tyr Ser Met Gly Tyr Asp
 50                  55                  60
Pro Tyr Asp Phe Phe Asp Leu Gly Glu Tyr Asp Gln Lys Gly Thr Val
 65                  70                  75                  80
Glu Thr Arg Phe Gly Ser Lys Gln Glu Leu Val Asn Met Ile Asn Thr
                 85                  90                  95
Ala His Ala Tyr Gly Ile Lys Val Ile Ala Asp Ile Val Ile Asn His
            100                 105                 110
Arg Ala Gly Gly Asp Leu Glu Trp Asn Pro Phe Val Asn Asp Tyr Thr
        115                 120                 125
Trp Thr Asp Phe Ser Lys Val Ala Ser Gly Lys Tyr Thr Ala Asn Tyr
    130                 135                 140
Leu Asp Phe His Pro Asn Glu Leu His Ala Gly Asp Ser Gly Thr Phe
145                 150                 155                 160
Gly Gly Tyr Pro Asp Ile Cys His Asp Lys Ser Trp Asp Gln Tyr Trp
                165                 170                 175
Leu Trp Ala Ser Gln Glu Ser Tyr Ala Ala Tyr Leu Arg Ser Ile Gly
            180                 185                 190
Ile Asp Ala Trp Arg Phe Asp Tyr Val Lys Gly Tyr Ala Pro Trp Val
        195                 200                 205
Val Lys Asp Trp Leu Asn Trp Trp Gly Gly Trp Ala Val Gly Glu Tyr
    210                 215                 220
Trp Asp Thr Asn Val Asp Ala Val Leu Asn Trp Ala Tyr Ser Ser Gly
225                 230                 235                 240
Ala Lys Val Phe Asp Phe Ala Leu Tyr Tyr Lys Met Asp Glu Ala Phe
                245                 250                 255
Asp Asn Lys Asn Ile Pro Ala Leu Val Ser Ala Leu Gln Asn Gly Gln
            260                 265                 270
Thr Val Val Ser Arg Asp Pro Phe Lys Ala Val Thr Phe Val Ala Asn
        275                 280                 285
His Asp Thr Asp Ile Ile Trp Asn Lys Tyr Pro Ala Tyr Ala Phe Ile
    290                 295                 300
Leu Thr Tyr Glu Gly Gln Pro Thr Ile Phe Tyr Arg Asp Tyr Glu Glu
305                 310                 315                 320
Trp Leu Asn Lys Asp Lys Leu Lys Asn Leu Ile Trp Ile His Asp Asn
                325                 330                 335
Leu Ala Gly Gly Ser Thr Asp Ile Val Tyr Tyr Asp Asn Asp Glu Leu
            340                 345                 350
Ile Phe Val Arg Asn Gly Tyr Gly Ser Lys Pro Gly Leu Ile Thr Tyr
        355                 360                 365
Ile Asn Leu Ala Ser Ser Glu Ala Gly Arg Trp Val Tyr Val Pro Lys
    370                 375                 380
Phe Ala Gly Ala Cys Ile His Glu Tyr Thr Gly Asn Leu Gly Gly Trp
385                 390                 395                 400
Val Asp Lys Trp Val Asp Ser Ser Gly Trp Val Tyr Leu Glu Ala Pro
                405                 410                 415
Ala His Asp Pro Ala Asn Gly Tyr Tyr Gly Tyr Ser Val Trp Ser Tyr
            420                 425                 430
Cys Gly Val Gly
        435
```

<210> SEQ ID NO 38
<211> LENGTH: 1311
<212> TYPE: DNA
<213> ORGANISM: Artificial Sequence
<220> FEATURE:
<223> OTHER INFORMATION: DNA sequence coding for an amylase

<400> SEQUENCE: 38

```
atggcaaagt actccgagct ggaagagggc ggcgttataa tgcaggcctt ctactgggac    60
gtcccaggtg aggaatctg gtgggacacc atcaggagca ggataccgga gtggtacgag    120
gcgggaatat ccgccatttg gattcccccg gcgagcaagg gcatgggcgg cgcctattcg    180
atgggctacg accctacga cttctttgac ctcggtgagt acgaccagaa gggaacggta    240
gagacgcgct ttggctccaa gcaggagctc gtgaacatga taaacacggc ccatgcctac    300
ggcataaagg tcatagcgga catcgtcata aaccaccgcg caggcggaga cctcgagtgg    360
aacccgttcg ttggggacta cacctggacg gacttctcaa aggtggcctc gggcaaatat    420
actgccaact acctcgactt ccaccccgaa cgagctccatg cgggcgattc cggaacattt    480
ggaggctatc ccgacatatg ccacgacaag agctgggacc agtactggct ctgggccagc    540
caggagagct acgcggcata tctcaggagc atcggcatcg atgcctggcg ctttgactac    600
gtgaagggct acggagcgtg ggtcgtcaag gactggctca actggtgggg cggctgggcc    660
gttggcgagt actgggacac caacgttgat gcactcctca actgggccta ctcgagcggc    720
gccaaggtct tcgacttccc gctctactac aagatggacg aggccttcga taacaacaac    780
attcccgccc tggtggacgc cctcagatac ggtcagacag tggtcagccg cgacccgttc    840
aaggctgtga cgtttgtagc caaccacgat accgatataa tctggaacaa gtatccagcc    900
tacgcgttca tcctcaccta cgagggccag ccgacaatat tctaccgcga ctacgaggag    960
tggctcaaca aggataagct caagaaccctc atctggatac atgacaacct ggccggagga    1020
agcacgagca tagtttacta cgacagcgac gagatgatct tcgtgaggac cggctatgga    1080
agcaagcctg gccttataac ttacatcaac ctcggctcga gcaaggttgg aaggtgggtt    1140
tatgtgccga agttcgcggg gcgtgcatc cacgagtata ctggtaacct cggaggctgg    1200
gtagacaagt acgtctactc aagcggctgg gtctatctcg aagctccagc ttacgaccct    1260
gccaacgggc agtatggcta ctccgtgtgg agctattgcg gtgttggctg a              1311
```

<210> SEQ ID NO 39
<211> LENGTH: 436
<212> TYPE: PRT
<213> ORGANISM: Artificial Sequence
<220> FEATURE:
<223> OTHER INFORMATION: protein sequence of an amylase

<400> SEQUENCE: 39

```
Met Ala Lys Tyr Ser Glu Leu Glu Glu Gly Gly Val Ile Met Gln Ala
1               5                   10                  15

Phe Tyr Trp Asp Val Pro Gly Gly Ile Trp Trp Asp Thr Ile Arg
            20                  25                  30

Ser Arg Ile Pro Glu Trp Tyr Glu Ala Gly Ile Ser Ala Ile Trp Ile
        35                  40                  45

Pro Pro Ala Ser Lys Gly Met Gly Gly Ala Tyr Ser Met Gly Tyr Asp
    50                  55                  60

Pro Tyr Asp Phe Phe Asp Leu Gly Glu Tyr Asp Gln Lys Gly Thr Val
65                  70                  75                  80
```

Glu Thr Arg Phe Gly Ser Lys Gln Glu Leu Val Asn Met Ile Asn Thr
                85                  90                  95

Ala His Ala Tyr Gly Ile Lys Val Ile Ala Asp Ile Val Ile Asn His
            100                 105                 110

Arg Ala Gly Gly Asp Leu Glu Trp Asn Pro Phe Val Gly Asp Tyr Thr
            115                 120                 125

Trp Thr Asp Phe Ser Lys Val Ala Ser Gly Lys Tyr Thr Ala Asn Tyr
130                 135                 140

Leu Asp Phe His Pro Asn Glu Leu His Ala Gly Asp Ser Gly Thr Phe
145                 150                 155                 160

Gly Gly Tyr Pro Asp Ile Cys His Asp Lys Ser Trp Asp Gln Tyr Trp
                165                 170                 175

Leu Trp Ala Ser Gln Glu Ser Tyr Ala Ala Tyr Leu Arg Ser Ile Gly
            180                 185                 190

Ile Asp Ala Trp Arg Phe Asp Tyr Val Lys Gly Tyr Gly Ala Trp Val
            195                 200                 205

Val Lys Asp Trp Leu Asn Trp Trp Gly Gly Trp Ala Val Gly Glu Tyr
210                 215                 220

Trp Asp Thr Asn Val Asp Ala Leu Leu Asn Trp Ala Tyr Ser Ser Gly
225                 230                 235                 240

Ala Lys Val Phe Asp Phe Pro Leu Tyr Tyr Lys Met Asp Glu Ala Phe
                245                 250                 255

Asp Asn Asn Asn Ile Pro Ala Leu Val Asp Ala Leu Arg Tyr Gly Gln
                260                 265                 270

Thr Val Val Ser Arg Asp Pro Phe Lys Ala Val Thr Phe Val Ala Asn
            275                 280                 285

His Asp Thr Asp Ile Ile Trp Asn Lys Tyr Pro Ala Tyr Ala Phe Ile
            290                 295                 300

Leu Thr Tyr Glu Gly Gln Pro Thr Ile Phe Tyr Arg Asp Tyr Glu Glu
305                 310                 315                 320

Trp Leu Asn Lys Asp Lys Leu Lys Asn Leu Ile Trp Ile His Asp Asn
                325                 330                 335

Leu Ala Gly Gly Ser Thr Ser Ile Val Tyr Tyr Asp Ser Asp Glu Met
            340                 345                 350

Ile Phe Val Arg Thr Gly Tyr Gly Ser Lys Pro Gly Leu Ile Thr Tyr
            355                 360                 365

Ile Asn Leu Gly Ser Ser Lys Val Gly Arg Trp Val Tyr Val Pro Lys
370                 375                 380

Phe Ala Gly Ala Cys Ile His Glu Tyr Thr Gly Asn Leu Gly Gly Trp
385                 390                 395                 400

Val Asp Lys Tyr Val Tyr Ser Ser Gly Trp Val Tyr Leu Glu Ala Pro
                405                 410                 415

Ala Tyr Asp Pro Ala Asn Gly Gln Tyr Gly Tyr Ser Val Trp Ser Tyr
                420                 425                 430

Cys Gly Val Gly
            435

<210> SEQ ID NO 40
<211> LENGTH: 1311
<212> TYPE: DNA
<213> ORGANISM: Artificial Sequence
<220> FEATURE:
<223> OTHER INFORMATION: DNA sequence coding for an amylase

<400> SEQUENCE: 40

```
atggccaagt actccgagct ggaagagggc ggggtcataa tgcaggcgtt ctactgggac      60
gtgccttcag gaggaatatg gtgggacaca atacggcaga agataccgga gtggtacgat     120
gccggaatct ccgcaatatg gattcctccc gcgagcaagg gtatgagcgg cggctattcg     180
atgggctacg accctacga ttattttgac ctcggtgagt actaccagaa gggaacggtg     240
gaaacgaggt tcggctcaaa gcaggagctc ataaacatga taaacacggc ccatgcctac     300
ggcataaagg tcatagcgga catcgtcata aaccaccgcg caggcggaga cctcgagtgg     360
aacccgttcg ttggggacta cacctggacg gacttctcaa aggtggcctc gggcaaatat     420
actgccaact acctcgactt ccacccgaac gagctccatg cgggcgattc cggaacattt     480
ggaggctatc ccgacatatg ccacgacaag agctgggacc agtactgct ctgggccagc     540
caggagagct acgcggcata tctcaggagc atcggcatcg atgcctggcg ctttgactac     600
gtgaagggct acgagcgtg gtcgtcaag gactggctca actggtgggg cggctgggcc     660
gttggcgagt actgggacac caacgttgat gcactcctca actgggccta ctcgagcggc     720
gccaaggtct tcgactttcc gctctactac aagatggacg cggcctttga caacaagaac     780
attcccgcac tcgtcgaggc cctcaagaac ggggcacag tcgtcagccg cgacccgttt     840
aaggccgtaa ccttcgttgc aaaccacgac accgatataa tctggaccaa gtaccttgct     900
tatgctttca tcctcaccta cgaaggccag cccgtcatat tctaccgcga ctacgaggag     960
tggctcaaca aggacaggtt gaacaacctc atatggatac acgaccacct cgcaggtgga    1020
agcaccgaca tagtctacta cgataacgat gaactcatct tcgtcaggaa cggctacggg    1080
gacaagccgg ggcttataac ctacatcaac ctaggctcga gcaaggccgg aaggtgggtt    1140
tacgttccga agttcgcagg ctcgtgcata cacgagtaca ccggcaatct cggcggctgg    1200
gtggacaagt gggtggactc aagcggctgg gtctacctcg aggctcctgc ccacgacccg    1260
gccaacggcc agtacggcta ctccgtctgg agctactgcg gtgttggctg a             1311
```

<210> SEQ ID NO 41
<211> LENGTH: 436
<212> TYPE: PRT
<213> ORGANISM: Artificial Sequence
<220> FEATURE:
<223> OTHER INFORMATION: protein sequence of an amylase

<400> SEQUENCE: 41

```
Met Ala Lys Tyr Ser Glu Leu Glu Glu Gly Gly Val Ile Met Gln Ala
1               5                   10                  15

Phe Tyr Trp Asp Val Pro Ser Gly Gly Ile Trp Trp Asp Thr Ile Arg
            20                  25                  30

Gln Lys Ile Pro Glu Trp Tyr Asp Ala Gly Ile Ser Ala Ile Trp Ile
        35                  40                  45

Pro Pro Ala Ser Lys Gly Met Ser Gly Gly Tyr Ser Met Gly Tyr Asp
    50                  55                  60

Pro Tyr Asp Tyr Phe Asp Leu Gly Glu Tyr Tyr Gln Lys Gly Thr Val
65                  70                  75                  80

Glu Thr Arg Phe Gly Ser Lys Gln Glu Leu Ile Asn Met Ile Asn Thr
                85                  90                  95

Ala His Ala Tyr Gly Ile Lys Val Ile Ala Asp Ile Val Ile Asn His
            100                 105                 110

Arg Ala Gly Gly Asp Leu Glu Trp Asn Pro Phe Val Gly Asp Tyr Thr
        115                 120                 125
```

Trp Thr Asp Phe Ser Lys Val Ala Ser Gly Lys Tyr Thr Ala Asn Tyr
130                 135                 140

Leu Asp Phe His Pro Asn Glu Leu His Ala Gly Asp Ser Gly Thr Phe
145                 150                 155                 160

Gly Gly Tyr Pro Asp Ile Cys His Asp Lys Ser Trp Asp Gln Tyr Trp
                165                 170                 175

Leu Trp Ala Ser Gln Glu Ser Tyr Ala Ala Tyr Leu Arg Ser Ile Gly
                180                 185                 190

Ile Asp Ala Trp Arg Phe Asp Tyr Val Lys Gly Tyr Gly Ala Trp Val
                195                 200                 205

Val Lys Asp Trp Leu Asn Trp Trp Gly Gly Trp Ala Val Gly Glu Tyr
210                 215                 220

Trp Asp Thr Asn Val Asp Ala Leu Leu Asn Trp Ala Tyr Ser Ser Gly
225                 230                 235                 240

Ala Lys Val Phe Asp Phe Pro Leu Tyr Tyr Lys Met Asp Ala Ala Phe
                245                 250                 255

Asp Asn Lys Asn Ile Pro Ala Leu Val Glu Ala Leu Lys Asn Gly Gly
                260                 265                 270

Thr Val Val Ser Arg Asp Pro Phe Lys Ala Val Thr Phe Val Ala Asn
                275                 280                 285

His Asp Thr Asp Ile Ile Trp Thr Lys Tyr Leu Ala Tyr Ala Phe Ile
290                 295                 300

Leu Thr Tyr Glu Gly Gln Pro Val Ile Phe Tyr Arg Asp Tyr Glu Glu
305                 310                 315                 320

Trp Leu Asn Lys Asp Arg Leu Asn Asn Leu Ile Trp Ile His Asp His
                325                 330                 335

Leu Ala Gly Gly Ser Thr Asp Ile Val Tyr Tyr Asp Asn Asp Glu Leu
                340                 345                 350

Ile Phe Val Arg Asn Gly Tyr Gly Asp Lys Pro Gly Leu Ile Thr Tyr
                355                 360                 365

Ile Asn Leu Gly Ser Ser Lys Ala Gly Arg Trp Val Tyr Val Pro Lys
370                 375                 380

Phe Ala Gly Ser Cys Ile His Glu Tyr Thr Gly Asn Leu Gly Gly Trp
385                 390                 395                 400

Val Asp Lys Trp Val Asp Ser Ser Gly Trp Val Tyr Leu Glu Ala Pro
                405                 410                 415

Ala His Asp Pro Ala Asn Gly Gln Tyr Gly Tyr Ser Val Trp Ser Tyr
                420                 425                 430

Cys Gly Val Gly
        435

<210> SEQ ID NO 42
<211> LENGTH: 1311
<212> TYPE: DNA
<213> ORGANISM: Artificial Sequence
<220> FEATURE:
<223> OTHER INFORMATION: DNA sequence coding for an amylase

<400> SEQUENCE: 42
atggccaagt actccgagct ggaagagggc ggcgttataa tgcaggcctt ctactgggac     60
gtcccaggtg gaggaatctg gtgggacacc atcaggagca agataccgga gtggtacgag    120
gcgggaatat ccgccatttg gattcccccg gcgagcaagg gcatgggcgg cgcctattcg    180
atgggctacg accctacga cttctttgac ctcggtgagt acgaccagaa gggaacggta    240
gagacgcgct ttggctccaa gcaggagctc gtgaacatga taaacaccgc ccacgcctac    300

```
ggcatcaagg tcatcgcaga catagtaatc aaccaccgcg ccggaggaga ccttgagtgg    360
aaccccttcg tcaatgacta cacctggacg gacttctcga aggtcgcttc cggcaagtac    420
acggccaact acctcgactt ccaccccaac gaggtcaagt gctgtgacga gggcacattt    480
ggaggcttcc cagacatagc ccacgagaag agctgggacc agcactggct ctgggcgagc    540
gatgagagct acgccgccta cctaaggagc atcggcgttg atgcctggcg cttcgactac    600
gtcaagggct atgctccctg ggtcgtcaag gactggctga actggtgggg aggctgggcg    660
gttggagagt actgggacac caacgtcgac gctgttctca actgggcata ctcgagcggt    720
gccaaggtct ttgacttcgc cctctactac aagatggacg cggcctttga caacaagaac    780
attcccgcac tcgtcgaggc cctcaagaac gggggcacag tcgtcagccg cgacccgttt    840
aaggccgtaa ccttcgttgc aaaccacgac accgatataa tctggaacaa gtatccagcc    900
tacgcgttca tcctcaccta cgagggccag ccgacaatat tctaccgcga ctacgaggag    960
tggctcaaca aggataagct caagaacctc atctggatac atgacaacgt cgccggagga   1020
agcaccgaca tagtctacta cgataacgat gaactcatct tcgtcaggaa cggctacggg   1080
gacaagccgg ggcttataac ctacatcaac ctaggctcga gcaaggccgg aaggtgggtt   1140
tacgttccga agttcgcagg ctcgtgcata cacgagtaca ccggcaatct cggcggctgg   1200
gtggacaagt gggtggactc aagcggctgg gtctacctcg aggctcctgc ccacgacccg   1260
gccaacggcc agtacggcta ctccgtctgg agctactgcg tgttgggtg a              1311
```

<210> SEQ ID NO 43
<211> LENGTH: 436
<212> TYPE: PRT
<213> ORGANISM: Artificial Sequence
<220> FEATURE:
<223> OTHER INFORMATION: protein sequence of an amylase

<400> SEQUENCE: 43

```
Met Ala Lys Tyr Ser Glu Leu Glu Glu Gly Gly Val Ile Met Gln Ala
1               5                   10                  15

Phe Tyr Trp Asp Val Pro Gly Gly Ile Trp Trp Asp Thr Ile Arg
            20                  25                  30

Ser Lys Ile Pro Glu Trp Tyr Glu Ala Gly Ile Ser Ala Ile Trp Ile
        35                  40                  45

Pro Pro Ala Ser Lys Gly Met Gly Gly Ala Tyr Ser Met Gly Tyr Asp
    50                  55                  60

Pro Tyr Asp Phe Phe Asp Leu Gly Glu Tyr Asp Gln Lys Gly Thr Val
65                  70                  75                  80

Glu Thr Arg Phe Gly Ser Lys Gln Glu Leu Val Asn Met Ile Asn Thr
                85                  90                  95

Ala His Ala Tyr Gly Ile Lys Val Ile Ala Asp Ile Val Ile Asn His
            100                 105                 110

Arg Ala Gly Gly Asp Leu Glu Trp Asn Pro Phe Val Asn Asp Tyr Thr
        115                 120                 125

Trp Thr Asp Phe Ser Lys Val Ala Ser Gly Lys Tyr Thr Ala Asn Tyr
    130                 135                 140

Leu Asp Phe His Pro Asn Glu Val Lys Cys Cys Asp Glu Gly Thr Phe
145                 150                 155                 160

Gly Gly Phe Pro Asp Ile Ala His Glu Lys Ser Trp Asp Gln His Trp
                165                 170                 175

Leu Trp Ala Ser Asp Glu Ser Tyr Ala Ala Tyr Leu Arg Ser Ile Gly
            180                 185                 190
```

```
Val Asp Ala Trp Arg Phe Asp Tyr Val Lys Gly Tyr Ala Pro Trp Val
            195                 200                 205

Val Lys Asp Trp Leu Asn Trp Trp Gly Gly Trp Ala Val Gly Glu Tyr
    210                 215                 220

Trp Asp Thr Asn Val Asp Ala Val Leu Asn Trp Ala Tyr Ser Ser Gly
225                 230                 235                 240

Ala Lys Val Phe Asp Phe Ala Leu Tyr Tyr Lys Met Asp Ala Ala Phe
                245                 250                 255

Asp Asn Lys Asn Ile Pro Ala Leu Val Glu Ala Leu Lys Asn Gly Gly
            260                 265                 270

Thr Val Val Ser Arg Asp Pro Phe Lys Ala Val Thr Phe Val Ala Asn
    275                 280                 285

His Asp Thr Asp Ile Ile Trp Asn Lys Tyr Pro Ala Tyr Ala Phe Ile
290                 295                 300

Leu Thr Tyr Glu Gly Gln Pro Thr Ile Phe Tyr Arg Asp Tyr Glu Glu
305                 310                 315                 320

Trp Leu Asn Lys Asp Lys Leu Lys Asn Leu Ile Trp Ile His Asp Asn
                325                 330                 335

Val Ala Gly Gly Ser Thr Asp Ile Val Tyr Tyr Asp Asn Asp Glu Leu
            340                 345                 350

Ile Phe Val Arg Asn Gly Tyr Gly Asp Lys Pro Gly Leu Ile Thr Tyr
    355                 360                 365

Ile Asn Leu Gly Ser Ser Lys Ala Gly Arg Trp Val Tyr Val Pro Lys
370                 375                 380

Phe Ala Gly Ser Cys Ile His Glu Tyr Thr Gly Asn Leu Gly Gly Trp
385                 390                 395                 400

Val Asp Lys Trp Val Asp Ser Ser Gly Trp Val Tyr Leu Glu Ala Pro
                405                 410                 415

Ala His Asp Pro Ala Asn Gly Gln Tyr Gly Tyr Ser Val Trp Ser Tyr
            420                 425                 430

Cys Gly Val Gly
        435

<210> SEQ ID NO 44
<211> LENGTH: 1311
<212> TYPE: DNA
<213> ORGANISM: Artificial Sequence
<220> FEATURE:
<223> OTHER INFORMATION: DNA sequence coding for an amylase

<400> SEQUENCE: 44
atggccaagt acctggagct cgaagagggc ggggtcataa tgcaggcgtt ctactgggac       60
gtgccttcag gaggaatatg gtgggacaca atacggcaga agataccgga gtggtacgat      120
gccggaatct ccgcaatatg gattcccccg gcgagcaagg gcatgggcgg cgcctattcg      180
atgggctacg accctacga cttctttgac ctcggtgagt acgaccagaa gggaacggta      240
gagacgcgct ttggctccaa gcaggagctc gtgaacatga taaacaccgc ccacgcctat      300
ggcatgaagg taatagccga tatagtcatc aaccaccgcg ccggcggtga cctggagtgg      360
aaccccttcg tgaacgacta tacctggacc gacttctcaa aggtcgcgtc gggtaaatac      420
acggccaact acctcgactt ccacccgaac gagctccatg cgggcgattc cggaacattt      480
ggaggctatc ccgacatatg ccacgacaag agctgggacc agtactggct ctgggccagc      540
caggagagct acgcggcata tctcaggagc atcggcatcg atgcctggcg ctttgactac      600
gtgaagggct acggagcgcg ggtcgtcaag gactggctca actggtgggg cggctgggcc      660
```

```
gttggcgagt actgggacac caacgttgat gcactcctca actgggccta ctcgagcggc    720
gccaaggtct tcgacttccc gctctactac aagatggatg aggcctttga caacaaaaac    780
attccagcgc tcgtctctgc ccttcagaac ggccagactg ttgtctcccg cgacccgttc    840
aaggccgtaa cctttgtagc aaaccacgac accgatataa tctggaacaa gtatccagcc    900
tacgcgttca tcctcaccta cgagggccag ccgacaatat tctatcgcga ctacgaggag    960
tggctcaaca aggataagct caagaacctc atctggatac atgacaacct cgccggagga   1020
agcactgaca tcgtttacta cgacaacgac gagctgatat tcgtgagaaa cggctacgga   1080
agcaagccgg gactgataac atacatcaac ctcgcctcaa gcaaagccgg aaggtgggtt   1140
tacgttccga agttcgcagg ctcgtgcata cacgagtaca ccggcaatct cggcggctgg   1200
gtggacaagt gggtggactc aagcggctgg gtctacctcg aggctcctgc ccacgacccg   1260
gccaacggcc agtacggcta ctccgtctgg agctactgcg ggtggggtg a              1311
```

<210> SEQ ID NO 45
<211> LENGTH: 436
<212> TYPE: PRT
<213> ORGANISM: Artificial Sequence
<220> FEATURE:
<223> OTHER INFORMATION: protein sequence of an amylase

<400> SEQUENCE: 45

```
Met Ala Lys Tyr Leu Glu Leu Glu Glu Gly Gly Val Ile Met Gln Ala
1               5                   10                  15

Phe Tyr Trp Asp Val Pro Ser Gly Gly Ile Trp Trp Asp Thr Ile Arg
            20                  25                  30

Gln Lys Ile Pro Glu Trp Tyr Asp Ala Gly Ile Ser Ala Ile Trp Ile
        35                  40                  45

Pro Pro Ala Ser Lys Gly Met Gly Gly Ala Tyr Ser Met Gly Tyr Asp
    50                  55                  60

Pro Tyr Asp Phe Phe Asp Leu Gly Glu Tyr Asp Gln Lys Gly Thr Val
65                  70                  75                  80

Glu Thr Arg Phe Gly Ser Lys Gln Glu Leu Val Asn Met Ile Asn Thr
                85                  90                  95

Ala His Ala Tyr Gly Met Lys Val Ile Ala Asp Ile Val Ile Asn His
            100                 105                 110

Arg Ala Gly Gly Asp Leu Glu Trp Asn Pro Phe Val Asn Asp Tyr Thr
        115                 120                 125

Trp Thr Asp Phe Ser Lys Val Ala Ser Gly Lys Tyr Thr Ala Asn Tyr
    130                 135                 140

Leu Asp Phe His Pro Asn Glu Leu His Ala Gly Asp Ser Gly Thr Phe
145                 150                 155                 160

Gly Gly Tyr Pro Asp Ile Cys His Asp Lys Ser Trp Asp Gln Tyr Trp
                165                 170                 175

Leu Trp Ala Ser Gln Glu Ser Tyr Ala Ala Tyr Leu Arg Ser Ile Gly
            180                 185                 190

Ile Asp Ala Trp Arg Phe Asp Tyr Val Lys Gly Tyr Gly Ala Arg Val
        195                 200                 205

Val Lys Asp Trp Leu Asn Trp Trp Gly Gly Trp Ala Val Gly Glu Tyr
    210                 215                 220

Trp Asp Thr Asn Val Asp Ala Leu Leu Asn Trp Ala Tyr Ser Ser Gly
225                 230                 235                 240

Ala Lys Val Phe Asp Phe Pro Leu Tyr Tyr Lys Met Asp Glu Ala Phe
                245                 250                 255
```

Asp Asn Lys Asn Ile Pro Ala Leu Val Ser Ala Leu Gln Asn Gly Gln
            260                 265                 270

Thr Val Val Ser Arg Asp Pro Phe Lys Ala Val Thr Phe Val Ala Asn
            275                 280                 285

His Asp Thr Asp Ile Ile Trp Asn Lys Tyr Pro Ala Tyr Ala Phe Ile
            290                 295                 300

Leu Thr Tyr Glu Gly Gln Pro Thr Ile Phe Tyr Arg Asp Tyr Glu Glu
305                 310                 315                 320

Trp Leu Asn Lys Asp Lys Leu Lys Asn Leu Ile Trp Ile His Asp Asn
                325                 330                 335

Leu Ala Gly Gly Ser Thr Asp Ile Val Tyr Tyr Asp Asn Asp Glu Leu
            340                 345                 350

Ile Phe Val Arg Asn Gly Tyr Gly Ser Lys Pro Gly Leu Ile Thr Tyr
            355                 360                 365

Ile Asn Leu Ala Ser Ser Lys Ala Gly Arg Trp Val Tyr Val Pro Lys
            370                 375                 380

Phe Ala Gly Ser Cys Ile His Glu Tyr Thr Gly Asn Leu Gly Gly Trp
385                 390                 395                 400

Val Asp Lys Trp Val Asp Ser Ser Gly Trp Val Tyr Leu Glu Ala Pro
                405                 410                 415

Ala His Asp Pro Ala Asn Gly Gln Tyr Gly Tyr Ser Val Trp Ser Tyr
            420                 425                 430

Cys Gly Val Gly
        435

<210> SEQ ID NO 46
<211> LENGTH: 1311
<212> TYPE: DNA
<213> ORGANISM: Artificial Sequence
<220> FEATURE:
<223> OTHER INFORMATION: DNA sequence coding for an amylase

<400> SEQUENCE: 46
atggccaagt acctggagct cgaagagggc ggggtcataa tgcaggcgtt ctactgggac      60
gtgccttcag gaggaatatg gtgggacaca atacggcaga agataccgga gtggtacgat     120
gccggaatct ccgcaatatg gattcctccc gcgagcaggg gtatgagcgg cggctattcg     180
atgggctacg acccctacga ttattttgac ctcggtgagt actaccagaa gggaacggtg     240
gaaacgaggt tcggctcaaa gcaggagctc ataaacatga taaacaccgc ccacgcctat     300
ggcatgaagg taatagccga tatagtcatc aaccaccgcg ccggcggtga cctggagtgg     360
aaccccttcg tgaacgacta tacctggacc gacttctcaa aggtcgcgtc gggtaaatac     420
acggccaact acctcgactt ccacccgaac gagctccatg cgggcgattc cggaacattt     480
ggaggctatc ccgacatatg ccacgacaag agctgggacc agtactggct ctgggccagc     540
caggagagct acgcggcata tctcaggagc atcggtatcg atgcctggcg ctttgactac     600
gtgaagggct acggagcgtg ggtcgtcaag gactggctca ctggtggggg cggctgggcc     660
gttggcgagt actgggaccc caacgttgat gccctcctcc cctgggccta ctcgagcggc     720
gccaaggtct tcgacttccc gctctactac aagatggatg aggcctttga caacaaaaac     780
attccagcgc tcgtctctgc ccttcagaac ggccagactg ttgtctcccg cgaccgttc      840 aaggccgtaa cctttgtagc caaccacgat accgatataa tctggaacaa gtatccagcc     900
tacgcgttca tcctcaccta cgagggccag ccgacaatat tctaccgcga ctacgaggag     960
tggctcaaca aggataagct caagaacctc atctggatac atgacaacct cgccggagga    1020

-continued

```
agcaccgaca tagtctacta cgataacgat gaactcatct tcgtcaggaa cggctacggg    1080
gacaagccgg ggcttataac ctacatcaac ctaggctcga gcaaggccgg aaggtgggtc    1140
tacgttccga agttcgcggg agcgtgcatc cacgagtaca ccggcaacct cggcggctgg    1200
gtggacaagt gggtggactc aagcgggtgg gtgtacctcg aggcccctgc ccacgacccg    1260
gccaacggct attacggcta ctccgtctgg agctactgcg gggtgggctg a             1311
```

<210> SEQ ID NO 47
<211> LENGTH: 436
<212> TYPE: PRT
<213> ORGANISM: Artificial Sequence
<220> FEATURE:
<223> OTHER INFORMATION: protein sequence of an amylase

<400> SEQUENCE: 47

```
Met Ala Lys Tyr Leu Glu Leu Glu Glu Gly Gly Val Ile Met Gln Ala
1               5                   10                  15

Phe Tyr Trp Asp Val Pro Ser Gly Gly Ile Trp Trp Asp Thr Ile Arg
            20                  25                  30

Gln Lys Ile Pro Glu Trp Tyr Asp Ala Gly Ile Ser Ala Ile Trp Ile
        35                  40                  45

Pro Pro Ala Ser Arg Gly Met Ser Gly Gly Tyr Ser Met Gly Tyr Asp
    50                  55                  60

Pro Tyr Asp Tyr Phe Asp Leu Gly Glu Tyr Tyr Gln Lys Gly Thr Val
65                  70                  75                  80

Glu Thr Arg Phe Gly Ser Lys Gln Glu Leu Ile Asn Met Ile Asn Thr
                85                  90                  95

Ala His Ala Tyr Gly Met Lys Val Ile Ala Asp Ile Val Ile Asn His
            100                 105                 110

Arg Ala Gly Gly Asp Leu Glu Trp Asn Pro Phe Val Asn Asp Tyr Thr
        115                 120                 125

Trp Thr Asp Phe Ser Lys Val Ala Ser Gly Lys Tyr Thr Ala Asn Tyr
    130                 135                 140

Leu Asp Phe His Pro Asn Glu Leu His Ala Gly Asp Ser Gly Thr Phe
145                 150                 155                 160

Gly Gly Tyr Pro Asp Ile Cys His Asp Lys Ser Trp Asp Gln Tyr Trp
                165                 170                 175

Leu Trp Ala Ser Gln Glu Ser Tyr Ala Ala Tyr Leu Arg Ser Ile Gly
            180                 185                 190

Ile Asp Ala Trp Arg Phe Asp Tyr Val Lys Gly Tyr Gly Ala Trp Val
        195                 200                 205

Val Lys Asp Trp Leu Asn Trp Trp Gly Gly Trp Ala Val Gly Glu Tyr
    210                 215                 220

Trp Asp Pro Asn Val Asp Ala Leu Leu Pro Trp Ala Tyr Ser Ser Gly
225                 230                 235                 240

Ala Lys Val Phe Asp Phe Pro Leu Tyr Tyr Lys Met Asp Glu Ala Phe
                245                 250                 255

Asp Asn Lys Asn Ile Pro Ala Leu Val Ser Ala Leu Gln Asn Gly Gln
            260                 265                 270

Thr Val Val Ser Arg Asp Pro Phe Lys Ala Val Thr Phe Val Ala Asn
        275                 280                 285

His Asp Thr Asp Ile Ile Trp Asn Lys Tyr Pro Ala Tyr Ala Phe Ile
    290                 295                 300

Leu Thr Tyr Glu Gly Gln Pro Thr Ile Phe Tyr Arg Asp Tyr Glu Glu
305                 310                 315                 320
```

```
Trp Leu Asn Lys Asp Lys Leu Lys Asn Leu Ile Trp Ile His Asp Asn
                325                 330                 335

Leu Ala Gly Gly Ser Thr Asp Ile Val Tyr Tyr Asp Asn Asp Glu Leu
            340                 345                 350

Ile Phe Val Arg Asn Gly Tyr Gly Asp Lys Pro Gly Leu Ile Thr Tyr
        355                 360                 365

Ile Asn Leu Gly Ser Ser Lys Ala Gly Arg Trp Val Tyr Val Pro Lys
    370                 375                 380

Phe Ala Gly Ala Cys Ile His Glu Tyr Thr Gly Asn Leu Gly Gly Trp
385                 390                 395                 400

Val Asp Lys Trp Val Asp Ser Ser Gly Trp Val Tyr Leu Glu Ala Pro
                405                 410                 415

Ala His Asp Pro Ala Asn Gly Tyr Tyr Gly Tyr Ser Val Trp Ser Tyr
            420                 425                 430

Cys Gly Val Gly
        435

<210> SEQ ID NO 48
<211> LENGTH: 1311
<212> TYPE: DNA
<213> ORGANISM: Artificial Sequence
<220> FEATURE:
<223> OTHER INFORMATION: DNA sequence coding for an amylase

<400> SEQUENCE: 48
atggccaagt actccgagct ggaagagggc ggcgttataa tgcaggcctt ctactgggac      60
gtcccaggtg gaggaatctg gtgggacacc atcaggagca agataccgga gtggtacgag     120
gcgggaatat ccgccatttg gattcccccg gcgagcaagg gcatgggcgg cgcctattcg     180
atgggctacg acccctacga cttctttgac ctcggtgagt acgaccagaa gggaacggta     240
gagacgcgct ttggctccaa gcaggagctc gtgaacatga taaacacggc ccatgcctac     300
ggcataaagg tcatagcgga catcgtcata aaccaccgcg caggcggaga cctcgagtgg     360
aacccgttcg ttggggacta cacctggacg gacttctcaa aggtggcctc gggcaaatat     420
actgccaact acctcgactt ccaccccaac gaggtcaagt gctgtgacga gggcacattt     480
ggaggcttcc cagacatagc ccacgagaag agctgggacc agcactggct ctgggcgagc     540
gatgagagct acgccgccta cctaaggagc atcggcgttg atgcctggcg cttcgactac     600
gtcaagggct acggagcgtg ggtcgtcaag gactggctgg actggtgggg aggctgggcc     660
gtcggggagt actgggacac aaacgttgat gcactgctca actgggccta ctcgagcgat     720
gcaaaagtct tcgacttccc gctctactac aagatggatg aggcctttga caacaaaaac     780
attccagcgc tcgtctctgc ccttcagaac ggccagactg ttgtctcccg gacccgttc      840 aaggccgtaa cctttgtagc aaaccacgac accgatataa tctggaacaa gtatccagcc     900
tacgcgttca tcctcaccta cgagggccag ccgacaatat tctaccgcga ctacgaggag     960
tggctcaaca aggataagct caagaacctc atctggatac atgacaacct cgtcggagga    1020
agcacgagca tagtttacta cgacagcgac gagatgatct tcgtgaggaa cggctatgga    1080
agcaagcctg gccttataac ttacatcaac ctcggctcga gcaaggttgg aaggtgggtt    1140
tacgttccga agttcgcagg ctcgtgcata cacgagtaca ccggcaatct cggcggctgg    1200
gtggacaagt gggtggactc aagcggctgg gtctacctcg aggctcctgc ccacgacccg    1260
gccaacggcc agtacggcta ctccgtctgg agctactgcg gtgttggctg a             1311
```

-continued

```
<210> SEQ ID NO 49
<211> LENGTH: 436
<212> TYPE: PRT
<213> ORGANISM: Artificial Sequence
<220> FEATURE:
<223> OTHER INFORMATION: protein sequence of an amylase

<400> SEQUENCE: 49
```

Met Ala Lys Tyr Ser Glu Leu Glu Glu Gly Val Ile Met Gln Ala
1               5                   10                  15

Phe Tyr Trp Asp Val Pro Gly Gly Ile Trp Trp Asp Thr Ile Arg
            20                  25                  30

Ser Lys Ile Pro Glu Trp Tyr Glu Ala Gly Ile Ser Ala Ile Trp Ile
            35                  40                  45

Pro Pro Ala Ser Lys Gly Met Gly Gly Ala Tyr Ser Met Gly Tyr Asp
50                  55                  60

Pro Tyr Asp Phe Phe Asp Leu Gly Glu Tyr Asp Gln Lys Gly Thr Val
65                  70                  75                  80

Glu Thr Arg Phe Gly Ser Lys Gln Glu Leu Val Asn Met Ile Asn Thr
                85                  90                  95

Ala His Ala Tyr Gly Ile Lys Val Ile Ala Asp Ile Val Ile Asn His
            100                 105                 110

Arg Ala Gly Gly Asp Leu Glu Trp Asn Pro Phe Val Gly Asp Tyr Thr
            115                 120                 125

Trp Thr Asp Phe Ser Lys Val Ala Ser Gly Lys Tyr Thr Ala Asn Tyr
            130                 135                 140

Leu Asp Phe His Pro Asn Glu Val Lys Cys Cys Asp Glu Gly Thr Phe
145                 150                 155                 160

Gly Gly Phe Pro Asp Ile Ala His Glu Lys Ser Trp Asp Gln His Trp
                165                 170                 175

Leu Trp Ala Ser Asp Glu Ser Tyr Ala Ala Tyr Leu Arg Ser Ile Gly
            180                 185                 190

Val Asp Ala Trp Arg Phe Asp Tyr Val Lys Gly Tyr Gly Ala Trp Val
            195                 200                 205

Val Lys Asp Trp Leu Asp Trp Trp Gly Gly Trp Ala Val Gly Glu Tyr
210                 215                 220

Trp Asp Thr Asn Val Asp Ala Leu Leu Asn Trp Ala Tyr Ser Ser Asp
225                 230                 235                 240

Ala Lys Val Phe Asp Phe Pro Leu Tyr Tyr Lys Met Asp Glu Ala Phe
                245                 250                 255

Asp Asn Lys Asn Ile Pro Ala Leu Val Ser Ala Leu Gln Asn Gly Gln
            260                 265                 270

Thr Val Val Ser Arg Asp Pro Phe Lys Ala Val Thr Phe Val Ala Asn
            275                 280                 285

His Asp Thr Asp Ile Ile Trp Asn Lys Tyr Pro Ala Tyr Ala Phe Ile
290                 295                 300

Leu Thr Tyr Glu Gly Gln Pro Thr Ile Phe Tyr Arg Asp Tyr Glu Glu
305                 310                 315                 320

Trp Leu Asn Lys Asp Lys Leu Lys Asn Leu Ile Trp Ile His Asp Asn
                325                 330                 335

Leu Val Gly Gly Ser Thr Ser Ile Val Tyr Tyr Asp Ser Asp Glu Met
            340                 345                 350

Ile Phe Val Arg Asn Gly Tyr Gly Ser Lys Pro Gly Leu Ile Thr Tyr
            355                 360                 365

```
Ile Asn Leu Gly Ser Ser Lys Val Gly Arg Trp Val Tyr Val Pro Lys
        370                 375                 380
Phe Ala Gly Ser Cys Ile His Glu Tyr Thr Gly Asn Leu Gly Gly Trp
385                 390                 395                 400
Val Asp Lys Trp Val Asp Ser Ser Gly Trp Val Tyr Leu Glu Ala Pro
                405                 410                 415
Ala His Asp Pro Ala Asn Gly Gln Tyr Gly Tyr Ser Val Trp Ser Tyr
                420                 425                 430
Cys Gly Val Gly
        435

<210> SEQ ID NO 50
<211> LENGTH: 1311
<212> TYPE: DNA
<213> ORGANISM: Artificial Sequence
<220> FEATURE:
<223> OTHER INFORMATION: DNA sequence coding for an amylase

<400> SEQUENCE: 50
atggccaagt actccgacct ggaagagggc ggcgttataa tgcaggcctt ctactgggac    60
gtcccaggtg gaggaatctg gtgggacacc atcaggagca agataccgga gtggtacgag   120
gcgggaatat ccgccatttg gattcccccg gcgagcaagg gcatgggcgg cgcctattcg   180
atgggctacg accctacga cttctttgac ctcggtgagt acgaccagaa gggaacggta   240
gagacgcgct ttggctccaa gcaggagctc gtgaacatga taaacacggc ccatgcctac   300
ggcataaagg tcatagcgga catcgtcata accaccgcg caggcggaga cctcgagtgg   360
aacccgttcg ttggggacta cacctggacg gacttctcaa aggtggcctc gggcaaatat   420
actgccaact acctcgactt ccaccccaac gaggtcaagt gctgtgacga gggcacattt   480
ggaggcttcc cagacatagc ccacgagaag agctgggacc agcactggct ctgggcgagc   540
gatgagagct acgccgccta cctaaggagc atcggcgttg atgcctggcg ctttgactac   600
gtgaagggct acggagcgtg ggtcgtcaag gactggctca actggtgggg cggctgggcc   660
gttggcgagt actgggacac caacgttgat gcactcctca ctgggccta ctcgagcggc   720 gccaaggtct cgacttccc gctctactac aagatggatg aggcctttga acaaaaaac   780 attccagcgc tcgtctctgc ccttcagaac ggccagactg ttgtctcccg cgacccgttc   840
aaggccgtaa cctttgtagc aaaccacgac accgatataa tctggaacaa gtatccagcc   900
tacgcgttca tcctcaccta cgagggccag ccgacaatat tctaccgcga ctacgaggag   960
tggctcaaca aggataagct caagaacctc atctggatac atgacaacct cgccggagga  1020
agcaccgaca tagtctacta cgataacgat gaactcatct tcgtcaggaa cggctacggg  1080
gacaagccgg ggcttataac ctacatcaac ctaggctcga gcaaggccgg aaggtgggtt  1140
tatgtgccga agttcgcggg cgcgtgcatc acgagtata ctggtaacct cggaggctgg  1200
gtagacaagt acgtctactc aagcggctgg gtctatctcg aagctccagc ttacgaccct  1260
gccaacgggc agtatggcta ctccgtgtgg agctattgcg gtgttgggtg a            1311

<210> SEQ ID NO 51
<211> LENGTH: 436
<212> TYPE: PRT
<213> ORGANISM: Artificial Sequence
<220> FEATURE:
<223> OTHER INFORMATION: protein sequence of an amylase
```

<400> SEQUENCE: 51

```
Met Ala Lys Tyr Ser Asp Leu Glu Glu Gly Gly Val Ile Met Gln Ala
1               5                   10                  15

Phe Tyr Trp Asp Val Pro Gly Gly Ile Trp Trp Asp Thr Ile Arg
            20                  25                  30

Ser Lys Ile Pro Glu Trp Tyr Glu Ala Gly Ile Ser Ala Ile Trp Ile
                35                  40                  45

Pro Pro Ala Ser Lys Gly Met Gly Gly Ala Tyr Ser Met Gly Tyr Asp
            50                  55                  60

Pro Tyr Asp Phe Phe Asp Leu Gly Glu Tyr Asp Gln Lys Gly Thr Val
65                  70                  75                  80

Glu Thr Arg Phe Gly Ser Lys Gln Glu Leu Val Asn Met Ile Asn Thr
                85                  90                  95

Ala His Ala Tyr Gly Ile Lys Val Ile Ala Asp Ile Val Ile Asn His
            100                 105                 110

Arg Ala Gly Gly Asp Leu Glu Trp Asn Pro Phe Val Gly Asp Tyr Thr
                115                 120                 125

Trp Thr Asp Phe Ser Lys Val Ala Ser Gly Lys Tyr Thr Ala Asn Tyr
        130                 135                 140

Leu Asp Phe His Pro Asn Glu Val Lys Cys Cys Asp Glu Gly Thr Phe
145                 150                 155                 160

Gly Gly Phe Pro Asp Ile Ala His Glu Lys Ser Trp Asp Gln His Trp
                165                 170                 175

Leu Trp Ala Ser Asp Glu Ser Tyr Ala Ala Tyr Leu Arg Ser Ile Gly
            180                 185                 190

Val Asp Ala Trp Arg Phe Asp Tyr Val Lys Gly Tyr Gly Ala Trp Val
        195                 200                 205

Val Lys Asp Trp Leu Asn Trp Trp Gly Gly Trp Ala Val Gly Glu Tyr
        210                 215                 220

Trp Asp Thr Asn Val Asp Ala Leu Leu Asn Trp Ala Tyr Ser Ser Gly
225                 230                 235                 240

Ala Lys Val Phe Asp Phe Pro Leu Tyr Tyr Lys Met Asp Glu Ala Phe
            245                 250                 255

Asp Asn Lys Asn Ile Pro Ala Leu Val Ser Ala Leu Gln Asn Gly Gln
            260                 265                 270

Thr Val Val Ser Arg Asp Pro Phe Lys Ala Val Thr Phe Val Ala Asn
            275                 280                 285

His Asp Thr Asp Ile Ile Trp Asn Lys Tyr Pro Ala Tyr Ala Phe Ile
    290                 295                 300

Leu Thr Tyr Glu Gly Gln Pro Thr Ile Phe Tyr Arg Asp Tyr Glu Glu
305                 310                 315                 320

Trp Leu Asn Lys Asp Lys Leu Lys Asn Leu Ile Trp Ile His Asp Asn
                325                 330                 335

Leu Ala Gly Gly Ser Thr Asp Ile Val Tyr Tyr Asp Asn Asp Glu Leu
            340                 345                 350

Ile Phe Val Arg Asn Gly Tyr Gly Asp Lys Pro Gly Leu Ile Thr Tyr
        355                 360                 365

Ile Asn Leu Gly Ser Ser Lys Ala Gly Arg Trp Val Tyr Val Pro Lys
    370                 375                 380

Phe Ala Gly Ala Cys Ile His Glu Tyr Thr Gly Asn Leu Gly Gly Trp
385                 390                 395                 400

Val Asp Lys Tyr Val Tyr Ser Ser Gly Trp Val Tyr Leu Glu Ala Pro
            405                 410                 415
```

```
Ala Tyr Asp Pro Ala Asn Gly Gln Tyr Gly Tyr Ser Val Trp Ser Tyr
            420                 425                 430

Cys Gly Val Gly
        435
```

<210> SEQ ID NO 52
<211> LENGTH: 1311
<212> TYPE: DNA
<213> ORGANISM: Artificial Sequence
<220> FEATURE:
<223> OTHER INFORMATION: DNA sequence coding for an amylase

<400> SEQUENCE: 52

```
atggccaagt acaccgagct ggaagagggc ggcgttataa tgcaggcctt ctactgggac      60
gtcccaggtg gaggaatctg gtgggacacc atcaggagca agataccgga gtggtacgag     120
gcgggaatat ccgccatttg gattcccccg gcgagcaagg gcatgggcgg cgcctattcg     180
atgggctacg accctacga cttctttgac ctcggtgagt acgaccagaa gggaacggta     240
gagacgcgct ttggctccaa gcaggagctc gtgaacatga taaacaccgc ccacgcctat     300
ggcatgaagg taatagccga tatagtcatc aaccaccgcg ccggcggtga cctggagtgg     360
aaccccttcg tgaacgacta tacctggacc gacttctcaa aggtcgcgtc gggtaaatac     420
acggccaact acctcgactt ccaccccaac gaggtcaagt gctgtgacga gggcacattt     480
ggaggcttcc cagacatagc ccacgagaag agctgggacc agcactggct ctgggcgagc     540
gatgagagct acgccgccta cctaaggagc atcgcgttg atgcctggcg ctttgactac     600
gtgaagggct acggagcgtg gtcgtcaag actggctca actggtgggg cggttgggcc     660
gttggcgagt actgggacac caacgttgat gcactcctca actgggccta ctcgagcggc     720
gccaaggtct cgacttccc gctctactac aagatggatg aggcctttga caacaaaaac     780
attccagcgc tcgtctctgc ccttcagaac ggccagactg ttgtctcccg gacccgttc     840
aaggccgtaa cctttgtagc aaaccacgac accgatataa tctggaacaa gtaccttgct     900
tatgctttca tcctcaccta cgaaggccag cccgtcatat tctaccgcga ctacgaggag     960
tggctcaaca aggacaggtt gaacaaccct atatggatac acgaccacct cgcaggtgga    1020
agcacgagca tagtttacta cgacagcgac gagatgatct tcgtgaggaa cggctatgga    1080
agcaagcctg gccttataac ttacatcaac ctcggctcga gcaaggttgg aaggtgggtt    1140
tacgttccga agttcgcagg cccgtgcata cacgagtaca ccggcaatct cggcggctgg    1200
gtggacaagt gggtggactc aagcggctgg gtctacctcg aggctcctgc ccacgacccg    1260
gccaacggcc agtacggcta ctccgtctgg agctactgcg gtgttgggta g             1311
```

<210> SEQ ID NO 53
<211> LENGTH: 436
<212> TYPE: PRT
<213> ORGANISM: Artificial Sequence
<220> FEATURE:
<223> OTHER INFORMATION: protein sequence of an amylase

<400> SEQUENCE: 53

```
Met Ala Lys Tyr Thr Glu Leu Glu Glu Gly Gly Val Ile Met Gln Ala
1               5                   10                  15

Phe Tyr Trp Asp Val Pro Gly Gly Ile Trp Trp Asp Thr Ile Arg
            20                  25                  30

Ser Lys Ile Pro Glu Trp Tyr Glu Ala Gly Ile Ser Ala Ile Trp Ile
        35                  40                  45
```

-continued

```
Pro Pro Ala Ser Lys Gly Met Gly Gly Ala Tyr Ser Met Gly Tyr Asp
    50              55                  60
Pro Tyr Asp Phe Phe Asp Leu Gly Glu Tyr Asp Gln Lys Gly Thr Val
 65              70              75                  80
Glu Thr Arg Phe Gly Ser Lys Gln Glu Leu Val Asn Met Ile Asn Thr
                85              90                  95
Ala His Ala Tyr Gly Met Lys Val Ile Ala Asp Ile Val Ile Asn His
                100             105                 110
Arg Ala Gly Gly Asp Leu Glu Trp Asn Pro Phe Val Asn Asp Tyr Thr
            115             120             125
Trp Thr Asp Phe Ser Lys Val Ala Ser Gly Lys Tyr Thr Ala Asn Tyr
    130             135             140
Leu Asp Phe His Pro Asn Glu Val Lys Cys Cys Asp Glu Gly Thr Phe
145             150             155                 160
Gly Gly Phe Pro Asp Ile Ala His Glu Lys Ser Trp Asp Gln His Trp
                165             170             175
Leu Trp Ala Ser Asp Glu Ser Tyr Ala Ala Tyr Leu Arg Ser Ile Gly
            180             185             190
Val Asp Ala Trp Arg Phe Asp Tyr Val Lys Gly Tyr Gly Ala Trp Val
        195             200             205
Val Lys Asp Trp Leu Asn Trp Trp Gly Gly Trp Ala Val Gly Glu Tyr
    210             215                 220
Trp Asp Thr Asn Val Asp Ala Leu Leu Asn Trp Ala Tyr Ser Ser Gly
225             230              235                240
Ala Lys Val Phe Asp Phe Pro Leu Tyr Tyr Lys Met Asp Glu Ala Phe
            245             250             255
Asp Asn Lys Asn Ile Pro Ala Leu Val Ser Ala Leu Gln Asn Gly Gln
            260             265             270
Thr Val Val Ser Arg Asp Pro Phe Lys Ala Val Thr Phe Val Ala Asn
        275             280             285
His Asp Thr Asp Ile Ile Trp Asn Lys Tyr Leu Ala Tyr Ala Phe Ile
    290             295             300
Leu Thr Tyr Glu Gly Gln Pro Val Ile Phe Tyr Arg Asp Tyr Glu Glu
305             310             315                 320
Trp Leu Asn Lys Asp Arg Leu Asn Asn Leu Ile Trp Ile His Asp His
                325             330             335
Leu Ala Gly Gly Ser Thr Ser Ile Val Tyr Tyr Asp Ser Asp Glu Met
            340             345             350
Ile Phe Val Arg Asn Gly Tyr Gly Ser Lys Pro Gly Leu Ile Thr Tyr
            355             360             365
Ile Asn Leu Gly Ser Ser Lys Val Gly Arg Trp Val Tyr Val Pro Lys
            370             375             380
Phe Ala Gly Pro Cys Ile His Glu Tyr Thr Gly Asn Leu Gly Gly Trp
385             390             395                 400
Val Asp Lys Trp Val Asp Ser Ser Gly Trp Val Tyr Leu Glu Ala Pro
            405             410             415
Ala His Asp Pro Ala Asn Gly Gln Tyr Gly Tyr Ser Val Trp Ser Tyr
            420             425             430
Cys Gly Val Gly
            435
```

<210> SEQ ID NO 54
<211> LENGTH: 1311
<212> TYPE: DNA
<213> ORGANISM: Artificial Sequence
<220> FEATURE:
<223> OTHER INFORMATION: DNA sequence coding for an amylase

<400> SEQUENCE: 54

```
atggccaagt actccgagct ggaagagggc ggcgttataa tgcaggcctt ctactgggac      60
gtcccaggtg aggaatctg gtgggacacc atcaggagca agataccgga gtggtacgag      120
gcgggaatat ccgccatttg gattccccg gcaagcaagg gcatgggcgg cgcctattcg      180
atgggctacg accctacga cttctttgac ctcggtgagt acgaccagaa gggaacggta      240
gagacgcgct ttggctccaa gcaggagctc gtgaacatga taaacaccgc ccacgcctat      300
ggcatgaagg taatagccga tatagtcatc aaccaccgcg ccggcggtga cctggagtgg      360
aaccccttcg tgaacgacta tacctggacc gacttctcaa aggtcgcgtc gggtaaatac      420
acggccaact acctcgactt ccacccgaac gagctccatg cgggcgattc cggaacattt      480
ggaggctatc ccgacatatg ccacgacaag agctgggacc agtactggct ctgggccagc      540
caggagagct acgcggcata tctcaggagc atcggcatcg atgcctggcg cttcgactac      600
gtcaagggct atgctccctg gtcgtcaag gactggctga actggtgggg aggctgggcg      660
gttgagagt actgggacac caacgtcgac gctgttctca actgggcata ctcgagcggt      720
gccaaggtct ttgacttcgc cctctactac aagatggatg aggcctttga caacaaaaac      780
attccagcgc tcgtctctgc ccttcagaac ggccagactg ttgtctcccg cgacccgttc      840
aaggccgtaa cctttgtagc aaaccacgac accgatataa tctggaacaa gtaccttgct      900
tatgctttca tcctcaccta cgaaggccag cccgtcatat tctaccgcga ccacgaggag      960
tggctcaaca aggacaggtt gaacaacctc atatggatac acgaccacct cgcaggtgga      1020
agcaccgaca tagtctacta cgataacgat gaactcatct tcgtcaggaa cggctacggg      1080
gacaagccgg ggcttataac ctacatcaac ctaggctcga gcaaggccgg aaggtgggtt      1140
tatgtgccga agttcgcggg cgcgtgcatc cacgagtata ctggtaacct cggaggctgg      1200
gtagacaagt acgtctactc aagcggctgg gtctatctcg aagctccagc ttacgaccct      1260
gccaacgggc agtatggcta ctccgtgtgg agctactgcg gggtgggctg a                1311
```

<210> SEQ ID NO 55
<211> LENGTH: 436
<212> TYPE: PRT
<213> ORGANISM: Artificial Sequence
<220> FEATURE:
<223> OTHER INFORMATION: protein sequence of an amylase

<400> SEQUENCE: 55

Met Ala Lys Tyr Ser Glu Leu Glu Glu Gly Gly Val Ile Met Gln Ala
1               5                   10                  15

Phe Tyr Trp Asp Val Pro Gly Gly Gly Ile Trp Trp Asp Thr Ile Arg
            20                  25                  30

Ser Lys Ile Pro Glu Trp Tyr Glu Ala Gly Ile Ser Ala Ile Trp Ile
        35                  40                  45

Pro Pro Ala Ser Lys Gly Met Gly Gly Ala Tyr Ser Met Gly Tyr Asp
    50                  55                  60

Pro Tyr Asp Phe Phe Asp Leu Gly Glu Tyr Asp Gln Lys Gly Thr Val
65                  70                  75                  80

-continued

```
Glu Thr Arg Phe Gly Ser Lys Gln Glu Leu Val Asn Met Ile Asn Thr
                85                  90                  95
Ala His Ala Tyr Gly Met Lys Val Ile Ala Asp Ile Val Ile Asn His
            100                 105                 110
Arg Ala Gly Gly Asp Leu Glu Trp Asn Pro Phe Val Asn Asp Tyr Thr
        115                 120                 125
Trp Thr Asp Phe Ser Lys Val Ala Ser Gly Lys Tyr Thr Ala Asn Tyr
130                 135                 140
Leu Asp Phe His Pro Asn Glu Leu His Ala Gly Asp Ser Gly Thr Phe
145                 150                 155                 160
Gly Gly Tyr Pro Asp Ile Cys His Asp Lys Ser Trp Asp Gln Tyr Trp
                165                 170                 175
Leu Trp Ala Ser Gln Glu Ser Tyr Ala Ala Tyr Leu Arg Ser Ile Gly
            180                 185                 190
Ile Asp Ala Trp Arg Phe Asp Tyr Val Lys Gly Tyr Ala Pro Trp Val
        195                 200                 205
Val Lys Asp Trp Leu Asn Trp Trp Gly Gly Trp Ala Val Gly Glu Tyr
210                 215                 220
Trp Asp Thr Asn Val Asp Ala Val Leu Asn Trp Ala Tyr Ser Ser Gly
225                 230                 235                 240
Ala Lys Val Phe Asp Phe Ala Leu Tyr Tyr Lys Met Asp Glu Ala Phe
                245                 250                 255
Asp Asn Lys Asn Ile Pro Ala Leu Val Ser Ala Leu Gln Asn Gly Gln
            260                 265                 270
Thr Val Val Ser Arg Asp Pro Phe Lys Ala Val Thr Phe Val Ala Asn
        275                 280                 285
His Asp Thr Asp Ile Ile Trp Asn Lys Tyr Leu Ala Tyr Ala Phe Ile
290                 295                 300
Leu Thr Tyr Glu Gly Gln Pro Val Ile Phe Tyr Arg Asp His Glu Glu
305                 310                 315                 320
Trp Leu Asn Lys Asp Arg Leu Asn Asn Leu Ile Trp Ile His Asp His
                325                 330                 335
Leu Ala Gly Gly Ser Thr Asp Ile Val Tyr Tyr Asp Asn Asp Glu Leu
            340                 345                 350
Ile Phe Val Arg Asn Gly Tyr Gly Asp Lys Pro Gly Leu Ile Thr Tyr
        355                 360                 365
Ile Asn Leu Gly Ser Ser Lys Ala Gly Arg Trp Val Tyr Val Pro Lys
370                 375                 380
Phe Ala Gly Ala Cys Ile His Glu Tyr Thr Gly Asn Leu Gly Gly Trp
385                 390                 395                 400
Val Asp Lys Tyr Val Tyr Ser Ser Gly Trp Val Tyr Leu Glu Ala Pro
                405                 410                 415
Ala Tyr Asp Pro Ala Asn Gly Gln Tyr Gly Tyr Ser Val Trp Ser Tyr
            420                 425                 430
Cys Gly Val Gly
        435

<210> SEQ ID NO 56
<211> LENGTH: 1311
<212> TYPE: DNA
<213> ORGANISM: Artificial Sequence
<220> FEATURE:
<223> OTHER INFORMATION: DNA sequence coding for an amylase
```

<400> SEQUENCE: 56

```
atggccaagt acctggagct cgaagagggc ggggtcataa tgcaggcgtt ctactgggac      60
gtgccttcag gaggaatatg gtgggacaca atacggcaga agataccgga gtggtacgat     120
gccggaatct ccgcaatatg gattcccccg gcgagcaagg gcatgggcgg cgcctattcg     180
atgggctacg accctacga cttctttgac ctcggtgagt acgaccagaa gggaacggta     240
gagacgcgct ttggctccaa gcaggagctc gtgaacatga taaacaccgc ccacgcctat     300
ggcatgaagg taatagccga tatagtcatc aaccaccgcg ccggcggtga cctggagtgg     360
aaccccttcg tgaacgacta tacctggacc gacttctcaa aggtcgcgtc gggtaaatac     420
acggccaact acctcgactt ccaccccaac gaggtcaagt gctgtgacga gggcacattt     480
ggaggcttcc cagacatagc ccacgagaag agctgggacc agcactggct ctgggcgagc     540
gatgagagct acgccgccta cctaaggagc atcggcgttg atgcctggcg ctttgactac     600
gtgaagggct acggagcgtg ggtcgtcaag gactggctca actggtgggg cggctgggcc     660
gttggcgagt actgggacac caacgttgat gcactcctca actgggccta ctcgagcggc     720
gccaaggtct tcgacttccc gctctactac aagatggatg aggcctttga caacaaaaac     780
attccagcgc tcgtctctgc ccttcagaac ggccagactg ttgtctcccg cgacccgttc     840
aaggccgtaa cctttgtagc aaaccacgac accgatataa tctggaacaa gtatccagcc     900
tacgcgttca tcctcaccta cgagggccag ccgacaatat tctaccgcga ctacgaggag     960
tggctcaaca aggataagct caagaacctc atctggatac atgacaacct cgccggagga    1020
agcactgaca tcgtttacta cgacaacgac gagctgatat tcgtgagaaa cggctacgga    1080
agcaagccgg gactgataac atacatcaac ctcgcctcaa gcaaagccgg aaggtgggtt    1140
tacgttccga agttcgcagg ctcgtgcata cacgagtaca ccggcaatct cggcggctgg    1200
gtggacaagt gggtggactc aagcggctgg gtctacctcg aggctcctgc ccacgacccg    1260
gccaacggcc agtacggcta ctccgtctgg agctattgcg gtgttggctg a             1311
```

<210> SEQ ID NO 57
<211> LENGTH: 436
<212> TYPE: PRT
<213> ORGANISM: Artificial Sequence
<220> FEATURE:
<223> OTHER INFORMATION: protein sequence of an amylase

<400> SEQUENCE: 57

```
Met Ala Lys Tyr Leu Glu Leu Glu Glu Gly Gly Val Ile Met Gln Ala
1               5                  10                  15

Phe Tyr Trp Asp Val Pro Ser Gly Gly Ile Trp Trp Asp Thr Ile Arg
            20                  25                  30

Gln Lys Ile Pro Glu Trp Tyr Asp Ala Gly Ile Ser Ala Ile Trp Ile
        35                  40                  45

Pro Pro Ala Ser Lys Gly Met Gly Gly Ala Tyr Ser Met Gly Tyr Asp
    50                  55                  60

Pro Tyr Asp Phe Phe Asp Leu Gly Glu Tyr Asp Gln Lys Gly Thr Val
65                  70                  75                  80

Glu Thr Arg Phe Gly Ser Lys Gln Glu Leu Val Asn Met Ile Asn Thr
                85                  90                  95

Ala His Ala Tyr Gly Met Lys Val Ile Ala Asp Ile Val Ile Asn His
            100                 105                 110

Arg Ala Gly Gly Asp Leu Glu Trp Asn Pro Phe Val Asn Asp Tyr Thr
        115                 120                 125
```

```
Trp Thr Asp Phe Ser Lys Val Ala Ser Gly Lys Tyr Thr Ala Asn Tyr
    130                 135                 140

Leu Asp Phe His Pro Asn Glu Val Lys Cys Cys Asp Glu Gly Thr Phe
145                 150                 155                 160

Gly Gly Phe Pro Asp Ile Ala His Glu Lys Ser Trp Asp Gln His Trp
                165                 170                 175

Leu Trp Ala Ser Asp Glu Ser Tyr Ala Ala Tyr Leu Arg Ser Ile Gly
                180                 185                 190

Val Asp Ala Trp Arg Phe Asp Tyr Val Lys Gly Tyr Gly Ala Trp Val
                195                 200                 205

Val Lys Asp Trp Leu Asn Trp Trp Gly Gly Trp Ala Val Gly Glu Tyr
210                 215                 220

Trp Asp Thr Asn Val Asp Ala Leu Leu Asn Trp Ala Tyr Ser Ser Gly
225                 230                 235                 240

Ala Lys Val Phe Asp Phe Pro Leu Tyr Tyr Lys Met Asp Glu Ala Phe
                245                 250                 255

Asp Asn Lys Asn Ile Pro Ala Leu Val Ser Ala Leu Gln Asn Gly Gln
                260                 265                 270

Thr Val Val Ser Arg Asp Pro Phe Lys Ala Val Thr Phe Val Ala Asn
                275                 280                 285

His Asp Thr Asp Ile Ile Trp Asn Lys Tyr Pro Ala Tyr Ala Phe Ile
290                 295                 300

Leu Thr Tyr Glu Gly Gln Pro Thr Ile Phe Tyr Arg Asp Tyr Glu Glu
305                 310                 315                 320

Trp Leu Asn Lys Asp Lys Leu Lys Asn Leu Ile Trp Ile His Asp Asn
                325                 330                 335

Leu Ala Gly Gly Ser Thr Asp Ile Val Tyr Tyr Asp Asn Asp Glu Leu
                340                 345                 350

Ile Phe Val Arg Asn Gly Tyr Gly Ser Lys Pro Gly Leu Ile Thr Tyr
                355                 360                 365

Ile Asn Leu Ala Ser Ser Lys Ala Gly Arg Trp Val Tyr Val Pro Lys
                370                 375                 380

Phe Ala Gly Ser Cys Ile His Glu Tyr Thr Gly Asn Leu Gly Gly Trp
385                 390                 395                 400

Val Asp Lys Trp Val Asp Ser Ser Gly Trp Val Tyr Leu Glu Ala Pro
                405                 410                 415

Ala His Asp Pro Ala Asn Gly Gln Tyr Gly Tyr Ser Val Trp Ser Tyr
                420                 425                 430

Cys Gly Val Gly
            435

<210> SEQ ID NO 58
<211> LENGTH: 1311
<212> TYPE: DNA
<213> ORGANISM: Artificial Sequence
<220> FEATURE:
<223> OTHER INFORMATION: DNA sequence coding for an amylase

<400> SEQUENCE: 58
atggccaagt actccgagct ggaagagggc ggcgttataa tgcaggcctt ctactgggac      60
gtcccaggtg gaggaatctg gtgggacacc atcaggagca agataccgga gtggtacgag     120
gcgggaatat ccgccatttg gattcccccg gcgagcaagg gcatgggcgg cgcctattcg     180
atgggctacg accctacga cttctttgac ctcggtgagt acgaccagaa gggaacggta     240
gagacgcgct ttggctccaa gcaggagctc gtgaacatga taaacacggc ccatgcctac     300
```

-continued

```
ggcataaagg tcatagcgga catcgtcata aaccaccgca caggcggaga cctcgagtgg    360
aacccgttcg ttggggacta cacctggacg gacttctcaa aggtggcctc gggcaaatat    420
actgccaact acctcgactt ccaccccaac gaggtcaagt gctgtgacga gggcacattt    480
ggaggcttcc cagacatagc ccacgagaag agctgggacc agcactggct ctgggcgagc    540
gatgagagct acgccgccta cctaaggagc atcggcgttg atgcctggcg cttcgactac    600
gtcaagggct acggagcgtg ggtcgtcaag gactggctgg actggtgggg aggctgggcc    660
gtcggggagt actgggacac aaacgttgat gcactgctca actgggccta ctcgagcgat    720
gcaaaagtct tcgacttccc gctctactac aagatggatg aggcctttga caacaaaaac    780
attccagcgc tcgtctctgc ccttcagaac ggccagactg ttgtctcccg cgacccgttc    840
aaggccgtaa cctttgtagc aaaccacgac accgatataa tctggaacaa gtatccagcc    900
tacgcgttca tcctcaccta cgagggccag ccgacaatat tctaccgcga ctacgaggag    960
tggctcaaca aggataagct caagaacctc atctggatac atgacaacct cgccggagga   1020
agcactgaca tcgtttacta cgacaacgac gagctgtatt tcgtgagaaa cggctacgga   1080
agcaagccgg gactgataac atacatcaac ctcgcctcaa gcaaagccgg aaggtgggtc   1140
tacgttccga agttcgcggg agcgtgcatc cacgagtaca ccggcaacct cggcggctgg   1200
gtggacaagt gggtggactc aagcgggtgg gtgtacctcg aggcccctgc ccacgacccg   1260
gccaacggct attacggcta ctccgtctgg agctactgcg gtgttggctg a             1311
```

<210> SEQ ID NO 59
<211> LENGTH: 436
<212> TYPE: PRT
<213> ORGANISM: Artificial Sequence
<220> FEATURE:
<223> OTHER INFORMATION: protein sequence of an amylase

<400> SEQUENCE: 59

```
Met Ala Lys Tyr Ser Glu Leu Glu Glu Gly Gly Val Ile Met Gln Ala
1               5                   10                  15

Phe Tyr Trp Asp Val Pro Gly Gly Ile Trp Trp Asp Thr Ile Arg
            20                  25                  30

Ser Lys Ile Pro Glu Trp Tyr Glu Ala Gly Ile Ser Ala Ile Trp Ile
        35                  40                  45

Pro Pro Ala Ser Lys Gly Met Gly Gly Ala Tyr Ser Met Gly Tyr Asp
    50                  55                  60

Pro Tyr Asp Phe Phe Asp Leu Gly Glu Tyr Asp Gln Lys Gly Thr Val
65                  70                  75                  80

Glu Thr Arg Phe Gly Ser Lys Gln Glu Leu Val Asn Met Ile Asn Thr
                85                  90                  95

Ala His Ala Tyr Gly Ile Lys Val Ile Ala Asp Ile Val Ile Asn His
            100                 105                 110

Arg Thr Gly Gly Asp Leu Glu Trp Asn Pro Phe Val Gly Asp Tyr Thr
        115                 120                 125

Trp Thr Asp Phe Ser Lys Val Ala Ser Gly Lys Tyr Thr Ala Asn Tyr
    130                 135                 140

Leu Asp Phe His Pro Asn Glu Val Lys Cys Cys Asp Glu Gly Thr Phe
145                 150                 155                 160

Gly Gly Phe Pro Asp Ile Ala His Glu Lys Ser Trp Asp Gln His Trp
                165                 170                 175

Leu Trp Ala Ser Asp Glu Ser Tyr Ala Ala Tyr Leu Arg Ser Ile Gly
            180                 185                 190
```

Val Asp Ala Trp Arg Phe Asp Tyr Val Lys Gly Tyr Gly Ala Trp Val
                195                 200                 205

Val Lys Asp Trp Leu Asp Trp Trp Gly Gly Trp Ala Val Gly Glu Tyr
210                 215                 220

Trp Asp Thr Asn Val Asp Ala Leu Leu Asn Trp Ala Tyr Ser Ser Asp
225                 230                 235                 240

Ala Lys Val Phe Asp Phe Pro Leu Tyr Tyr Lys Met Asp Glu Ala Phe
                245                 250                 255

Asp Asn Lys Asn Ile Pro Ala Leu Val Ser Ala Leu Gln Asn Gly Gln
                260                 265                 270

Thr Val Val Ser Arg Asp Pro Phe Lys Ala Val Thr Phe Val Ala Asn
                275                 280                 285

His Asp Thr Asp Ile Ile Trp Asn Lys Tyr Pro Ala Tyr Ala Phe Ile
                290                 295                 300

Leu Thr Tyr Glu Gly Gln Pro Thr Ile Phe Tyr Arg Asp Tyr Glu Glu
305                 310                 315                 320

Trp Leu Asn Lys Asp Lys Leu Lys Asn Leu Ile Trp Ile His Asp Asn
                325                 330                 335

Leu Ala Gly Gly Ser Thr Asp Ile Val Tyr Tyr Asp Asn Asp Glu Leu
                340                 345                 350

Ile Phe Val Arg Asn Gly Tyr Gly Ser Lys Pro Gly Leu Ile Thr Tyr
                355                 360                 365

Ile Asn Leu Ala Ser Ser Lys Ala Gly Arg Trp Val Tyr Val Pro Lys
                370                 375                 380

Phe Ala Gly Ala Cys Ile His Glu Tyr Thr Gly Asn Leu Gly Gly Trp
385                 390                 395                 400

Val Asp Lys Trp Val Asp Ser Ser Gly Trp Val Tyr Leu Glu Ala Pro
                405                 410                 415

Ala His Asp Pro Ala Asn Gly Tyr Tyr Gly Tyr Ser Val Trp Ser Tyr
                420                 425                 430

Cys Gly Val Gly
        435

<210> SEQ ID NO 60
<211> LENGTH: 1311
<212> TYPE: DNA
<213> ORGANISM: Artificial Sequence
<220> FEATURE:
<223> OTHER INFORMATION: DNA sequence coding for an amylase

<400> SEQUENCE: 60
atggccaagt acctggagct cgaggagggc ggggtcataa tgcaggcgtt ctactgggac     60
gtgccttcag aggaatatg gtgggacaca atacggcaga agataccgga gtggtacgat    120
gccggaatct ccgcaatatg gattcccccg gcgagcaagg gcatgggcgg cgcctattcg    180
atgggctacg accctacga cttctttgac ctcggtgagt acgaccagaa gggaacggta    240
gagacgcgct ttggctccaa gcaggagctc gtgaacatga taaacaccgc ccacgcctat    300
ggcatgaagg taatagccga tatagtcatc aaccaccgcg ccggcggtga cctggagtgg    360
aaccccttcg tgaacgacta tacctggacc gacttctcaa aggtcgcgtc gggtaaatac    420
acggccaact acctcgactt ccacccgaac gagctccatg cgggcgattc cggaacattt    480
ggaggctatc ccgacatatg ccacgacaag agctgggacc agtactggct ctgggccagc    540
caggagagct acgcggcata tctcaggagc atcggcatcg atgcctggcg ctttgactac    600
gtgaagggct acggagcgtg ggtcgtcaag gactggctca actggtgggg cggctgggcc    660

```
gttggcgagt actgggacac caacgttgat gcactcctca actgggccta ctcgagcggc    720
gccaaggtct tcgacttccc gctctactac aagatggatg aggcctttga caacaaaaac    780
attccagcgc tcgtctctgc ccttcagaac ggccagactg ttgtctcccg cgacccgttc    840
aaggccgtaa cctttgtagc aaaccacgac accgatataa tctggaacaa gtaccttgct    900
tatgctttca tcctcaccta cgaaggccag cccgtcatat tctaccgcga ctacgaggag    960
tggctcaaca aggacaggtt gaacaacctc atatggatac acgaccacct cgcaggtgga   1020
agcacgagca tagtttacta cgacagcgac gagatgatct tcgtgaggaa cggctatgga   1080
agcaagcctg gccttataac ttacatcaac ctcggctcga gcaaggttgg aaggtgggtt   1140
tacgttccga agttcgcagg ctcgtgcata cacgagtaca ccggcaatct cggcggctgg   1200
gtggacaagt gggtggactc aagcggctgg gtctacctcg aggctcctgc ccacgacccg   1260
gccaacggcc agtacggcta ctccgtctgg agctattgcg tgttggctg a              1311
```

<210> SEQ ID NO 61
<211> LENGTH: 436
<212> TYPE: PRT
<213> ORGANISM: Artificial Sequence
<220> FEATURE:
<223> OTHER INFORMATION: protein sequence of an amylase

<400> SEQUENCE: 61

```
Met Ala Lys Tyr Leu Glu Leu Glu Glu Gly Gly Val Ile Met Gln Ala
1               5                   10                  15

Phe Tyr Trp Asp Val Pro Ser Gly Gly Ile Trp Trp Asp Thr Ile Arg
            20                  25                  30

Gln Lys Ile Pro Glu Trp Tyr Asp Ala Gly Ile Ser Ala Ile Trp Ile
        35                  40                  45

Pro Pro Ala Ser Lys Gly Met Gly Gly Ala Tyr Ser Met Gly Tyr Asp
    50                  55                  60

Pro Tyr Asp Phe Phe Asp Leu Gly Glu Tyr Asp Gln Lys Gly Thr Val
65                  70                  75                  80

Glu Thr Arg Phe Gly Ser Lys Gln Glu Leu Val Asn Met Ile Asn Thr
                85                  90                  95

Ala His Ala Tyr Gly Met Lys Val Ile Ala Asp Ile Val Ile Asn His
            100                 105                 110

Arg Ala Gly Gly Asp Leu Glu Trp Asn Pro Phe Val Asn Asp Tyr Thr
        115                 120                 125

Trp Thr Asp Phe Ser Lys Val Ala Ser Gly Lys Tyr Thr Ala Asn Tyr
    130                 135                 140

Leu Asp Phe His Pro Asn Glu Leu His Ala Gly Asp Ser Gly Thr Phe
145                 150                 155                 160

Gly Gly Tyr Pro Asp Ile Cys His Asp Lys Ser Trp Asp Gln Tyr Trp
                165                 170                 175

Leu Trp Ala Ser Gln Glu Ser Tyr Ala Ala Tyr Leu Arg Ser Ile Gly
            180                 185                 190

Ile Asp Ala Trp Arg Phe Asp Tyr Val Lys Gly Tyr Gly Ala Trp Val
        195                 200                 205

Val Lys Asp Trp Leu Asn Trp Trp Gly Gly Trp Ala Val Gly Glu Tyr
    210                 215                 220

Trp Asp Thr Asn Val Asp Ala Leu Leu Asn Trp Ala Tyr Ser Ser Gly
225                 230                 235                 240

Ala Lys Val Phe Asp Phe Pro Leu Tyr Tyr Lys Met Asp Glu Ala Phe
                245                 250                 255
```

```
Asp Asn Lys Asn Ile Pro Ala Leu Val Ser Ala Leu Gln Asn Gly Gln
            260                 265                 270

Thr Val Val Ser Arg Asp Pro Phe Lys Ala Val Thr Phe Val Ala Asn
        275                 280                 285

His Asp Thr Asp Ile Ile Trp Asn Lys Tyr Leu Ala Tyr Ala Phe Ile
    290                 295                 300

Leu Thr Tyr Glu Gly Gln Pro Val Ile Phe Tyr Arg Asp Tyr Glu Glu
305                 310                 315                 320

Trp Leu Asn Lys Asp Arg Leu Asn Asn Leu Ile Trp Ile His Asp His
                325                 330                 335

Leu Ala Gly Gly Ser Thr Ser Ile Val Tyr Tyr Asp Ser Asp Glu Met
            340                 345                 350

Ile Phe Val Arg Asn Gly Tyr Gly Ser Lys Pro Gly Leu Ile Thr Tyr
        355                 360                 365

Ile Asn Leu Gly Ser Ser Lys Val Gly Arg Trp Val Tyr Val Pro Lys
    370                 375                 380

Phe Ala Gly Ser Cys Ile His Glu Tyr Thr Gly Asn Leu Gly Gly Trp
385                 390                 395                 400

Val Asp Lys Trp Val Asp Ser Ser Gly Trp Val Tyr Leu Glu Ala Pro
                405                 410                 415

Ala His Asp Pro Ala Asn Gly Gln Tyr Gly Tyr Ser Val Trp Ser Tyr
            420                 425                 430

Cys Gly Val Gly
        435

<210> SEQ ID NO 62
<211> LENGTH: 1311
<212> TYPE: DNA
<213> ORGANISM: Artificial Sequence
<220> FEATURE:
<223> OTHER INFORMATION: DNA sequence coding for an amylase

<400> SEQUENCE: 62
atggccaagt acctggagct cgaagagagc ggggtcataa tgcaggcgtt ctactgggac      60
gtgccttcag gaggaatatg gtgggacaca atacggcaga agataccgga gtggtacgat     120
gccggaatct ccgcaatatg gattcctccc gcgagcaagg gtatgagcgg cggctattcg     180
atgggctacg acccctacga ttattttgac ctcggtgagt actaccagaa gggaacggtg     240
gaaacgaggt tcggctcaaa gcaggagctc ataaacatga taaacaccgc ccacgcctac     300
ggcatcaagg tcatcgcaga catagtaatc aaccaccgcg ccggaggaga ccttgagtgg     360 aacccccttcg tcaatgacta cacctggacg gacttctcga aggtcgcttc cggcaagtac     420
acggccaact acctcgactt ccaccccaac gaggtcaagt gctgtgacga ggcacattt     480 ggaggcttcc cagacatagc ccacgagaag agctgggacc agcactggct ctgggcgagc     540
gatgagagct acgccgccta cctaaggagc atcggcgttg atgcctggcg ctttgactac     600
gtgaagggct acggagcgtg gtcgtcaag gactggctca actggtgggg tggctgggcc     660 gtcgggagt actgggacac aaacgttgat gcactgctca ctgggccta ctcgagcgat     720 gcaaaagtct tcgacttccc gctctactac aagatggacg aggccttcga taacaacaac     780 attccccgccc tggtggacgc cctcagatac ggtcagacag tggtcagccg cgaccgttc     840 aaggctgtga cgtttgtagc caaccacgat accgatataa tctggaacaa gtaccttgct     900
tatgctttca tcctcaccta cgaaggccag cccgtcatat tctaccgcga ctacgaggag     960
tggctcaaca aggacaggtt gaacaacctc atatggatac acgaccacct cgcaggtgga    1020
```

```
agcactgaca tcgtttacta cgacaacgac gagctgatat tcgtgagaaa cggctacgga   1080
agcaagccgg gactgataac atacatcaac ctcgcctcaa gcaaagccgg aaggtgggtc   1140
tacgttccga agttcgcggg agcgtgcatc cacgagtaca ccggcaacct cggcggctgg   1200
gtggacaagt gggtggactc aagcgggtgg gtgtacctcg aggcccctgc ccacgacccg   1260
gccaacggct attacggcta ctccgtctgg agctattgcg gtgttggctg a             1311
```

<210> SEQ ID NO 63
<211> LENGTH: 436
<212> TYPE: PRT
<213> ORGANISM: Artificial Sequence
<220> FEATURE:
<223> OTHER INFORMATION: protein sequence of an amylase

<400> SEQUENCE: 63

```
Met Ala Lys Tyr Leu Glu Leu Glu Glu Ser Gly Val Ile Met Gln Ala
1               5                   10                  15

Phe Tyr Trp Asp Val Pro Ser Gly Gly Ile Trp Trp Asp Thr Ile Arg
            20                  25                  30

Gln Lys Ile Pro Glu Trp Tyr Asp Ala Gly Ile Ser Ala Ile Trp Ile
        35                  40                  45

Pro Pro Ala Ser Lys Gly Met Ser Gly Gly Tyr Ser Met Gly Tyr Asp
    50                  55                  60

Pro Tyr Asp Tyr Phe Asp Leu Gly Glu Tyr Tyr Gln Lys Gly Thr Val
65                  70                  75                  80

Glu Thr Arg Phe Gly Ser Lys Gln Glu Leu Ile Asn Met Ile Asn Thr
                85                  90                  95

Ala His Ala Tyr Gly Ile Lys Val Ile Ala Asp Ile Val Ile Asn His
            100                 105                 110

Arg Ala Gly Gly Asp Leu Glu Trp Asn Pro Phe Val Asn Asp Tyr Thr
        115                 120                 125

Trp Thr Asp Phe Ser Lys Val Ala Ser Gly Lys Tyr Thr Ala Asn Tyr
    130                 135                 140

Leu Asp Phe His Pro Asn Glu Val Lys Cys Cys Asp Glu Gly Thr Phe
145                 150                 155                 160

Gly Gly Phe Pro Asp Ile Ala His Glu Lys Ser Trp Asp Gln His Trp
                165                 170                 175

Leu Trp Ala Ser Asp Glu Ser Tyr Ala Ala Tyr Leu Arg Ser Ile Gly
            180                 185                 190

Val Asp Ala Trp Arg Phe Asp Tyr Val Lys Gly Tyr Gly Ala Trp Val
        195                 200                 205

Val Lys Asp Trp Leu Asn Trp Trp Gly Gly Trp Ala Val Gly Glu Tyr
    210                 215                 220

Trp Asp Thr Asn Val Asp Ala Leu Leu Asn Trp Ala Tyr Ser Ser Asp
225                 230                 235                 240

Ala Lys Val Phe Asp Phe Pro Leu Tyr Tyr Lys Met Asp Glu Ala Phe
                245                 250                 255

Asp Asn Asn Asn Ile Pro Ala Leu Val Asp Ala Leu Arg Tyr Gly Gln
            260                 265                 270

Thr Val Val Ser Arg Asp Pro Phe Lys Ala Val Thr Phe Val Ala Asn
        275                 280                 285

His Asp Thr Asp Ile Ile Trp Asn Lys Tyr Leu Ala Tyr Ala Phe Ile
    290                 295                 300

Leu Thr Tyr Glu Gly Gln Pro Val Ile Phe Tyr Arg Asp Tyr Glu Glu
305                 310                 315                 320
```

Trp Leu Asn Lys Asp Arg Leu Asn Asn Leu Ile Trp Ile His Asp His
            325                 330                 335

Leu Ala Gly Gly Ser Thr Asp Ile Val Tyr Tyr Asp Asn Asp Glu Leu
        340                 345                 350

Ile Phe Val Arg Asn Gly Tyr Gly Ser Lys Pro Gly Leu Ile Thr Tyr
            355                 360                 365

Ile Asn Leu Ala Ser Ser Lys Ala Gly Arg Trp Val Tyr Val Pro Lys
        370                 375                 380

Phe Ala Gly Ala Cys Ile His Glu Tyr Thr Gly Asn Leu Gly Gly Trp
385                 390                 395                 400

Val Asp Lys Trp Val Asp Ser Ser Gly Trp Val Tyr Leu Glu Ala Pro
                405                 410                 415

Ala His Asp Pro Ala Asn Gly Tyr Tyr Gly Tyr Ser Val Trp Ser Tyr
            420                 425                 430

Cys Gly Val Gly
        435

<210> SEQ ID NO 64
<211> LENGTH: 1311
<212> TYPE: DNA
<213> ORGANISM: Artificial Sequence
<220> FEATURE:
<223> OTHER INFORMATION: DNA sequence coding for an amylase

<400> SEQUENCE: 64
atggccaagt acctggagct cgaagagggc ggggtcataa tgcaggcgtt ctactgggac      60
gtgccttcag gaggaatatg gtgggacaca atacggcaga agataccgga gtggtacgat     120
gccggaatct ccgcaatatg gattcctccc gcgagcaagg gtatgagcgg cggctattcg     180
atgggctacg accctacga ttattttgac ctcggtgagt actaccagaa gggaacggtg      240
gaaacgaggt tcggctcaaa gcaggagctc ataaacatga taaacaccgc ccacgcctac     300
ggcatcaagg tcatcgcaga catagtaatc aaccaccgcg ccggaggaga ccttgagtgg     360
aaccccttcg tcaatgacta cacctggacg gacttctcga aggtcgcttc cggcaagtac     420
acggccaact acctcgactt ccacccgaac gagctccatg cgggcgattc cggaacattt     480
ggaggctatc ccgacatatg ccacgacaag agctgggacc agtactggct ctgggccagc     540
caggagagct acgcggcata tctcaggagc atcggcatcg atgcctggcg cttcgactac     600
gtcaagggct atgctccctg gtcgtcaag gactggctga actggtgggg aggctgggcg      660
gttggagagt actgggacac caacgtcgac gctgttctca actgggcata ctcgagcggt     720
gccaaggtct ttgacttcgc cctctactac aagatggacg aggccttcga taacaacaac     780
attcccgccc tggtggacgc cctcagatac ggtcagacag tggtcagccg cgaccgttc      840 aaggctgtga cgtttgtagc caaccacgat accgatataa tttggaacaa gtacccggcc     900
tacgccttca tcctcaccta cgagggccag ccgacgatat tctaccgcga ctacgaggag     960
tggctcaaca aggacaggct caagaacctc atctggatac acgaccacct cgccggtgga    1020
agcactgaca tcgtttacta cgacaacgac gagctgatat cgtgagaaaa cggctacgga    1080
agcaagccgg gactgataac atacatcaac ctcgcgtcaa gcaaagccgg aaggtgggtt    1140
tatgtgccga gttcgcgggc gcgtgcatc acgagtata ctggtaacct cggaggctgg       1200
gtagacaagt acgtctactc aagcggctgg gtctatctcg aagctccagc ttacgaccct    1260
gccaacgggc agtatggcta ctccgtgtgg agctattgcg gtgttgggtg a              1311

```
<210> SEQ ID NO 65
<211> LENGTH: 436
<212> TYPE: PRT
<213> ORGANISM: Artificial Sequence
<220> FEATURE:
<223> OTHER INFORMATION: protein sequence of an amylase

<400> SEQUENCE: 65
```

| | | | | | | | | | | | | | | |
|---|---|---|---|---|---|---|---|---|---|---|---|---|---|---|
| Met | Ala | Lys | Tyr | Leu | Glu | Leu | Glu | Glu | Gly | Val | Ile | Met | Gln | Ala |
| 1 | | | | 5 | | | | | 10 | | | | | 15 |
| Phe | Tyr | Trp | Asp | Val | Pro | Ser | Gly | Gly | Ile | Trp | Trp | Asp | Thr | Ile | Arg |
| | | | 20 | | | | | 25 | | | | | 30 | | |
| Gln | Lys | Ile | Pro | Glu | Trp | Tyr | Asp | Ala | Gly | Ile | Ser | Ala | Ile | Trp | Ile |
| | | | 35 | | | | | 40 | | | | | 45 | | |
| Pro | Pro | Ala | Ser | Lys | Gly | Met | Ser | Gly | Gly | Tyr | Ser | Met | Gly | Tyr | Asp |
| | 50 | | | | | 55 | | | | | 60 | | | | |
| Pro | Tyr | Asp | Tyr | Phe | Asp | Leu | Gly | Glu | Tyr | Tyr | Gln | Lys | Gly | Thr | Val |
| 65 | | | | | 70 | | | | | 75 | | | | | 80 |
| Glu | Thr | Arg | Phe | Gly | Ser | Lys | Gln | Glu | Leu | Ile | Asn | Met | Ile | Asn | Thr |
| | | | | 85 | | | | | 90 | | | | | 95 | |
| Ala | His | Ala | Tyr | Gly | Ile | Lys | Val | Ile | Ala | Asp | Ile | Val | Ile | Asn | His |
| | | | 100 | | | | | 105 | | | | | 110 | | |
| Arg | Ala | Gly | Gly | Asp | Leu | Glu | Trp | Asn | Pro | Phe | Val | Asn | Asp | Tyr | Thr |
| | | | 115 | | | | | 120 | | | | | 125 | | |
| Trp | Thr | Asp | Phe | Ser | Lys | Val | Ala | Ser | Gly | Lys | Tyr | Thr | Ala | Asn | Tyr |
| | | 130 | | | | | 135 | | | | | 140 | | | |
| Leu | Asp | Phe | His | Pro | Asn | Glu | Leu | His | Ala | Gly | Asp | Ser | Gly | Thr | Phe |
| 145 | | | | | 150 | | | | | 155 | | | | | 160 |
| Gly | Gly | Tyr | Pro | Asp | Ile | Cys | His | Asp | Lys | Ser | Trp | Asp | Gln | Tyr | Trp |
| | | | | 165 | | | | | 170 | | | | | 175 | |
| Leu | Trp | Ala | Ser | Gln | Glu | Ser | Tyr | Ala | Ala | Tyr | Leu | Arg | Ser | Ile | Gly |
| | | | 180 | | | | | 185 | | | | | 190 | | |
| Ile | Asp | Ala | Trp | Arg | Phe | Asp | Tyr | Val | Lys | Gly | Tyr | Ala | Pro | Trp | Val |
| | | | 195 | | | | | 200 | | | | | 205 | | |
| Val | Lys | Asp | Trp | Leu | Asn | Trp | Trp | Gly | Gly | Trp | Ala | Val | Gly | Glu | Tyr |
| | | 210 | | | | | 215 | | | | | 220 | | | |
| Trp | Asp | Thr | Asn | Val | Asp | Ala | Val | Leu | Asn | Trp | Ala | Tyr | Ser | Ser | Gly |
| 225 | | | | | 230 | | | | | 235 | | | | | 240 |
| Ala | Lys | Val | Phe | Asp | Phe | Ala | Leu | Tyr | Tyr | Lys | Met | Asp | Glu | Ala | Phe |
| | | | | 245 | | | | | 250 | | | | | 255 | |
| Asp | Asn | Asn | Asn | Ile | Pro | Ala | Leu | Val | Asp | Ala | Leu | Arg | Tyr | Gly | Gln |
| | | | | 260 | | | | | 265 | | | | | 270 | |
| Thr | Val | Val | Ser | Arg | Asp | Pro | Phe | Lys | Ala | Val | Thr | Phe | Val | Ala | Asn |
| | | | 275 | | | | | 280 | | | | | 285 | | |
| His | Asp | Thr | Asp | Ile | Ile | Trp | Asn | Lys | Tyr | Pro | Ala | Tyr | Ala | Phe | Ile |
| | | 290 | | | | | 295 | | | | | 300 | | | |
| Leu | Thr | Tyr | Glu | Gly | Gln | Pro | Thr | Ile | Phe | Tyr | Arg | Asp | Tyr | Glu | Glu |
| 305 | | | | | 310 | | | | | 315 | | | | | 320 |
| Trp | Leu | Asn | Lys | Asp | Arg | Leu | Lys | Asn | Leu | Ile | Trp | Ile | His | Asp | His |
| | | | | 325 | | | | | 330 | | | | | 335 | |
| Leu | Ala | Gly | Gly | Ser | Thr | Asp | Ile | Val | Tyr | Tyr | Asp | Asn | Asp | Glu | Leu |
| | | | | 340 | | | | | 345 | | | | | 350 | |
| Ile | Phe | Val | Arg | Asn | Gly | Tyr | Gly | Ser | Lys | Pro | Gly | Leu | Ile | Thr | Tyr |
| | | | 355 | | | | | 360 | | | | | 365 | | |

```
Ile Asn Leu Ala Ser Ser Lys Ala Gly Arg Trp Val Tyr Val Pro Lys
        370                 375                 380

Phe Ala Gly Ala Cys Ile His Glu Tyr Thr Gly Asn Leu Gly Gly Trp
    385                 390                 395                 400

Val Asp Lys Tyr Val Tyr Ser Ser Gly Trp Val Tyr Leu Glu Ala Pro
                405                 410                 415

Ala Tyr Asp Pro Ala Asn Gly Gln Tyr Gly Tyr Ser Val Trp Ser Tyr
                420                 425                 430

Cys Gly Val Gly
        435

<210> SEQ ID NO 66
<211> LENGTH: 1311
<212> TYPE: DNA
<213> ORGANISM: Artificial Sequence
<220> FEATURE:
<223> OTHER INFORMATION: DNA sequence coding for an amylase

<400> SEQUENCE: 66
atggccaagt actccgagct gaaaaagggc ggggtcataa tgcaggcgtt ctactgggac      60
gtgccttcag gaggaatatg gtgggacaca atacggcaga agataccgga gtggtacgag     120
gcgggaatat ccgccatttg gattcctccc gcgagcaagg gtatgagcgg cggctattcg     180
atgggctacg acccctacga ttattttgac ctcggtgagt actaccagaa gggaacggtg     240
gaaacgaggt tcggctcaaa gcaggagctc ataaacatga taaacaccgc ccacgcctac     300
ggcatcaagg tcatcgcaga catagtaatc aaccaccgcg ccggaggaga ccttgagtgg     360
aaccccttcg tcaatgacta cacctggacg gacttctcga aggtcgcttc cggcaagtac     420
acggccaact acctcaactt ccacccgaac gagctccatg cgggcgattc cggaacattt     480
ggaggctatc ccgacatatg ccacgacaag agctgggacc agtactggct ctgggccagc     540
caggagagct acgcggcata tctcaggagc atcggcatcg atgcctggcg cttcgactac     600
gtcaagggct acgagcgtgg ggtcgtcaag gactggctgg actggtgggg aggctgggcc     660 gtcgggagt actgggacac aaaacgttga tgcactgctca actgggccta ctcgagcgat     720
gcaaaagtct tcgacttccc gctctactac aagatggatg aggcctttga acaaaaaac     780 attccagcgc tcgtctctgc ccttcagaac ggccagactg ttgtctcccg cgacccgttc     840
aaggccgtaa cctttgtagc aaaccatgac accgatataa tctggaacaa gtatccagcc     900
tacgcgttca tcctcaccta cgagggccag ccgacaatat tctaccgcga ctacgaggag     960
tggctcaaca aggataagct caagaacctc atctggatac atgacaacct cgccggagga    1020
agcaccgaca tagtctacta cgataacgat gaactcatct tcgtcaggaa cggctacggg    1080
gacaagccgg ggcttataac ctacatcaac ctaggctcga gcaaggccgg aaggtgggtc    1140
tacgttccga agttcgcggg agcgtgcatc cacgagtaca ccggcaacct cggcggctgg    1200
gtggacaagt gggtggactc aagcgggtgg gtgtacctcg aggcccctgc ccacgacccg    1260
gccaacggct attacggcta ctccgtctgg agctactgcg gggtgggctg a             1311

<210> SEQ ID NO 67
<211> LENGTH: 436
<212> TYPE: PRT
<213> ORGANISM: Artificial Sequence
<220> FEATURE:
<223> OTHER INFORMATION: protein sequence of an amylase
```

```
<400> SEQUENCE: 67

Met Ala Lys Tyr Ser Glu Leu Lys Lys Gly Gly Val Ile Met Gln Ala
1               5                   10                  15

Phe Tyr Trp Asp Val Pro Ser Gly Gly Ile Trp Trp Asp Thr Ile Arg
                20                  25                  30

Gln Lys Ile Pro Glu Trp Tyr Glu Ala Gly Ile Ser Ala Ile Trp Ile
            35                  40                  45

Pro Pro Ala Ser Lys Gly Met Ser Gly Gly Tyr Ser Met Gly Tyr Asp
        50                  55                  60

Pro Tyr Asp Tyr Phe Asp Leu Gly Glu Tyr Tyr Gln Lys Gly Thr Val
65                  70                  75                  80

Glu Thr Arg Phe Gly Ser Lys Gln Glu Leu Ile Asn Met Ile Asn Thr
                85                  90                  95

Ala His Ala Tyr Gly Ile Lys Val Ile Ala Asp Ile Val Ile Asn His
            100                 105                 110

Arg Ala Gly Gly Asp Leu Glu Trp Asn Pro Phe Val Asn Asp Tyr Thr
        115                 120                 125

Trp Thr Asp Phe Ser Lys Val Ala Ser Gly Lys Tyr Thr Ala Asn Tyr
130                 135                 140

Leu Asn Phe His Pro Asn Glu Leu His Ala Gly Asp Ser Gly Thr Phe
145                 150                 155                 160

Gly Gly Tyr Pro Asp Ile Cys His Asp Lys Ser Trp Asp Gln Tyr Trp
                165                 170                 175

Leu Trp Ala Ser Gln Glu Ser Tyr Ala Ala Tyr Leu Arg Ser Ile Gly
            180                 185                 190

Ile Asp Ala Trp Arg Phe Asp Tyr Val Lys Gly Tyr Gly Ala Trp Val
        195                 200                 205

Val Lys Asp Trp Leu Asp Trp Trp Gly Gly Trp Ala Val Gly Glu Tyr
210                 215                 220

Trp Asp Thr Asn Val Asp Ala Leu Leu Asn Trp Ala Tyr Ser Ser Asp
225                 230                 235                 240

Ala Lys Val Phe Asp Phe Pro Leu Tyr Tyr Lys Met Asp Glu Ala Phe
                245                 250                 255

Asp Asn Lys Asn Ile Pro Ala Leu Val Ser Ala Leu Gln Asn Gly Gln
            260                 265                 270

Thr Val Val Ser Arg Asp Pro Phe Lys Ala Val Thr Phe Val Ala Asn
        275                 280                 285

His Asp Thr Asp Ile Ile Trp Asn Lys Tyr Pro Ala Tyr Ala Phe Ile
290                 295                 300

Leu Thr Tyr Glu Gly Gln Pro Thr Ile Phe Tyr Arg Asp Tyr Glu Glu
305                 310                 315                 320

Trp Leu Asn Lys Asp Lys Leu Lys Asn Leu Ile Trp Ile His Asp Asn
                325                 330                 335

Leu Ala Gly Gly Ser Thr Asp Ile Val Tyr Tyr Asp Asn Asp Glu Leu
            340                 345                 350

Ile Phe Val Arg Asn Gly Tyr Gly Asp Lys Pro Gly Leu Ile Thr Tyr
        355                 360                 365

Ile Asn Leu Gly Ser Ser Lys Ala Gly Arg Trp Val Tyr Val Pro Lys
370                 375                 380

Phe Ala Gly Ala Cys Ile His Glu Tyr Thr Gly Asn Leu Gly Gly Trp
                385                 390                 395                 400

Val Asp Lys Trp Val Asp Ser Ser Gly Trp Val Tyr Leu Glu Ala Pro
            405                 410                 415
```

Ala His Asp Pro Ala Asn Gly Tyr Tyr Gly Tyr Ser Val Trp Ser Tyr
            420                 425                 430

Cys Gly Val Gly
        435

<210> SEQ ID NO 68
<211> LENGTH: 1311
<212> TYPE: DNA
<213> ORGANISM: Artificial Sequence
<220> FEATURE:
<223> OTHER INFORMATION: DNA sequence coding for an amylase

<400> SEQUENCE: 68

```
atggccaagt acctggagct cgaagagggc ggggtcataa tgcaggcgtt ctactgggac      60
gtgccttcag gaggaatatg gtgggacaca atacggcaga agataccgga gtggtacgat     120
gccggaatct ccgcaatatg gattcccccg gcgagcaagg gcatgggcgg cgcctattcg     180
atgggctacg accctacga cttctttgac ctcggtgagt acgaccagaa gggaacggta     240
gagacgcgct ttggctccaa gcaggagctc gtgaacatga taaacacggc ccatgcctac     300
ggcataaagg ccatagcgga catcgtcata aaccaccgcg caggcggaga cctcgagtgg     360
aacccgttcg ttggggacta cacctggacg gacttctcaa aggtggcctc gggcaaatat     420
actgccaact acctcgactt ccaccccaac gaggtcaagt gctgtgacga gggcacattt     480
ggaggcttcc cagacatagc ccacgagaag agctgggacc agcactggct ctgggcgagc     540
gatgagagct acgccgccta cctaaggagc atcggcgttg atgcctggcg ctttgactac     600
gtgaagggct acggagcgtg ggtcgtcaag gactggctca ctggtgggg cggctgggcc     660
gttggcgagt actgggacac caacgttgat gcactcctca actgggccta ctcgagcggc     720
gccaaggtct tcgacttccc gctctactac aagatggacg cggcctttga caacaagaac     780
attcccgcac tcgtcgaggc cctcaagaac gggggcacag tcgtcagccg cgaccgtttt     840
aaggccgtaa ccttcgttgc aaaccacgac accgatataa tctggaacaa gtatccagcc     900
tacgcgttca tcctcaccta cgagggccag ccgacaatat tctaccgcga ctacgaggag     960
tggctcaaca aggataagct caagaaccta atctggatac atgacaacct cgccggagga    1020
agcaccgaca tagtctacta cgataacgat gaactcatct tcgtcaggaa cggctacggg    1080
gacaagccgg ggcttataac ctacatcaac ctaggctgga gcaaggccgg aaggtggggt    1140
tatgtgccga agttcgcggg cgcgtgcatc cacgagtata ctggtaacct cggaggctgg    1200
gtagacaagt acgtctactc aagcggctgg gtctatctcg aagctccagc ttacgaccct    1260
gccaacgggc agtatggcta ctccgtgtgg agctactgcg gggtggggtg a             1311
```

<210> SEQ ID NO 69
<211> LENGTH: 436
<212> TYPE: PRT
<213> ORGANISM: Artificial Sequence
<220> FEATURE:
<223> OTHER INFORMATION: protein sequence of an amylase

<400> SEQUENCE: 69

Met Ala Lys Tyr Leu Glu Leu Glu Glu Gly Gly Val Ile Met Gln Ala
1               5                   10                  15

Phe Tyr Trp Asp Val Pro Ser Gly Gly Ile Trp Trp Asp Thr Ile Arg
            20                  25                  30

Gln Lys Ile Pro Glu Trp Tyr Asp Ala Gly Ile Ser Ala Ile Trp Ile
        35                  40                  45

```
Pro Pro Ala Ser Lys Gly Met Gly Gly Ala Tyr Ser Met Gly Tyr Asp
    50                  55                  60
Pro Tyr Asp Phe Phe Asp Leu Gly Glu Tyr Asp Gln Lys Gly Thr Val
65                  70                  75                  80
Glu Thr Arg Phe Gly Ser Lys Gln Glu Leu Val Asn Met Ile Asn Thr
                    85                  90                  95
Ala His Ala Tyr Gly Ile Lys Ala Ile Ala Asp Ile Val Ile Asn His
                100                 105                 110
Arg Ala Gly Gly Asp Leu Glu Trp Asn Pro Phe Val Gly Asp Tyr Thr
                115                 120                 125
Trp Thr Asp Phe Ser Lys Val Ala Ser Gly Lys Tyr Thr Ala Asn Tyr
    130                 135                 140
Leu Asp Phe His Pro Asn Glu Val Lys Cys Cys Asp Glu Gly Thr Phe
145                 150                 155                 160
Gly Gly Phe Pro Asp Ile Ala His Glu Lys Ser Trp Asp Gln His Trp
                165                 170                 175
Leu Trp Ala Ser Asp Glu Ser Tyr Ala Ala Tyr Leu Arg Ser Ile Gly
                180                 185                 190
Val Asp Ala Trp Arg Phe Asp Tyr Val Lys Gly Tyr Gly Ala Trp Val
                195                 200                 205
Val Lys Asp Trp Leu Asn Trp Trp Gly Gly Trp Ala Val Gly Glu Tyr
    210                 215                 220
Trp Asp Thr Asn Val Asp Ala Leu Leu Asn Trp Ala Tyr Ser Ser Gly
225                 230                 235                 240
Ala Lys Val Phe Asp Phe Pro Leu Tyr Tyr Lys Met Asp Ala Ala Phe
                245                 250                 255
Asp Asn Lys Asn Ile Pro Ala Leu Val Glu Ala Leu Lys Asn Gly Gly
                260                 265                 270
Thr Val Val Ser Arg Asp Pro Phe Lys Ala Val Thr Phe Val Ala Asn
    275                 280                 285
His Asp Thr Asp Ile Ile Trp Asn Lys Tyr Pro Ala Tyr Ala Phe Ile
    290                 295                 300
Leu Thr Tyr Glu Gly Gln Pro Thr Ile Phe Tyr Arg Asp Tyr Glu Glu
305                 310                 315                 320
Trp Leu Asn Lys Asp Lys Leu Lys Asn Leu Ile Trp Ile His Asp Asn
                325                 330                 335
Leu Ala Gly Gly Ser Thr Asp Ile Val Tyr Tyr Asp Asn Asp Glu Leu
                340                 345                 350
Ile Phe Val Arg Asn Gly Tyr Gly Asp Lys Pro Gly Leu Ile Thr Tyr
                355                 360                 365
Ile Asn Leu Gly Trp Ser Lys Ala Gly Arg Trp Val Tyr Val Pro Lys
    370                 375                 380
Phe Ala Gly Ala Cys Ile His Glu Tyr Thr Gly Asn Leu Gly Gly Trp
385                 390                 395                 400
Val Asp Lys Tyr Val Tyr Ser Ser Gly Trp Val Tyr Leu Glu Ala Pro
                405                 410                 415
Ala Tyr Asp Pro Ala Asn Gly Gln Tyr Gly Tyr Ser Val Trp Ser Tyr
                420                 425                 430
Cys Gly Val Gly
            435
```

-continued

<210> SEQ ID NO 70
<211> LENGTH: 1311
<212> TYPE: DNA
<213> ORGANISM: Artificial Sequence
<220> FEATURE:
<223> OTHER INFORMATION: DNA sequence coding for an amylase

<400> SEQUENCE: 70

```
atggccaagt actccgagct ggaagaaggc ggcgttataa tgcaggcctt ctactgggac      60
gtcccaggtg gaggaatctg tggggcacc atcaggagca agataccgga gtggtacgag     120
gcgggaatat ccgccatttg gattcctccc gcgagcaagg gtatgagcgg cggctattcg     180
atgggctacg accctacga ttattttgac ctcggtgagt actaccagaa gggaacggtg     240
gaaacgaggt tcggctcaaa gcaggagctc ataaacatga taaacaccgc ccacgcctat     300
ggcatgaagg taatagccga tatagtcatc aaccaccgcg ccggcggtga cctggagtgg     360
aaccccttcg tgaacgacta tacctggacc gacttctcaa aggtcgcgtc gggtaaatac     420
acggccaact acctcgactt ccacccgaac gagctccatg cgggcgattc cggaacattt     480
ggaggctatc ccgacatatg ccacgacaag agctgggacc agtactggct ctgggccagc     540
caggagagct acgcggcata tctcaggagc atcggcatcg atgcctggcg cttcgactac     600
gtcaagggct atgctccctg gtcgtcaag gactggctga actggtgggg aggctgggcg     660
gttggagagt actgggacac caacgtcgac gctgttctca actgggcata ctcgagcggt     720
gccaaggtct ttgacttcgc cctctactac aagatggacg aggccttcga taacaacaac     780
attcccgccc tggtggacgc cctcagatac ggtcagacag tggtcagccg cgacccgttc     840
aaggctgtga cgtttgtagc caaccacgat accgatataa tttggaacaa gtacccggcc     900
tacgccttca tcctcaccta cgagggccag ccgacgatat tctaccgcga ctacgaggag    960
tggctcaaca aggacaggct caagaacctc atctggatac acgaccacct cgccggtgga    1020
agcacgagca tagtttacta cgacagcgac gagatgatct tcgtgaggaa cggctatgga    1080
agcaagcctg gccttataac ttacatcaac ctcggctcga gcaaggttgg aaggtgggtt    1140
tacgttccga agttcgcagg ctcgtgcata cacgagtaca ccggcaatct cggcggctgg    1200
gtggacaagt gggtggactc aagcggctgg gtctacctcg aggctcctgc ccacgacccg    1260
gccaacggcc agtacggcta ctccgtctgg agctattgcg gtgttggctg a             1311
```

<210> SEQ ID NO 71
<211> LENGTH: 436
<212> TYPE: PRT
<213> ORGANISM: Artificial Sequence
<220> FEATURE:
<223> OTHER INFORMATION: protein sequence of an amylase

<400> SEQUENCE: 71

```
Met Ala Lys Tyr Ser Glu Leu Glu Glu Gly Gly Val Ile Met Gln Ala
1               5                   10                  15

Phe Tyr Trp Asp Val Pro Gly Gly Gly Ile Trp Trp Gly Thr Ile Arg
            20                  25                  30

Ser Lys Ile Pro Glu Trp Tyr Glu Ala Gly Ile Ser Ala Ile Trp Ile
        35                  40                  45

Pro Pro Ala Ser Lys Gly Met Ser Gly Gly Tyr Ser Met Gly Tyr Asp
    50                  55                  60

Pro Tyr Asp Tyr Phe Asp Leu Gly Glu Tyr Tyr Gln Lys Gly Thr Val
65                  70                  75                  80
```

```
Glu Thr Arg Phe Gly Ser Lys Gln Glu Leu Ile Asn Met Ile Asn Thr
                85                  90                  95
Ala His Ala Tyr Gly Met Lys Val Ile Ala Asp Ile Val Ile Asn His
            100                 105                 110
Arg Ala Gly Gly Asp Leu Glu Trp Asn Pro Phe Val Asn Asp Tyr Thr
        115                 120                 125
Trp Thr Asp Phe Ser Lys Val Ala Ser Gly Lys Tyr Thr Ala Asn Tyr
130                 135                 140
Leu Asp Phe His Pro Asn Glu Leu His Ala Gly Asp Ser Gly Thr Phe
145                 150                 155                 160
Gly Gly Tyr Pro Asp Ile Cys His Asp Lys Ser Trp Asp Gln Tyr Trp
                165                 170                 175
Leu Trp Ala Ser Gln Glu Ser Tyr Ala Ala Tyr Leu Arg Ser Ile Gly
            180                 185                 190
Ile Asp Ala Trp Arg Phe Asp Tyr Val Lys Gly Tyr Ala Pro Trp Val
        195                 200                 205
Val Lys Asp Trp Leu Asn Trp Trp Gly Gly Trp Ala Val Gly Glu Tyr
210                 215                 220
Trp Asp Thr Asn Val Asp Ala Val Leu Asn Trp Ala Tyr Ser Ser Gly
225                 230                 235                 240
Ala Lys Val Phe Asp Phe Ala Leu Tyr Tyr Lys Met Asp Glu Ala Phe
                245                 250                 255
Asp Asn Asn Asn Ile Pro Ala Leu Val Asp Ala Leu Arg Tyr Gly Gln
            260                 265                 270
Thr Val Val Ser Arg Asp Pro Phe Lys Ala Val Thr Phe Val Ala Asn
        275                 280                 285
His Asp Thr Asp Ile Ile Trp Asn Lys Tyr Pro Ala Tyr Ala Phe Ile
290                 295                 300
Leu Thr Tyr Glu Gly Gln Pro Thr Ile Phe Tyr Arg Asp Tyr Glu Glu
305                 310                 315                 320
Trp Leu Asn Lys Asp Arg Leu Lys Asn Leu Ile Trp Ile His Asp His
                325                 330                 335
Leu Ala Gly Gly Ser Thr Ser Ile Val Tyr Tyr Asp Ser Asp Glu Met
            340                 345                 350
Ile Phe Val Arg Asn Gly Tyr Gly Ser Lys Pro Gly Leu Ile Thr Tyr
        355                 360                 365
Ile Asn Leu Gly Ser Ser Lys Val Gly Arg Trp Val Tyr Val Pro Lys
370                 375                 380
Phe Ala Gly Ser Cys Ile His Glu Tyr Thr Gly Asn Leu Gly Gly Trp
385                 390                 395                 400
Val Asp Lys Trp Val Asp Ser Ser Gly Trp Val Tyr Leu Glu Ala Pro
                405                 410                 415
Ala His Asp Pro Ala Asn Gly Gln Tyr Gly Tyr Ser Val Trp Ser Tyr
            420                 425                 430
Cys Gly Val Gly
        435

<210> SEQ ID NO 72
<211> LENGTH: 1311
<212> TYPE: DNA
<213> ORGANISM: Artificial Sequence
<220> FEATURE:
<223> OTHER INFORMATION: DNA sequence coding for an amylase
```

<400> SEQUENCE: 72

```
atggccaagt acctggagct cgaagagggc ggggtcataa tgcaggcgtt ctactgggac      60
gtgccttcgg gaggaatatg gtgggacaca atacggcaga agataccgga gtggtacgat     120
gccggaatct ccgcaatatg gattcctccc gcgagcaagg gtatgagcgg cggctattcg     180
atgggctacg accctacga ttattttgac ctcggtgagt actaccagaa gggaacggtg      240
gaaacgaggt tcggctcaaa gcaggagctc ataaacatga taaacacggc ccatgcctac     300
ggcataaagg tcatagcgga catcgtcata aaccaccgcg caggcggaga cctcgagtgg     360
aacccgttcg ttggggacta cacctggacg gacttctcaa aggtggcctc gggcaaatat     420
actgccaact acctcgactt ccaccccaac gaggtcaagt gctgtgacga gggcacattt     480
ggaggcttcc cagacatagc ccacgagaag agctgggacc agcactggct ctgggcgagc     540
gatgagagct acgccgccta cctaaggagc atcggcgttg atgcctggcg cttcgactac     600
gtcaagggct acgagcgtg gtcgtcaag gactggctgg actggtgggg aggctgggcc       660
gtcgggagt actgggacac aaacgttgat gcactgctca actgggccta ctcgagcgat     720
gcaaaagtct tcgacttccc gctctactac aagatggacg aggccttcga taacaacaac     780
attcccgccc tggtggacgc cctcagatac ggtcagacag tggtcagccg cgacccgttc     840
aaggctgtga cgtttgtagc caaccacgat accgatataa tctggaacaa gtatccagcc     900
tacgcgttca tcctcaccta cgagggccag ccgacaatat tctaccgcga ctacgaggag     960
tggctcaaca aggataagct caagaacctc atctggatac atgacaacct cgccggagga    1020
agcacgagca tagttttacta cgacagcgac gagatgatct tcgtgaggaa cggctatgga    1080
agcaagcctg gccttataac ttacatcaac ctcggctcga gcaaggttgg aaggtgggtc    1140
tacgttccga gttcgcggg agcgtgcatc cacgagtaca ccggcaacct cggcggctgg    1200
gtggacaagt gggtggactc aagcgggtgg gtgtacctcg aggcccctgc ccacgacccg    1260
gccaacggct attacggcta ctccgtctgg agctactgcg tggtgggctg a             1311
```

<210> SEQ ID NO 73
<211> LENGTH: 436
<212> TYPE: PRT
<213> ORGANISM: Artificial Sequence
<220> FEATURE:
<223> OTHER INFORMATION: protein sequence of an amylase

<400> SEQUENCE: 73

```
Met Ala Lys Tyr Leu Glu Leu Glu Glu Gly Gly Val Ile Met Gln Ala
1               5                   10                  15

Phe Tyr Trp Asp Val Pro Ser Gly Gly Ile Trp Trp Asp Thr Ile Arg
            20                  25                  30

Gln Lys Ile Pro Glu Trp Tyr Asp Ala Gly Ile Ser Ala Ile Trp Ile
        35                  40                  45

Pro Pro Ala Ser Lys Gly Met Ser Gly Gly Tyr Ser Met Gly Tyr Asp
    50                  55                  60

Pro Tyr Asp Tyr Phe Asp Leu Gly Glu Tyr Tyr Gln Lys Gly Thr Val
65                  70                  75                  80

Glu Thr Arg Phe Gly Ser Lys Gln Glu Leu Ile Asn Met Ile Asn Thr
                85                  90                  95

Ala His Ala Tyr Gly Ile Lys Val Ile Ala Asp Ile Val Ile Asn His
            100                 105                 110

Arg Ala Gly Gly Asp Leu Glu Trp Asn Pro Phe Val Gly Asp Tyr Thr
        115                 120                 125
```

Trp Thr Asp Phe Ser Lys Val Ala Ser Gly Lys Tyr Thr Ala Asn Tyr
130                 135                 140

Leu Asp Phe His Pro Asn Glu Val Lys Cys Cys Asp Glu Gly Thr Phe
145                 150                 155                 160

Gly Gly Phe Pro Asp Ile Ala His Glu Lys Ser Trp Asp Gln His Trp
                165                 170                 175

Leu Trp Ala Ser Asp Glu Ser Tyr Ala Ala Tyr Leu Arg Ser Ile Gly
                180                 185                 190

Val Asp Ala Trp Arg Phe Asp Tyr Val Lys Gly Tyr Gly Ala Trp Val
                195                 200                 205

Val Lys Asp Trp Leu Asp Trp Trp Gly Gly Trp Ala Val Gly Glu Tyr
210                 215                 220

Trp Asp Thr Asn Val Asp Ala Leu Leu Asn Trp Ala Tyr Ser Ser Asp
225                 230                 235                 240

Ala Lys Val Phe Asp Phe Pro Leu Tyr Tyr Lys Met Asp Glu Ala Phe
                245                 250                 255

Asp Asn Asn Asn Ile Pro Ala Leu Val Asp Ala Leu Arg Tyr Gly Gln
                260                 265                 270

Thr Val Val Ser Arg Asp Pro Phe Lys Ala Val Thr Phe Val Ala Asn
                275                 280                 285

His Asp Thr Asp Ile Ile Trp Asn Lys Tyr Pro Ala Tyr Ala Phe Ile
                290                 295                 300

Leu Thr Tyr Glu Gly Gln Pro Thr Ile Phe Tyr Arg Asp Tyr Glu Glu
305                 310                 315                 320

Trp Leu Asn Lys Asp Lys Leu Lys Asn Leu Ile Trp Ile His Asp Asn
                325                 330                 335

Leu Ala Gly Gly Ser Thr Ser Ile Val Tyr Tyr Asp Ser Asp Glu Met
                340                 345                 350

Ile Phe Val Arg Asn Gly Tyr Gly Ser Lys Pro Gly Leu Ile Thr Tyr
                355                 360                 365

Ile Asn Leu Gly Ser Ser Lys Val Gly Arg Trp Val Tyr Val Pro Lys
                370                 375                 380

Phe Ala Gly Ala Cys Ile His Glu Tyr Thr Gly Asn Leu Gly Gly Trp
385                 390                 395                 400

Val Asp Lys Trp Val Asp Ser Ser Gly Trp Val Tyr Leu Glu Ala Pro
                405                 410                 415

Ala His Asp Pro Ala Asn Gly Tyr Tyr Gly Tyr Ser Val Trp Ser Tyr
                420                 425                 430

Cys Val Val Gly
                435

<210> SEQ ID NO 74
<211> LENGTH: 1311
<212> TYPE: DNA
<213> ORGANISM: Artificial Sequence
<220> FEATURE:
<223> OTHER INFORMATION: DNA sequence coding for an amylase

<400> SEQUENCE: 74
atggccaagt acctggagct cgaagagggc ggggtcataa tgcaggcgtt ctactgggac      60
gtgccttcag gaggaatatg gtgggacaca atacggcaga agataccgga gtggtacgat     120
gccggaatct ccgcaatatg gattcccccg gcgagcaagg gcatgggcgg cgcctattcg     180
atgggctacg accectacga cttctttgac ctcggtgagt acgaccagaa gggaacggta     240
gagacgcgct ttggctccaa gcaggagctc gtgaacatga taaacacggc ccatgcctac     300

-continued

```
ggcataaagg tcatagcgga catcgtcata aaccaccgcg caggcggaga cctcgagtgg    360
aacccgttcg ttggggacta cacctggacg gacttctcaa aggtagcctc gggcaaatat    420
actgccaact acctcgactt ccacccgaac gagctccatg cgggcgattc cggaacattt    480
ggaggctatc ccgacatatg ccacgacaag agctgggacc agtactggct ctgggccagc    540
caggagagct acgcggcata tctcaggagc atcggcatcg atgcctggcg cttcgactac    600
gtcaagggct atgctccctg gtcgtcaag gactggctga actggtgggg aggctgggcg     660
gttggagagt actgggacac caacgtcgac gctgttctca actgggcata ctcgagcggt    720
gccaaggtct ttgacttcgc cctctactac aagatggatg aggcctttga caacaaaaac    780
attccagcgc tcgtctctgc ccttcagaac ggccagactg ttgtctcccg cgacccgttc    840
aaggccgtaa cctttgtagc aaaccacgac accgatataa tctggaacaa gtatccagcc    900
tacgcgttca tcctcaccta cgagggccag ccgacaatat tctaccgcga ctacgaggag    960
tggctcaaca aggataagct caagaacctc atctggatac atgacaacct cgccggagga   1020
agcactgaca tcgtttacta cgacaacgac gagctgtatat tcgtgagaaa cggctacgga   1080
agcaagccgg gactgataac atacatcaac ctcgcctcaa gcaaagccgg aaggtgggtt   1140
tatgtgccga agttcgcggg cgcgtgcatc cacgagtata ctggtaacct cggaggctgg   1200
gtagacaagt acgtctactc aagcggctgg gtctatctcg aagctccagc ttacgaccct   1260
gccaacgggc agtatggcta ctccgtgtgg agctactgcg gggtgggctg a            1311
```

<210> SEQ ID NO 75
<211> LENGTH: 436
<212> TYPE: PRT
<213> ORGANISM: Artificial Sequence
<220> FEATURE:
<223> OTHER INFORMATION: protein sequence of an amylase

<400> SEQUENCE: 75

```
Met Ala Lys Tyr Leu Glu Leu Glu Gly Gly Val Ile Met Gln Ala
1               5                   10                  15

Phe Tyr Trp Asp Val Pro Ser Gly Gly Ile Trp Trp Asp Thr Ile Arg
            20                  25                  30

Gln Lys Ile Pro Glu Trp Tyr Asp Ala Gly Ile Ser Ala Ile Trp Ile
        35                  40                  45

Pro Pro Ala Ser Lys Gly Met Gly Gly Ala Tyr Ser Met Gly Tyr Asp
    50                  55                  60

Pro Tyr Asp Phe Phe Asp Leu Gly Glu Tyr Gln Lys Gly Thr Val
65                  70                  75                  80

Glu Thr Arg Phe Gly Ser Lys Gln Glu Leu Val Asn Met Ile Asn Thr
                85                  90                  95

Ala His Ala Tyr Gly Ile Lys Val Ile Ala Asp Ile Val Ile Asn His
            100                 105                 110

Arg Ala Gly Gly Asp Leu Glu Trp Asn Pro Phe Val Gly Asp Tyr Thr
        115                 120                 125

Trp Thr Asp Phe Ser Lys Val Ala Ser Gly Lys Tyr Thr Ala Asn Tyr
    130                 135                 140

Leu Asp Phe His Pro Asn Glu Leu His Ala Gly Asp Ser Gly Thr Phe
145                 150                 155                 160

Gly Gly Tyr Pro Asp Ile Cys His Asp Lys Ser Trp Asp Gln Tyr Trp
                165                 170                 175

Leu Trp Ala Ser Gln Glu Ser Tyr Ala Ala Tyr Leu Arg Ser Ile Gly
            180                 185                 190
```

```
Ile Asp Ala Trp Arg Phe Asp Tyr Val Lys Gly Tyr Ala Pro Trp Val
            195                 200                 205

Val Lys Asp Trp Leu Asn Trp Trp Gly Gly Trp Ala Val Gly Glu Tyr
        210                 215                 220

Trp Asp Thr Asn Val Asp Ala Val Leu Asn Trp Ala Tyr Ser Ser Gly
225                 230                 235                 240

Ala Lys Val Phe Asp Phe Ala Leu Tyr Tyr Lys Met Asp Glu Ala Phe
                245                 250                 255

Asp Asn Lys Asn Ile Pro Ala Leu Val Ser Ala Leu Gln Asn Gly Gln
            260                 265                 270

Thr Val Val Ser Arg Asp Pro Phe Lys Ala Val Thr Phe Val Ala Asn
        275                 280                 285

His Asp Thr Asp Ile Ile Trp Asn Lys Tyr Pro Ala Tyr Ala Phe Ile
    290                 295                 300

Leu Thr Tyr Glu Gly Gln Pro Thr Ile Phe Tyr Arg Asp Tyr Glu Glu
305                 310                 315                 320

Trp Leu Asn Lys Asp Lys Leu Lys Asn Leu Ile Trp Ile His Asp Asn
                325                 330                 335

Leu Ala Gly Gly Ser Thr Asp Ile Val Tyr Tyr Asp Asn Asp Glu Leu
            340                 345                 350

Ile Phe Val Arg Asn Gly Tyr Gly Ser Lys Pro Gly Leu Ile Thr Tyr
        355                 360                 365

Ile Asn Leu Ala Ser Ser Lys Ala Gly Arg Trp Val Tyr Val Pro Lys
    370                 375                 380

Phe Ala Gly Ala Cys Ile His Glu Tyr Thr Gly Asn Leu Gly Gly Trp
385                 390                 395                 400

Val Asp Lys Tyr Val Tyr Ser Ser Gly Trp Val Tyr Leu Glu Ala Pro
                405                 410                 415

Ala Tyr Asp Pro Ala Asn Gly Gln Tyr Gly Tyr Ser Val Trp Ser Tyr
            420                 425                 430

Cys Gly Val Gly
        435

<210> SEQ ID NO 76
<211> LENGTH: 1311
<212> TYPE: DNA
<213> ORGANISM: Artificial Sequence
<220> FEATURE:
<223> OTHER INFORMATION: DNA sequence coding for an amylase

<400> SEQUENCE: 76
atggccaagt actccgagct ggaagagggc gggctcataa tgcaggcctt ctactgggac     60
gtccccatgg gaggaatctg gtgggacacg atagcccaga agatacccga ctgggcaagc    120
gccgggattt cggcgatatg gattcccccg gcgagcaagg gcatgggcgg cgcctattcg    180
atgggctacg accctacga cttctttgac ctcggtgagt acgaccagaa gggaacggta    240
gagacgcgct ttggctccaa gcaggagctc gtgaacatga taaacacggc ccatgcctac    300
ggcataaagg tcatagcgga catcgtcata aaccaccgcg caggcggaga cctcgagtgg    360
aacccgttcg ttggggacta cacctggacg gacttctcaa aggtggcctc gggcaaatat    420
actgccaact acctcgactt ccacccgaac gagctccatg cgggcgattc cggaacattt    480
ggaggctatc ccgacatatg ccacgacaag agctgggacc agtactggct ctgggccagc    540
caggagagct acgcggcata tctcaggagc atcggcatcg atgcctggcg cttcgactac    600
gtcaagggct atgctcccctg gtcgtcaag gactggctga actggtgggg aggctgggcg    660
```

```
gttggagagt actgggacac caacgtcgac gctgttctca actgggcata ctcgagcggt    720
gccaaggtct ttgacttcgc cctctactac aagatggacg aggccttcga taacaacaac    780
attcccgccc tggtggacgc cctcagatac ggtcagacag tggtcagccg cgacccgttc    840
aaggctgtga cgtttgtagc caaccacgat accgatataa tctggaacaa gtatccagcc    900
tacgcgttca tcctcaccta cgagggccag ccgacaatat tctaccgcga ctacgaggag    960
tggctcaaca aggataagct caagaacctc atctggatac atgacaacct cgccggagga    1020
agcactgaca tcgtttacta cgacaacgac gagctgatat tcgcgagaaa cggctacgga    1080
agcaagccgg gactgataac atacatcaac ctcgcctcaa gcaaagccgg aaggtgggtt    1140
tacgttccga agttcgcagg ctcgtgcata cacgagtaca ccggcaatct cggcggctgg    1200
gtggacaagt gggtggactc aagcggctgg gtctacctcg aggctcctgc ccacgacccg    1260
gccaacggcc agtacggcta ctccgtctgg agctactgcg tgttgggtg a              1311
```

<210> SEQ ID NO 77
<211> LENGTH: 436
<212> TYPE: PRT
<213> ORGANISM: Unknown
<220> FEATURE:
<223> OTHER INFORMATION: protein sequence of an amylase

<400> SEQUENCE: 77

```
Met Ala Lys Tyr Ser Glu Leu Glu Glu Gly Gly Leu Ile Met Gln Ala
1               5                   10                  15

Phe Tyr Trp Asp Val Pro Met Gly Gly Ile Trp Trp Asp Thr Ile Ala
                20                  25                  30

Gln Lys Ile Pro Asp Trp Ala Ser Ala Gly Ile Ser Ala Ile Trp Ile
            35                  40                  45

Pro Pro Ala Ser Lys Gly Met Gly Gly Ala Tyr Ser Met Gly Tyr Asp
        50                  55                  60

Pro Tyr Asp Phe Phe Asp Leu Gly Glu Tyr Asp Gln Lys Gly Thr Val
65                  70                  75                  80

Glu Thr Arg Phe Gly Ser Lys Gln Glu Leu Val Asn Met Ile Asn Thr
                85                  90                  95

Ala His Ala Tyr Gly Ile Lys Val Ile Ala Asp Ile Val Ile Asn His
            100                 105                 110

Arg Ala Gly Gly Asp Leu Glu Trp Asn Pro Phe Val Gly Asp Tyr Thr
        115                 120                 125

Trp Thr Asp Phe Ser Lys Val Ala Ser Gly Lys Tyr Thr Ala Asn Tyr
    130                 135                 140

Leu Asp Phe His Pro Asn Glu Leu His Ala Gly Asp Ser Gly Thr Phe
145                 150                 155                 160

Gly Gly Tyr Pro Asp Ile Cys His Asp Lys Ser Trp Asp Gln Tyr Trp
                165                 170                 175

Leu Trp Ala Ser Gln Glu Ser Tyr Ala Ala Tyr Leu Arg Ser Ile Gly
            180                 185                 190

Ile Asp Ala Trp Arg Phe Asp Tyr Val Lys Gly Tyr Ala Pro Trp Val
        195                 200                 205

Val Lys Asp Trp Leu Asn Trp Trp Gly Gly Trp Ala Val Gly Glu Tyr
    210                 215                 220

Trp Asp Thr Asn Val Asp Ala Val Leu Asn Trp Ala Tyr Ser Ser Gly
225                 230                 235                 240

Ala Lys Val Phe Asp Phe Ala Leu Tyr Tyr Lys Met Asp Glu Ala Phe
                245                 250                 255
```

Asp Asn Asn Asn Ile Pro Ala Leu Val Asp Ala Leu Arg Tyr Gly Gln
            260                 265                 270

Thr Val Val Ser Arg Asp Pro Phe Lys Ala Val Thr Phe Val Ala Asn
        275                 280                 285

His Asp Thr Asp Ile Ile Trp Asn Lys Tyr Pro Ala Tyr Ala Phe Ile
    290                 295                 300

Leu Thr Tyr Glu Gly Gln Pro Thr Ile Phe Tyr Arg Asp Tyr Glu Glu
305                 310                 315                 320

Trp Leu Asn Lys Asp Lys Leu Lys Asn Leu Ile Trp Ile His Asp Asn
                325                 330                 335

Leu Ala Gly Gly Ser Thr Asp Ile Val Tyr Tyr Asp Asn Asp Glu Leu
            340                 345                 350

Ile Phe Ala Arg Asn Gly Tyr Gly Ser Lys Pro Gly Leu Ile Thr Tyr
        355                 360                 365

Ile Asn Leu Ala Ser Ser Lys Ala Gly Arg Trp Val Tyr Val Pro Lys
    370                 375                 380

Phe Ala Gly Ser Cys Ile His Glu Tyr Thr Gly Asn Leu Gly Gly Trp
385                 390                 395                 400

Val Asp Lys Trp Val Asp Ser Ser Gly Trp Val Tyr Leu Glu Ala Pro
                405                 410                 415

Ala His Asp Pro Ala Asn Gly Gln Tyr Gly Tyr Ser Val Trp Ser Tyr
            420                 425                 430

Cys Gly Val Gly
        435

<210> SEQ ID NO 78
<211> LENGTH: 1299
<212> TYPE: DNA
<213> ORGANISM: Unknown
<220> FEATURE:
<223> OTHER INFORMATION: DNA sequence coding for an amylase

<400> SEQUENCE: 78
atggctctgg aagagggcgg gctcataatg caggccttct actgggacgt ccccatggga      60
ggaatctggt gggacacgat agcccagaag atacccgact gggcaagcgc cgggatttcg     120
gcgatatgga tccctcccgc gagcaagggt atgagcggcg gctattcgat gggctacgac     180
ccctacgatt attttgacct cggtgagtac taccagaagg gaacggtgga aacgaggttc     240
ggctcaaagc aggagctcat aaacatgata aacaccgccc acgcctatgg catgaaggta     300
atagccgata tagtcatcaa ccaccgcgcc ggcggtgacc tggagtggaa ccccttcgtg     360
aacgactata cctggaccga cttctcaaag gtcgcgtcgg gtaaatacac ggccaactac     420
ctcgacttcc acccgaacga gctccatgcg ggcgattccg aacatttgg aggctatccc     480 gacatatgcc acgacaagag ctgggaccag tactggctct gggccagcca ggagagctac     540
gcggcatatc tcaggagcat cggcatcgat gcctggcgct cgactacgt caagggctat     600 gctcccctgg tcgtcaagga ctggctgaac tggtggggag ctggcgcgt tggagagtac     660 tgggacacca acgtcgacgc tgttctcaac tgggcatact cgagcggtgc caaggtcttt     720
gacttcgccc tctactacaa gatggacgag gccttcgata caacaacat tcccgccctg     780 gtggacgccc tcagatacgg tcagacagtg gtcagccgcg acccgttcaa ggctgtgacg     840
tttgtagcca accacgatac cgacataatc tggaacaagt atccagccta cgcgttcatc     900
ctcacctacg agggccagcc gacaatattc taccgcgact acgaggagtg gctcaacaag     960
gataagctca agaacctcat ctggatacat gacaacctcg ccggagggag cactgacatc    1020

```
gtttactacg acaacgacga gctgatattc gtgagaaacg gctacggaag caagccggga    1080
ctgataacat acatcaacct cgcctcaagc aaagccggaa ggtgggttta cgttccgaag    1140
ttcgcaggct cgtgcataca cgagtacacc ggcaatctcg gcggctgggt ggacaagtgg    1200
gtggactcaa gcggctgggt ctacctcgag gctcctgccc acgacccggc caacggccag    1260
tacggctact ccgtctggag ctactgcggt gttgggtga                           1299
```

<210> SEQ ID NO 79
<211> LENGTH: 432
<212> TYPE: PRT
<213> ORGANISM: Unknown
<220> FEATURE:
<223> OTHER INFORMATION: protein sequence of an amylase

<400> SEQUENCE: 79

```
Met Ala Leu Glu Glu Gly Gly Leu Ile Met Gln Ala Phe Tyr Trp Asp
1               5                   10                  15

Val Pro Met Gly Gly Ile Trp Trp Asp Thr Ile Ala Gln Lys Ile Pro
                20                  25                  30

Asp Trp Ala Ser Ala Gly Ile Ser Ala Ile Trp Ile Pro Pro Ala Ser
            35                  40                  45

Lys Gly Met Ser Gly Gly Tyr Ser Met Gly Tyr Asp Pro Tyr Asp Tyr
        50                  55                  60

Phe Asp Leu Gly Glu Tyr Tyr Gln Lys Gly Thr Val Glu Thr Arg Phe
65                  70                  75                  80

Gly Ser Lys Gln Glu Leu Ile Asn Met Ile Asn Thr Ala His Ala Tyr
                85                  90                  95

Gly Met Lys Val Ile Ala Asp Ile Val Ile Asn His Arg Ala Gly Gly
                100                 105                 110

Asp Leu Glu Trp Asn Pro Phe Val Asn Asp Tyr Thr Trp Thr Asp Phe
            115                 120                 125

Ser Lys Val Ala Ser Gly Lys Tyr Thr Ala Asn Tyr Leu Asp Phe His
        130                 135                 140

Pro Asn Glu Leu His Ala Gly Asp Ser Gly Thr Phe Gly Gly Tyr Pro
145                 150                 155                 160

Asp Ile Cys His Asp Lys Ser Trp Asp Gln Tyr Trp Leu Trp Ala Ser
                165                 170                 175

Gln Glu Ser Tyr Ala Ala Tyr Leu Arg Ser Ile Gly Ile Asp Ala Trp
            180                 185                 190

Arg Phe Asp Tyr Val Lys Gly Tyr Ala Pro Trp Val Val Lys Asp Trp
        195                 200                 205

Leu Asn Trp Trp Gly Gly Trp Ala Val Gly Glu Tyr Trp Asp Thr Asn
    210                 215                 220

Val Asp Ala Val Leu Asn Trp Ala Tyr Ser Ser Gly Ala Lys Val Phe
225                 230                 235                 240

Asp Phe Ala Leu Tyr Tyr Lys Met Asp Glu Ala Phe Asp Asn Asn
                245                 250                 255

Ile Pro Ala Leu Val Asp Ala Leu Arg Tyr Gly Gln Thr Val Val Ser
                260                 265                 270

Arg Asp Pro Phe Lys Ala Val Thr Phe Val Ala Asn His Asp Thr Asp
        275                 280                 285

Ile Ile Trp Asn Lys Tyr Pro Ala Tyr Ala Phe Ile Leu Thr Tyr Glu
    290                 295                 300

Gly Gln Pro Thr Ile Phe Tyr Arg Asp Tyr Glu Glu Trp Leu Asn Lys
305                 310                 315                 320
```

```
Asp Lys Leu Lys Asn Leu Ile Trp Ile His Asp Asn Leu Ala Gly Gly
            325                 330                 335

Ser Thr Asp Ile Val Tyr Tyr Asp Asn Asp Glu Leu Ile Phe Val Arg
            340                 345                 350

Asn Gly Tyr Gly Ser Lys Pro Gly Leu Ile Thr Tyr Ile Asn Leu Ala
            355                 360                 365

Ser Ser Lys Ala Gly Arg Trp Val Tyr Val Pro Lys Phe Ala Gly Ser
        370                 375                 380

Cys Ile His Glu Tyr Thr Gly Asn Leu Gly Gly Trp Val Asp Lys Trp
385                 390                 395                 400

Val Asp Ser Ser Gly Trp Val Tyr Leu Glu Ala Pro Ala His Asp Pro
                405                 410                 415

Ala Asn Gly Gln Tyr Gly Tyr Ser Val Trp Ser Tyr Cys Gly Val Gly
            420                 425                 430

<210> SEQ ID NO 80
<211> LENGTH: 1386
<212> TYPE: DNA
<213> ORGANISM: Unknown
<220> FEATURE:
<223> OTHER INFORMATION: DNA sequence coding for an amylase

<400> SEQUENCE: 80
atgaagcctg cgaaactcct cgtctttgtg ctcgtagtct ctatcctcgc ggggctctac      60
gcccagcccg cggggcggc caagtacctg gagctcgaag agggcggcgt cataatgcag     120
gcgttctact gggacgtgcc ttcaggagga atatggtggg acacaatacg gcagaagata     180
ccggagtggt acgatgccgg aatctccgca atatggattc ccccggcgag caagggcatg     240
ggcggcgcct attcgatggg ctacgacccc tacgacttct tgacctcgg tgagtacgac     300 cagaagggaa cggtagagac gcgctttggc tccaagcagg agctcgtgaa catgataaac     360
accgcccacg cctacggcat caaggtcatc gcagacatag taatcaacca ccgcgccgga     420
ggagaccttg agtggaaccc cttcgtcaat gactacacct ggacggactt ctcgaaggtc     480
gcttccggca agtacacggc caactacctc gacttccacc caacgaggt caagtgctgc     540 gacgagggca ccttggagg gttcccggac atagcccacg agaagagctg ggaccagtac     600
tggctctggg cgagcaacga gagctacgcc gcctacctca ggagcatcgg cgttgacgca     660
tggcgcttcg actacgtcaa gggctacgga gcgtgggtcg tcaaggactg gctggactgg     720
tggggaggct gggccgtcgg ggagtactgg gacacaaacg ttgatgcact gctcaactgg     780
gcctactcga gcgatgcaaa agtcttcgac ttcccgctct actacaagat ggacgcggcc     840
tttgacaaca agaacattcc cgcactcgtc gaggccctca agaacggggg cacagtcgtc     900
agccgcgacc cgtttaaggc cgtaaccttc gttgcaaacc acgacacgga cataatttgg     960
aacaagtacc cggcctacgc cttcatcctc acctacgagg ccagccgac gatattctac    1020 cgcgactacg aggagtggct caacaaggac aggctcaaga acctcatctg gatacacgac    1080
cacctcgccg gtggaagcac cgacatagtc tactacgata cgatgaact catcttcgtc    1140 aggaacggct acgggacaa gccgggctt ataacctaca tcaacctagg ctcgagcaag    1200
gccgggaggt gggtctacgt tccgaagttc gcgggagcgt gcatccacga gtacaccggc    1260
aacctcggcg gctgggtgga caagtgggtg gactcaagcg gtggtgta cctcgaggcc    1320 cctgcccacg acccggccaa cggctattac ggctactccg tctggagcta ctgcggggtg    1380
ggctga                                                              1386
```

```
<210> SEQ ID NO 81
<211> LENGTH: 461
<212> TYPE: PRT
<213> ORGANISM: Unknown
<220> FEATURE:
<223> OTHER INFORMATION: protein sequence of an amylase

<400> SEQUENCE: 81
```

Met Lys Pro Ala Lys Leu Leu Val Phe Val Leu Val Val Ser Ile Leu
1               5                   10                  15

Ala Gly Leu Tyr Ala Gln Pro Ala Gly Ala Ala Lys Tyr Leu Glu Leu
                20                  25                  30

Glu Glu Gly Gly Val Ile Met Gln Ala Phe Tyr Trp Asp Val Pro Ser
            35                  40                  45

Gly Gly Ile Trp Trp Asp Thr Ile Arg Gln Lys Ile Pro Glu Trp Tyr
        50                  55                  60

Asp Ala Gly Ile Ser Ala Ile Trp Ile Pro Pro Ala Ser Lys Gly Met
65                  70                  75                  80

Gly Gly Ala Tyr Ser Met Gly Tyr Asp Pro Tyr Asp Phe Phe Asp Leu
                85                  90                  95

Gly Glu Tyr Asp Gln Lys Gly Thr Val Glu Thr Arg Phe Gly Ser Lys
            100                 105                 110

Gln Glu Leu Val Asn Met Ile Asn Thr Ala His Ala Tyr Gly Ile Lys
        115                 120                 125

Val Ile Ala Asp Ile Val Ile Asn His Arg Ala Gly Gly Asp Leu Glu
130                 135                 140

Trp Asn Pro Phe Val Asn Asp Tyr Thr Trp Thr Asp Phe Ser Lys Val
145                 150                 155                 160

Ala Ser Gly Lys Tyr Thr Ala Asn Tyr Leu Asp Phe His Pro Asn Glu
                165                 170                 175

Val Lys Cys Cys Asp Glu Gly Thr Phe Gly Gly Phe Pro Asp Ile Ala
            180                 185                 190

His Glu Lys Ser Trp Asp Gln Tyr Trp Leu Trp Ala Ser Asn Glu Ser
        195                 200                 205

Tyr Ala Ala Tyr Leu Arg Ser Ile Gly Val Asp Ala Trp Arg Phe Asp
210                 215                 220

Tyr Val Lys Gly Tyr Gly Ala Trp Val Val Lys Asp Trp Leu Asp Trp
225                 230                 235                 240

Trp Gly Gly Trp Ala Val Gly Glu Tyr Trp Asp Thr Asn Val Asp Ala
                245                 250                 255

Leu Leu Asn Trp Ala Tyr Ser Ser Asp Ala Lys Val Phe Asp Phe Pro
            260                 265                 270

Leu Tyr Tyr Lys Met Asp Ala Ala Phe Asp Asn Lys Asn Ile Pro Ala
        275                 280                 285

Leu Val Glu Ala Leu Lys Asn Gly Gly Thr Val Val Ser Arg Asp Pro
290                 295                 300

Phe Lys Ala Val Thr Phe Val Ala Asn His Asp Thr Asp Ile Ile Trp
305                 310                 315                 320

Asn Lys Tyr Pro Ala Tyr Ala Phe Ile Leu Thr Tyr Glu Gly Gln Pro
                325                 330                 335

Thr Ile Phe Tyr Arg Asp Tyr Glu Glu Trp Leu Asn Lys Asp Arg Leu
            340                 345                 350

Lys Asn Leu Ile Trp Ile His Asp His Leu Ala Gly Gly Ser Thr Asp
        355                 360                 365

```
Ile Val Tyr Tyr Asp Asn Asp Glu Leu Ile Phe Val Arg Asn Gly Tyr
        370                 375                 380

Gly Asp Lys Pro Gly Leu Ile Thr Tyr Ile Asn Leu Gly Ser Ser Lys
385                 390                 395                 400

Ala Gly Arg Trp Val Tyr Val Pro Lys Phe Ala Gly Ala Cys Ile His
            405                 410                 415

Glu Tyr Thr Gly Asn Leu Gly Gly Trp Val Asp Lys Trp Val Asp Ser
            420                 425                 430

Ser Gly Trp Val Tyr Leu Glu Ala Pro Ala His Asp Pro Ala Asn Gly
        435                 440                 445

Tyr Tyr Gly Tyr Ser Val Trp Ser Tyr Cys Gly Val Gly
    450                 455                 460
```

<210> SEQ ID NO 82
<211> LENGTH: 1386
<212> TYPE: DNA
<213> ORGANISM: Unknown
<220> FEATURE:
<223> OTHER INFORMATION: DNA sequence coding for an amylase

<400> SEQUENCE: 82

```
atgaagaagt tgtcgccct gttcataacc atgttttttcg tagtgagcat ggcagtcgtt      60
gcacagccag ctagcgccgc aaagtattcc gagctcgaag aaggcggcgt tataatgcag     120
gccttctact gggacgtccc aggtggagga atctggtggg acaccatcag gagcaagata     180
ccggagtggt acgaggcggg aatatccgcc atttggattc cgccagccag caaggggatg     240
agcggcggtt actcgatggg ctacgatccc tacgatttct ttgacctcgg cgagtacaac     300
cagaagggaa ccatcgaaac gcgctttggc tctaaacagg agctcatcaa tatgataaac     360
acggcccatg cctacggcat aaaggtcata gcggacatcg tcataaacca ccgcgcaggc     420
ggagacctcg agtggaaccc gttcgttggg gactacacct ggacggactt ctcaaaggtg     480
gcctcgggca atatactgc caactacctc gacttccacc caacgaggt caagtgctgt     540 gacgagggca catttggagg cttcccagac atagcccacg agaagagctg ggaccagcac     600
tggctctggg cgagcgatga gagctacgcc gcctacctaa ggagcatcgg cgttgatgcc     660
tggcgctttg actacgtgaa gggctacgga gcgtgggtcg tcaaggactg gctcaactgg     720
tggggcggct gggccgttgg cgagtactgg gacaccaacg ttgatgcact cctcaactgg     780
gcctactcga gcggcgccaa ggtcttcgac ttcccgctct actacaagat ggatgaggcc     840
tttgacaaca aaaacattcc agcgctcgtc tctgcccttc agaacggcca gactgttgtc     900
tcccgcgacc cgttcaaggc cgtaaccttt gtagcaaacc acgacaccga taatctgg      960 aacaagtacc ttgcttatgc tttcatcctc acctacgaag ccagcccgt catattctac    1020 cgcgactacg aggagtggct caacaaggac aggttgaaca acctcatatg gatacacgac    1080
cacctcgcag gtggaagcac gagcatagtc tactacgaca gcgacgagat gatcttcgtg    1140
aggaacggct atgaagcaa gcctggcctt ataacttaca tcaacctcgg ctcgagcaag    1200
gttggaaggt gggtttatgt gccgaagttc gcgggcgcgt gcatccacga gtatactggt    1260
aacctcggag ctgggtaga caagtacgtc tactcaagcg gctgggtcta tctcgaagct    1320
ccagcttacg accctgccaa cgggcagtat ggctactccg tgtggagcta ttgcggtgtt    1380
gggtga                                                              1386
```

```
<210> SEQ ID NO 83
<211> LENGTH: 461
<212> TYPE: PRT
<213> ORGANISM: Unknown
<220> FEATURE:
<223> OTHER INFORMATION: protein sequence of an amylase

<400> SEQUENCE: 83
```

Met Lys Lys Phe Val Ala Leu Phe Ile Thr Met Phe Val Val Ser
1               5                   10                  15

Met Ala Val Val Ala Gln Pro Ala Ser Ala Ala Lys Tyr Ser Glu Leu
            20                  25                  30

Glu Glu Gly Gly Val Ile Met Gln Ala Phe Tyr Trp Asp Val Pro Gly
            35                  40                  45

Gly Gly Ile Trp Trp Asp Thr Ile Arg Ser Lys Ile Pro Glu Trp Tyr
        50                  55                  60

Glu Ala Gly Ile Ser Ala Ile Trp Ile Pro Pro Ala Ser Lys Gly Met
65                  70                  75                  80

Ser Gly Gly Tyr Ser Met Gly Tyr Asp Pro Tyr Asp Phe Phe Asp Leu
                85                  90                  95

Gly Glu Tyr Asn Gln Lys Gly Thr Ile Glu Thr Arg Phe Gly Ser Lys
            100                 105                 110

Gln Glu Leu Ile Asn Met Ile Asn Thr Ala His Ala Tyr Gly Ile Lys
        115                 120                 125

Val Ile Ala Asp Ile Val Ile Asn His Arg Ala Gly Gly Asp Leu Glu
    130                 135                 140

Trp Asn Pro Phe Val Gly Asp Tyr Thr Trp Thr Asp Phe Ser Lys Val
145                 150                 155                 160

Ala Ser Gly Lys Tyr Thr Ala Asn Tyr Leu Asp Phe His Pro Asn Glu
                165                 170                 175

Val Lys Cys Cys Asp Glu Gly Thr Phe Gly Gly Phe Pro Asp Ile Ala
            180                 185                 190

His Glu Lys Ser Trp Asp Gln His Trp Leu Trp Ala Ser Asp Glu Ser
        195                 200                 205

Tyr Ala Ala Tyr Leu Arg Ser Ile Gly Val Asp Ala Trp Arg Phe Asp
    210                 215                 220

Tyr Val Lys Gly Tyr Gly Ala Trp Val Val Lys Asp Trp Leu Asn Trp
225                 230                 235                 240

Trp Gly Gly Trp Ala Val Gly Glu Tyr Trp Asp Thr Asn Val Asp Ala
                245                 250                 255

Leu Leu Asn Trp Ala Tyr Ser Ser Gly Ala Lys Val Phe Asp Phe Pro
            260                 265                 270

Leu Tyr Tyr Lys Met Asp Glu Ala Phe Asp Asn Lys Asn Ile Pro Ala
        275                 280                 285

Leu Val Ser Ala Leu Gln Asn Gly Gln Thr Val Val Ser Arg Asp Pro
    290                 295                 300

Phe Lys Ala Val Thr Phe Val Ala Asn His Asp Thr Asp Ile Ile Trp
305                 310                 315                 320

Asn Lys Tyr Leu Ala Tyr Ala Phe Ile Leu Thr Tyr Glu Gly Gln Pro
                325                 330                 335

Val Ile Phe Tyr Arg Asp Tyr Glu Glu Trp Leu Asn Lys Asp Arg Leu
            340                 345                 350

Asn Asn Leu Ile Trp Ile His Asp His Leu Ala Gly Gly Ser Thr Ser
        355                 360                 365

-continued

```
Ile Val Tyr Tyr Asp Ser Asp Glu Met Ile Phe Val Arg Asn Gly Tyr
    370             375             380

Gly Ser Lys Pro Gly Leu Ile Thr Tyr Ile Asn Leu Gly Ser Ser Lys
385             390             395             400

Val Gly Arg Trp Val Tyr Val Pro Lys Phe Ala Gly Ala Cys Ile His
            405             410             415

Glu Tyr Thr Gly Asn Leu Gly Gly Trp Val Asp Lys Tyr Val Tyr Ser
            420             425             430

Ser Gly Trp Val Tyr Leu Glu Ala Pro Ala Tyr Asp Pro Ala Asn Gly
        435             440             445

Gln Tyr Gly Tyr Ser Val Trp Ser Tyr Cys Gly Val Gly
    450             455             460
```